United States Patent
Chesworth et al.

(10) Patent No.: US 9,718,816 B2
(45) Date of Patent: Aug. 1, 2017

(54) 1-PHENOXY-3-(ALKYLAMINO)-PROPAN-2-OL DERIVATIVES AS CARM1 INHIBITORS AND USES THEREOF

(71) Applicant: Epizyme, Inc., Cambridge, MA (US)

(72) Inventors: Richard Chesworth, Concord, MA (US); Oscar Miguel Moradei, Burlington, MA (US); Gideon Shapiro, Gainesville, FL (US); Kenneth W. Duncan, Westwood, MA (US); Lorna Helen Mitchell, Cambridge, MA (US); Lei Jin, Wellesley, MA (US); Robert E. Babine, Carlsbad, CA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/775,197

(22) PCT Filed: Mar. 14, 2014

(86) PCT No.: PCT/US2014/028874
§ 371 (c)(1),
(2) Date: Sep. 11, 2015

(87) PCT Pub. No.: WO2014/144455
PCT Pub. Date: Sep. 18, 2014

(65) Prior Publication Data
US 2016/0052922 A1   Feb. 25, 2016

Related U.S. Application Data

(60) Provisional application No. 61/798,109, filed on Mar. 15, 2013.

(51) Int. Cl.
| C07D 471/04 | (2006.01) |
| C07D 498/08 | (2006.01) |
| C07D 487/04 | (2006.01) |

(52) U.S. Cl.
CPC ......... *C07D 471/04* (2013.01); *C07D 487/04* (2013.01); *C07D 498/08* (2013.01)

(58) Field of Classification Search
None
See application file for complete search history.

(56) References Cited

U.S. PATENT DOCUMENTS

| 4,011,321 | A | 3/1977 | Coates et al. |
| 5,221,675 | A | 6/1993 | Chung et al. |
| 6,710,052 | B2 | 3/2004 | Pease et al. |
| 6,730,792 | B2 | 5/2004 | Evers et al. |
| 6,864,267 | B2 | 3/2005 | Bhatnagar et al. |
| 7,098,207 | B2 | 8/2006 | Niewohner et al. |
| 7,485,722 | B2 | 2/2009 | Egle et al. |
| 8,063,071 | B2 | 11/2011 | Kerns et al. |
| 8,110,579 | B2 | 2/2012 | Altenburger et al. |
| 8,338,437 | B2 | 12/2012 | Wahhab et al. |
| 8,906,900 | B2 | 12/2014 | Duncan et al. |
| 8,940,726 | B2 | 1/2015 | Duncan et al. |
| 8,952,026 | B2 | 2/2015 | Mitchell et al. |
| 8,993,555 | B2 | 3/2015 | Duncan et al. |
| 9,023,883 | B2 | 5/2015 | Kuntz et al. |

(Continued)

FOREIGN PATENT DOCUMENTS

| DE | 100 10 067 A1 | 9/2001 |
| GB | 1488330 A | 10/1977 |

(Continued)

OTHER PUBLICATIONS

International Search Report and Written Opinion for International Application No. PCT/US2014/028874 mailed May 21, 2014.
International Search Report and Written Opinion for International Application No. PCT/US2014/028463 mailed Jun. 10, 2014.
International Search Report and Written Opinion for International Application No. PCT/US2015/050712 mailed Dec. 15, 2015.
International Search Report and Written Opinion for International Application No. PCT/US2015/050776 mailed Dec. 14, 2015.
International Search Report and Written Opinion for International Application No. PCT/US2015/050788 mailed Dec. 17, 2015.
International Search Report and Written Opinion for International Application No. PCT/US2015/050675 mailed Dec. 17, 2015.
International Search Report and Written Opinion for International Application No. PCT/US2015/050647 mailed Dec. 14, 2015.
Al-Dhaheri et al., CARM1 is an important determinant of ERα-dependent breast cancer cell differentiation and proliferation in breast cancer cells. Cancer Res. Mar. 15, 2011;71(6):2118-28.doi: 10.1158/0008-5472.CAN-10-2426. Epub Jan. 31, 2011.

(Continued)

*Primary Examiner* — Brian J Davis
(74) *Attorney, Agent, or Firm* — Wolf, Greenfield & Sacks, P.C.

(57) ABSTRACT

Provided herein are compounds of Formula (I): and pharmaceutically acceptable salts thereof, and pharmaceutical compositions thereof; wherein X, $R^1$, $R^{2a}$, $R^{2b}$, $R^{2c}$, $R^{2d}$, are as defined herein, and Ring HET is an optionally substituted 6,5-bicyclic heteroaryl ring system comprising 2 to 5 nitrogen atoms, inclusive, wherein the point of attachment is provided on the 6-membered ring of the 6,5-bicyclic heteroaryl ring system, and wherein the 6-membered ring is further substituted with a group of formula $-L^1-R^3$, wherein $L^1$ and $R^3$ are as defined herein. Compounds of the present invention are useful for inhibiting CARM1 activity. Methods of using the compounds for treating CARM1-mediated disorders are also described.

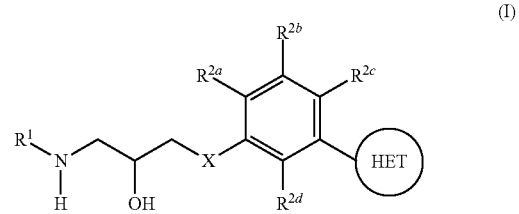

(I)

28 Claims, No Drawings

(56) References Cited

U.S. PATENT DOCUMENTS

| | | | |
|---|---|---|---|
| 9,045,455 | B2 | 6/2015 | Mitchell et al. |
| 9,120,757 | B2 | 9/2015 | Chesworth et al. |
| 9,133,189 | B2 | 9/2015 | Chesworth et al. |
| 9,221,794 | B2 | 12/2015 | Duncan et al. |
| 9,266,836 | B2 | 2/2016 | Duncan et al. |
| 9,346,761 | B2 | 5/2016 | Chesworth et al. |
| 9,346,802 | B2 | 5/2016 | Chesworth et al. |
| 9,365,519 | B2 | 6/2016 | Duncan et al. |
| 9,365,527 | B2 | 6/2016 | Chesworth et al. |
| 9,365,555 | B2 | 6/2016 | Duncan et al. |
| 9,388,173 | B2 | 7/2016 | Duncan et al. |
| 9,394,258 | B2 | 7/2016 | Chesworth et al. |
| 9,440,950 | B2 | 9/2016 | Mitchell et al. |
| 9,447,079 | B2 | 9/2016 | Mitchell et al. |
| 9,475,776 | B2 | 10/2016 | Kuntz et al. |
| 2003/0055244 | A1 | 3/2003 | Scarborough et al. |
| 2004/0242633 | A1 | 12/2004 | Evers et al. |
| 2005/0124001 | A1 | 6/2005 | Coats et al. |
| 2006/0235037 | A1 | 10/2006 | Purandare et al. |
| 2009/0318473 | A1 | 12/2009 | Altenburger et al. |
| 2010/0144722 | A1 | 6/2010 | Alexander et al. |
| 2011/0065681 | A1 | 3/2011 | Wei et al. |
| 2011/0098268 | A1 | 4/2011 | Mampreian et al. |
| 2014/0163049 | A1 | 6/2014 | Duffy et al. |
| 2014/0221310 | A1 | 8/2014 | Eccles et al. |
| 2014/0228360 | A1 | 8/2014 | Duncan et al. |
| 2014/0288067 | A1 | 9/2014 | Chesworth et al. |
| 2014/0288105 | A1 | 9/2014 | Chesworth et al. |
| 2014/0288129 | A1 | 9/2014 | Mitchell et al. |
| 2014/0323537 | A1 | 10/2014 | Chesworth et al. |
| 2015/0284334 | A1 | 10/2015 | Kuntz et al. |
| 2015/0344433 | A1 | 12/2015 | Duncan et al. |
| 2015/0344434 | A1 | 12/2015 | Duncan et al. |
| 2015/0344457 | A1 | 12/2015 | Duncan et al. |
| 2015/0344463 | A1 | 12/2015 | Duncan et al. |
| 2015/0361042 | A1 | 12/2015 | Duncan et al. |
| 2016/0024016 | A1 | 1/2016 | Chesworth et al. |
| 2016/0024017 | A1 | 1/2016 | Chesworth et al. |
| 2016/0031839 | A1 | 2/2016 | Chesworth et al. |
| 2016/0039767 | A1 | 2/2016 | Mitchell et al. |
| 2016/0039834 | A1 | 2/2016 | Chesworth et al. |
| 2016/0108018 | A1 | 4/2016 | Mitchell et al. |
| 2016/0137609 | A1 | 5/2016 | Chesworth et al. |
| 2016/0137631 | A1 | 5/2016 | Duncan et al. |
| 2016/0184267 | A1 | 6/2016 | Chesworth et al. |
| 2016/0185772 | A1 | 6/2016 | Chesworth et al. |
| 2016/0214985 | A1 | 7/2016 | Duncan et al. |
| 2016/0368907 | A1 | 12/2016 | Duncan et al. |

FOREIGN PATENT DOCUMENTS

| | | |
|---|---|---|
| GB | 1548601 A | 7/1979 |
| WO | WO 95/15952 A1 | 6/1995 |
| WO | WO 99/59959 A1 | 11/1999 |
| WO | WO 00/39101 A1 | 7/2000 |
| WO | WO 01/64653 A1 | 9/2001 |
| WO | WO 2004/078114 A2 | 9/2004 |
| WO | WO 2008/104077 A1 | 9/2008 |
| WO | WO 2011/115183 A1 | 9/2011 |
| WO | WO 2012/121939 A2 | 9/2012 |
| WO | WO 2012/173689 A2 | 12/2012 |
| WO | WO 2014/100695 A1 | 6/2014 |
| WO | WO 2014/100716 A1 | 6/2014 |
| WO | WO 2014/100719 A1 | 6/2014 |
| WO | WO 2014/100730 A1 | 6/2014 |
| WO | WO 2014/100734 A1 | 6/2014 |
| WO | WO 2014/100764 A1 | 6/2014 |
| WO | WO 2014/144169 A1 | 9/2014 |
| WO | WO 2014/144455 A1 | 9/2014 |
| WO | WO 2014/144659 A1 | 9/2014 |
| WO | WO 2014/153090 A1 | 9/2014 |
| WO | WO 2014/153100 A1 | 9/2014 |
| WO | WO 2014/153172 A1 | 9/2014 |
| WO | WO 2014/153208 A1 | 9/2014 |
| WO | WO 2014/153214 A1 | 9/2014 |
| WO | WO 2014/153226 A1 | 9/2014 |
| WO | WO 2014/153235 A1 | 9/2014 |
| WO | WO 2014/178954 A1 | 11/2014 |
| WO | WO 2015/200677 A1 | 12/2015 |
| WO | WO 2015/200680 A1 | 12/2015 |
| WO | WO 2016/022605 A1 | 2/2016 |
| WO | WO 2016/044556 A2 | 3/2016 |
| WO | WO 2016/044569 A1 | 3/2016 |
| WO | WO 2016/044576 A1 | 3/2016 |
| WO | WO 2016/044585 A1 | 3/2016 |
| WO | WO 2016/044604 A1 | 3/2016 |
| WO | WO 2016/044626 A1 | 3/2016 |
| WO | WO 2016/044641 A1 | 3/2016 |
| WO | WO 2016/044650 A1 | 3/2016 |

OTHER PUBLICATIONS

Copeland, Protein methyltransferase inhibitors as personalized cancer therapeutics. Drug Discovery Today. Therapeutic Strategies. 2012;9(2-3):e83-90.

Di Lorenzo et al., Castration-resistant prostate cancer: current and emerging treatment strategies. Drugs. May 28, 2010;70(8):983-1000. doi: 10.2165/10898600-000000000-00000.

El Messaoudi et al., Coactivator-associated arginine methyltransferase 1 (CARM1) is a positive regulator of the Cyclin E1 gene. Proc Natl Acad Sci U S A. Sep. 5, 2006;103(36):13351-6. Epub Aug. 28, 2006.

Engelmann et al., the dark side of E2F1: in transit beyond apoptosis. Cancer Res. Feb. 1, 2012;72(3):571-5. doi: 10.1158/0008-5472.CAN-11-2575.

Eymin et al., Distinct pattern of E2F1 expression in human lung tumours: E2F1 is upregulated in small cell lung carcinoma. Oncogene. Mar. 29, 2001;20(14):1678-87.

Frietze et al., CARM1 regulates estrogen-stimulated breast cancer growth through up-regulation of E2F1. Cancer Res. Jan. 1, 2008;68(1):301-6. doi: 10.1158/0008-5472.CAN-07-1983.

Hong et al., Aberrant expression of CARM1, a transcriptional coactivator of androgen receptor, in the development of prostate carcinoma and androgen-independent status. Cancer. Jul. 1, 2004;101(1):83-9.

Kim et al., Differential CARM1 expression in prostate and colorectal cancers. BMC Cancer. May 13, 2010;10:197. doi: 10.1186/1471-2407-10-197.

Majumder et al., Involvement of arginine methyltransferase CARM1 in androgen receptor function and prostate cancer cell viability. Prostate. Sep. 1, 2006;66(12):1292-301.

Ou et al., A coactivator role of CARM1 in the dysregulation of β-catenin activity in colorectal cancer cell growth and gene expression. Mol Cancer Res. May 2011;9(5):660-70. doi: 10.1158/1541-7786.MCR-10-0223. Epub Apr. 8, 2011.

Pubchem Submission; NIH/NCBI, Compound Identifier 90425581. Feb 13, 2015. 9 pages.

Purandare et al., Pyrazole inhibitors of coactivator associated arginine methyltransferase 1 (CARM1). Bioorg Med Chem Lett. Aug. 1, 2008;18(15):4438-41. doi: 10.1016/j.bmcl.2008.06.026. Epub Jun. 12, 2008.

Sack et al., Structural basis for CARM1 inhibition by indole and pyrazole inhibitors. Biochem J. Jun. 1, 2011;436(2):331-9. doi: 10.1042/BJ20102161.

Teyssier et al., Protein arginine methylation in estrogen signaling and estrogen-related cancers. Trends Endocrinol Metab. Mar. 2010;21(3):181-9. doi: 10.1016/j.tem.2009.11.002. Epub Dec. 11, 2009.

Therrien et al., 1,2-Diamines as inhibitors of co-activator associated arginine methyltransferase 1 (CARM1). Bioorg Med Chem Lett. Dec. 1, 2009;19(23):6725-32. doi: 10.1016/j.bmcl.2009.09.110. Epub Oct. 2, 2009.

Wan et al., Benzo[d]imidazole inhibitors of Coactivator Associated Arginine Methyltransferase 1 (CARM1)—Hit to Lead studies. Bioorg Med Chem Lett. Sep. 1, 2009;19(17):5063-6. doi: 10.1016/j.bmcl.2009.07.040. Epub Jul. 10, 2009.

Wang et al., CARM1/PRMT4 is necessary for the glycogen gene expression programme in skeletal muscle cells. Biochem J. Jun. 1, 2012;444(2):323-31. doi: 10.1042/BJ20112033.

(56) References Cited

OTHER PUBLICATIONS

Vu et al., PRMT4 blocks myeloid differentiation by assembling a methyl-RUNX1-dependent repressor complex. Cell Rep. Dec. 26, 2013;5(6):1625-38. doi: 10.1016/j.celrep.2013.11.025.

Zauli et al., miR-34a induces the downregulation of both E2F1 and B-Myb oncogenes in leukemic cells. Clin Cancer Res. May 1, 2011;17(9):2712-24. doi:10.1158/1078-0432.CCR-10-3244.

1-PHENOXY-3-(ALKYLAMINO)-PROPAN-2-OL DERIVATIVES AS CARM1 INHIBITORS AND USES THEREOF

RELATED APPLICATIONS

The present application is a national stage filing under 35 U.S.C. §371 of International PCT application PCT/US2014/028874, filed Mar. 14, 2014 which claims priority under 35 U.S.C. §119(e) to U.S. provisional patent application, U.S. Ser. No. 61/798,109, filed Mar. 15, 2013, the entire contents of each of which is incorporated herein by reference.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., CARM1 (co-activator-associated arginine methyltransferase 1; PRMT4)), many of which are associated with specific genetic alterations that can cause human disease.

Disease-associated chromatin-modifying enzymes play a role in diseases such as proliferative disorders, autoimmune disorders, muscular disorders, and neurological disorders. Thus, there is a need for the development of small molecules that are capable of inhibiting the activity of CARM1.

DETAILED DESCRIPTION OF CERTAIN EMBODIMENTS

CARM1 is an attractive target for modulation given its role in the regulation of diverse biological processes. It has now been found that compounds described herein, and pharmaceutically acceptable salts and compositions thereof, are effective as inhibitors of CARM1. Such compounds have the general Formula (I):

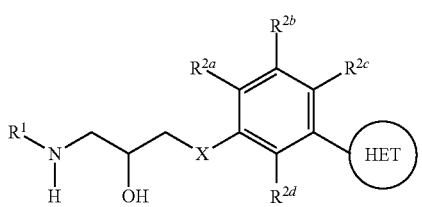

(I)

or a pharmaceutically acceptable salt thereof; wherein X, $R^1$, $R^{2a}$, $R^{2b}$, $R^{2c}$, $R^{2d}$, are as defined herein, and Ring HET is an optionally substituted 6,5-bicyclic heteroaryl ring system comprising 2 to 5 nitrogen atoms, inclusive, wherein the point of attachment is provided on the 6-membered ring of the 6,5-bicyclic heteroaryl ring system, and wherein the 6-membered ring is further substituted with a group of formula -$L^1$-$R^3$, wherein $L^1$ and $R^3$ are as defined herein.

In some embodiments, pharmaceutical compositions are provided which comprise a compound described herein (e.g., a compound of Formula (I), or a pharmaceutically acceptable salt thereof) and optionally a pharmaceutically acceptable excipient.

In certain embodiments, compounds described herein inhibit activity of CARM1. In certain embodiments, methods of inhibiting CARM1 are provided which comprise contacting CARM1 with an effective amount of a compound of Formula (I), or a pharmaceutically acceptable salt thereof. The CARM1 may be purified or crude, and may be present in a cell, tissue, or a subject. Thus, such methods encompass inhibition of CARM1 activity both in vitro and in vivo. In certain embodiments, the CARM1 is wild-type CARM1. In certain embodiments, the CARM1 is overexpressed. In certain embodiments, the CARM1 is a mutant. In certain embodiments, the CARM1 is in a cell. In certain embodiments, the CARM1 is in an animal, e.g., a human. In some embodiments, the CARM1 is expressed at normal levels in a subject, but the subject would benefit from CARM1 inhibition (e.g., because the subject has one or more mutations in an CARM1 substrate that causes an increase in methylation of the substrate with normal levels of CARM1). In some embodiments, the CARM1 is in a subject known or identified as having abnormal CARM1 activity (e.g., overexpression). In some embodiments, a provided compound is selective for CARM1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective relative to one or more other methyltransferases.

In certain embodiments, methods of modulating gene expression or activity in a cell are provided which comprise contacting a cell with an effective amount of a compound of Formula (I), or a pharmaceutically acceptable salt thereof, or a pharmaceutical composition thereof. In certain embodiments, the cell in culture in vitro. In certain embodiments, cell is in an animal, e.g., a human.

In certain embodiments, methods of modulating transcription in a cell are provided which comprise contacting a cell with an effective amount of a compound of Formula (I), or a pharmaceutically acceptable salt thereof, or a pharmaceutical composition thereof. In certain embodiments, the cell in culture in vitro. In certain embodiments, the cell is in an animal, e.g., a human.

In some embodiments, methods of treating a CARM1-mediated disorder are provided which comprise administering to a subject suffering from a CARM1-mediated disorder an effective amount of a compound described herein (e.g., a compound of Formula (I), or a pharmaceutically acceptable salt thereof), or a pharmaceutical composition thereof. In certain embodiments, the CARM1-mediated disorder is a proliferative disorder. In certain embodiments, compounds described herein are useful for treating cancer. In certain embodiments, compounds described herein are useful for treating breast cancer or prostate cancer. In certain embodiments, the CARM1-mediated disorder is a metabolic disorder.

Compounds described herein are also useful for the study of CARM1 in biological and pathological phenomena, the study of intracellular signal transduction pathways mediated by CARM1, and the comparative evaluation of new CARM1 inhibitors.

This application refers to various issued patent, published patent applications, journal articles, and other publications, all of which are incorporated herein by reference.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$-or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Aliphatic" refers to alkyl, alkenyl, alkynyl, and carbocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., $CH_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds (e.g., 1, 2, 3, or 4 double bonds), and optionally one or more triple bonds (e.g., 1, 2, 3, or 4 triple bonds) ("$C_{2-20}$ alkenyl"). In certain embodiments, alkenyl does not comprise triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl")

or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms and one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). In certain embodiments, alkynyl does not comprise double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") or tricyclic system ("tricyclic carbocyclyl"), and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl") or tricyclic system ("tricyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P$^3$(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14-membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$alkyl)$_2$, —OP(=O)(OC$_{1-6}$ alkyl)$_2$, C$_1$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Hydroxyl" or "hydroxy" refers to the group —OH. "Substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

"Thiol" or "thio" refers to the group —SH. "Substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

"Amino" refers to the group —NH$_2$. "Substituted amino," by extension, refers to a monosubstituted amino, a disubstituted amino, or a trisubstituted amino, as defined herein. In certain embodiments, the "substituted amino" is a monosubstituted amino or a disubstituted amino group.

"Monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

"Disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

"Trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

"Sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

"Sulfinyl" refers to the group —S(=O)R$^{aa}$, wherein R$^{aa}$ is as defined herein.

"Carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., S(=O)$_2$R$^{aa}$) include, but are not limited to, p-toluenesulfonamide (Ts), benzenesulfonamide, 2,3,6,trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5- dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, t-butyl carbonate (Boc), 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g., infant, child, adolescent) or adult subject (e.g., young adult, middleaged adult or senior adult)) and/or other nonhuman animals, for example, non-human mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), rodents (e.g., rats and/or mice), reptiles, amphibians, and fish. In certain embodiments, the nonhuman animal is a mammal. The non-human animal may be a male or female at any stage of development. A nonhuman animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methytransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

As generally described above, provided herein are compounds useful as CARM1 inhibitors. In some embodiments, the present disclosure provides a compound of Formula (I):

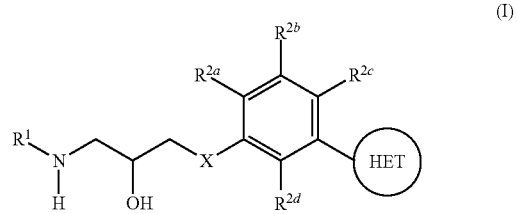

or a pharmaceutically acceptable salt thereof;
wherein:
X is —O—, —S—, or —CH$_2$—;
R$^1$ is hydrogen or optionally substituted C$_{1-4}$ aliphatic;
each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring;

Ring HET is an optionally substituted 6,5-bicyclic heteroaryl ring system comprising 2 to 5 nitrogen atoms, inclusive, wherein the point of attachment is provided on the 6-membered ring of the 6,5-bicyclic heteroaryl ring system, and wherein the 6-membered ring is further substituted with a group of formula -$L^1$-$R^3$;

$L^1$ is a bond, —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(=$NR^L$)—, —C(=$NNR^L$)—, —C(=$NOR^L$)—, —C(=$NR^L$)N($R^L$)—, —$NR^L$C(=$NR^L$)—, —C(S)—, —C(S)N($R^L$)—, —$NR^L$C(S)—, —S(O)—, —OS(O)$_2$—, —S(O)$_2$O—, —SO$_2$—, —N($R^L$)SO$_2$—, —SO$_2$N($R^L$)—, —N($R^L$)SO$_2$N($R^L$)—, or an optionally substituted $C_{1-10}$ saturated or unsaturated hydrocarbon chain, wherein one or more moieties selected from the group consisting of —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(=$NR^L$)—, —C(=$NNR^L$)—, —C(=$NOR^L$)—, —C(=$NR^L$)N($R^L$)—, —$NR^L$C(=$NR^L$)—, —C(S)—, —C(S)N($R^L$)—, —$NR^L$C(S)—, —S(O)—, —OS(O)$_2$—, —S(O)$_2$O—, —SO$_2$—, —N($R^L$)SO$_2$—, —SO$_2$N($R^L$)—, and —N($R^L$)SO$_2$N($R^L$)— is optionally and independently present between two carbon atoms of the hydrocarbon chain, and optionally and independently present at one or both ends of the hydrocarbon chain;

each $R^L$ is independently hydrogen, optionally substituted alkyl, or a nitrogen protecting group, or $R^L$ and $R^3$ taken together form an optionally substituted heterocyclyl or optionally substituted heteroaryl ring; and $R^3$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided when $R^3$ is hydrogen, then $L^1$ is not a bond.

It is generally understood that compounds of Formula (I), as described herein, comprises one or more asymmetric centers, and thus can exist in various isomeric forms, e.g., enantiomeric and/or diastereomeric forms. In certain embodiments, the compound of Formula (I) has the following stereochemistry (I-a) or (I-b):

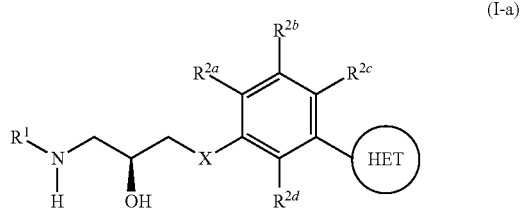

(I-a)

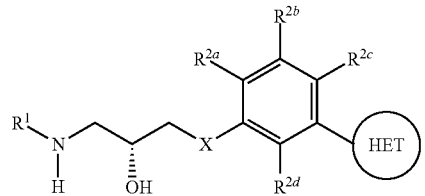

(I-b)

As generally defined herein, X is —O—, —S—, or —CH$_2$—. In certain embodiments, X is —O—. In certain embodiments, X is —S—. In certain embodiments, X is —O—.

As generally defined herein, $R^1$ is hydrogen or optionally substituted $C_{1-4}$ aliphatic. In certain embodiments, $R^1$ is hydrogen. In certain embodiments, $R^1$ is optionally substituted $C_{1-4}$ aliphatic, e.g., optionally substituted $C_1$ aliphatic, optionally substituted $C_2$ aliphatic, optionally substituted $C_3$ aliphatic, or optionally substituted $C_4$ aliphatic. It is understood that aliphatic, as used herein, encompasses alkyl, alkenyl, alkynyl, and carbocyclic groups. In certain embodiments, $R^1$ is optionally substituted $C_{1-4}$ alkyl, e.g., optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. Exemplary $R^1C_1$ alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), or iso-butyl ($C_4$), each of which may be substituted or unsubstituted. In certain embodiments, $R^1$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, $R^1$ is optionally substituted $C_{2-4}$ alkynyl, e.g., optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, $R^1$ is optionally substituted $C_3$carbocylyl, e.g., optionally substituted cyclopropyl. In certain embodiments, $R^1$ is hydrogen or an unsubstituted $C_{1-4}$ aliphatic group, e.g., for example, in certain embodiments, $R^1$ is hydrogen, methyl, ethyl, n-propyl, isopropyl, or cyclopropyl.

As generally defined herein, each of $R^{2a}$, $R^{2b}$, $R^{2c}$, and $R^{2d}$ is independently hydrogen, halo, —CN, —NO$_2$, —C(=O)$R^{A2}$, —C(=O)O$R^{A2}$, —C(=O)N($R^{A2}$)$_2$, —O$R^{A2}$, —S$R^{A2}$, —N($R^{A2}$)$_2$, —S(=O)$R^{A2}$, —S(=O)$_2R^{A2}$, optionally substituted alkyl, optionally substituted alkenyl, optionally substituted alkynyl, optionally substituted carbocyclyl, optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring.

In certain embodiments, at least one of (e.g., one, two, three, each of) $R^{2a}$, $R^{2b}$, $R^{2c}$, and $R^{2d}$ is hydrogen. In certain embodiments, at least one of $R^{2a}$, $R^{2b}$, $R^{2c}$, and $R^{2d}$ is halo, e.g., fluoro, chloro, bromo, or iodo. In certain embodiments, at least one of $R^{2a}$, $R^{2b}$, $R^{2c}$, and $R^{2d}$ is chloro. In certain embodiments, at least one of $R^{2a}$, $R^{2b}$, $R^{2c}$, and $R^{2d}$ is —CN.

In certain embodiments, at least one of $R^{2a}$, $R^{2b}$, $R^{2c}$, and $R^{2d}$ is —$NO_2$. In certain embodiments, at least one of $R^{2a}$, $R^{2b}$, $R^{2c}$, and $R^{2d}$ is —C(=O)$R^{A2}$, e.g., wherein $R^{A2}$ is hydrogen or optionally substituted alkyl (e.g., methyl). In certain embodiments, at least one of $R^{2a}$, $R^{2b}$, $R^{2c}$, and $R^{2d}$ is —C(=O)O$R^{A2}$, e.g., wherein $R^{A2}$ is hydrogen or optionally substituted alkyl (e.g., methyl). In certain embodiments, at least one of $R^{2a}$, $R^{2b}$, $R^{2c}$, and $R^{2d}$ is —C(=O)N($R^{A2}$)$_2$, e.g., wherein each instance of $R^{A2}$ is hydrogen or optionally substituted alkyl (e.g., methyl), or two $R^{A2}$ groups attached to the same nitrogen atom are joined to form an optionally substituted heterocyclyl or optionally substituted heteroaryl ring. In certain embodiments, at least one of $R^{2a}$, $R^{2b}$, $R^{2c}$, and $R^{2d}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl. Exemplary $R^{2a}$, $R^{2b}$, $R^{2c}$, and $R^{2d}$ $C_{1-4}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), and iso-butyl ($C_4$), each of which may be substituted or unsubstituted. In certain embodiments, at least one of $R^{2a}$, $R^{2b}$, $R^{2c}$, and $R^{2d}$ is alkyl substituted with hydroxy or substituted hydroxy, e.g., —(CH$_2$)$_a$OH or —(CH$_2$)$_a$OCH$_3$, wherein a is 1, 2, 3, 4, 5, or 6. In certain embodiments, at least one of $R^{2a}$, $R^{2b}$, $R^{2c}$, and $R^{2d}$ is alkyl substituted with halogen (e.g., fluoro), e.g., at least one of $R^{2a}$, $R^{2b}$, $R^{2c}$, and $R^{2d}$ is —CF$_3$. In certain embodiments, at least one of $R^{2a}$, $R^{2b}$, $R^{2c}$, and $R^{2d}$ is optionally substituted alkenyl, e.g., optionally substituted $C_{2-4}$ alkenyl, optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, at least one of $R^{2a}$, $R^{2b}$, $R^{2c}$, and $R^{2d}$ is optionally substituted $C_2$alkenyl or optionally substituted $C_3$alkenyl, e.g., vinyl or allyl. In certain embodiments, at least one of $R^{2a}$, $R^{2b}$, $R^{2c}$, and $R^{2d}$ is optionally substituted alkynyl, e.g., optionally substituted $C_{2-4}$ alkynyl, optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, at least one of $R^{2a}$, $R^{2b}$, $R^{2c}$, and $R^{2d}$ is optionally substituted $C_2$alkynyl, e.g., acetylene. In certain embodiments, at least one of $R^{2a}$, $R^{2b}$, $R^{2c}$, and $R^{2d}$ is optionally substituted carbocyclyl, e.g., optionally substituted $C_{3-5}$carbocyclyl, optionally substituted $C_{3-4}$carbocyclyl, optionally substituted $C_{4-5}$ carbocyclyl, optionally substituted $C_3$carbocyclyl, optionally substituted $C_4$carbocyclyl, or optionally substituted $C_5$carbocyclyl. In certain embodiments, at least one of $R^{2a}$, $R^{2b}$, $R^{2c}$, and $R^{2d}$ is optionally substituted $C_3$carbocyclyl, e.g., cyclopropyl. In certain embodiments, at least one of $R^{2a}$, $R^{2b}$, $R^{2c}$, and $R^{2d}$ is optionally substituted heterocyclyl, e.g., optionally substituted 3- to 5-membered heterocyclyl, optionally substituted 3- to 4-membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one of $R^{2a}$, $R^{2b}$, $R^{2c}$, and $R^{2d}$ is —O$R^{A2}$, —S$R^{A2}$, or —N($R^{A2}$)$_2$, wherein $R^{A2}$ is as defined herein. In certain embodiments, at least one of $R^{2a}$, $R^{2b}$, $R^{2c}$, and $R^{2d}$ is —S(=O)$R^{A2}$ or —S(=O)$_2R^{A2}$, wherein $R^{A2}$ is as defined herein. In certain embodiments, at least one $R^{A2}$ is hydrogen, e.g., for example, to provide at least one of $R^{2a}$, $R^{2b}$, $R^{2c}$, and $R^{2d}$ as —OH, —SH, —NH$_2$, or —NH$R^{A2}$. In certain embodiments, at least one of $R^{A2}$ is optionally substituted alkyl, e.g., optionally substituted $C_{1-4}$ alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, or optionally substituted $C_4$alkyl, e.g., for example, at least one of $R^{A2}$ is methyl to provide a group $R^{2a}$, $R^{2b}$, $R^{2c}$, and $R^{2d}$ of formula —OCH$_3$, —SCH$_3$, —NHCH$_3$, —N(CH$_3$)$_2$, or —NCH$_3R^{A2}$. In certain embodiments, at least one of $R^{A2}$ is alkyl substituted with halogen (e.g., fluoro), e.g., to provide a group $R^{2a}$, $R^{2b}$, $R^{2c}$, and $R^{2d}$ of formula —OCF$_3$, —SCF$_3$, —NHCF$_3$, —N(CF$_3$)$_2$, or —NCF$_3R^{A2}$. In certain embodiments, at least one of $R^{A2}$ is a group of formula —CH$_2$CH(OH)CH$_2$NHR$^1$, wherein R$^1$ is as defined herein, e.g., to provide a group $R^{2a}$, $R^{2b}$, $R^{2c}$, and $R^{2d}$ of formula —OCH$_2$CH(OH)CH$_2$NHR$^1$, —SCH$_2$CH(OH)CH$_2$NHR$^1$, —NHCH$_2$CH(OH)CH$_2$NHR$^1$, or —N($R^{A2}$)CH$_2$CH(OH)CH$_2$NHR$^1$. In certain embodiments, at least one of $R^{A2}$ is alkyl substituted with an optionally substituted aryl (e.g., optionally substituted phenyl) or optionally substituted heteroaryl (e.g., optionally substituted pyridinyl), e.g., to provide a group $R^{2a}$, $R^{2b}$, $R^{2c}$, and $R^{2d}$ of formula —O(CH$_2$)$_a$Ar, —S(CH$_2$)$_a$Ar, —NH(CH$_2$)$_a$Ar, or —N($R^{A2}$)(CH$_2$)$_a$Ar, wherein a is 1, 2, 3, 4, 5, or 6, and Ar is optionally substituted aryl (e.g., optionally substituted phenyl) or optionally substituted heteroaryl (e.g., optionally substituted pyridinyl). In certain embodiments, at least one of $R^{A2}$ is optionally substituted alkenyl, e.g., optionally substituted $C_{2-4}$ alkenyl, optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, at least one of $R^{A2}$ is optionally substituted alkynyl, e.g., optionally substituted $C_{2-4}$ alkynyl, optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, at least one of $R^{A2}$ is optionally substituted carbocyclyl, e.g., optionally substituted $C_{3-5}$carbocyclyl, optionally substituted $C_{3-4}$carbocyclyl, optionally substituted $C_{4-5}$ carbocyclyl, optionally substituted $C_3$carbocyclyl, optionally substituted $C_4$carbocyclyl, or optionally substituted $C_5$carbocyclyl. In certain embodiments, at least one of $R^{A2}$ is optionally substituted heterocyclyl, e.g., optionally substituted 3- to 5-membered heterocyclyl, optionally substituted 3- to 4-membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one of $R^{A2}$ is optionally substituted aryl (e.g., optionally substituted phenyl) or optionally substituted heteroaryl (e.g., optionally substituted pyridinyl). In certain embodiments, two $R^{A2}$ groups, e.g., of —N($R^{A2}$)$_2$, are joined to form an optionally substituted heterocyclyl or optionally substituted heteroaryl ring.

In certain embodiments, at least one of $R^{2a}$, $R^{2b}$, $R^{2c}$, and $R^{2d}$ is hydrogen. In certain embodiments, at least two of $R^{2a}$, $R^{2b}$, $R^{2c}$, and $R^{2d}$ are hydrogen. In certain embodiments, at least three of $R^{2a}$, $R^{2b}$, $R^{2c}$, and $R^{2d}$ are hydrogen. In certain embodiments, each of $R^{2a}$, $R^{2b}$, $R^{2c}$, and $R^{2d}$ are hydrogen, e.g., to provide a compound of Formula (I-c):

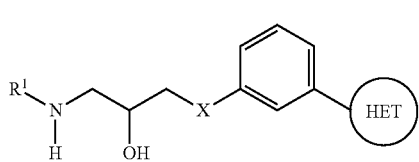

(I-c)

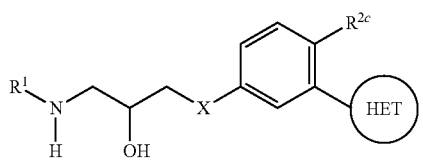

(I-f)

or a pharmaceutically acceptable salt thereof.

However, in certain embodiments, at least one of $R^{2a}$, $R^{2b}$, $R^{2c}$, and $R^{2d}$ is a non-hydrogen group. For example, in certain embodiments, $R^{2a}$ is a non-hydrogen group. In certain embodiments, $R^{2a}$ is a non-hydrogen group, and each of $R^{2b}$, $R^{2c}$, and $R^{2d}$ is hydrogen, e.g., to provide a compound of Formula (I-d):

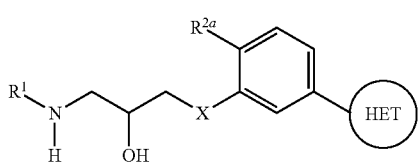

(I-d)

or a pharmaceutically acceptable salt thereof. In certain embodiments, $R^{2a}$ is a non-hydrogen group selected from the group consisting of halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, and optionally substituted $C_{2-4}$alkynyl, wherein $R^{A2}$ is optionally substituted alkyl.

In certain embodiments, $R^{2b}$ is a non-hydrogen group. In certain embodiments, $R^{2b}$ is a non-hydrogen group, and each of $R^{2a}$, $R^{2c}$, and $R^{2d}$ is hydrogen, e.g., to provide a compound of Formula (I-e):

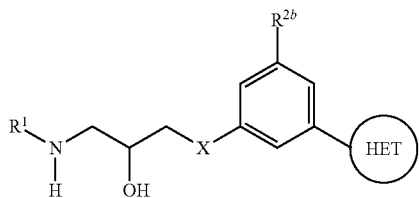

(I-e)

or a pharmaceutically acceptable salt thereof. In certain embodiments, $R^{2b}$ is a non-hydrogen group selected from the group consisting of halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, and optionally substituted $C_{2-4}$alkynyl, wherein $R^{A2}$ is optionally substituted alkyl.

In certain embodiments, $R^{2c}$ is a non-hydrogen group. In certain embodiments, $R^{2c}$ is a non-hydrogen group, and each of $R^{2a}$, $R^{2b}$, and $R^{2d}$ is hydrogen, e.g., to provide a compound of Formula (I-f):

or a pharmaceutically acceptable salt thereof. In certain embodiments, $R^{2c}$ is a non-hydrogen group selected from the group consisting of halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, and optionally substituted $C_{2-4}$alkynyl, wherein $R^{A2}$ is optionally substituted alkyl.

In certain embodiments, $R^{2d}$ is a non-hydrogen group. In certain embodiments, $R^{2d}$ is a non-hydrogen group, and each of $R^{2a}$, $R^{2b}$, and $R^{2c}$ is hydrogen, e.g., to provide a compound of Formula (I-g):

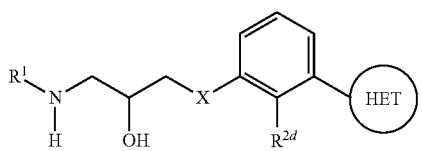

(I-g)

or a pharmaceutically acceptable salt thereof. In certain embodiments, $R^{2d}$ is a non-hydrogen group selected from the group consisting of halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, and optionally substituted $C_{2-4}$alkynyl, wherein $R^{A2}$ is optionally substituted alkyl.

As generally understood from the present disclosure, Ring HET comprising 2 to 5 nitrogen atoms, inclusive, wherein the point of attachment is provided on the 6-membered ring of the 6,5-bicyclic heteroaryl ring system, and wherein the 6-membered ring is further substituted with a group of formula -$L^1$-$R^3$ attached directly (wherein $L^1$ is a bond) or indirectly (wherein $L^1$ is a linking group), wherein $R^3$ is an acyclic moiety selected from the group consisting of hydrogen (provided that when $R^3$ is hydrogen then $L^1$ is not a bond), optionally substituted alkyl, optionally substituted alkenyl, or optionally substituted alkynyl; or $R^3$ is a cyclic moiety selected from the group consisting of optionally substituted carbocyclyl, optionally substituted heterocyclyl, optionally substituted aryl, and optionally substituted heteroaryl. In certain embodiments, $R^3$ is an acyclic moiety. In certain embodiments, $R^3$ is a cyclic moiety.

It is further understood that the point of attachment of the bicyclic Ring HET to the parent moiety is provided on the 6-membered ring of the 6,5 bicyclic heteroaryl ring system.

In certain embodiments, -$L^1$-$R^3$ is meta to the point of attachment of Ring HET to the parent moiety. Exemplary optionally substituted 6,5 bicyclic heteroaryl ring system include, but are not limited to, optionally substituted pyrrolopyridinyl, optionally substituted pyrazolopyridinyl, optionally substituted imidazopyridinyl, optionally substituted triazolopyridinyl, optionally substituted pyrazolopyrimidinyl, optionally substituted pyrrolopyrimidinyl, optionally substituted purinyl, optionally substituted triazolopyrimidinyl, optionally substituted imidazopyridazinyl, optionally substituted triazolopyridazinyl, optionally substituted imidazotriazinyl, and optionally substituted pyrazolotriazinyl. In certain embodiments, Ring HET is optionally substituted pyrrolopyridinyl ring system. In certain embodiments, Ring HET is optionally substituted pyrazolopyridinyl ring system. In certain embodiments, Ring HET is optionally substituted imidazopyridinyl ring system. In certain embodiments, Ring HET is optionally substituted triazolopyridinyl ring system. In certain embodiments, Ring HET is optionally substituted pyrazolopyrimidinyl ring system. In certain embodiments, Ring HET is optionally substituted pyrrolopyrimidinyl ring system. In certain embodiments, Ring HET is optionally substituted purinyl ring system. In certain embodiments, Ring HET is optionally substituted triazolopyrimidinyl ring system. In certain embodiments, Ring HET is optionally substituted imidazopyridazinyl ring system. In certain embodiments, Ring HET is optionally substituted triazolopyridazinyl ring system. In certain embodiments, Ring HET is optionally substituted imidazotriazinyl ring system.

As generally defined herein, $L^1$ is a bond, —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —N$R^L$C(O)—, —N$R^L$C(O)N($R^L$)—, —N$R^L$C(O)N($R^L$)N($R^L$)—, —N$R^L$C(O)O—, —SC(O)—, C(=N$R^L$)—, —C(=NN$R^L$)—, —C(=NO$R^L$)—, —C(=N$R^L$)N($R^L$)—, —N$R^L$C(=N$R^L$)—, —C(S)—, —C(S)N($R^L$)—, —N$R^L$C(S)—, —S(O)—, —OS(O)$_2$—, —S(O)$_2$O—, —SO$_2$—, —N($R^L$)SO$_2$—, —SO$_2$N($R^L$)—, —N($R^L$)SO$_2$N($R^L$)—, or an optionally substituted $C_{1-10}$ saturated or unsaturated hydrocarbon chain, wherein one or more moieties selected from the group consisting of —O—, —N($R^L$)—, —S—, —C(O)—, —C(O)O—, —C(O)S—, —C(O)N($R^L$)—, C(O)N($R^L$)N($R^L$)—, —OC(O)—, —OC(O)N($R^L$)—, —N$R^L$C(O)—, —N$R^L$C(O)N($R^L$)—, —N$R^L$C(O)N($R^L$)N($R^L$)—, —N$R^L$C(O)O—, —SC(O)—, —C(=N$R^L$)—, —C(=NN$R^L$)—, —C(=NO$R^L$)—, —C(=N$R^L$)N($R^L$)—, —N$R^L$C(=N$R^L$)—, —C(S)—, —C(S)N($R^L$)—, —N$R^L$C(S)—, —S(O)—, —OS(O)$_2$—, —S(O)$_2$O—, —SO$_2$—, —N($R^L$)SO$_2$—, —SO$_2$N($R^L$)—, and —N($R^L$)SO$_2$N($R^L$)— is optionally and independently present between two carbon atoms of the hydrocarbon chain, and optionally and independently present at one or both ends of the hydrocarbon chain. It is understood that the linker joining $R^3$ to Ring HET may comprise one or more of the above recited moieties in combination to form the group $L^1$.

In certain embodiments, $L^1$ is a bond. In certain embodiments, $L^1$ is a bond, and $R^3$ is optionally substituted alkyl, optionally substituted alkenyl, or optionally substituted alkynyl. In certain embodiments, $L^1$ is a bond, and $R^3$ is optionally substituted carbocyclyl, optionally substituted heterocyclyl, optionally substituted aryl, and optionally substituted heteroaryl.

In certain embodiments, $L^1$ is —O—. In certain embodiments, $L^1$ is —N($R^L$)—. In certain embodiments, $L^1$ is —S—. In certain embodiments, $L^1$ is —C(O)—. In certain embodiments, $L^1$ is —C(O)O—. In certain embodiments, $L^1$ is —C(O)S—. In certain embodiments, $L^1$ is —C(O)N($R^L$)—. In certain embodiments, $L^1$ is —C(O)N($R^L$)N($R^L$)—. In certain embodiments, $L^1$ is —OC(O)—. In certain embodiments, $L^1$ is —OC(O)N($R^L$)—. In certain embodiments, $L^1$ is —N$R^L$C(O)—. In certain embodiments, $L^1$ is —N$R^L$C(O)N($R^L$)—. In certain embodiments, $L^1$ is —N$R^L$C(O)N($R^L$)N($R^L$)—. In certain embodiments, $L^1$ is —N$R^L$C(O)O—. In certain embodiments, $L^1$ is —SC(O)—. In certain embodiments, $L^1$ is —C(=N$R^L$)—. In certain embodiments, $L^1$ is —C(=NN$R^L$)—. In certain embodiments, $L^1$ is —C(=NO$R^L$)—. In certain embodiments, $L^1$ is —C(=N$R^L$)N($R^L$)—. In certain embodiments, $L^1$ is —N$R^L$C(=N$R^L$)—. In certain embodiments, $L^1$ is —C(S)—. In certain embodiments, $L^1$ is —C(S)N($R^L$)—. In certain embodiments, $L^1$ is —N$R^L$C(S)—. In certain embodiments, $L^1$ is —S(O)—. In certain embodiments, $L^1$ is —OS(O)$_2$—. In certain embodiments, $L^1$ is —S(O)$_2$O—. In certain embodiments, $L^1$ is —SO$_2$—. In certain embodiments, $L^1$ is —N($R^L$)SO$_2$—. In certain embodiments, $L^1$ is —SO$_2$N($R^L$)—. In certain embodiments, $L^1$ is —N($R^L$)SO$_2$N($R^L$)—.

In certain embodiments, $L^1$ is an optionally substituted $C_{1-10}$ saturated or unsaturated hydrocarbon chain, e.g., in certain embodiments, $L^1$ is an optionally substituted $C_{1-10}$ alkyl chain, $L^1$ is an optionally substituted $C_{2-10}$ alkenyl chain, or $L^1$ is an optionally substituted $C_{2-10}$ alkynyl chain. In certain embodiments, $L^1$ is an optionally substituted $C_{1-10}$ alkyl chain, e.g., an optionally substituted $C_{1-8}$ alkyl chain, optionally substituted $C_{1-6}$ alkyl chain, optionally substituted $C_{1-4}$ alkyl chain, optionally substituted $C_{1-3}$ alkyl chain, or optionally substituted $C_{1-2}$ alkyl chain. In certain embodiments, $L^1$ is an unsubstituted $C_{1-10}$ n-alkyl chain of the formula —(CH$_2$)$_x$—, wherein x is 1, 2, 3, 4, 5, 6, 7, 8, 9, or 10. In certain embodiments, $L^1$ is an optionally substituted $C_{2-10}$ alkenyl chain, e.g., an optionally substituted $C_{2-8}$ alkenyl chain, optionally substituted $C_{2-6}$ alkenyl chain, optionally substituted $C_{2-4}$ alkenyl chain, optionally substituted $C_{2-3}$ alkenyl chain, or optionally substituted $C_2$ alkenyl chain. In certain embodiments, $L^1$ is an optionally substituted $C_{2-10}$ alkynyl chain, e.g., an optionally substituted $C_{2-8}$ alkynyl chain, optionally substituted $C_{2-6}$ alkynyl chain, optionally substituted $C_{2-4}$ alkynyl chain, optionally substituted $C_{2-3}$ alkynyl chain, or optionally substituted $C_2$ alkynyl chain.

In certain embodiments, $L^1$ is an optionally substituted $C_{1-10}$ saturated or unsaturated hydrocarbon chain, wherein one or more moieties selected from the group consisting of —O—, —N($R^L$)—, —S—, —C(O)O—, —C(O)S—, —C(O)N($R^L$)—, —C(O)N($R^L$)N($R^L$)—, —OC(O)—, —OC(O)N($R^L$)—, —N$R^L$C(O)—, —NRIC(O)N($R^L$)—, —N$R^L$C(O)N($R^L$)N($R^L$)—, —N$R^L$C(O)O—, —SC(O)—, —C(=N$R^L$)—, —C(=NN$R^L$)—, —C(=NO$R^L$)—, —C(=N$R^L$)N($R^L$)—, —N$R^L$C(=N$R^L$)—, —C(S)—, —C(S)N($R^L$)—, —N$R^L$C(S)—, —S(O)—, —OS(O)$_2$—, —S(O)$_2$O—, —SO$_2$—, —N($R^L$)SO$_2$—, —SO$_2$N($R^L$)—, or —N($R^L$)SO$_2$N($R^L$)— independently present between two carbon atoms of the hydrocarbon chain, or present at one or both ends of the hydrocarbon chain. In this instance, in certain embodiments, $L^1$ is a chain of at least 2 atoms, e.g., $L^1$ is a chain comprising 1 to 10 carbon atoms (e.g., 1, 2, 3, 4, 5, 6, 7, 8, 9, or 10 carbon atoms), and 1 or more of the above recited moieties (e.g., 1, 2, 3, or more), to provide a chain of between 2 and 20 atoms, inclusive, e.g., 2, 3, 4, 5, 6, 7, 8, 9, 10, 11, 12, 13, 14, 15, 16, 17, 18, 19, or 20 chain atoms. In certain embodiments, a moiety is present between two carbon atoms of the hydrocarbon chain. In certain embodiments, a moiety is present at one end of the hydrocarbon chain. In certain embodiments, a moiety is independently present at each end of the hydrocarbon chain. In certain embodiments, $L^1$ is an optionally substituted $C_{1-10}$ alkyl chain, $L^1$ is an optionally substituted $C_{2-10}$ alkenyl chain, or $L^1$ is an optionally substituted $C_{2-10}$ alkynyl chain comprising one or more of the above recited moieties independently present between two carbon atoms of the hydrocarbon chain, or present at one or both ends of the hydrocarbon chain. In certain embodiments, $L^1$ is an optionally substituted $C_{1-10}$ alkyl chain, e.g., an optionally substituted $C_{1-8}$ alkyl chain, optionally substituted $C_{1-6}$ alkyl chain, optionally substituted $C_{1-4}$ alkyl chain, optionally substituted $C_{1-3}$ alkyl chain, or optionally substituted $C_{1-2}$ alkyl chain, comprising one or more of the above recited moieties independently present between two carbon atoms of the hydrocarbon chain, or present at one or both ends of the hydrocarbon chain. In certain embodiments, $L^1$ is an unsubstituted $C_{1-10}$ n-alkyl chain of the formula —$(CH_2)_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^1$ is an optionally substituted $C_{2-10}$ alkenyl chain, e.g., an optionally substituted $C_{2-4}$ alkenyl chain, optionally substituted $C_{2-6}$alkenyl chain, optionally substituted $C_{2-4}$alkenyl chain, optionally substituted $C_{2-3}$ alkenyl chain, or optionally substituted $C_2$ alkenyl chain, comprising one or more of the above recited moieties independently present between two carbon atoms of the hydrocarbon chain, or present at one or both ends of the hydrocarbon chain. In certain embodiments, $L^1$ is an optionally substituted $C_{2-10}$ alkynyl chain, e.g., an optionally substituted $C_{2-8}$ alkynyl chain, optionally substituted $C_{2-6}$alkynyl chain, optionally substituted $C_{2-4}$alkynyl chain, optionally substituted $C_{2-3}$ alkynyl chain, or optionally substituted $C_2$ alkynyl chain, comprising one or more of the above recited moieties independently present between two carbon atoms of the hydrocarbon chain, or present at one or both ends of the hydrocarbon chain.

As described above, in certain embodiments, $L^1$ is an unsubstituted $C_{1-10}$ n-alkyl chain of the formula —$(CH_2)_x$—, wherein x is 1, 2, 3, 4, 5, 6, 7, 8, 9, or 10, comprising one or more of the above recited moieties independently present between two carbon atoms of the hydrocarbon chain, or present at one or both ends of the hydrocarbon chain. In certain embodiments, $L^1$ is —O—$(CH_2)$—, —$(CH_2)_x$—O—, or —O—$(CH_2)_x$—O—. In certain embodiments, $L^1$ is —N($R^L$)—$(CH_2)_x$—, —$(CH_2)_x$—N($R^L$)—, —N($R^L$)—$(CH_2)_x$N($R^L$)—, —O—$(CH_2)_x$—N($R^L$)—, —N($R^L$)—$(CH_2)_x$—O—, —$NR^L$—$(CH_2)_x$—C(O)O—, or —OC(O)—$(CH_2)_x$—N($R^L$)—. In certain embodiments, $L^1$ is —S—$(CH_2)_x$— or —$(CH_2)_x$—S—. In certain embodiments, $L^1$ is —C(O)—$(CH_2)_x$— or —$(CH_2)_x$—C(O)—. In certain embodiments, $L^1$ is —C(O)O—$(CH_2)_x$— or —$(CH_2)_x$—C(O)O—. In certain embodiments, $L^1$ is —C(O)S—$(CH_2)_x$— or —$(CH_2)_x$—C(O)S—. In certain embodiments, $L^1$ is —C(O)N($R^L$)—$(CH_2)_x$— or —$(CH_2)_x$—C(O)N($R^L$)—. In certain embodiments, $L^1$ is —C(O)N($R^L$)N($R^L$)—$(CH_2)_x$— or —$(CH_2)_x$—C(O)N($R^L$)N($R^L$)—. In certain embodiments, $L^1$ is —OC(O)—$(CH_2)_x$— or —$(CH_2)_x$—OC(O)—. In certain embodiments, $L^1$ is —OC(O)N($R^L$)—$(CH_2)_x$— or —$(CH_2)_x$—OC(O)N($R^L$)—. In certain embodiments, $L^1$ is —$NR^L$C(O)—$(CH_2)_x$— or —$(CH_2)_x$—$NR^L$C(O)—. In certain embodiments, $L^1$ is —$NR^L$C(O)N($R^L$)—$(CH_2)_x$— or —$(CH_2)_x$—$NR^L$C(O)N($R^L$)—. In certain embodiments, $L^1$ is —$NR^L$C(O)N($R^L$)N($R^L$)—$(CH_2)_x$— or —$(CH_2)_x$—$NR^L$C(O)N($R^L$)N($R^L$)—. In certain embodiments, $L^1$ is —$NR^L$C(O)O—$(CH_2)_x$— or —$(CH_2)_x$—$NR^L$C(O)O—. In certain embodiments, $L^1$ is —SC(O)—$(CH_2)_x$— or —$(CH_2)_x$—SC(O)—. In certain embodiments, $L^1$ is —C(=$NR^L$)—$(CH_2)_x$— or —$(CH_2)_x$—C(=$NR^L$)—. In certain embodiments, $L^1$ is —C(=$NNR^L$)—$(CH_2)_x$— or —$(CH_2)_x$—C(=$NNR^L$)—. In certain embodiments, $L^1$ is —C(=$NOR^L$)—$(CH_2)_x$— or —$(CH_2)_x$—C(=$NOR^L$)—. In certain embodiments, $L^1$ is —C(=$NR^L$)N($R^L$)—$(CH_2)_x$— or —$(CH_2)_x$—C(=$NR^L$)N($R^L$)—. In certain embodiments, $L^1$ is —$NR^L$C(=$NR^L$)—$(CH_2)_x$— or —$(CH_2)_x$—$NR^L$C(=$NR^L$)—. In certain embodiments, $L^1$ is —C(S)—$(CH_2)_x$— or —$(CH_2)_x$—C(S)—. In certain embodiments, $L^1$ is —C(S)N($R^L$)—$(CH_2)_x$— or —$(CH_2)_x$—C(S)N($R^L$)—. In certain embodiments, $L^1$ is —$NR^L$C(S)—$(CH_2)_x$— or —$(CH_2)_x$—$NR^L$C(S)—. In certain embodiments, $L^1$ is —S(O)—$(CH_2)_x$— or —$(CH_2)_x$—S(O)—. In certain embodiments, $L^1$ is —OS(O)$_2$—$(CH_2)_x$— or —$(CH_2)_x$—OS(O)$_2$—. In certain embodiments, $L^1$ is —S(O)$_2$O—$(CH_2)_x$— or —$(CH_2)_x$—S(O)$_2$O—. In certain embodiments, $L^1$ is —SO$_2$—$(CH_2)_x$— or —$(CH_2)_x$—SO$_2$—. In certain embodiments, $L^1$ is —N($R^L$)SO$_2$—$(CH_2)_x$— or —$(CH_2)_x$—N($R^L$)SO$_2$—. In certain embodiments, $L^1$ is —SO$_2$N($R^L$)—$(CH_2)_x$— or —$(CH_2)_x$—SO$_2$N($R^L$)—. In certain embodiments, $L^1$ is —N($R^L$)SO$_2$N($R^L$)—$(CH_2)_x$— or —$(CH_2)_x$—N($R^L$)SO$_2$N($R^L$)—. In certain embodiments, $L^1$ is a bond, —N($R^L$)—, —$NR^L$C(O)O—, —$NR^L$C(O)N($R^L$)—, —N($R^L$)—, —N($R^L$)SO$_2$N($R^L$)—, —$NR^L$—$(CH_2)_x$—C(O)O—, —$NR^L$—$(CH_2)_x$—O—, —$NR^L$C(O)N($R^L$)—, —$NR^L$—$(CH_2)_x$—, —$(CH_2)_x$—$NR^L$—, —$NR^L$C(O)O(CH_2)_x$—, —$NR^L$C(O)N$R^L$(CH_2)_x$—, or —$NR^L$(CH_2)_x$N$R^L$C(O)—.

In certain embodiments, $R^3$ is an acyclic moiety selected from the group consisting of hydrogen, optionally substituted alkyl, optionally substituted alkenyl, and optionally substituted alkynyl. In certain embodiments, $R^3$ is hydrogen, e.g., for example, when $L^1$ is —N($R^L$)— or —$NR^L$—$(CH_2)_x$—$NR^L$—. In certain embodiments, $R^3$ is optionally substituted alkyl, e.g., for example, when $L^1$ is —$NR^L$C(O)O—, —$NR^L$C(O)N($R^L$)—, —N($R^L$)—, —N($R^L$)SO$_2$N($R^L$)—, —$NR^L$—$(CH_2)_x$—C(O)O—, or —$NR^L$—$(CH_2)_x$—O—. In certain embodiments, $R^3$ is optionally substituted $C_{1-6}$ alkyl, e.g., optionally substituted $C_{1-5}$alkyl, optionally substituted $C_{1-4}$alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. Exemplary $R^3C_{1-6}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). In certain embodiments, $R^3$ is alkyl substituted with —CN, e.g., —$(CH_2)_y$CN, wherein y is 1, 2, 3, 4, 5, or 6. In certain embodiments, $R^3$ is alkyl substituted with hydroxy or substituted hydroxy, e.g., —$(CH_2)_y$OCH$_3$, wherein y is 1, 2, 3, 4, 5, or 6. In certain embodiments, $R^3$ is alkyl substituted with amino or substituted amino, e.g., —$(CH_2)_y$NH$_2$, wherein y is 1, 2, 3, 4, 5, or 6.

In certain embodiments, $R^3$ is optionally substituted alkenyl, e.g., for example, when $L^1$ is a bond. In certain embodiments, $R^3$ is optionally substituted $C_{2-4}$ alkenyl, e.g., optionally substituted $C_{2-3}$alkenyl, optionally substituted $C_{3-4}$alkenyl, optionally substituted $C_2$alkenyl, optionally substituted $C_3$alkenyl, or optionally substituted $C_4$alkenyl. In certain embodiments, $R^3$ is optionally substituted $C_2$alkenyl or $C_3$alkenyl, e.g., optionally substituted vinyl or optionally substituted allyl. In certain embodiments, $R^3$ is optionally substituted alkynyl, e.g., for example, when $L^1$ is a bond. In certain embodiments, $R^3$ is optionally substituted $C_{2-4}$ alkynyl, e.g., optionally substituted $C_{2-3}$alkynyl, optionally substituted $C_{3-4}$alkynyl, optionally substituted $C_2$alkynyl, optionally substituted $C_3$alkynyl, or optionally substituted $C_4$alkynyl. In certain embodiments, $R^3$ is optionally substituted $C_2$alkynyl, e.g., optionally substituted acetylene.

Alternatively, in certain embodiments, $R^3$ is a cyclic moiety selected from the group consisting of optionally substituted carbocyclyl, optionally substituted heterocyclyl, optionally substituted aryl, and optionally substituted heteroaryl. It is understood that the $R^3$ cyclic moiety may be monocyclic or polycyclic (e.g., bicyclic or tricyclic). In certain embodiments, $R^3$ is a monocylic optionally substituted carbocyclyl, monocylic optionally substituted heterocyclyl, monocylic optionally substituted aryl, or monocylic optionally substituted heteroaryl. In certain embodiments, $R^3$ is a bicyclic optionally substituted carbocyclyl, bicyclic optionally substituted heterocyclyl, bicyclic optionally substituted aryl, or bicyclic optionally substituted heteroaryl.

In certain embodiments, $R^3$ is an optionally substituted monocyclic or bicyclic carbocyclyl, e.g., an optionally substituted $C_{3-10}$ carbocyclyl, optionally substituted $C_{3-9}$ carbocyclyl, optionally substituted $C_{3-4}$ carbocyclyl, optionally substituted $C_{3-7}$ carbocyclyl, optionally substituted $C_{3-6}$ carbocyclyl, optionally substituted $C_{3-4}$carbocyclyl, optionally substituted $C_{5-10}$ carbocyclyl, optionally substituted $C_3$ carbocyclyl, optionally substituted $C_4$ carbocyclyl, optionally substituted $C_5$ carbocyclyl, optionally substituted $C_6$ carbocyclyl, optionally substituted $C_7$ carbocyclyl, optionally substituted $C_8$ carbocyclyl, optionally substituted $C_9$ carbocyclyl, or optionally substituted $C_{10}$ carbocyclyl. In certain embodiments, $R^3$ is an optionally substituted cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), or spiro[4.5]decanyl ($C_{10}$) ring.

In certain embodiments, $R^3$ is an optionally substituted monocyclic or bicyclic heterocyclyl, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl. In certain embodiments, $R^3$ is an optionally substituted azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, pyrrolidin-2-one, pyrrolyl-2,5-dione, dioxolanyl, oxasulfuranyl, disulfuranyl, oxazolidin-2-one, triazolinyl, oxadiazolinyl, thiadiazolinyl, piperidinyl, tetrahydropyranyl, dihydropyridinyl, thianyl, piperazinyl, morpholinyl, dithianyl, dioxanyl, triazinanyl, azepanyl, oxepanyl, thiepanyl, azocanyl, oxecanyl, thiocanyl, indolinyl, isoindolinyl, dihydrobenzofuranyl, dihydrobenzothienyl, benzoxazolinonyl, tetrahydroquinolinyl, tetrahydroisoquinolinyl, furo[2,3-b]furanyl, 2,3-dihydro-1,4-dioxinyl, 3-oxa-8-azabicyclo[3.2.1]octanyl, or 8-oxa-3-azabicyclo[3.2.1]octanyl ring.

In certain embodiments, $R^3$ is an optionally substituted monocyclic or bicyclic aryl, e.g., an optionally substituted phenyl, or optionally substituted naphthyl ring.

In certain embodiments, $R^3$ is an optionally substituted monocyclic or bicyclic heteroaryl, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl.

In certain embodiments, $R^3$ is an optionally substituted pyrrolyl, furanyl, thiophenyl, imidazolyl, pyrazolyl, oxazolyl, isoxazolyl, thiazolyl, isothiazolyl, tetrazolyl, pyridinyl, pyridazinyl, pyrimidinyl, pyrazinyl, triazinyl, tetrazinyl, azepinyl, oxepinyl, thiepinyl, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, purinyl, naphthyridinyl, pteridinyl, quinolinyl, isoquinolinyl, cinnolinyl, quinoxalinyl, phthalazinyl, or quinazolinyl ring.

In certain embodiments, $R^3$ is a cyclic moiety selected from the group consisting of

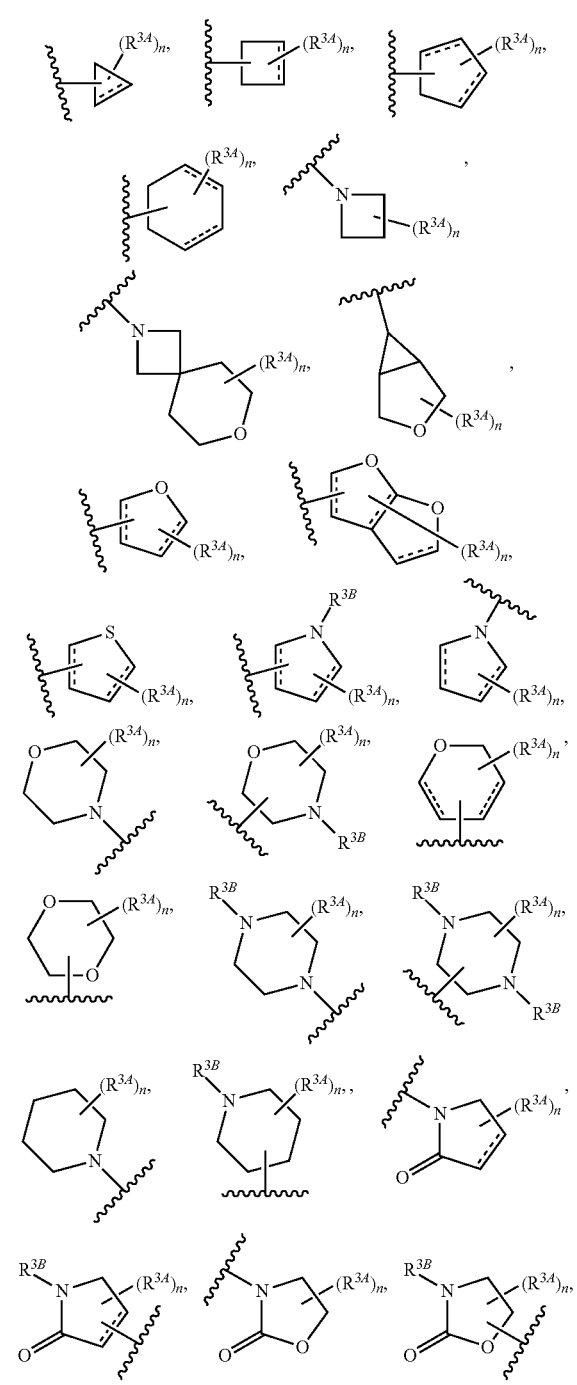

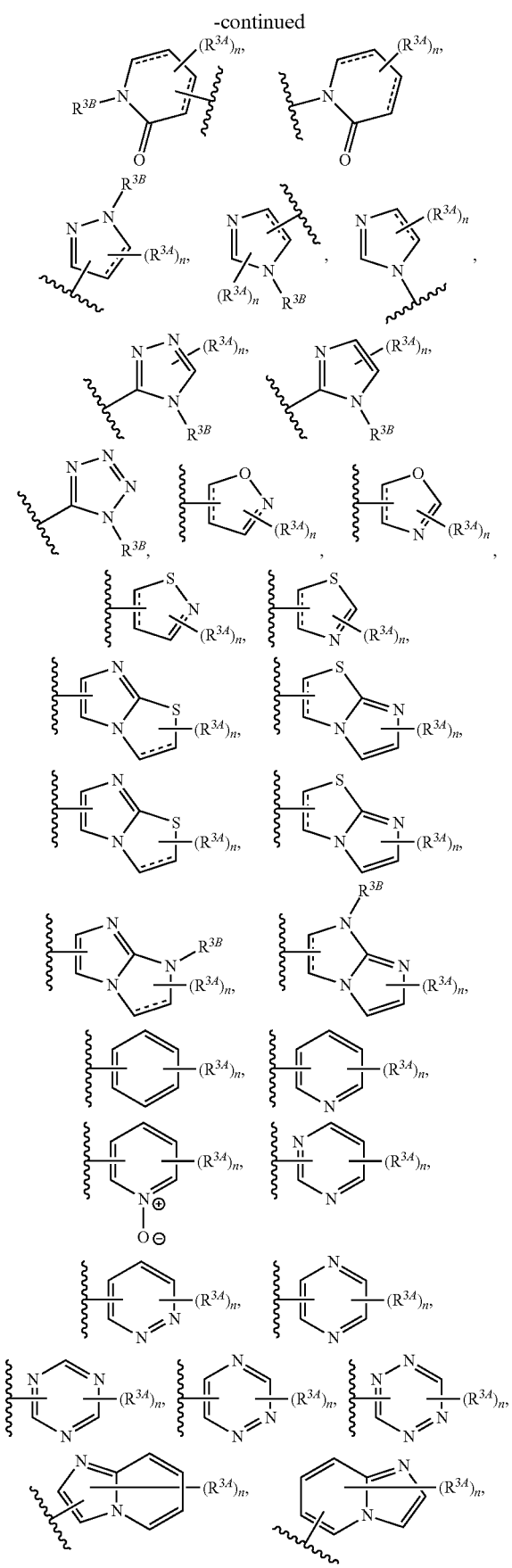
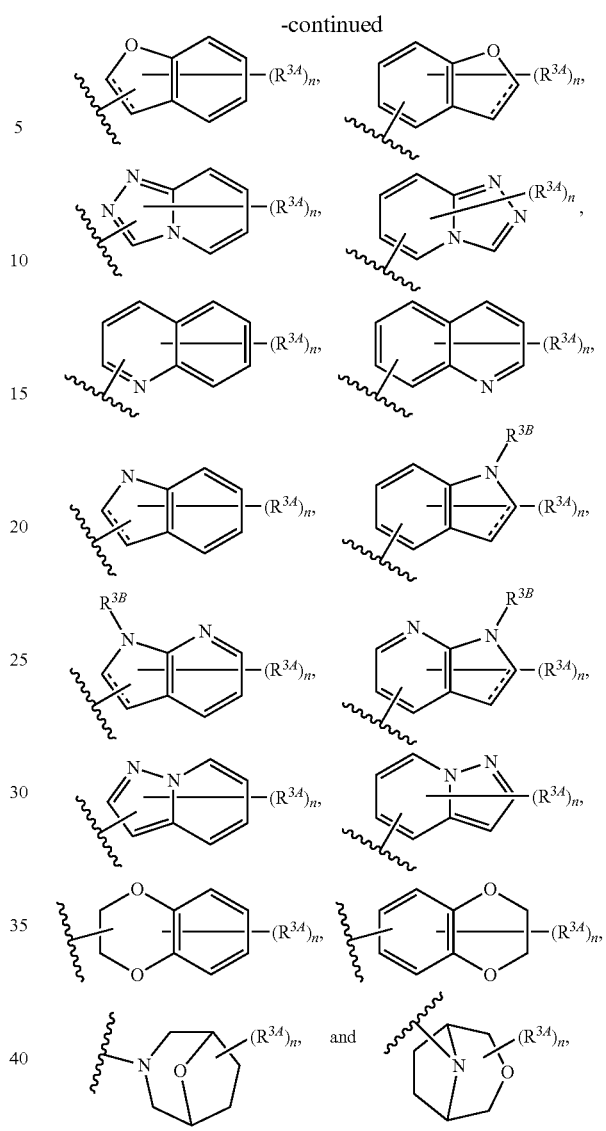

wherein:

each instance of ≡ independently represents a single or double bond;

n is 0, 1, 2, or 3;

each instance of $R^{3A}$ is independently hydroxyl, substituted hydroxyl, thiol, substituted thiol, amino, substituted amino, carbonyl, sulfonyl, sulfinyl, —CN, —NO$_2$, halogen, optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3B}$ groups are joined to form an optionally substituted carbocyclic, optionally substituted heterocyclic, optionally substituted aryl, or optionally substituted heteroaryl ring; and $R^{3B}$ is hydrogen, optionally substituted alkyl, or a nitrogen protecting group.

In certain embodiments, n is 0. In certain embodiments, n is 1. In certain embodiments, n is 2. In certain embodiments, n is 3. In certain embodiments, each instance of $R^{3A}$ is independently hydroxyl, —OCH$_3$, optionally substituted C$_{1-4}$alkyl (e.g., methyl, trifluoromethyl, ethyl, propyl, iso-propyl, butyl, iso-butyl, sec-butyl, tert-butyl), —CN, or sulfonyl (e.g., —S(O)$_2$CH$_3$).

As generally defined herein, each $R^L$ is independently hydrogen, optionally substituted alkyl, or a nitrogen protecting group, or $R^L$ and $R^3$ taken together form an optionally substituted heterocyclyl or optionally substituted heteroaryl ring. In certain embodiments, at least one instance of $R^L$ is hydrogen. In certain embodiments, each instance of $R^L$ is hydrogen. In certain embodiments, at least one instance of $R^L$ is optionally substituted alkyl, e.g., optionally substituted $C_{1-6}$ alkyl, optionally substituted $C_{1-5}$alkyl, optionally substituted $C_{1-4}$alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. Exemplary $R^LC_{1-6}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). In certain embodiments, at least one instance of $R^L$ is methyl. In certain embodiments, at least one instance of $R^L$ is alkyl substituted with —CN, e.g., —(CH$_2$)$_z$CN, wherein z is 1, 2, 3, 4, 5, or 6. In certain embodiments, at least one instance of $R^L$ is alkyl substituted with hydroxy or substituted hydroxy, e.g., —(CH$_2$)$_z$OCH$_3$, wherein z is 1, 2, 3, 4, 5, or 6. In certain embodiments, at least one instance of $R^L$ is alkyl substituted with amino or substituted substituted amino, e.g., —(CH$_2$)$_z$NH$_2$, wherein z is 1, 2, 3, 4, 5, or 6. In certain embodiments, at least one instance of $R^L$ is a nitrogen protecting group. In certain embodiments, $R^L$ and $R^3$ taken together form an optionally substituted heterocyclyl ring, e.g., an optionally substituted 3- to 10-membered heterocyclyl, 3- to 8-membered heterocyclyl, 3- to 6-membered heterocyclyl, 3- to 5-membered heterocyclyl, 3- to 4-membered heterocyclyl, 3-membered heterocyclyl, 4-membered heterocyclyl, 5-membered heterocyclyl, 6-membered heterocyclyl, 7-membered heterocyclyl, 8-membered heterocyclyl, 9-membered heterocyclyl, or 10-membered heterocyclyl ring. In certain embodiments, $R^L$ and $R^3$ taken together form an optionally substituted heteroaryl ring, e.g., an optionally substituted 5- to 10-membered heteroaryl, optionally substituted 5- to 8-membered heteroaryl, optionally substituted 5- to 6-membered heteroaryl, optionally substituted 5-membered heteroaryl, or optionally substituted 6-membered heteroaryl.

In certain embodiments, Ring HET is a 6,5-bicyclic ring system of the formula (i) or (ii):

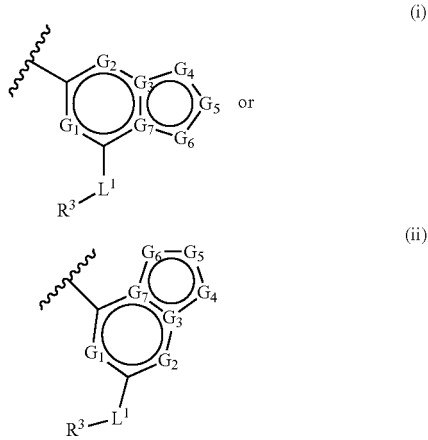

to respectively provide a compound of Formula (I-h) or (I-i):

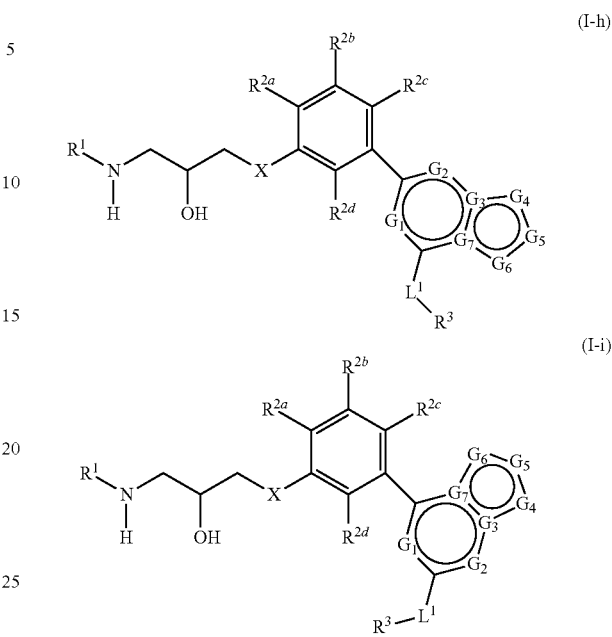

or a pharmaceutically acceptable salt thereof;
wherein:
$G_1$ is C—R$^7$ or N;
$G_2$ is C—R$^8$ or N;
$G_3$ and $G_7$ are each independently C or N;
$G_4$ is C—R$^4$, N, or N—R$^{4N}$;
$G_5$ is C—R$^5$, N, or N—R$^{5N}$;
$G_6$ is C—R$^6$, N, or N—R$^{6N}$;
provided at least two and not more than five instances of $G_1$, $G_2$, $G_3$, $G_4$, $G_5$, $G_6$, and $G_7$ is nitrogen;

each instance of R$^{4N}$, R$^{5N}$, and R$^{6N}$ independently hydrogen, —C(=O)R', —C(=O)OR', —C(=O)N(R')$_2$, —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of R$^4$, R$^5$, R$^6$, and R$^7$ is independently hydrogen, halo, —CN, —NO$_2$, —C(=O)R', —C(=O)OR', —C(=O)N(R')$_2$, —N(R')$_2$, —OR', —SR', —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, or optionally substituted heteroaryl; and each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring.

As generally defined above, between two and five instances, inclusive, of $G_1$, $G_2$, $G_3$, $G_4$, $G_5$, $G_6$, and $G_7$ is a nitrogen, e.g., two, three, four, or five instances of $G_1$, $G_2$, $G_3$, $G_4$, $G_5$, $G_6$, and $G_7$ is a nitrogen. In certain embodiments, $G_1$ is N. In certain embodiments, $G_2$ is N. In certain embodiments, $G_3$ is N. In certain embodiments, $G_4$ is N or N—$R^{4N}$. In certain embodiments, $G_5$ is N or N—$R^{5N}$. In certain embodiments, $G_6$ is N or N—$R^{6N}$. In certain embodiments, $G_1$ is N and $G_2$ is N. In certain embodiments, $G_1$ is N and $G_3$ is N. In certain embodiments, $G_1$ is N and $G_7$ is N. In certain embodiments, $G_1$ is N and $G_4$ is N or N—$R^{4N}$. In certain embodiments, $G_1$ is N and $G_5$ is N or N—$R^{5N}$. In certain embodiments, $G_1$ is N and $G_6$ is N or N—$R^{6N}$. In certain embodiments, $G_2$ is N and $G_3$ is N. In certain embodiments, $G_2$ is N and $G_7$ is N. In certain embodiments, $G_2$ is N and $G_4$ is N or N—$R^{4N}$. In certain embodiments, $G_2$ is N and $G_5$ is N or N—$R^{5N}$. In certain embodiments, $G_2$ is N and $G_6$ is N or N—$R^{6N}$. In certain embodiments, $G_3$ is N and $G_7$ is N. In certain embodiments, $G_3$ is N and $G_4$ is N or N—$R^{4N}$. In certain embodiments, $G_3$ is N and $G_5$ is N or N—$R^{5N}$. In certain embodiments, $G_3$ is N and $G_6$ is N or N—$R^{6N}$. In certain embodiments, $G_4$ is N or N—$R^{4N}$ and $G_7$ is N. In certain embodiments, $G_4$ is N or N—$R^{4N}$ and $G_5$ is N. In certain embodiments, $G_4$ is N or N—$R^{4N}$ and $G_6$ is N. In certain embodiments, $G_5$ is N or N—$R^{5N}$ and $G_7$ is N. In certain embodiments, $G_5$ is N or N—$R^{5N}$ and $G_4$ is N. In certain embodiments, $G_5$ is N or N—$R^{5N}$ and $G_6$ is N. In certain embodiments, $G_6$ is N or N—$R^{6N}$ and $G_7$ is N. In certain embodiments, $G_6$ is N or N—$R^{6N}$ and $G_4$ is N. In certain embodiments, $G_6$ is N or N—$R^{6N}$ and $G_5$ is N. Exemplary Ring HET groups of the formula (i) or (ii), include, but are not limited to, any one of the following ring systems, wherein one, two, three, four, or five instances of $G_1$, $G_2$, $G_3$, $G_4$, $G_5$, $G_6$, and $G_7$ is a nitrogen:

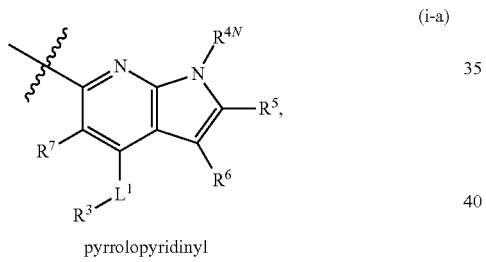

pyrrolopyridinyl (i-a)

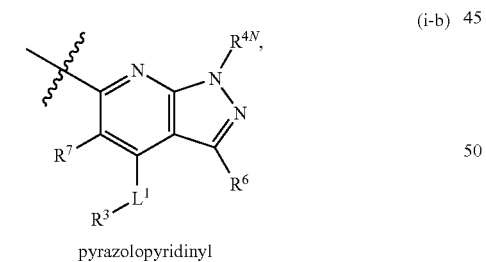

pyrazolopyridinyl (i-b)

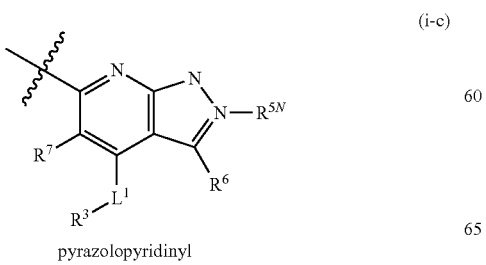

pyrazolopyridinyl (i-c)

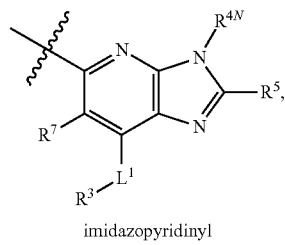

imidazopyridinyl (i-d)

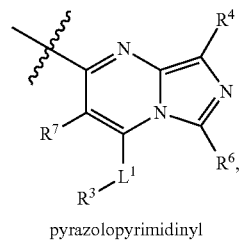

pyrazolopyrimidinyl (i-e)

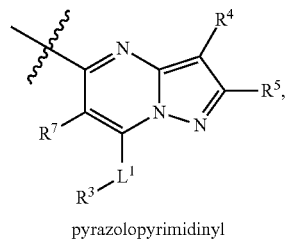

pyrazolopyrimidinyl (i-f)

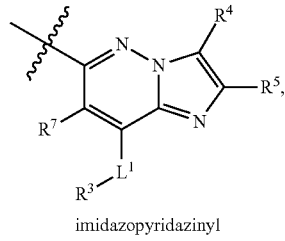

imidazopyridazinyl (i-g)

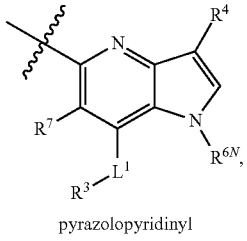

pyrazolopyridinyl (i-h)

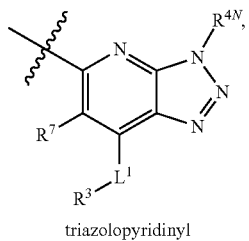

triazolopyridinyl (i-i)

-continued
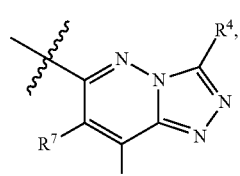
triazolopyridazinyl (i-j)
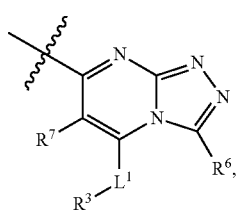
triazolopyrimidinyl (i-k)
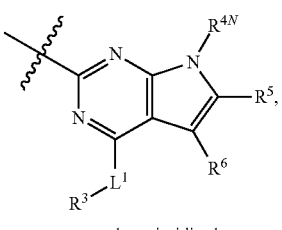
pyrazolopyrimidinyl (i-l)
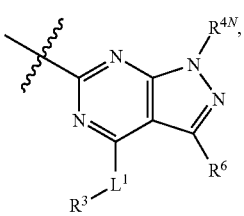
pyrazolopyrimidinyl (i-m)
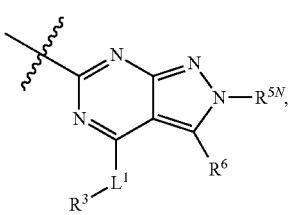
pyrazolopyrimidinyl (i-n)
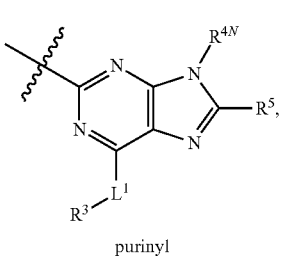
purinyl (i-o)
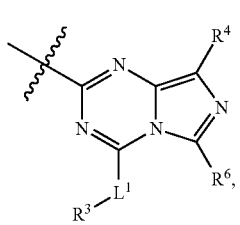
imidazotriazinyl (i-p)
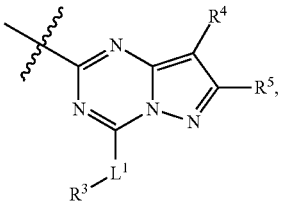
pyrazolotriazinyl (i-q)
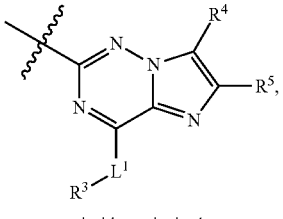
imidazotriazinyl (i-r)
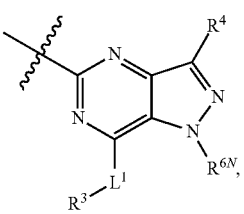
pyrazolopyrimidinyl (i-s)
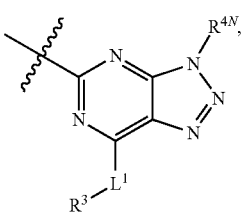
triazolopyrimidinyl (i-t)
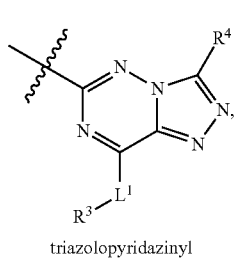
triazolopyridazinyl (i-u)

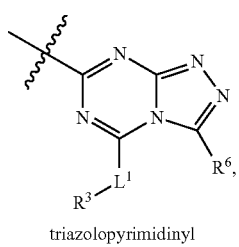
triazolopyrimidinyl (i-v)
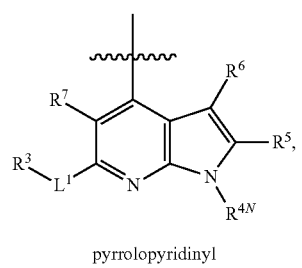
pyrrolopyridinyl (ii-a)
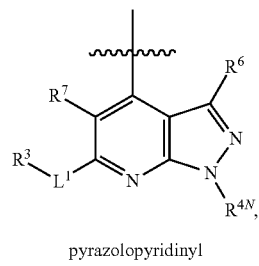
pyrazolopyridinyl (ii-b)
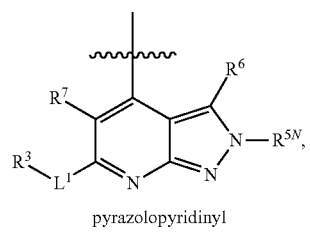
pyrazolopyridinyl (ii-c)
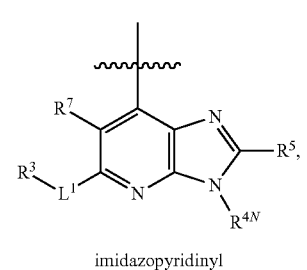
imidazopyridinyl (ii-d)
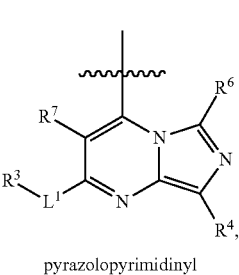
pyrazolopyrimidinyl (ii-e)
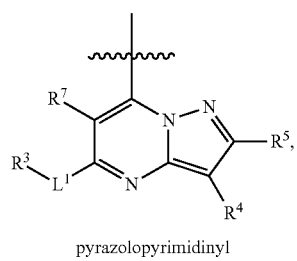
pyrazolopyrimidinyl (ii-f)
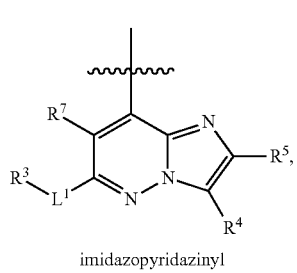
imidazopyridazinyl (ii-g)
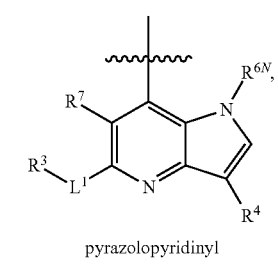
pyrazolopyridinyl (ii-h)
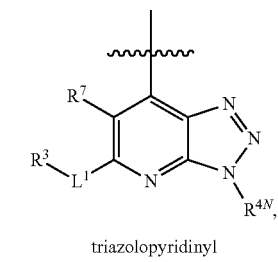
triazolopyridinyl (ii-i)
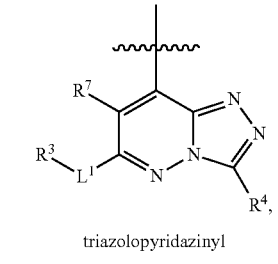
triazolopyridazinyl (ii-j)
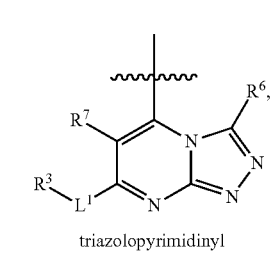
triazolopyrimidinyl (ii-k)

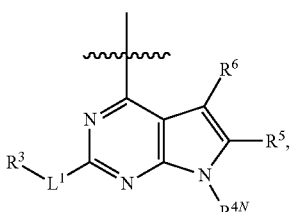

pyrrolopyrimidinyl (ii-l)

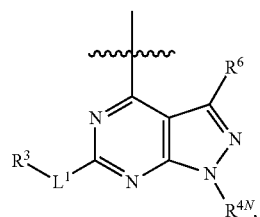

pyrazolopyrimidinyl (ii-m)

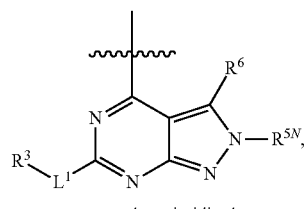

pyrazolopyrimidinyl (ii-n)

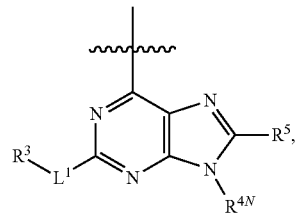

purinyl (ii-o)

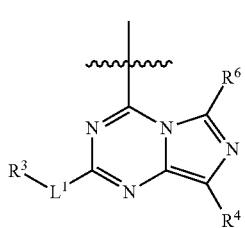

imidazotriazinyl (ii-p)

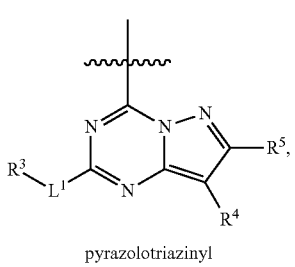

pyrazolotriazinyl (ii-q)

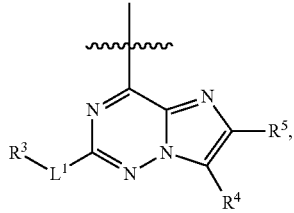

imidazotriazinyl (ii-r)

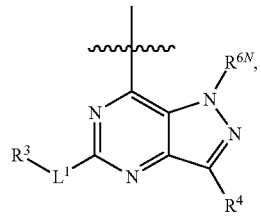

pyrazolopyrimidinyl (ii-s)

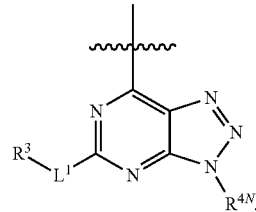

triazolopyrimidinyl (ii-t)

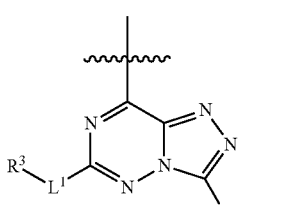

triazolopyridazinyl (ii-u)

and

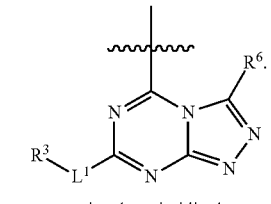

triazolopyrimidinyl (ii-v)

As generally defined herein, each instance of $R^{4N}$, $R^{5N}$, and $R^{6N}$ is independently hydrogen, —C(=O)R', —C(=O)OR', —C(=O)N(R')$_2$, —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group, wherein R' is as defined herein. In certain embodiments, at least one instance of $R^{4N}$, $R^{5N}$, or $R^{6N}$ is hydrogen. In certain embodiments, at least one instance of $R^{4N}$, $R^{5N}$, and $R^{6N}$ is —C(=O)R', —C(=O)OR', or —C(=O)N(R')$_2$, e.g., wherein R' is hydrogen or optionally substituted alkyl, e.g., methyl or ethyl. In certain embodiments, at least one instance of $R^{4N}$, $R^{5N}$, and $R^{6N}$ is —S(=O)R' or —S(=O)$_2$R', e.g., wherein R' is hydrogen or optionally substituted alkyl, e.g., methyl or ethyl. In certain embodiments, at least one instance of $R^{4N}$, $R^{5N}$, and $R^{6N}$ is optionally substituted alkyl, e.g., optionally substituted $C_{1-6}$ alkyl, optionally substituted $C_{1-5}$alkyl, optionally substituted $C_{1-4}$alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. Exemplary $R^{4N}$, $R^{5N}$, and $R^{6N}C_{1-6}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). In certain embodiments, at least one instance of $R^{4N}$, $R^{5N}$, and $R^{6N}$ is optionally substituted $C_{3-4}$alkyl, e.g., isopropyl ($C_3$) or tert-butyl ($C_4$). In certain embodiments, $R^{4N}$, $R^{5N}$, and $R^{6N}$ is optionally substituted alkenyl. In certain embodiments, at least one instance of $R^{4N}$, $R^{5N}$, and $R^{6N}$ is optionally substituted alkynyl. In certain embodiments, at least one instance of $R^{4N}$, $R^{5N}$, and $R^{6N}$ is optionally substituted carbocyclyl, e.g., optionally substituted $C_{3-5}$carbocyclyl, optionally substituted $C_{3-4}$carbocyclyl, optionally substituted $C_{4-5}$ carbocyclyl, optionally substituted $C_3$carbocyclyl, optionally substituted $C_4$carbocyclyl, or optionally substituted $C_5$carbocyclyl. In certain embodiments, at least one instance of $R^{4N}$, $R^{5N}$, and $R^{6N}$ is optionally substituted $C_3$carbocyclyl, e.g., optionally substituted cyclopropyl. In certain embodiments, at least one instance of $R^{4N}$, $R^{5N}$, and $R^{6N}$ is optionally substituted heterocyclyl, e.g., optionally substituted 3- to 5-membered heterocyclyl, optionally substituted 3- to 4 membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one instance of $R^{4N}$, $R^{5N}$, and $R^{6N}$ is optionally substituted aryl (e.g., optionally substituted phenyl) or optionally substituted heteroaryl (e.g., optionally substituted pyridinyl). In certain embodiments, at least one instance of $R^{4N}$, $R^{5N}$, and $R^{6N}$ is a nitrogen protecting group. In certain embodiments, at least one instance of $R^{4N}$, $R^{5N}$, and $R^{6N}$ is optionally substituted $C_3$carbocyclyl or optionally substituted $C_{1-4}$alkyl.

As generally defined herein, each instance of $R^4$, $R^5$, $R^6$, and $R^7$ is independently hydrogen, halo, —CN, —NO$_2$, —C(=O)R', —C(=O)OR', —C(=O)N(R')$_2$, —N(R')$_2$, —OR', —SR', —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, or optionally substituted heteroaryl, wherein R' is as defined herein. In certain embodiments, at least one instance of $R^4$, $R^5$, $R^6$, and $R^7$ is hydrogen. In certain embodiments, at least one instance of $R^4$, $R^5$, $R^6$, and $R^7$ is halo. In certain embodiments, at least one instance of $R^4$, $R^5$, $R^6$, and $R^7$ is independently —CN. In certain embodiments, at least one instance of $R^4$, $R^5$, $R^6$, and $R^7$ is —NO$_2$. In certain embodiments, at least one instance of $R^4$, $R^5$, $R^6$, and $R^7$ is —C(=O)R', —C(=O)OR', or —C(=O)N(R')$_2$, e.g., wherein R' is hydrogen or optionally substituted alkyl, e.g., methyl or ethyl. In certain embodiments, at least one instance of $R^4$, $R^5$, $R^6$, and $R^7$ is —N(R')$_2$. In certain embodiments, at least one instance of $R^4$, $R^5$, $R^6$, and $R^7$ is —OR'. In certain embodiments, at least one instance of $R^4$, $R^5$, $R^6$, and $R^7$ is —SR'. In certain embodiments, at least one instance of $R^4$, $R^5$, $R^6$, and $R^7$ is —S(=O)R' or —S(=O)$_2$R'. In certain embodiments, at least one instance of $R^4$, $R^5$, $R^6$, and $R^7$ is optionally substituted alkyl, e.g., optionally substituted $C_{1-6}$ alkyl, optionally substituted $C_{1-5}$alkyl, optionally substituted $C_{1-4}$alkyl, optionally substituted $C_{1-2}$alkyl, optionally substituted $C_{2-3}$alkyl, optionally substituted $C_{3-4}$alkyl, optionally substituted $C_1$alkyl, optionally substituted $C_2$alkyl, optionally substituted $C_3$alkyl, optionally substituted $C_4$alkyl, optionally substituted $C_5$alkyl, or optionally substituted $C_6$alkyl. Exemplary $R^4$, $R^5$, $R^6$, and $R^7C_{1-6}$alkyl groups include, but are not limited to, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). In certain embodiments, at least one instance of $R^4$, $R^5$, $R^6$, and $R^7$ is optionally substituted $C_{3-4}$alkyl, e.g., isopropyl ($C_3$) or tert-butyl ($C_4$). In certain embodiments, at least one instance of $R^4$, $R^5$, $R^6$, and $R^7$ is optionally substituted alkenyl. In certain embodiments, at least one instance of $R^4$, $R^5$, $R^6$, and $R^7$ is optionally substituted alkynyl. In certain embodiments, at least one instance of $R^4$, $R^5$, $R^6$, and $R^7$ is optionally substituted carbocyclyl, e.g., optionally substituted $C_{3-5}$carbocyclyl, optionally substituted $C_{3-4}$carbocyclyl, optionally substituted $C_{4-5}$ carbocyclyl, optionally substituted $C_3$carbocyclyl, optionally substituted $C_4$carbocyclyl, or optionally substituted $C_5$carbocyclyl. In certain embodiments, at least one instance of $R^4$, $R^5$, $R^6$, and $R^7$ is optionally substituted $C_3$carbocyclyl, e.g., optionally substituted cyclopropyl. In certain embodiments, at least one instance of $R^4$, $R^5$, $R^6$, and $R^7$ is optionally substituted heterocyclyl, e.g., optionally substituted 3- to 5-membered heterocyclyl, optionally substituted 3- to 4-membered heterocyclyl, optionally substituted 4- to 5-membered heterocyclyl, optionally substituted 3-membered heterocyclyl, optionally substituted 4-membered heterocyclyl, or optionally substituted 5-membered heterocyclyl. In certain embodiments, at least one instance of $R^4$, $R^5$, $R^6$, and $R^7$ is optionally substituted aryl (e.g., optionally substituted phenyl) or optionally substituted heteroaryl (e.g., optionally substituted pyridinyl). In certain embodiments, $R^{4N}$, $R^{5N}$, or $R^{6N}$ is a nitrogen protecting group. In certain embodiments, at least one instance of $R^4$, $R^5$, $R^6$, and $R^7$ is hydrogen, optionally substituted $C_{1-4}$alkyl, optionally substituted $C_3$carbocyclyl, —CN, —C(=O)R', —C(=O)OR', or —C(=O)N(R')$_2$.

Various combination of the above described embodiments are further contemplated herein. For example, in certain embodiments of Formula (I-h), wherein $G_2$ is N, provided is a compound of Formula (I-j):

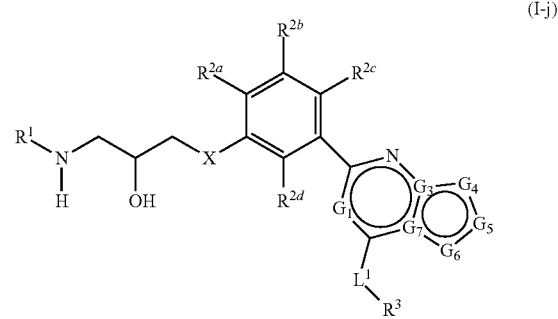

(I-j)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is optionally substituted heterocylyl or optionally substituted heteroaryl.

In certain embodiments of Formula (I-h), wherein $G_2$ is N, and $G_1$ is C—$R^7$, provided is a compound of Formula (I-k):

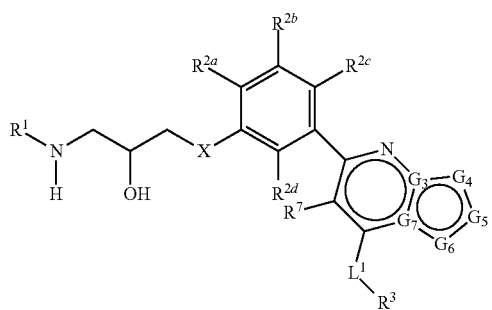

(I-k)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^1$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is optionally substituted heterocylyl or optionally substituted heteroaryl.

Alternatively, in certain embodiments of Formula (I-h), wherein $G_2$ is N, and $G_1$ is N, provided is a compound of Formula (I-l):

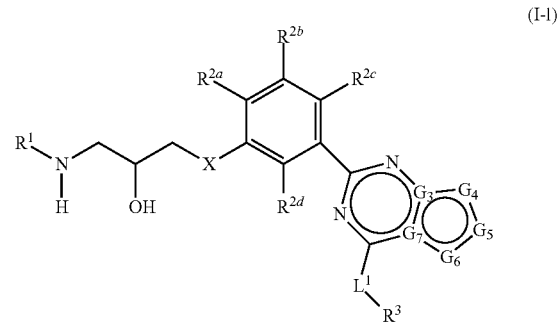

(I-l)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^A$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is optionally substituted heterocylyl or optionally substituted heteroaryl.

In certain embodiments of Formula (I-h), wherein $G_2$ is N, $G_4$ is N$R^{4N}$, and $G_5$ is N, provided is a compound of Formula (I-m):

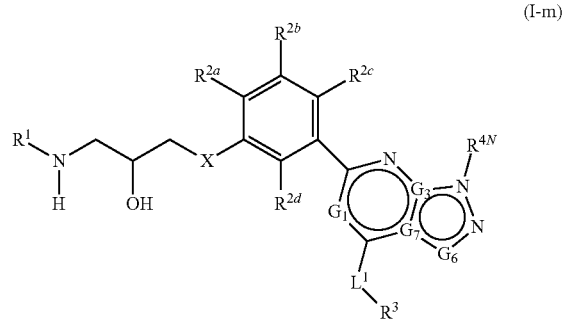

(I-m)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is optionally substituted heterocylyl or optionally substituted heteroaryl. In certain embodiments, $R^{4N}$ is optionally substituted $C_3$carbocyclyl or optionally substituted $C_{1-4}$alkyl.

Alternatively, in certain embodiments of Formula (I-h), wherein $G_2$ is N, $G_4$ is N, and $G_5$ is $NR^{5N}$, provided is a compound of Formula (I-n):

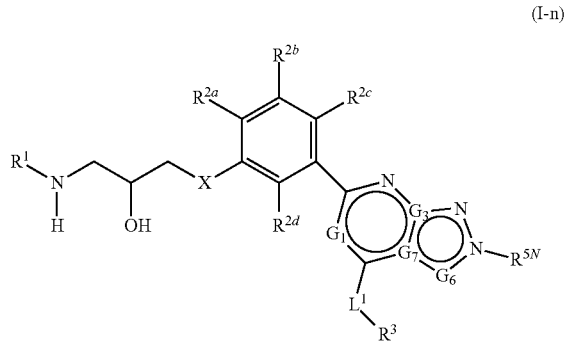

(I-n)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is optionally substituted heterocylyl or optionally substituted heteroaryl. In certain embodiments, $R^{5N}$ is optionally substituted $C_3$carbocyclyl or optionally substituted $C_{1-4}$alkyl.

In certain embodiments of Formula (I-h), wherein $G_2$ is N and $G_7$ is N, provided is a compound of Formula (I-o):

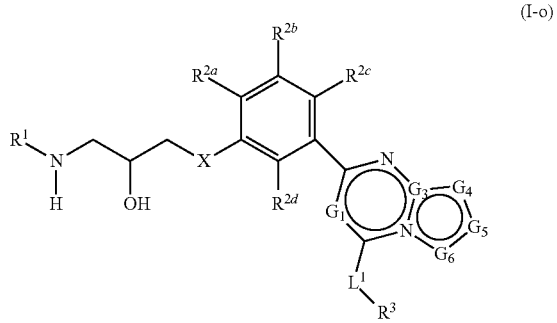

(I-o)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is optionally substituted heterocylyl or optionally substituted heteroaryl.

In certain embodiments of Formula (I-h), wherein $G_2$ is N, $G_7$ is N, and $G_6$ is N, provided is a compound of Formula (I-p):

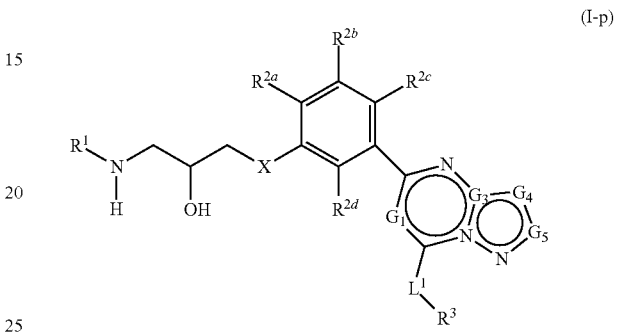

(I-p)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —N$R^L$C(O)O—, —N$R^L$C(O)N($R^L$)—, —N($R^L$)—, —N($R^L$)SO$_2$N($R^L$)—, —N$R^L$—(CH$_2$)$_x$—C(O)O—, —N$R^L$—(CH$_2$)$_x$—O—, —N$R^L$C(O)N($R^L$)—, —N$R^L$—(CH$_2$)$_x$—, —(CH$_2$)$_x$—N$R^L$—, —N$R^L$C(O)O(CH$_2$)$_x$—, —N$R^L$C(O)N$R^L$(CH$_2$)$_x$—, or —N$R^L$(CH$_2$)$_x$N$R^L$C(O)—. In certain embodiments, $R^3$ is optionally substituted heterocylyl or optionally substituted heteroaryl.

In certain embodiments of Formula (I-i), wherein $G_2$ is N, provided is a compound of Formula (I-q):

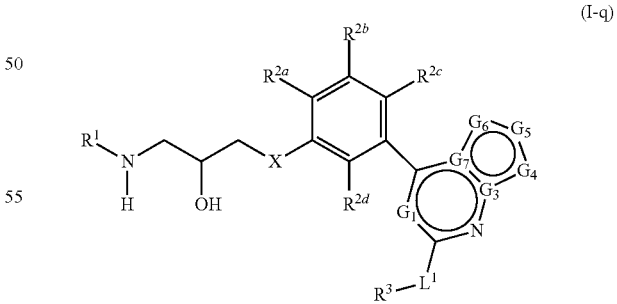

(I-q)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —$NR^L$C(O)O—, —$NR^L$C(O)N($R^L$)—, —N($R^L$)—, —N($R^L$)SO$_2$N($R^L$)—, —$NR^L$—(CH$_2$)$_x$—C(O)O—, —$NR^L$—(CH$_2$)$_x$—O—, —$NR^L$C(O)N($R^L$)—, —$NR^L$—(CH$_2$)$_x$—, —(CH$_2$)$_x$—$NR^L$—, —$NR^L$C(O)O(CH$_2$)$_x$—, —$NR^L$C(O)N$R^L$(CH$_2$)$_x$—, or —$NR^L$(CH$_2$)$_x$N$R^L$C(O)—. In certain embodiments, $R^3$ is optionally substituted heterocylyl or optionally substituted heteroaryl.

In certain embodiments of Formula (I-i), wherein $G_2$ is N, and $G_6$ is N, provided is a compound of Formula (I-r):

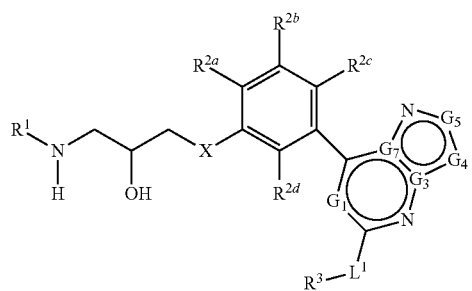

(I-r)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —$NR^L$C(O)O—, —$NR^L$C(O)N($R^L$)—, —N($R^L$)—, —N($R^L$)SO$_2$N($R^L$)—, —$NR^L$—(CH$_2$)$_x$—C(O)O—, —$NR^L$—(CH$_2$)$_x$—O—, —$NR^L$C(O)N($R^L$)—, —$NR^L$—(CH$_2$)$_x$—, —(CH$_2$)$_x$—$NR^L$—, —$NR^L$C(O)O(CH$_2$)$_x$—, —$NR^L$C(O)N$R^L$(CH$_2$)$_x$—, or —$NR^L$(CH$_2$)$_x$N$R^L$C(O)—. In certain embodiments, $R^3$ is optionally substituted heterocylyl or optionally substituted heteroaryl.

In certain embodiments of Formula (I-i), wherein $G_2$ is N, $G_6$ is N, and $G_7$ is N, provided is a compound of Formula (I-s):

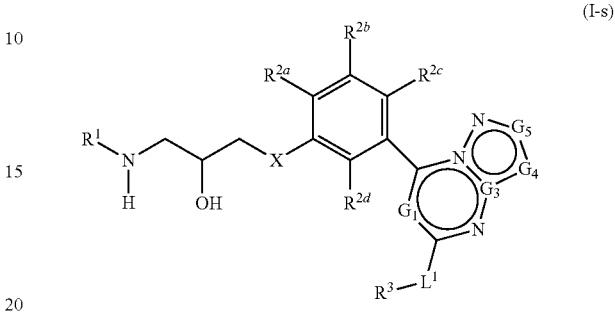

(I-s)

or a pharmaceutically acceptable salt thereof. In certain embodiments, X is —O—. In certain embodiments, $R^1$ is hydrogen, methyl, ethyl, n-propyl, isopropyl, or cyclopropyl. In certain embodiments, $R^{2a}$, $R^{2c}$, and $R^{2d}$ are hydrogen. In certain embodiments, $R^{2b}$ is halogen (e.g., chloro), —CN, —C(=O)$R^{A2}$, —O$R^{A2}$, —S$R^{A2}$, —N($R^{A2}$)$_2$, optionally substituted cyclopropyl, optionally substituted $C_{1-4}$alkyl, optionally substituted $C_{2-4}$alkenyl, optionally substituted $C_{2-4}$alkynyl, wherein $R^{A2}$ is optionally substituted alkyl. In certain embodiments, $L^1$ is a bond, —N($R^L$)—, —$NR^L$C(O)O—, —$NR^L$C(O)N($R^L$)—, —N($R^L$)—, —N($R^L$)SO$_2$N($R^L$)—, —$NR^L$—(CH$_2$)$_x$—C(O)O—, —$NR^L$—(CH$_2$)$_x$—O—, —$NR^L$C(O)N($R^L$)—, —$NR^L$—(CH$_2$)$_x$—, —(CH$_2$)$_x$—$NR^L$—, —$NR^L$C(O)O(CH$_2$)$_x$—, —$NR^L$C(O)N$R^L$(CH$_2$)$_x$—, — or $NR^L$(CH$_2$)$_x$N$R^L$C(O)—. In certain embodiments, $R^3$ is optionally substituted heterocylyl or optionally substituted heteroaryl.

In certain embodiments, a compound of Formula (I) is selected from any one of the compounds provided in Tables 1 to 7, or a pharmaceutically acceptable salt thereof.

TABLE 1

Exemplary Compounds

| # | Structure | LC-MS m/z (M + H) |
|---|-----------|-------------------|
| 1-1 | 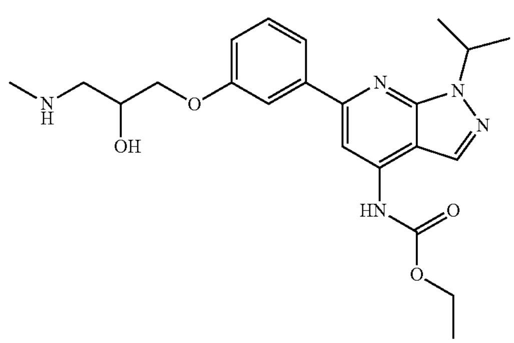 [SMILES: CCOC(=O)Nc1cc(-c2cccc(OCC(O)CNC)c2)nc2c1cnn2C(C)C] | 414.1 |

TABLE 1-continued

Exemplary Compounds

| # | Structure | LC-MS m/z (M + H) |
|---|---|---|
| 2-1 | 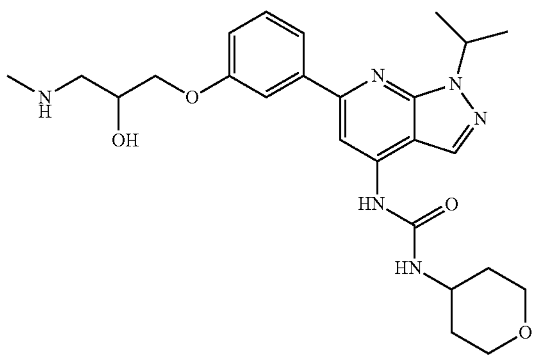 [SMILES: CNCC(O)COc1cccc(-c2cc(NC(=O)NC3CCOCC3)c3cnn(C(C)C)c3n2)c1] | 483.3 |
| 3-1 | 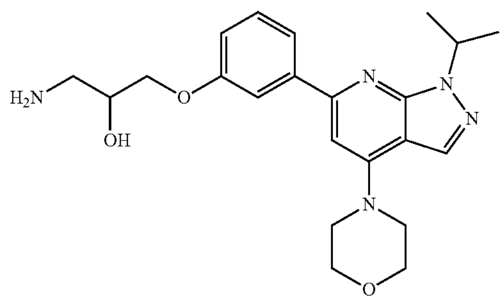 [SMILES: CC(C)n1ncc2c(N3CCOCC3)cc(-c3cccc(OCC(O)CN)c3)nc21] | 412.3 |
| 4-1 | 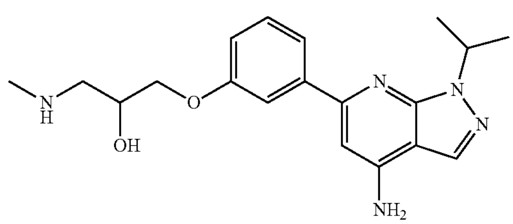 [SMILES: CNCC(O)COc1cccc(-c2cc(N)c3cnn(C(C)C)c3n2)c1] | 356.3 |
| 5-1 | 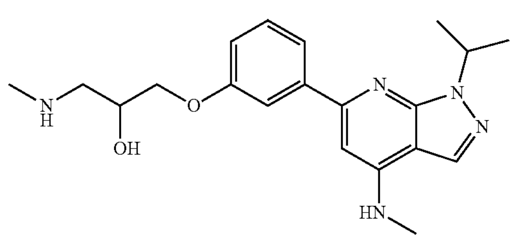 [SMILES: CNCC(O)COc1cccc(-c2cc(NC)c3cnn(C(C)C)c3n2)c1] | 370.3 |
| 6-1 | 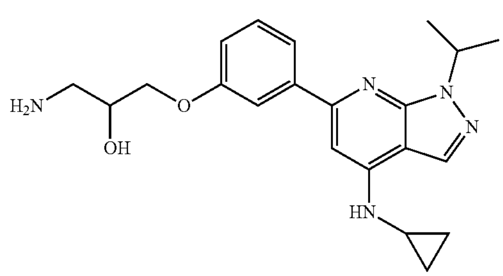 [SMILES: CC(C)n1ncc2c(NC3CC3)cc(-c3cccc(OCC(O)CN)c3)nc21] | 382.2 |

TABLE 1-continued

Exemplary Compounds

| # | Structure | LC-MS m/z (M + H) |
|---|---|---|
| 7-1 | 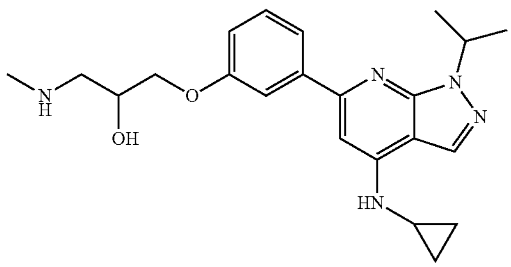 [SMILES: CNCC(O)COc1cccc(-c2cc(NC3CC3)c3cnn(C(C)C)c3n2)c1] | 396.3 |
| 8-1 | 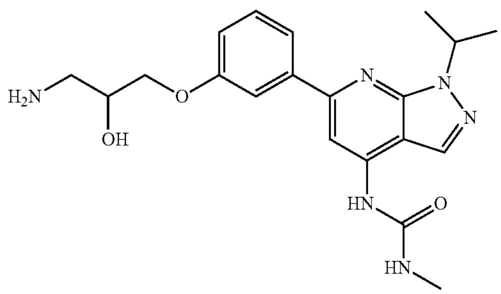 [SMILES: CNC(=O)Nc1cc(-c2cccc(OCC(O)CN)c2)nc2c1cnn2C(C)C] | 399.3 |
| 9-1 | 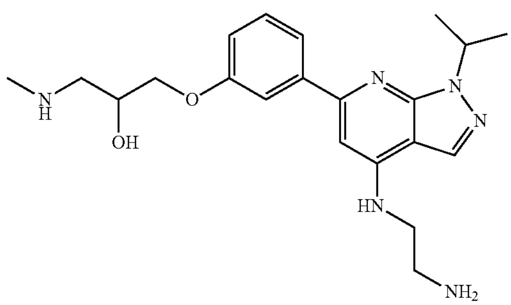 [SMILES: CNCC(O)COc1cccc(-c2cc(NCCN)c3cnn(C(C)C)c3n2)c1] | 399.2 |
| 10-1 | 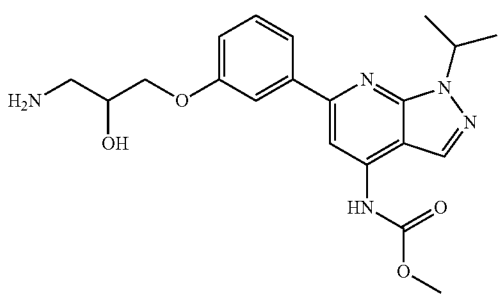 [SMILES: COC(=O)Nc1cc(-c2cccc(OCC(O)CN)c2)nc2c1cnn2C(C)C] | 400.3 |
| 11-1 | 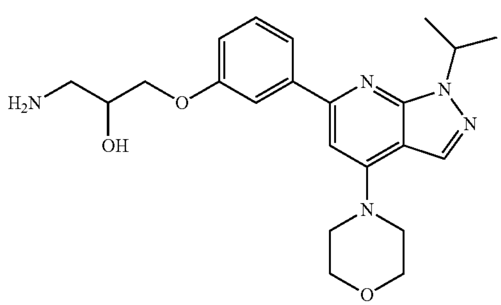 [SMILES: CC(C)n1ncc2c(N3CCOCC3)cc(-c3cccc(OCC(O)CN)c3)nc21] | 412.3 |

TABLE 1-continued

Exemplary Compounds

| # | Structure | LC-MS m/z (M + H) |
|---|---|---|
| 12-1 | 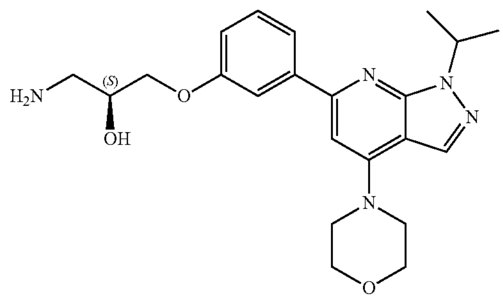 | 412.3 |
| 13-1 | 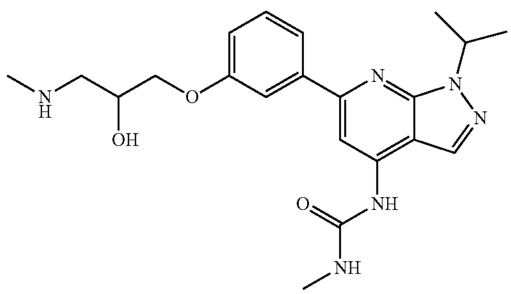 [SMILES: CNCC(O)COc1cccc(-c2cc(NC(=O)NC)c3cnn(C(C)C)c3n2)c1] | 413.3 |
| 14-1 | 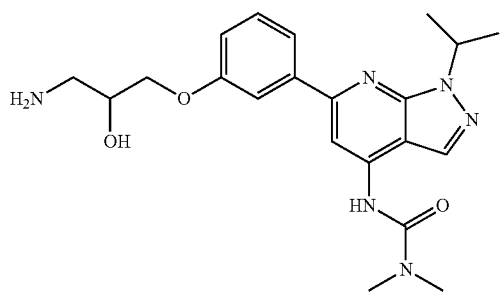 [SMILES: CC(C)n1ncc2c(NC(=O)N(C)C)cc(-c3cccc(OCC(O)CN)c3)nc21] | 413.3 |
| 15-1 | 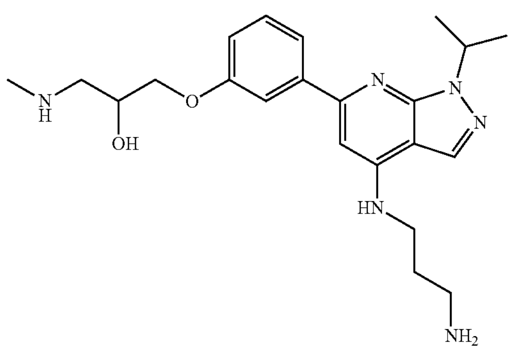 [SMILES: CNCC(O)COc1cccc(-c2cc(NCCCN)c3cnn(C(C)C)c3n2)c1] | 413.2 |
| 16-1 | 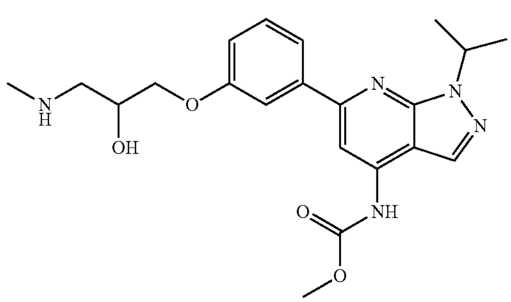 [SMILES: CNCC(O)COc1cccc(-c2cc(NC(=O)OC)c3cnn(C(C)C)c3n2)c1] | 414.3 |

TABLE 1-continued

Exemplary Compounds

| # | Structure | LC-MS m/z (M + H) |
|---|---|---|
| 17-1 | 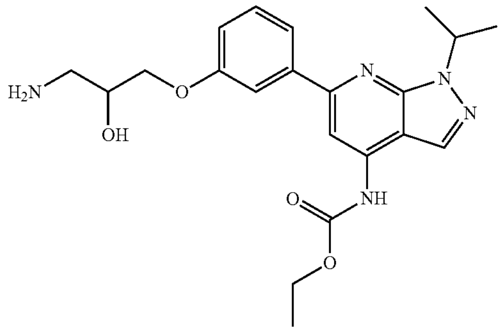 [SMILES: CCOC(=O)Nc1cc(-c2cccc(OCC(O)CN)c2)nc2c1cnn2C(C)C] | 414.3 |
| 18-1 | 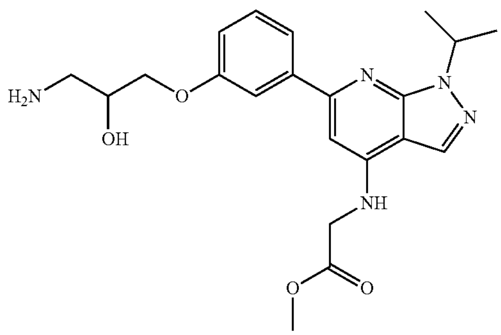 [SMILES: COC(=O)CNc1cc(-c2cccc(OCC(O)CN)c2)nc2c1cnn2C(C)C] | 414.2 |
| 19-1 | 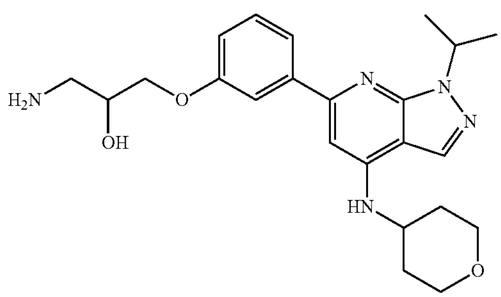 [SMILES: CC(C)n1ncc2c(NC3CCOCC3)cc(-c3cccc(OCC(O)CN)c3)nc21] | 426.2 |
| 20-1 | 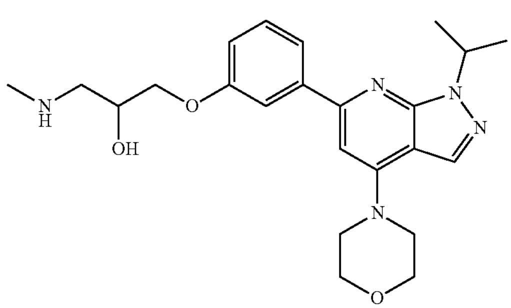 [SMILES: CNCC(O)COc1cccc(-c2cc(N3CCOCC3)c3cnn(C(C)C)c3n2)c1] | 426.3 |

TABLE 1-continued

Exemplary Compounds

| # | Structure | LC-MS m/z (M + H) |
|---|-----------|-------------------|
| 21-1 | 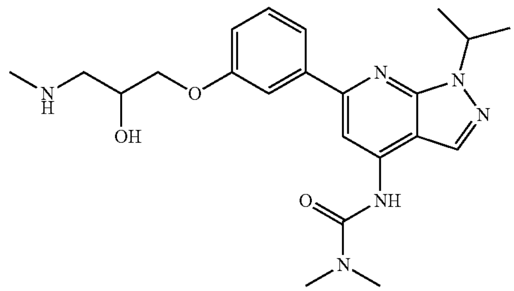 [SMILES: CNCC(O)COc1cccc(-c2cc(NC(=O)N(C)C)c3cnn(C(C)C)c3n2)c1] | 427.3 |
| 22-1 | 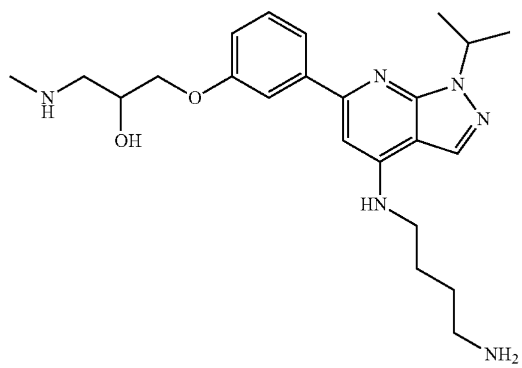 [SMILES: CNCC(O)COc1cccc(-c2cc(NCCCCN)c3cnn(C(C)C)c3n2)c1] | 427.2 |
| 23-1 | 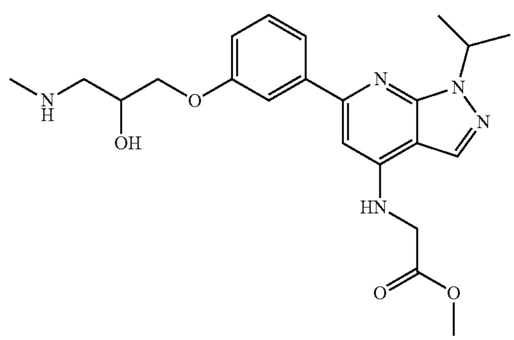 [SMILES: CNCC(O)COc1cccc(-c2cc(NCC(=O)OC)c3cnn(C(C)C)c3n2)c1] | 428.2 |
| 24-1 | 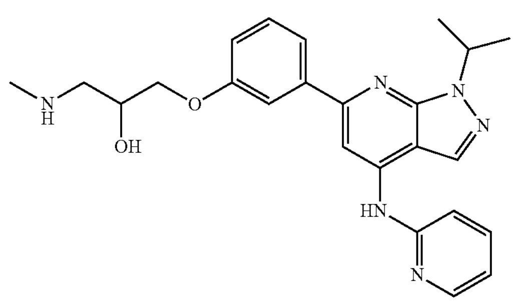 [SMILES: CNCC(O)COc1cccc(-c2cc(Nc3ccccn3)c3cnn(C(C)C)c3n2)c1] | 433.4 |

TABLE 1-continued

Exemplary Compounds

| # | Structure | LC-MS m/z (M + H) |
|---|---|---|
| 25-1 | 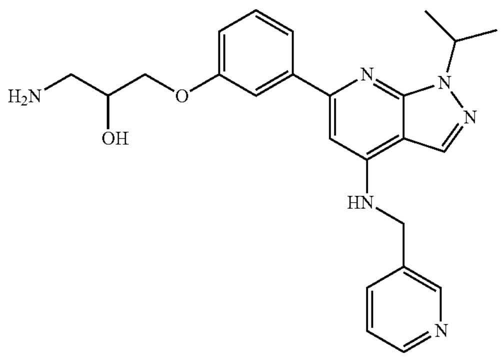 [SMILES: CC(C)n1ncc2c(NCc3cccnc3)cc(-c3cccc(OCC(O)CN)c3)nc21] | 217.5 (M + 2H)/2 |
| 26-1 | 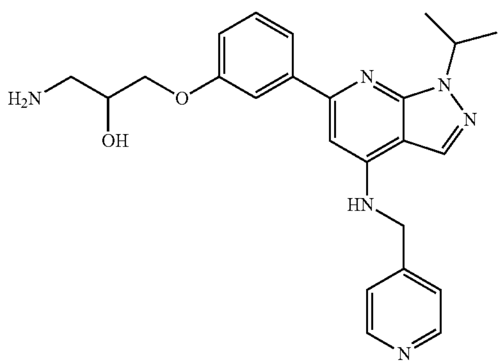 [SMILES: CC(C)n1ncc2c(NCc3ccncc3)cc(-c3cccc(OCC(O)CN)c3)nc21] | 433.3 |
| 27-1 | 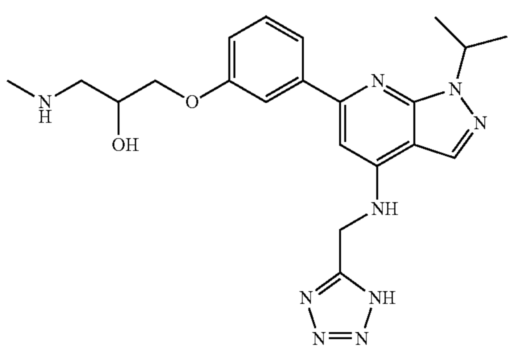 [SMILES: CNCC(O)COc1cccc(-c2cc(NCc3nnn[nH]3)c3cnn(C(C)C)c3n2)c1] | 438.3 |
| 28-1 | 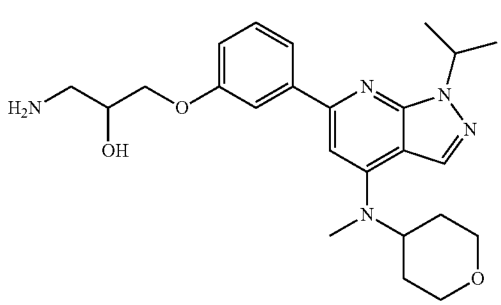 [SMILES: CC(C)n1ncc2c(N(C)C3CCOCC3)cc(-c3cccc(OCC(O)CN)c3)nc21] | 440.2 |

TABLE 1-continued

Exemplary Compounds

| # | Structure | LC-MS m/z (M + H) |
|---|---|---|
| 29-1 | 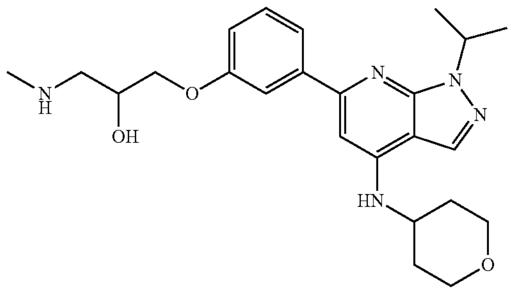 [SMILES: CNCC(O)COc1cccc(-c2cc(NC3CCOCC3)c3cnn(C(C)C)c3n2)c1] | 440.4 |
| 30-1 | 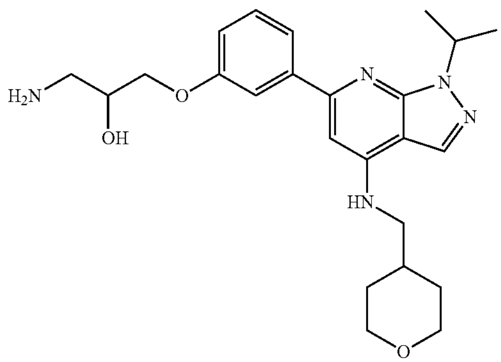 [SMILES: CC(C)n1ncc2c(NCC3CCOCC3)cc(-c3cccc(OCC(O)CN)c3)nc21] | 440.3 |
| 31-1 | 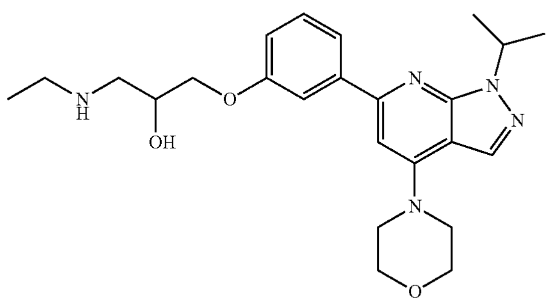 [SMILES: CCNCC(O)COc1cccc(-c2cc(N3CCOCC3)c3cnn(C(C)C)c3n2)c1] | 440.4 |
| 32-1 | 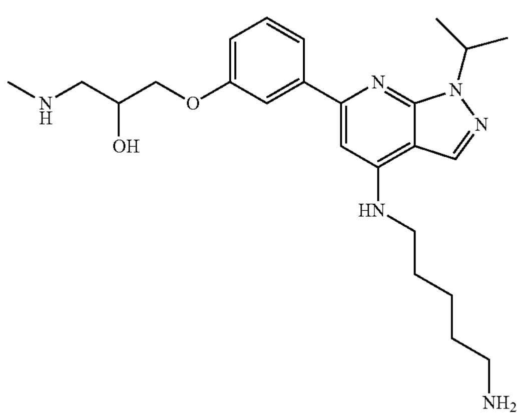 [SMILES: CNCC(O)COc1cccc(-c2cc(NCCCCCN)c3cnn(C(C)C)c3n2)c1] | 441.2 |

TABLE 1-continued

Exemplary Compounds

| # | Structure | LC-MS m/z (M + H) |
|---|---|---|
| 33-1 | 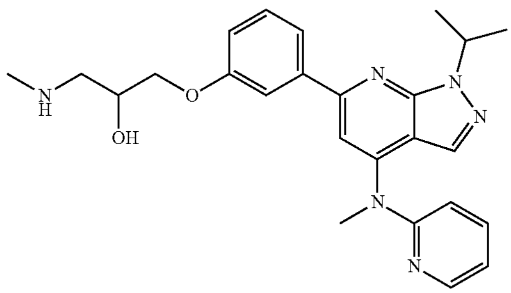 [SMILES: CNCC(O)COc1cccc(-c2cc(N(C)c3ccccn3)c3cnn(C(C)C)c3n2)c1] | 447.2 |
| 34-1 | 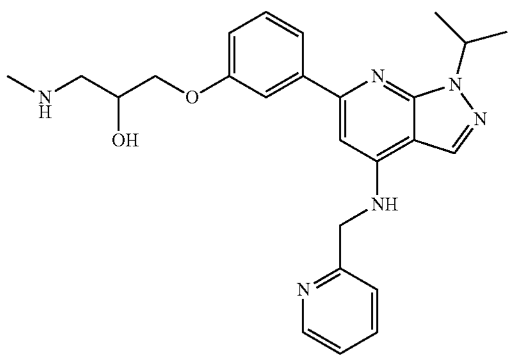 [SMILES: CNCC(O)COc1cccc(-c2cc(NCc3ccccn3)c3cnn(C(C)C)c3n2)c1] | 447.3 |
| 35-1 | 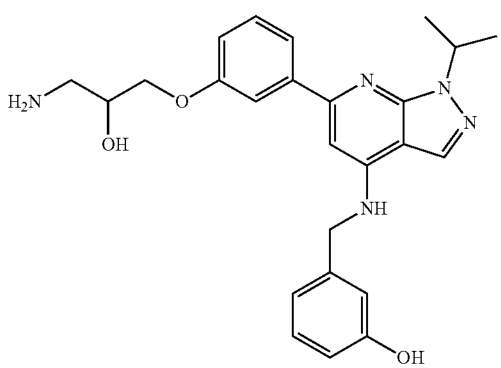 [SMILES: CC(C)n1ncc2c(NCc3cccc(O)c3)cc(-c3cccc(OCC(O)CN)c3)nc21] | 448.2 |
| 36-1 | 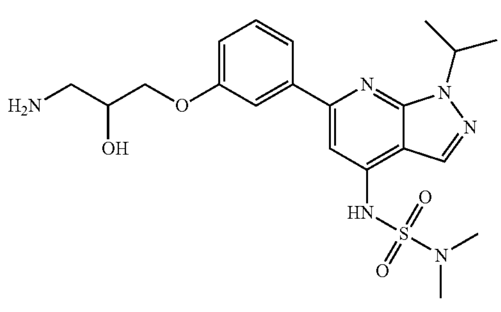 [SMILES: CC(C)n1ncc2c(NS(=O)(=O)N(C)C)cc(-c3cccc(OCC(O)CN)c3)nc21] | 449.3 |

TABLE 1-continued

Exemplary Compounds

| # | Structure | LC-MS m/z (M + H) |
|---|---|---|
| 37-1 | 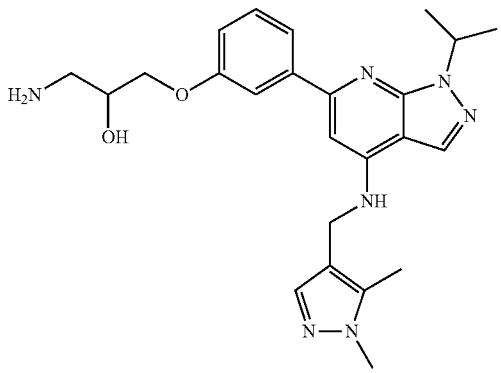 [SMILES: Cc1c(CNc2cc(-c3cccc(OCC(O)CN)c3)nc3c2cnn3C(C)C)cnn1C] | 450.2 |
| 38-1 | 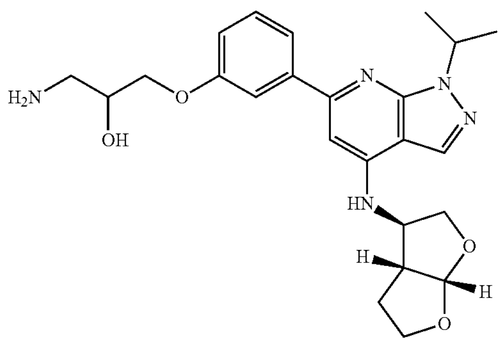 [SMILES: CC(C)n1ncc2c(N[C@H]3CO[C@@H]4OCC[C@@H]43)cc(-c3cccc(OCC(O)CN)c3)nc21] | 454.4 |
| 39-1 | 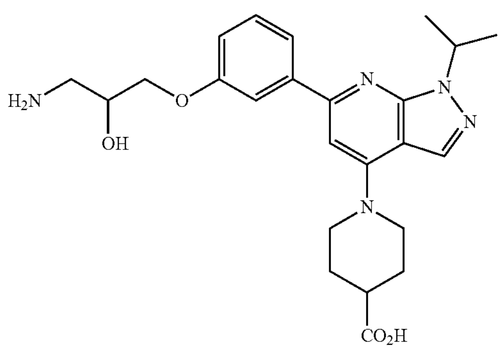 [SMILES: CC(C)n1ncc2c(N3CCC(C(=O)O)CC3)cc(-c3cccc(OCC(O)CN)c3)nc21] | 452.2 |
| 40-1 | 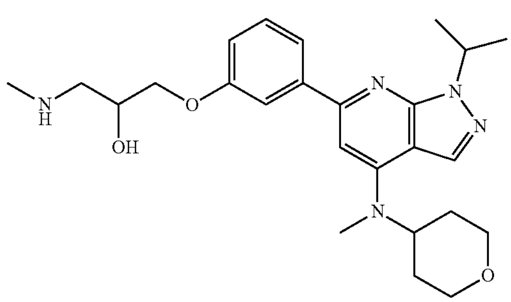 [SMILES: CNCC(O)COc1cccc(-c2cc(N(C)C3CCOCC3)c3cnn(C(C)C)c3n2)c1] | 454.4 |

TABLE 1-continued

Exemplary Compounds

| # | Structure | LC-MS m/z (M + H) |
|---|---|---|
| 41-1 | 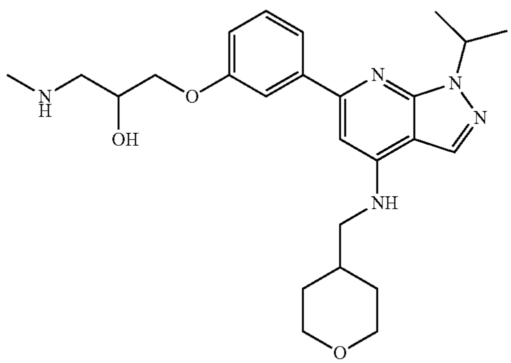 [SMILES: CNCC(O)COc1cccc(-c2cc(NCC3CCOCC3)c3cnn(C(C)C)c3n2)c1] | 454.4 |
| 42-1 | 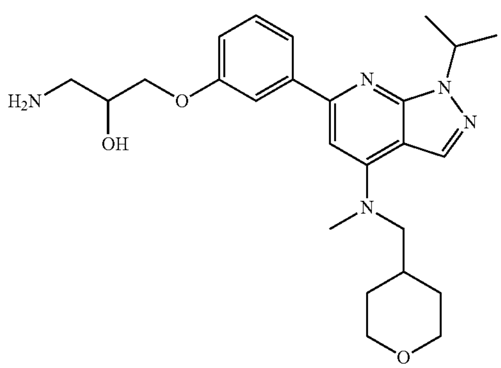 [SMILES: CC(C)n1ncc2c(N(C)CC3CCOCC3)cc(-c3cccc(OCC(O)CN)c3)nc21] | 454.2 |
| 43-1 | 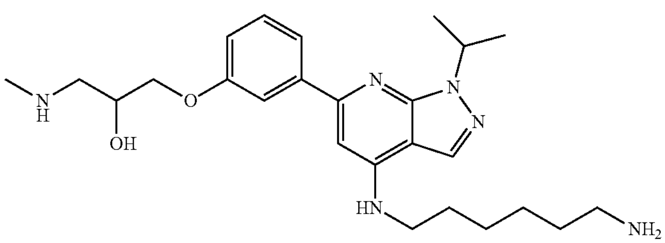 [SMILES: CNCC(O)COc1cccc(-c2cc(NCCCCCCN)c3cnn(C(C)C)c3n2)c1] | 455.3 |
| 44-1 | 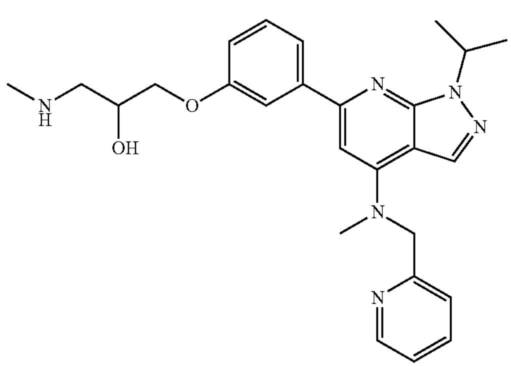 [SMILES: CNCC(O)COc1cccc(-c2cc(N(C)Cc3ccccn3)c3cnn(C(C)C)c3n2)c1] | 461.4 |

TABLE 1-continued

Exemplary Compounds

| # | Structure | LC-MS m/z (M + H) |
|---|---|---|
| 45-1 | 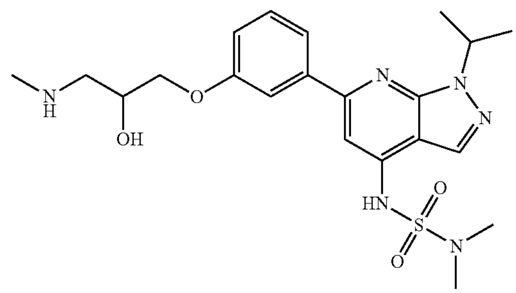 [SMILES: CNCC(O)COc1cccc(-c2cc(NS(=O)(=O)N(C)C)c3cnn(C(C)C)c3n2)c1] | 463.3 |
| 46-1 | 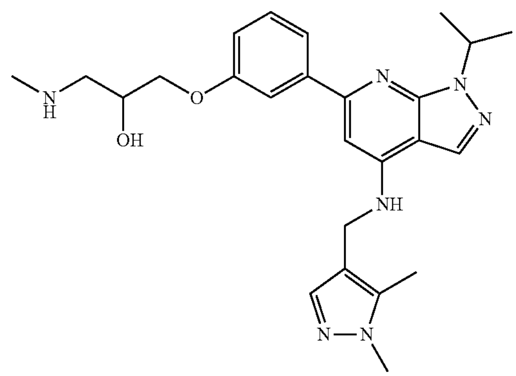 [SMILES: CNCC(O)COc1cccc(-c2cc(NCc3cnn(C)c3C)c3cnn(C(C)C)c3n2)c1] | 464.4 |
| 47-1 | 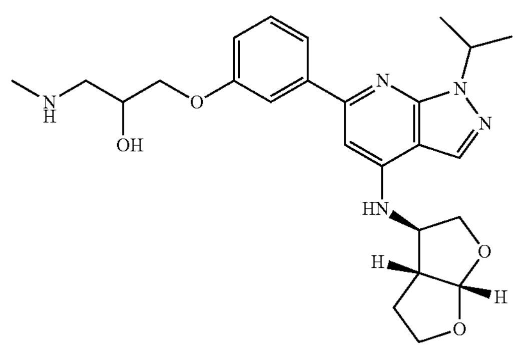 [SMILES: CNCC(O)COc1cccc(-c2cc(N[C@H]3CO[C@@H]4OCC[C@@H]43)c3cnn(C(C)C)c3n2)c1] | 467.9 |
| 48-1 | 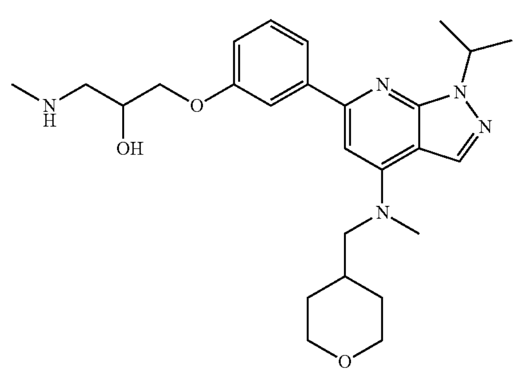 [SMILES: CNCC(O)COc1cccc(-c2cc(N(C)CC3CCOCC3)c3cnn(C(C)C)c3n2)c1] | 468.4 |

TABLE 1-continued

Exemplary Compounds

| # | Structure | LC-MS m/z (M + H) |
|---|-----------|-------------------|
| 49-1 | 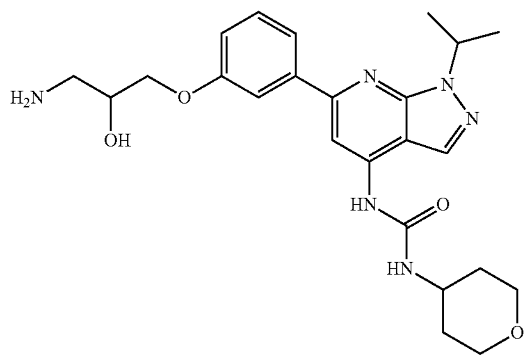 [SMILES: CC(C)n1ncc2c(NC(=O)NC3CCOCC3)cc(-c3cccc(OCC(O)CN)c3)nc21] | 469.2 |
| 50-1 | 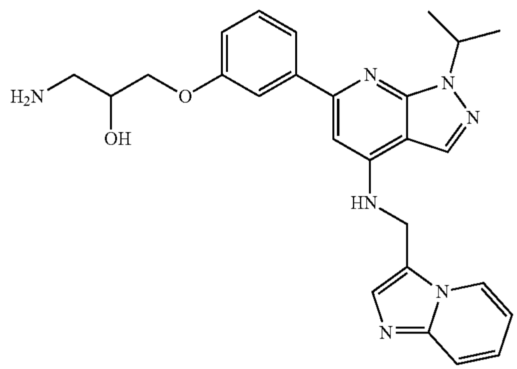 [SMILES: CC(C)n1ncc2c(NCc3cnc4ccccn34)cc(-c3cccc(OCC(O)CN)c3)nc21] | 472.2 |
| 51-1 | 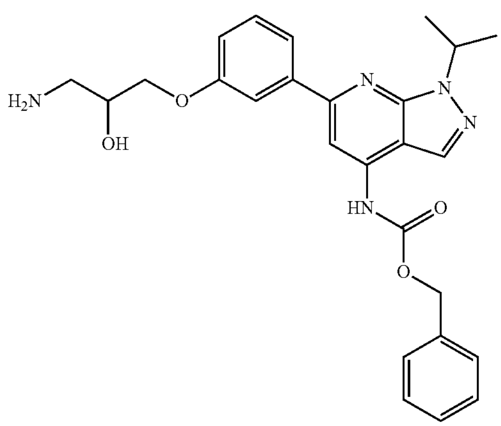 [SMILES: CC(C)n1ncc2c(NC(=O)OCc3ccccc3)cc(-c3cccc(OCC(O)CN)c3)nc21] | 476.3 |
| 52-1 | 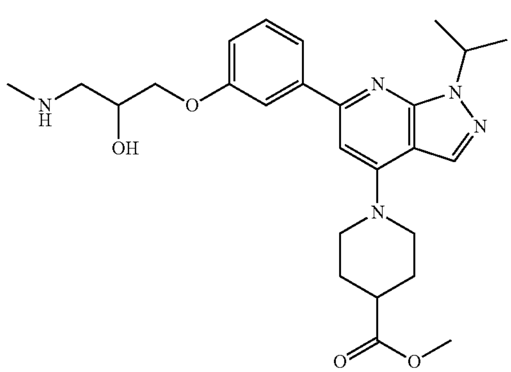 [SMILES: CNCC(O)COc1cccc(-c2cc(N3CCC(C(=O)OC)CC3)c3cnn(C(C)C)c3n2)c1] | 482.4 |

TABLE 1-continued
Exemplary Compounds
| # | Structure | LC-MS m/z (M + H) |
|---|---|---|
| 53-1 | 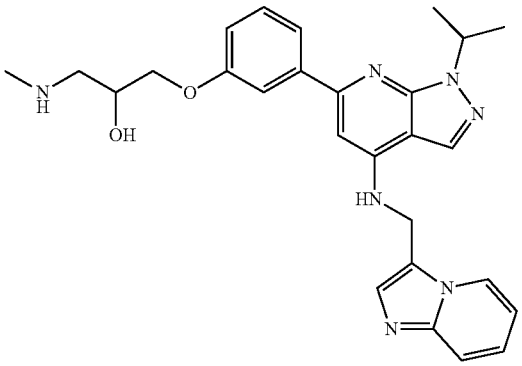 [SMILES: CNCC(O)COc1cccc(-c2cc(NCc3cnc4ccccn34)c3cnn(C(C)C)c3n2)c1] | 486.3 |
| 54-1 | 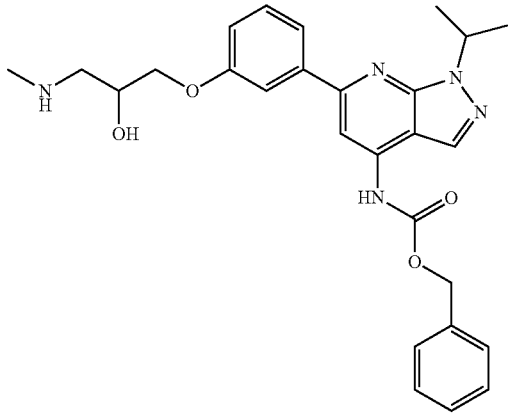 [SMILES: CNCC(O)COc1cccc(-c2cc(NC(=O)OCc3ccccc3)c3cnn(C(C)C)c3n2)c1] | 490.3 |
| 55-1 | 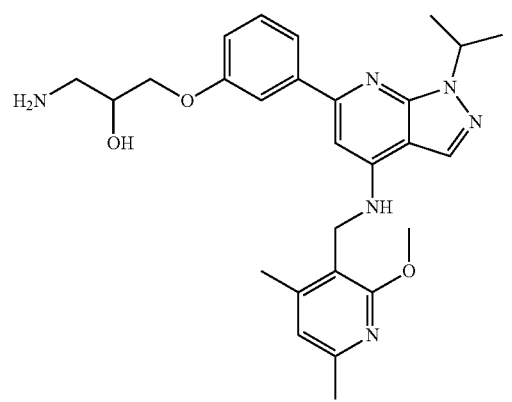 [SMILES: COc1nc(C)cc(C)c1CNc1cc(-c2cccc(OCC(O)CN)c2)nc2c1cnn2C(C)C] | 491.7 |

TABLE 1-continued

Exemplary Compounds

| # | Structure | LC-MS m/z (M + H) |
|---|---|---|
| 56-1 | 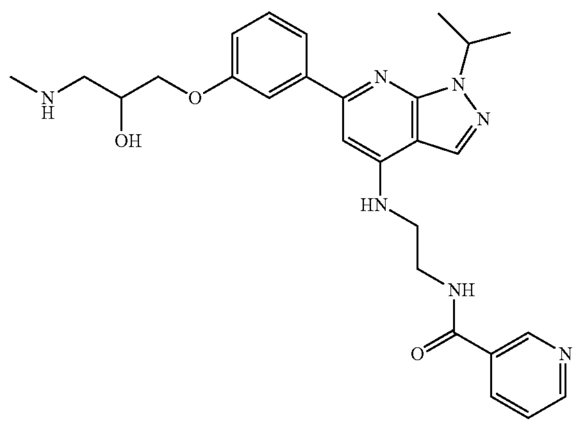 [SMILES: CNCC(O)COc1cccc(-c2cc(NCCNC(=O)c3cccnc3)c3cnn(C(C)C)c3n2)c1] | 504.2 |
| 57-1 | 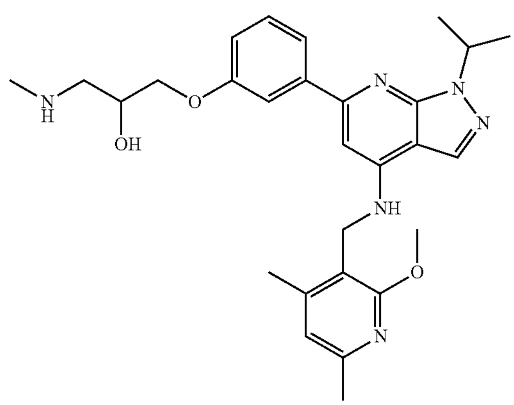 [SMILES: CNCC(O)COc1cccc(-c2cc(NCc3c(C)cc(C)nc3OC)c3cnn(C(C)C)c3n2)c1] | 505.4 |
| 58-1 | 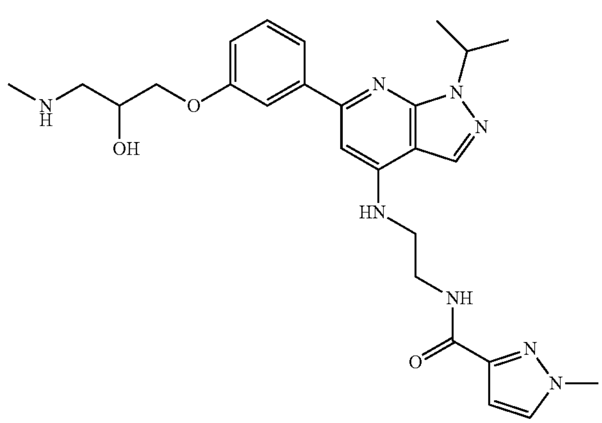 | 507.2 |

TABLE 1-continued

Exemplary Compounds

| # | Structure | LC-MS m/z (M + H) |
|---|---|---|
| 59-1 | 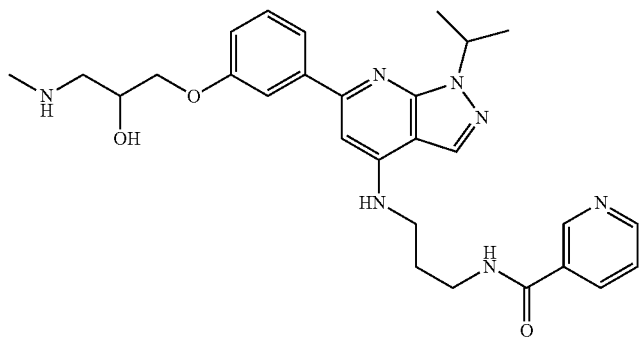 [SMILES: CNCC(O)COc1cccc(-c2cc(NCCCNC(=O)c3cccnc3)c3cnn(C(C)C)c3n2)c1] | 518.2 |
| 60-1 | 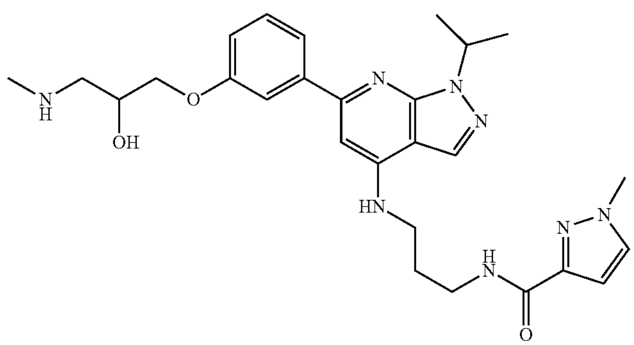 [SMILES: CNCC(O)COc1cccc(-c2cc(NCCCNC(=O)c3ccn(C)n3)c3cnn(C(C)C)c3n2)c1] | 521.3 |
| 61-1 | 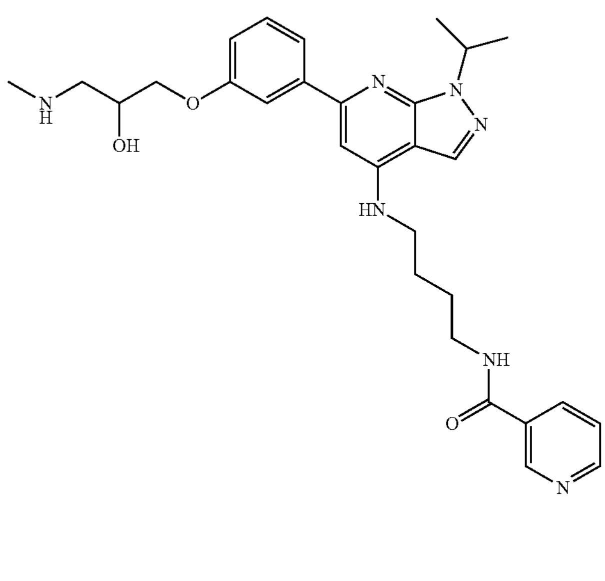 [SMILES: CNCC(O)COc1cccc(-c2cc(NCCCCNC(=O)c3cccnc3)c3cnn(C(C)C)c3n2)c1] | 532.3 |

TABLE 1-continued
Exemplary Compounds
| # | Structure | LC-MS m/z (M + H) |
|---|---|---|
| 62-1 | 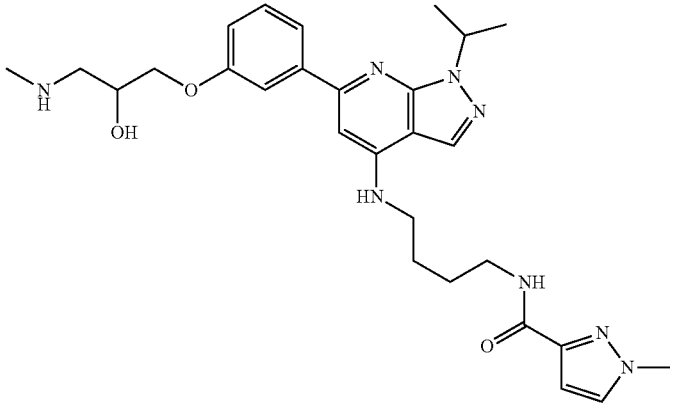 | 535.3 |
| 63-1 | 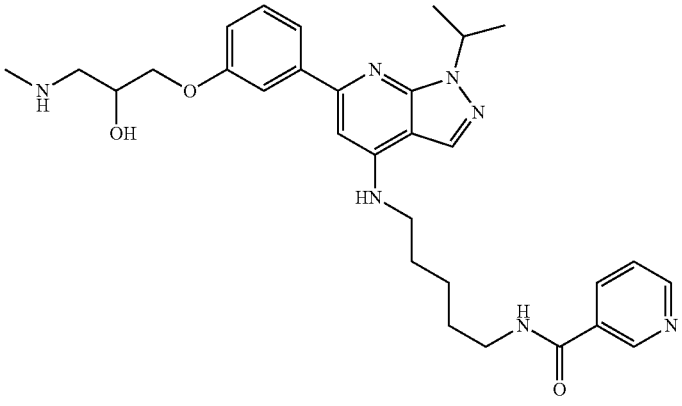 [SMILES: CNCC(O)COc1cccc(-c2cc(NCCCCCNC(=O)c3cccnc3)c3cnn(C(C)C)c3n2)c1] | 546.3 |
| 64-1 | 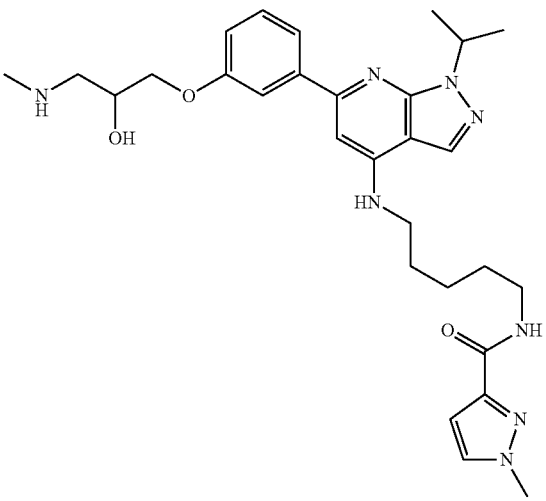 | 549.3 |

TABLE 1-continued
Exemplary Compounds
| # | Structure | LC-MS m/z (M + H) |
|---|---|---|
| 65-1 | 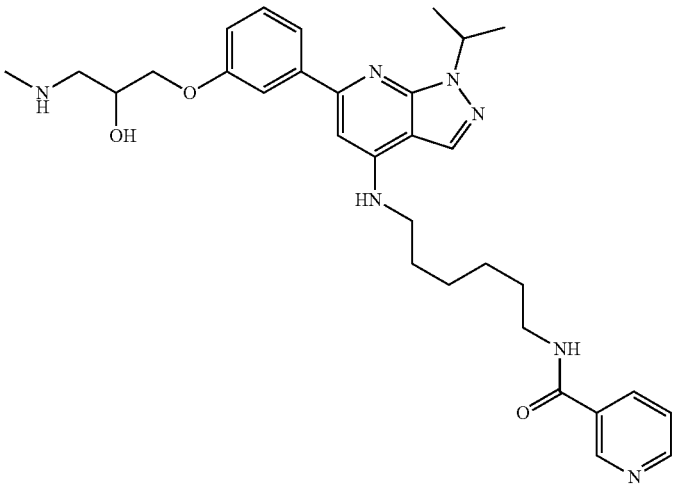 [SMILES: CNCC(O)COc1cccc(-c2cc(NCCCCCCNC(=O)c3cccnc3)c3cnn(C(C)C)c3n2)c1] | 560.3 |
| 66-1 | 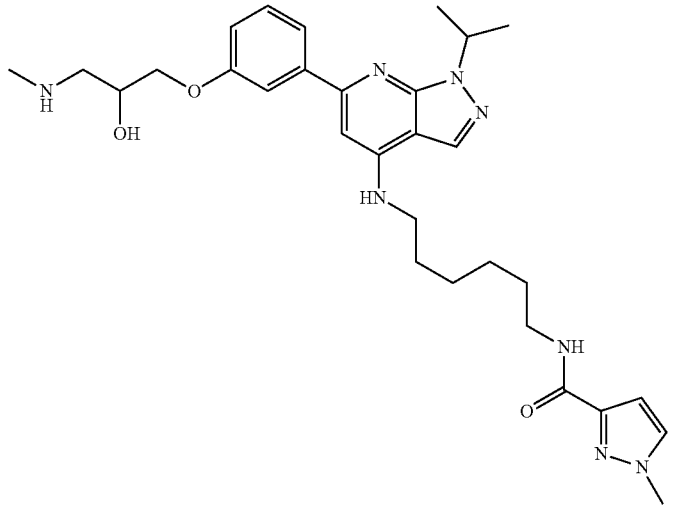 [SMILES: CNCC(O)COc1cccc(-c2cc(NCCCCCCNC(=O)c3ccn(C)n3)c3cnn(C(C)C)c3n2)c1] | 563.3 |
TABLE 2
Exemplary Compounds
| # | Structure | LC-MS m/z (M + H) |
|---|---|---|
| 1-2 | 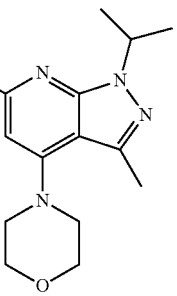 | 426.3 |

TABLE 2-continued
Exemplary Compounds
| # | Structure | LC-MS m/z (M + H) |
|---|---|---|
| 2-2 | 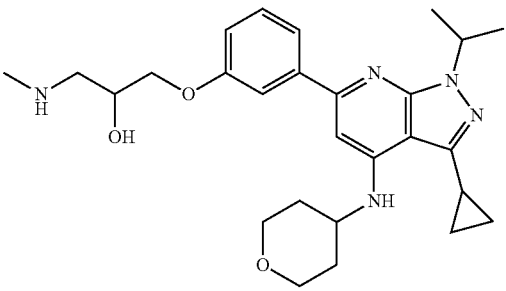 [SMILES: CNCC(O)COc1cccc(-c2cc(NC3CCOCC3)c3c(C4CC4)nn(C(C)C)c3n2)c1] | 480.3 |
| 3-2 | 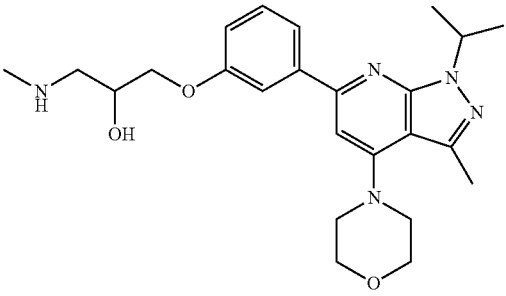 [SMILES: CNCC(O)COc1cccc(-c2cc(N3CCOCC3)c3c(C)nn(C(C)C)c3n2)c1] | 440.3 |
| 4-2 | 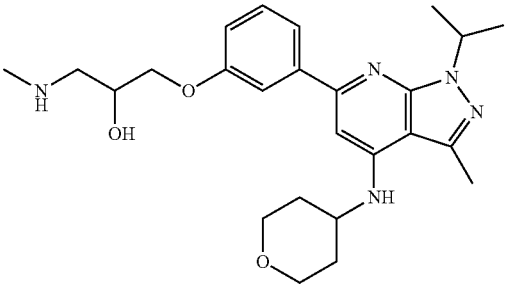 [SMILES: CNCC(O)COc1cccc(-c2cc(NC3CCOCC3)c3c(C)nn(C(C)C)c3n2)c1] | 454.4 |
| 5-2 | 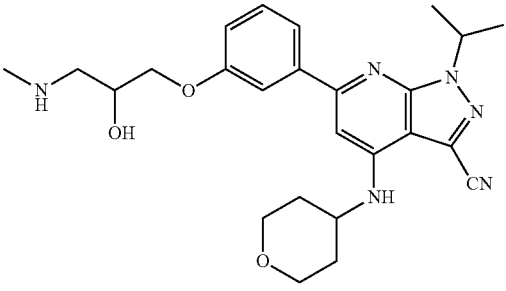 [SMILES: CNCC(O)COc1cccc(-c2cc(NC3CCOCC3)c3c(C#N)nn(C(C)C)c3n2)c1] | 465.3 |
| 6-2 | 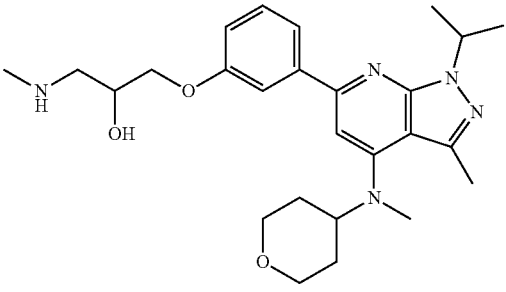 [SMILES: CNCC(O)COc1cccc(-c2cc(N(C)C3CCOCC3)c3c(C)nn(C(C)C)c3n2)c1] | 468.4 |

TABLE 3

Exemplary Compounds

| # | Structure | LC-MS m/z (M + H) |
|---|---|---|
| 1-3 | 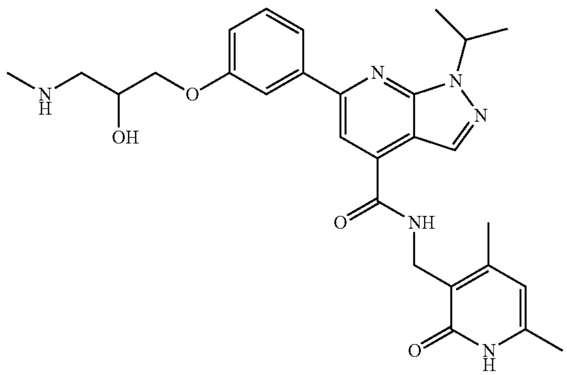 | 519.2 |
| 2-3 | 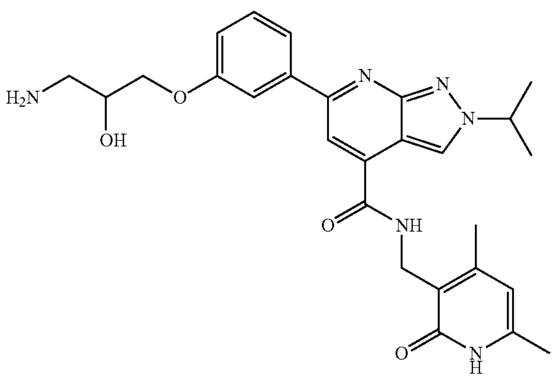 [SMILES: Cc1cc(C)c(CNC(=O)c2cc(-c3cccc(OCC(O)CN)c3)nc3nn(C(C)C)cc23)c(=O)[nH]1] | 505.3 |
| 3-3 | 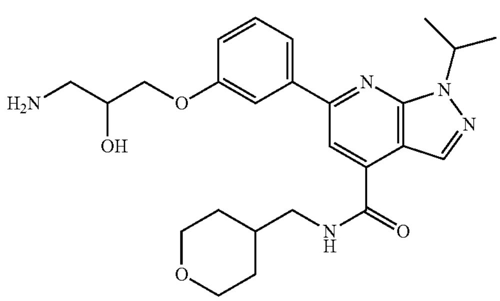 [SMILES: CC(C)n1ncc2c(C(=O)NCC3CCOCC3)cc(-c3cccc(OCC(O)CN)c3)nc21] | 468.3 |

TABLE 4
Exemplary compounds
| # | Structure | LC-MS m/z (M + H) |
|---|---|---|
| 1-4 | 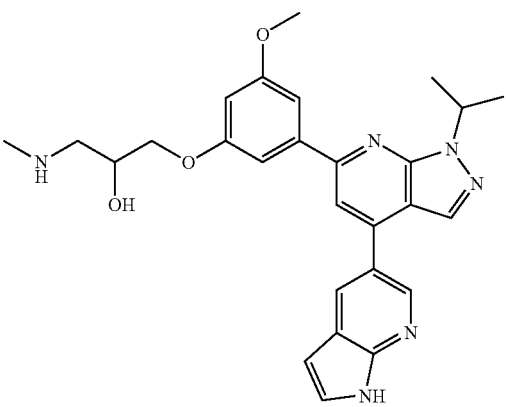 [SMILES: CNCC(O)COc1cc(OC)cc(-c2cc(-c3cnc4[nH]ccc4c3)c3cnn(C(C)C)c3n2)c1] | 487.2 |
| 2-4 | 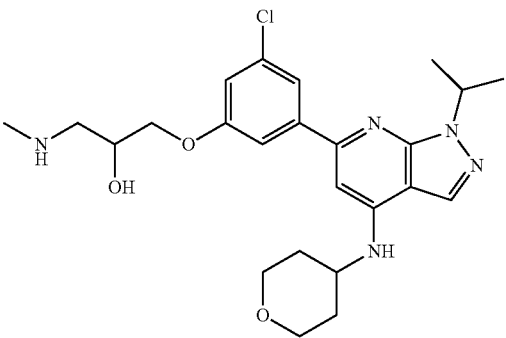 [SMILES: CNCC(O)COc1cc(Cl)cc(-c2cc(NC3CCOCC3)c3cnn(C(C)C)c3n2)c1] | 474.2 |
| 3-4 | 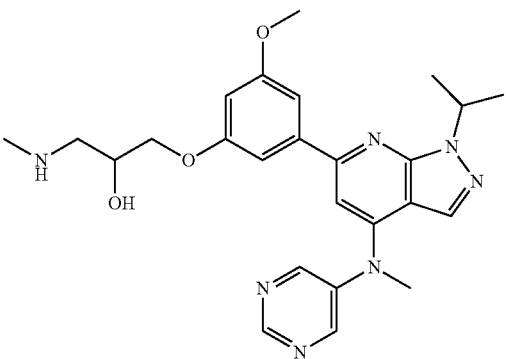 [SMILES: CNCC(O)COc1cc(OC)cc(-c2cc(N(C)c3cncnc3)c3cnn(C(C)C)c3n2)c1] | 478.2 |
| 4-4 | 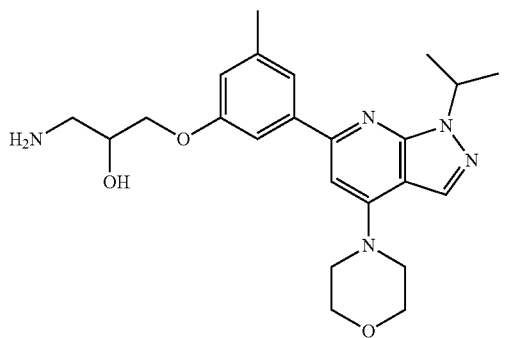 [SMILES: Cc1cc(OCC(O)CN)cc(-c2cc(N3CCOCC3)c3cnn(C(C)C)c3n2)c1] | 426.2 |

TABLE 4-continued

Exemplary compounds

| # | Structure | LC-MS m/z (M + H) |
|---|---|---|
| 5-4 | 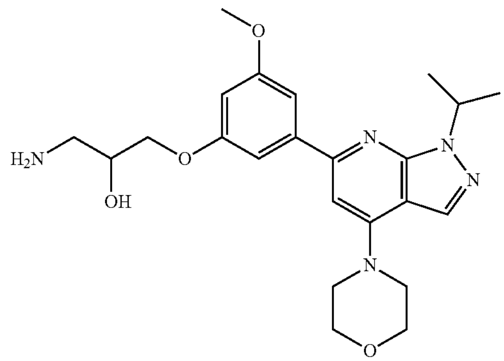 [SMILES: COc1cc(OCC(O)CN)cc(-c2cc(N3CCOCC3)c3cnn(C(C)C)c3n2)c1] | 442.3 |
| 6-4 | 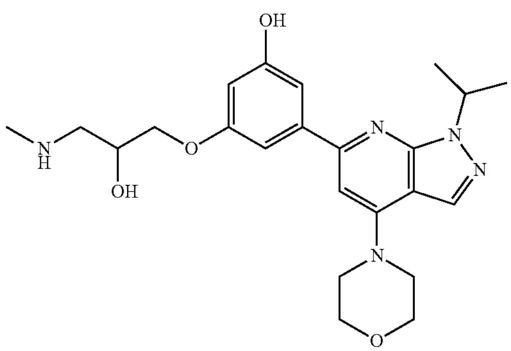 [SMILES: CNCC(O)COc1cc(O)cc(-c2cc(N3CCOCC3)c3cnn(C(C)C)c3n2)c1] | 442.3 |
| 7-4 | 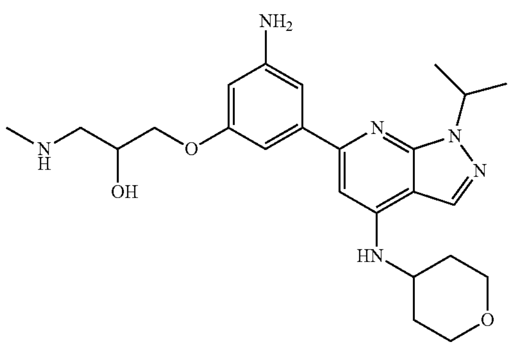 [SMILES: CNCC(O)COc1cc(N)cc(-c2cc(NC3CCOCC3)c3cnn(C(C)C)c3n2)c1] | 455.3 |
| 8-4 | 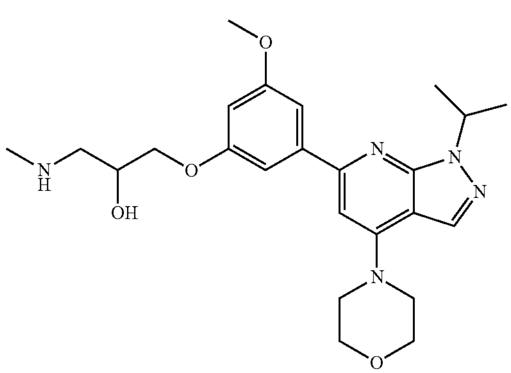 [SMILES: CNCC(O)COc1cc(OC)cc(-c2cc(N3CCOCC3)c3cnn(C(C)C)c3n2)c1] | 456.4 |

TABLE 4-continued

Exemplary compounds

| # | Structure | LC-MS m/z (M + H) |
|---|---|---|
| 9-4 | 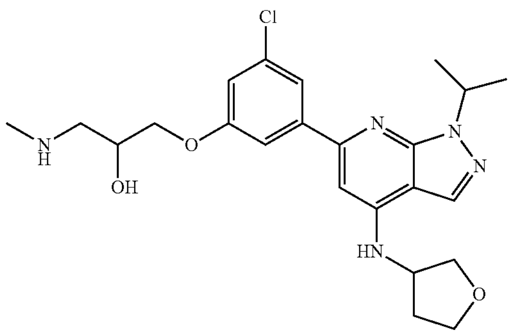 [SMILES: CNCC(O)COc1cc(Cl)cc(-c2cc(NC3CCOC3)c3cnn(C(C)C)c3n2)c1] | 460.3 |
| 10-4 | 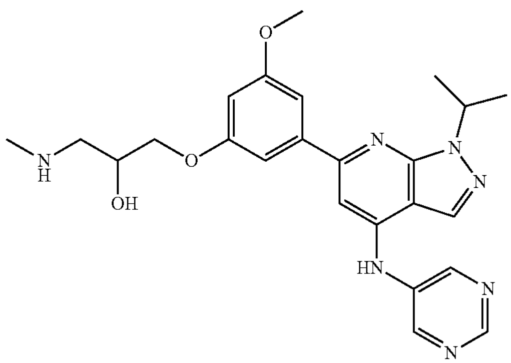 [SMILES: CNCC(O)COc1cc(OC)cc(-c2cc(Nc3cncnc3)c3cnn(C(C)C)c3n2)c1] | 464.2 |
| 11-4 | 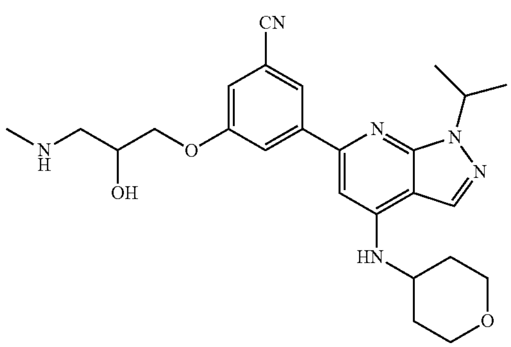 [SMILES: CNCC(O)COc1cc(C#N)cc(-c2cc(NC3CCOCC3)c3cnn(C(C)C)c3n2)c1] | 465.3 |
| 12-4 | 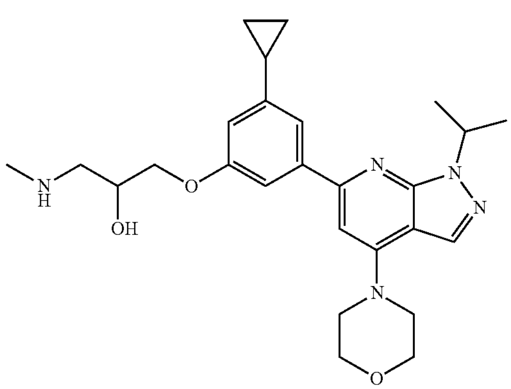 [SMILES: CNCC(O)COc1cc(-c2cc(N3CCOCC3)c3cnn(C(C)C)c3n2)cc(C2CC2)c1] | 466.4 |

TABLE 4-continued

Exemplary compounds

| # | Structure | LC-MS m/z (M + H) |
|---|---|---|
| 13-4 | 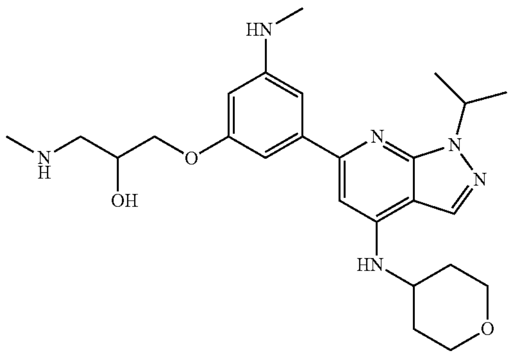 [SMILES: CNCC(O)COc1cc(NC)cc(-c2cc(NC3CCOCC3)c3cnn(C(C)C)c3n2)c1] | 469.3 |
| 14-4 | 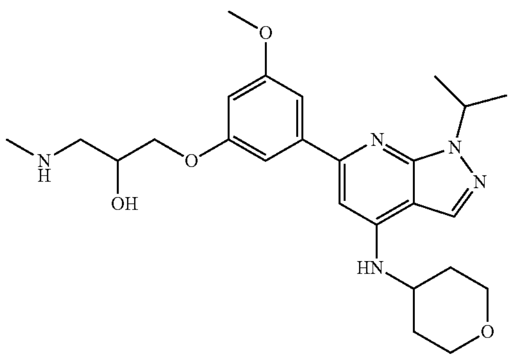 [SMILES: CNCC(O)COc1cc(OC)cc(-c2cc(NC3CCOCC3)c3cnn(C(C)C)c3n2)c1] | 470.4 |
| 15-4 | 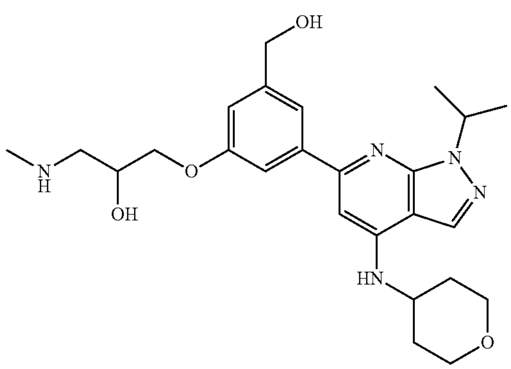 [SMILES: CNCC(O)COc1cc(CO)cc(-c2cc(NC3CCOCC3)c3cnn(C(C)C)c3n2)c1] | 470.2 |
| 16-4 | 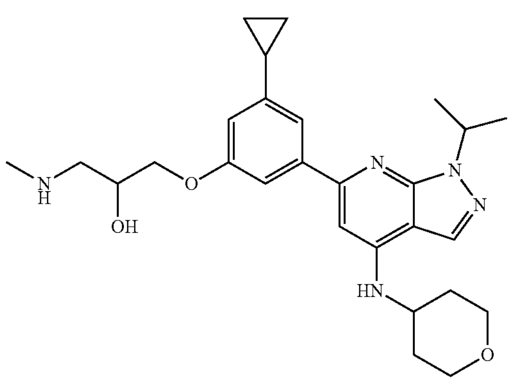 [SMILES: CNCC(O)COc1cc(-c2cc(NC3CCOCC3)c3cnn(C(C)C)c3n2)cc(C2CC2)c1] | 480.3 |

TABLE 4-continued

Exemplary compounds

| # | Structure | LC-MS m/z (M + H) |
|---|---|---|
| 17-4 | 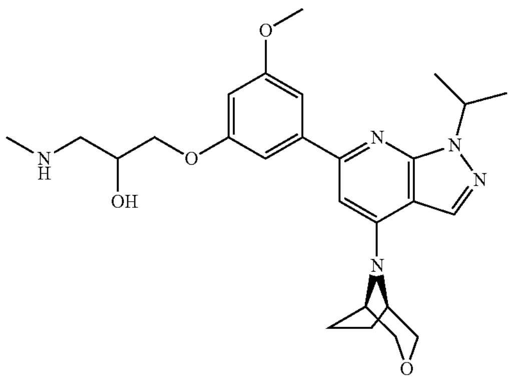 | 482.2 |
| 18-4 | 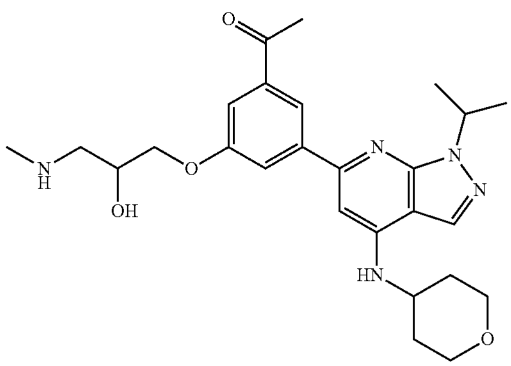 [SMILES: CNCC(O)COc1cc(C(C)=O)cc(-c2cc(NC3CCOCC3)c3cnn(C(C)C)c3n2)c1] | 482.3 |
| 19-4 | 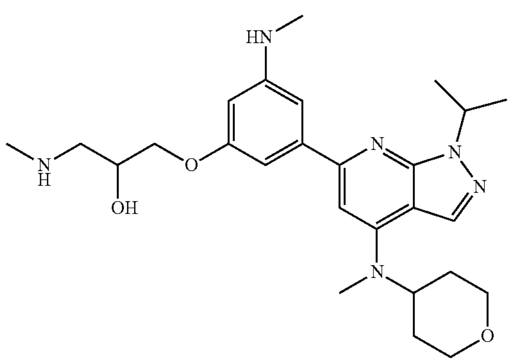 [SMILES: CNCC(O)COc1cc(NC)cc(-c2cc(N(C)C3CCOCC3)c3cnn(C(C)C)c3n2)c1] | 483.3 |
| 20-4 | 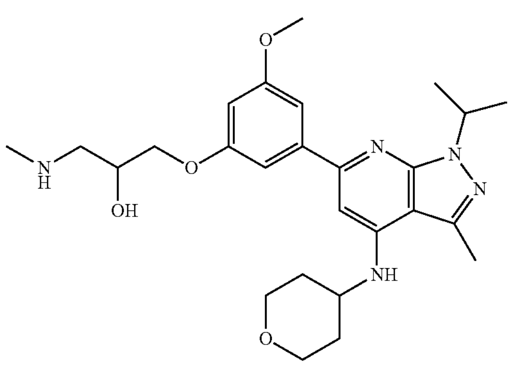 [SMILES: CNCC(O)COc1cc(OC)cc(-c2cc(NC3CCOCC3)c3c(C)nn(C(C)C)c3n2)c1] | 484.3 |

TABLE 4-continued

Exemplary compounds

| # | Structure | LC-MS m/z (M + H) |
|---|---|---|
| 21-4 | 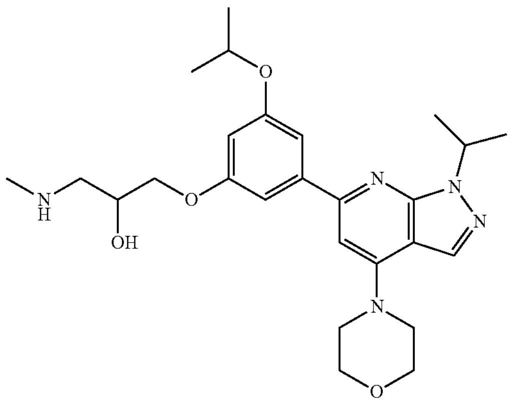 [SMILES: CNCC(O)COc1cc(OC(C)C)cc(-c2cc(N3CCOCC3)c3cnn(C(C)C)c3n2)c1] | 484.4 |
| 22-4 | 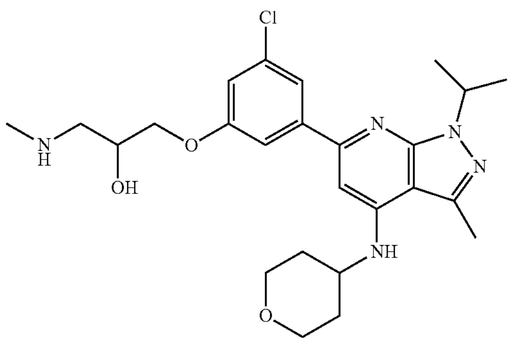 [SMILES: CNCC(O)COc1cc(Cl)cc(-c2cc(NC3CCOCC3)c3c(C)nn(C(C)C)c3n2)c1] | 488.3 |
| 23-4 | 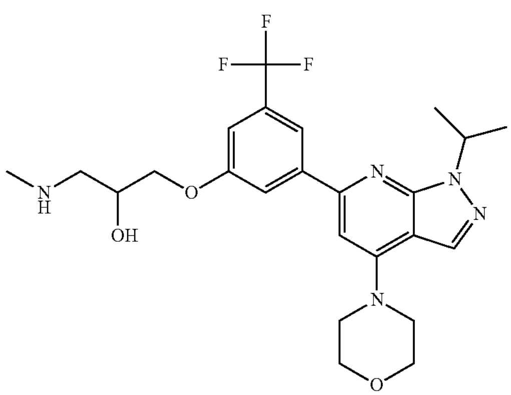 [SMILES: CNCC(O)COc1cc(-c2cc(N3CCOCC3)c3cnn(C(C)C)c3n2)cc(C(F)(F)F)c1] | 494.3 |
| 24-4 | 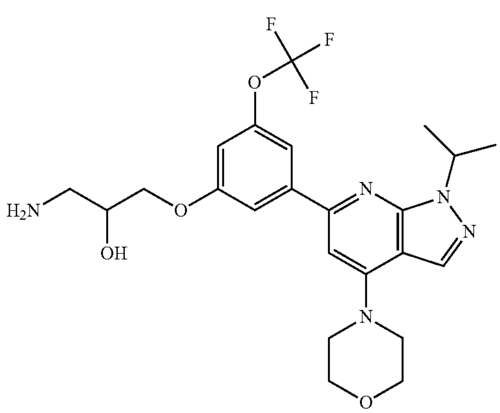 [SMILES: CC(C)n1ncc2c(N3CCOCC3)cc(-c3cc(OCC(O)CN)cc(OC(F)(F)F)c3)nc21] | 496.2 |

TABLE 4-continued
| # | Structure | LC-MS m/z (M + H) |
|---|---|---|
| 25-4 | 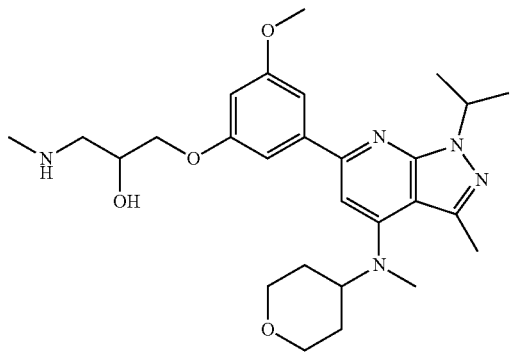 [SMILES: CNCC(O)COc1cc(OC)cc(-c2cc(N(C)C3CCOCC3)c3c(C)nn(C(C)C)c3n2)c1] | 498.3 |
| 26-4 | 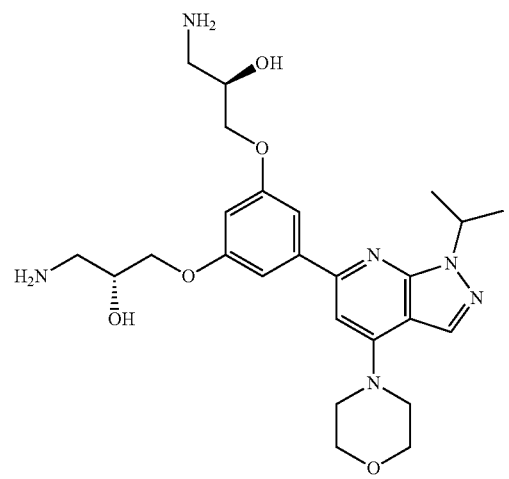 [SMILES: CC(C)n1ncc2c(N3CCOCC3)cc(-c3cc(OC[C@H](O)CN)cc(OC[C@H](O)CN)c3)nc21] | 501.4 |
| 27-4 | 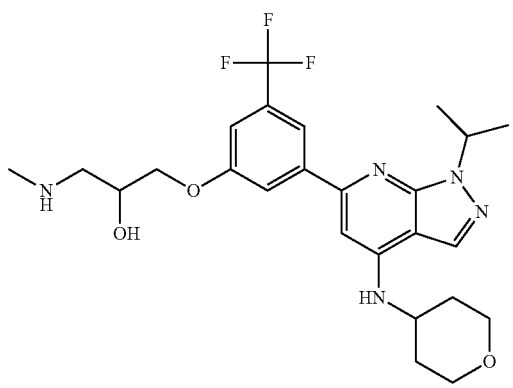 [SMILES: CNCC(O)COc1cc(-c2cc(NC3CCOCC3)c3cnn(C(C)C)c3n2)cc(C(F)(F)F)c1] | 508.4 |

TABLE 4-continued

Exemplary compounds

| # | Structure | LC-MS m/z (M + H) |
|---|---|---|
| 28-4 | 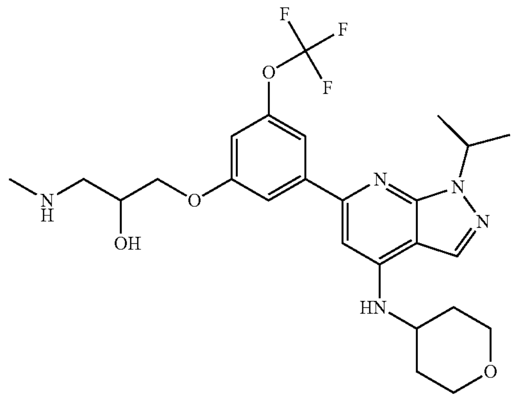 [SMILES: CNCC(O)COc1cc(OC(F)(F)F)cc(-c2cc(NC3CCOCC3)c3cnn(C(C)C)c3n2)c1] | 524.3 |
| 29-4 | 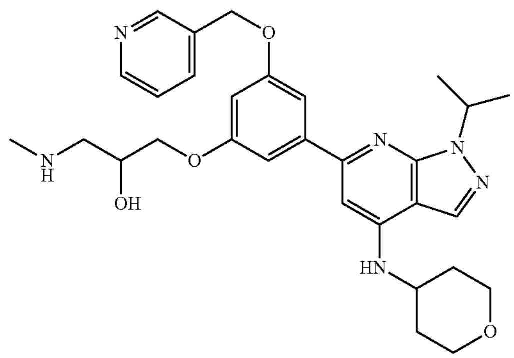 [SMILES: CNCC(O)COc1cc(OCc2cccnc2)cc(-c2cc(NC3CCOCC3)c3cnn(C(C)C)c3n2)c1] | 548.3 |

TABLE 5

Exemplary compounds

| # | Structure | LC-MS m/z (M + H) |
|---|---|---|
| 1-5 | 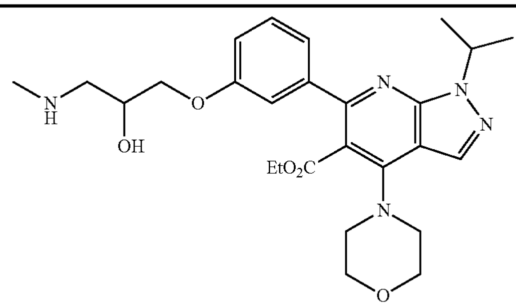 | 498.3 |
| 2-5 | 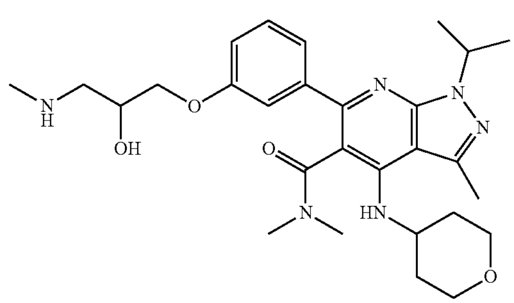 [SMILES: CNCC(O)COc1cccc(-c2nc3c(c(C)nn3C(C)C)c(NC3CCOCC3)c2C(=O)N(C)C)c1] | 525.3 |

TABLE 5-continued
Exemplary compounds
| # | Structure | LC-MS m/z (M + H) |
|---|---|---|
| 3-5 | 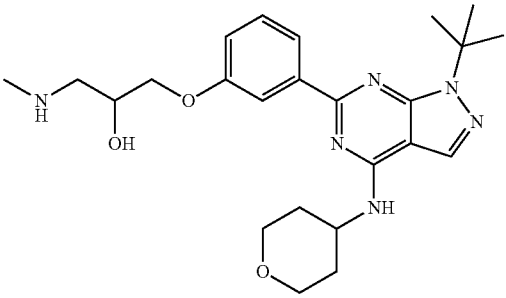 [SMILES: CNCC(O)COc1cccc(-c2nc(NC3CCOCC3)c3cnn(C(C)(C)C)c3n2)c1] | 455.4 |
| 4-5 | 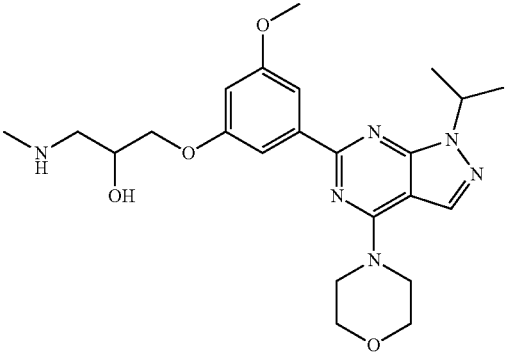 [SMILES: CNCC(O)COc1cc(OC)cc(-c2nc(N3CCOCC3)c3cnn(C(C)C)c3n2)c1] | 456.4 |
| 5-5 | 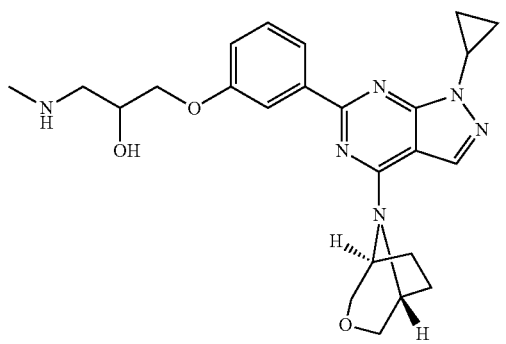 [SMILES: CNCC(O)COc1cccc(-c2nc(N3[C@@H]4CC[C@H]3COC4)c3cnn(C4CC4)c3n2)c1] | 451.2 |
| 6-5 | 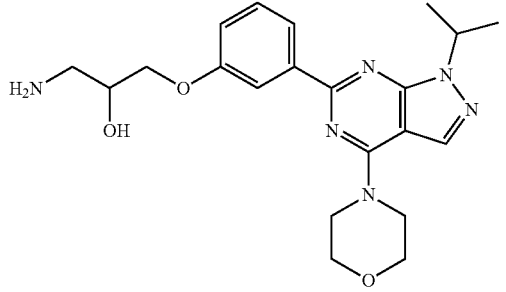 [SMILES: CC(C)n1ncc2c(N3CCOCC3)nc(-c3cccc(OCC(O)CN)c3)nc21] | 413.2 |

TABLE 5-continued

Exemplary compounds

| # | Structure | LC-MS m/z (M + H) |
|---|---|---|
| 7-5 | | 413.1 |
| 8-5 | | 427.2 |
| 9-5 | | 427.2 |
| 10-5 | | 427.2 |
| 11-5 | | 432.3 |

TABLE 5-continued

Exemplary compounds

| # | Structure | LC-MS m/z (M + H) |
|---|---|---|
| 12-5 | 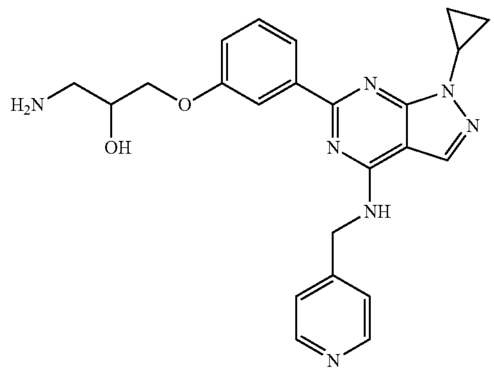 [SMILES: NCC(O)COc1cccc(-c2nc(NCc3ccncc3)c3cnn(C4CC4)c3n2)c1] | 432.2 |
| 13-5 | 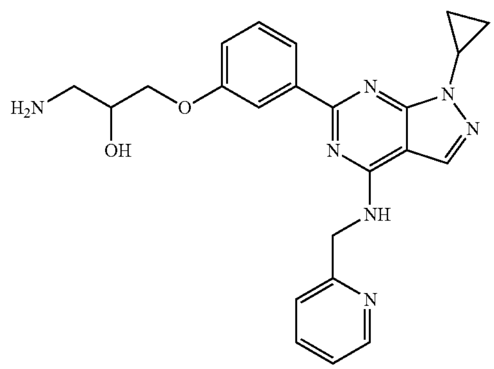 [SMILES: NCC(O)COc1cccc(-c2nc(NCc3ccccn3)c3cnn(C4CC4)c3n2)c1] | 432.2 |
| 14-5 | 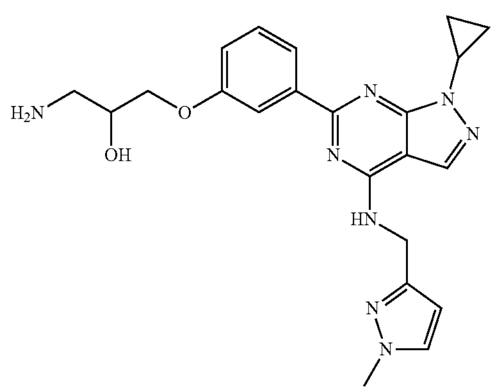 [SMILES: Cn1ccc(CNc2nc(-c3cccc(OCC(O)CN)c3)nc3c2cnn3C2CC2)n1] | 435.4 |
| 15-5 | 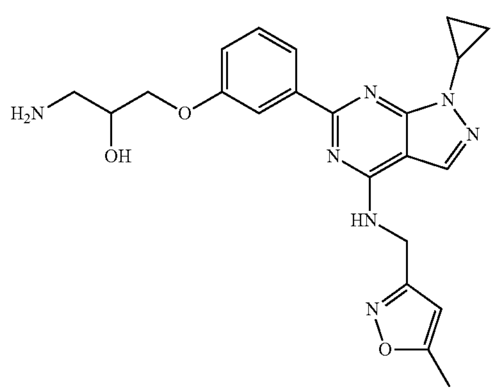 [SMILES: Cc1cc(CNc2nc(-c3cccc(OCC(O)CN)c3)nc3c2cnn3C2CC2)no1] | 436.2 |

TABLE 5-continued

Exemplary compounds

| # | Structure | LC-MS m/z (M + H) |
|---|---|---|
| 16-5 | 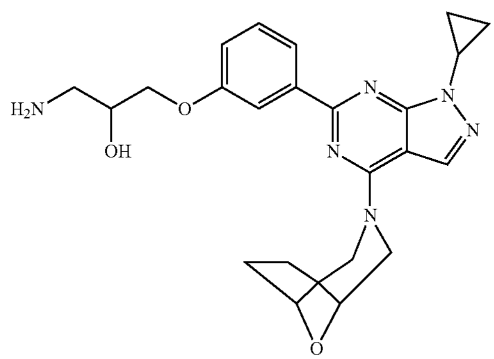 [SMILES: NCC(O)COc1cccc(-c2nc(N3CC4OC5CCC54C3)c3cnn(C4CC4)c3n2)c1] | 437.3 |
| 17-5 | 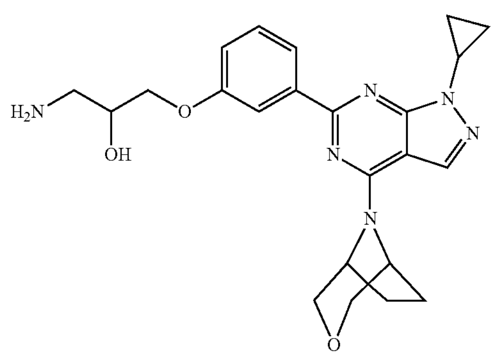 [SMILES: NCC(O)COc1cccc(-c2nc(N3C4CCC45COCC35)c3cnn(C4CC4)c3n2)c1] | 437.2 |
| 18-5 | 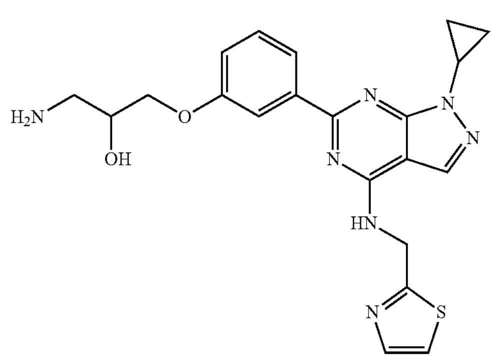 [SMILES: NCC(O)COc1cccc(-c2nc(NCc3nccs3)c3cnn(C4CC4)c3n2)c1] | 438.3 |
| 19-5 | 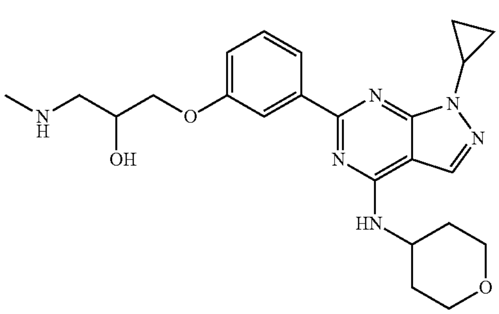 [SMILES: CNCC(O)COc1cccc(-c2nc(NC3CCOCC3)c3cnn(C4CC4)c3n2)c1] | 439.3 |

TABLE 5-continued
Exemplary compounds
| # | Structure | LC-MS m/z (M + H) |
|---|---|---|
| 20-5 | 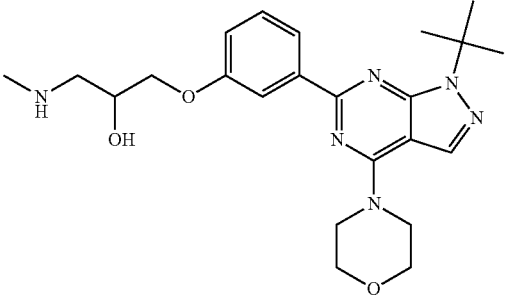 [SMILES: CNCC(O)COc1cccc(-c2nc(N3CCOCC3)c3cnn(C(C)(C)C)c3n2)c1] | 441.2 |
| 21-5 | 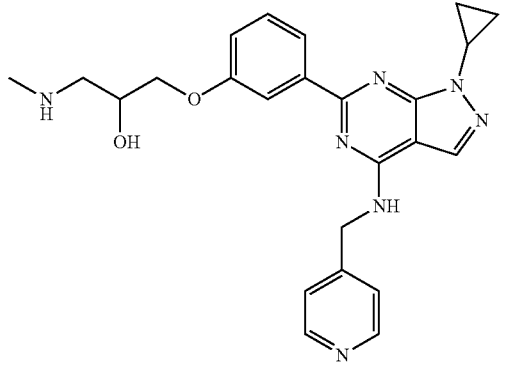 [SMILES: CNCC(O)COc1cccc(-c2nc(NCc3ccncc3)c3cnn(C4CC4)c3n2)c1] | 446.3 |
| 22-5 | 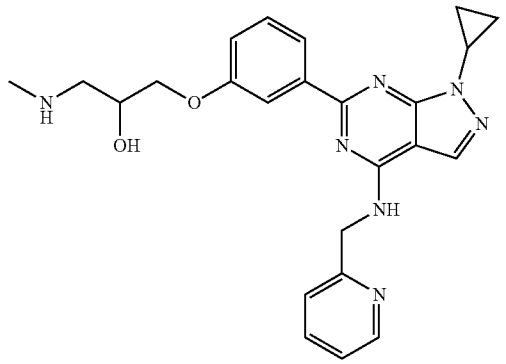 [SMILES: CNCC(O)COc1cccc(-c2nc(NCc3ccccn3)c3cnn(C4CC4)c3n2)c1] | 446.3 |
| 23-5 | 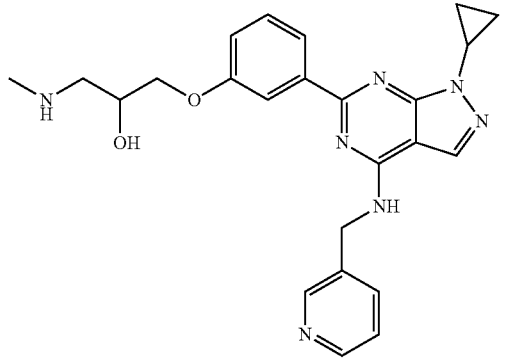 [SMILES: CNCC(O)COc1cccc(-c2nc(NCc3cccnc3)c3cnn(C4CC4)c3n2)c1] | 446.3 |

TABLE 5-continued

Exemplary compounds

| # | Structure | LC-MS m/z (M + H) |
|---|-----------|-------------------|
| 24-5 | 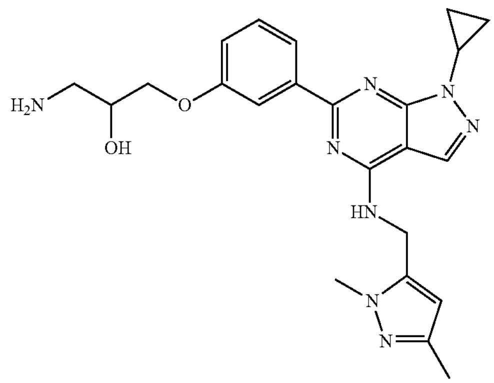 [SMILES: Cc1cc(CNc2nc(-c3cccc(OCC(O)CN)c3)nc3c2cnn3C2CC2)n(C)n1] | 449.3 |
| 25-5 | 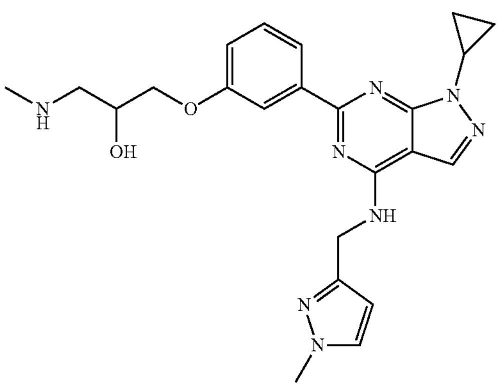 [SMILES: CNCC(O)COc1cccc(-c2nc(NCc3ccn(C)n3)c3cnn(C4CC4)c3n2)c1] | 449.3 |
| 26-5 | 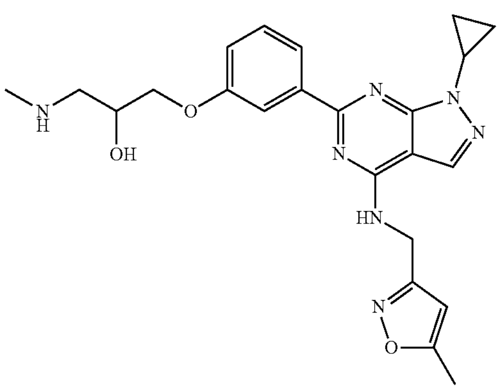 [SMILES: CNCC(O)COc1cccc(-c2nc(NCc3cc(C)on3)c3cnn(C4CC4)c3n2)c1] | 450.2 |
| 27-5 | 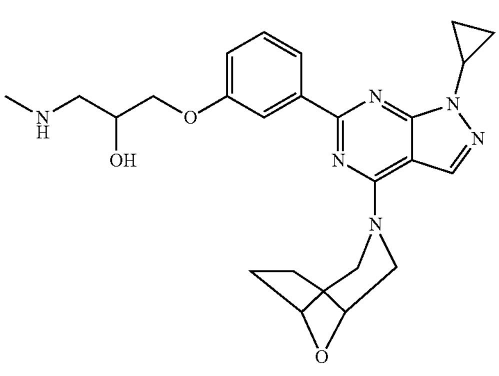 [SMILES: CNCC(O)COc1cccc(-c2nc(N3CC4OC5CCC54C3)c3cnn(C4CC4)c3n2)c1] | 451.3 |

TABLE 5-continued

Exemplary compounds

| # | Structure | LC-MS m/z (M + H) |
|---|---|---|
| 28-5 | 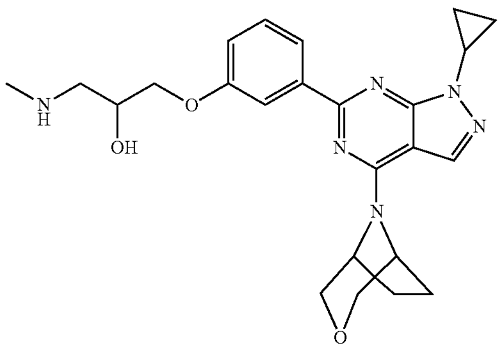 [SMILES: CNCC(O)COc1cccc(-c2nc(N3C4CCC45COCC35)c3cnn(C4CC4)c3n2)c1] | 451.2 |
| 29-5 | 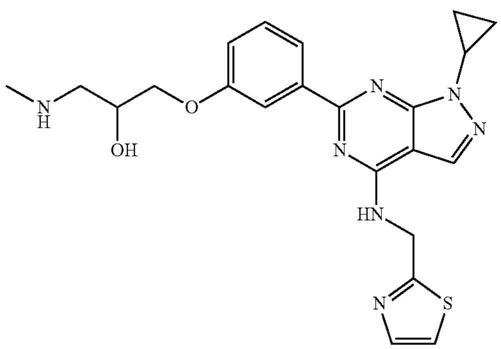 [SMILES: CNCC(O)COc1cccc(-c2nc(NCc3nccs3)c3cnn(C4CC4)c3n2)c1] | 452.3 |
| 30-5 | 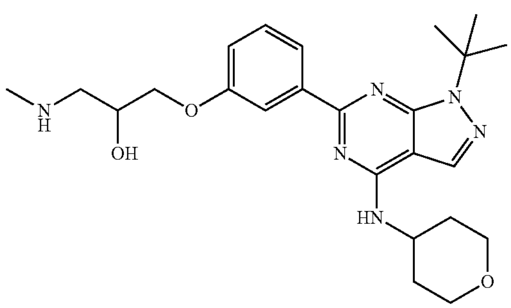 [SMILES: CNCC(O)COc1cccc(-c2nc(NC3CCOCC3)c3cnn(C(C)(C)C)c3n2)c1] | 455.4 |
| 31-5 | 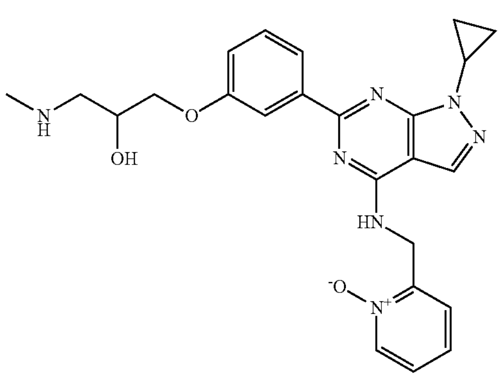 | 462.2 |

TABLE 5-continued

Exemplary compounds

| # | Structure | LC-MS m/z (M + H) |
|---|-----------|-------------------|
| 32-5 | 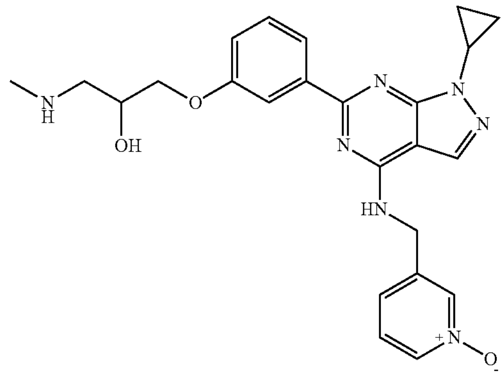 | 462.2 |
| 33-5 | 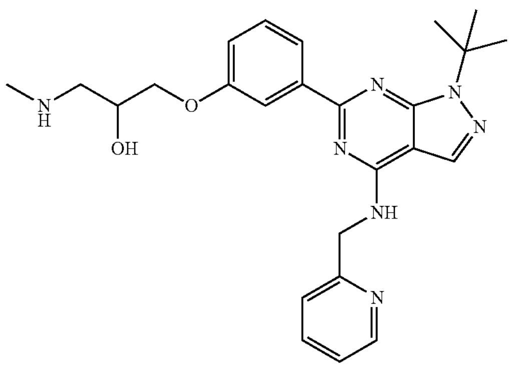 [SMILES: CNCC(O)COc1cccc(-c2nc(NCc3ccccn3)c3cnn(C(C)(C)C)c3n2)c1] | 462.3 |
| 34-5 | 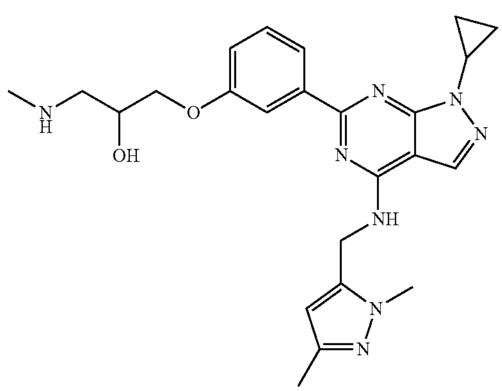 [SMILES: CNCC(O)COc1cccc(-c2nc(NCc3cc(C)nn3C)c3cnn(C4CC4)c3n2)c1] | 463.3 |
| 35-5 | 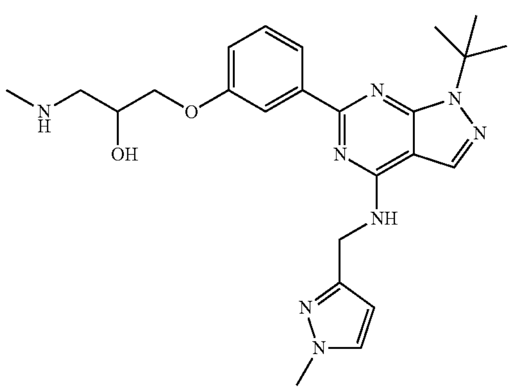 [SMILES: CNCC(O)COc1cccc(-c2nc(NCc3ccn(C)n3)c3cnn(C(C)(C)C)c3n2)c1] | 465.4 |

TABLE 5-continued

Exemplary compounds

| # | Structure | LC-MS m/z (M + H) |
|---|---|---|
| 36-5 | 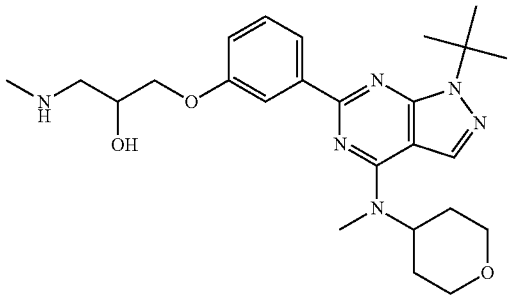 [SMILES: CNCC(O)COc1cccc(-c2nc(N(C)C3CCOCC3)c3cnn(C(C)(C)C)c3n2)c1] | 469.3 |
| 37-5 | 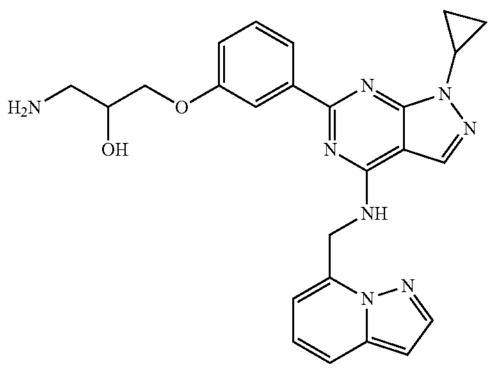 [SMILES: NCC(O)COc1cccc(-c2nc(NCc3cccc4ccnn34)c3cnn(C4CC4)c3n2)c1] | 471.1 |
| 38-5 | 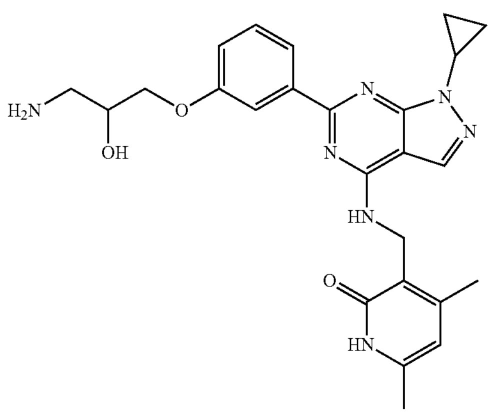 [SMILES: Cc1cc(C)c(CNc2nc(-c3cccc(OCC(O)CN)c3)nc3c2cnn3C2CC2)c(=O)[nH]1] | 476.3 |
| 39-5 | 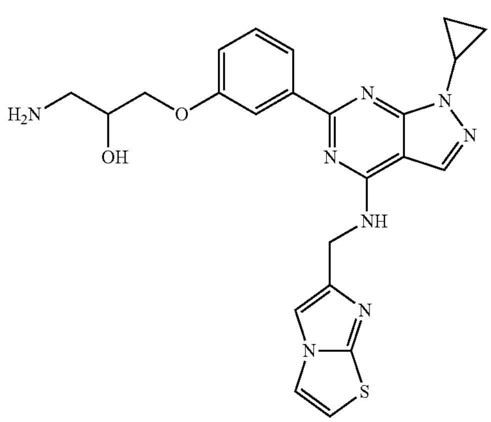 [SMILES: NCC(O)COc1cccc(-c2nc(NCc3cn4ccsc4n3)c3cnn(C4CC4)c3n2)c1] | 477.1 |

TABLE 5-continued
| # | Structure | LC-MS m/z (M + H) |
|---|---|---|
| 40-5 | 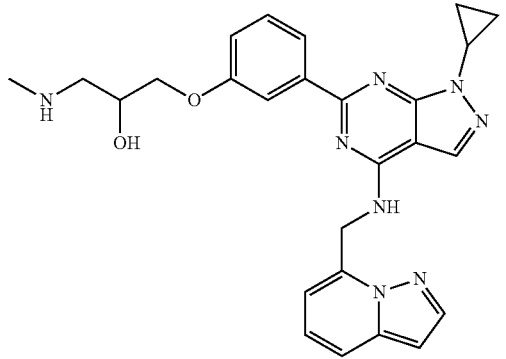 [SMILES: CNCC(O)COc1cccc(-c2nc(NCc3cccc4ccnn34)c3cnn(C4CC4)c3n2)c1] | 485.2 |
| 41-5 | 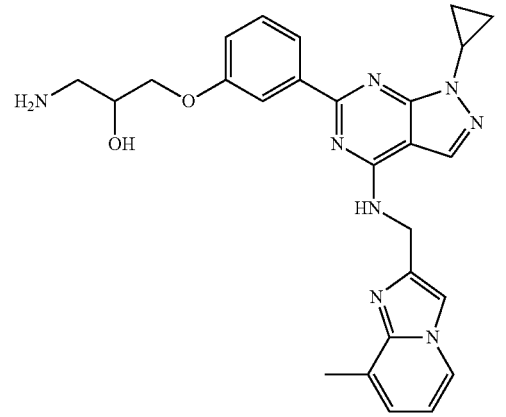 [SMILES: Cc1cccn2cc(CNc3nc(-c4cccc(OCC(O)CN)c4)nc4c3cnn4C3CC3)nc12] | 485.4 |
| 42-5 | 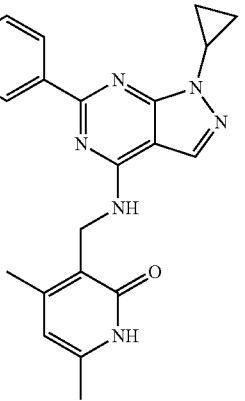 | 490.4 |

TABLE 5-continued
Exemplary compounds
| # | Structure | LC-MS m/z (M + H) |
|---|---|---|
| 43-5 | 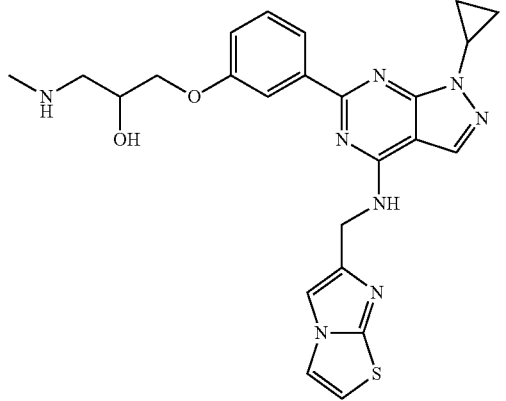 [SMILES: CNCC(O)COc1cccc(-c2nc(NCc3cn4ccsc4n3)c3cnn(C4CC4)c3n2)c1] | 491.2 |
| 44-5 | 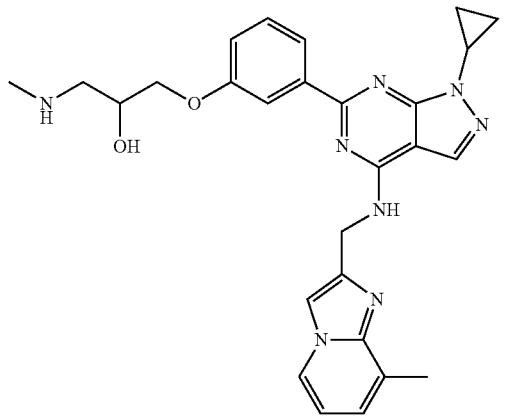 [SMILES: CNCC(O)COc1cccc(-c2nc(NCc3cn4cccc(C)c4n3)c3cnn(C4CC4)c3n2)c1] | 499.4 |
TABLE 6
Exemplary Compounds
| # | Structure | LC-MS m/z (M + H) |
|---|---|---|
| 1-6 | 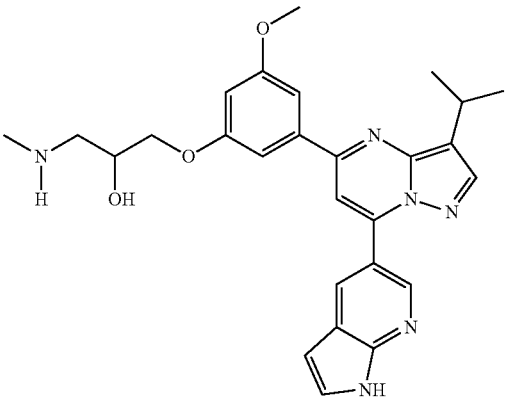 [SMILES: CNCC(O)COc1cc(OC)cc(-c2cc(-c3cnc4[nH]ccc4c3)n3ncc(C(C)C)c3n2)c1] | 487.3 |

TABLE 6-continued

Exemplary Compounds

| # | Structure | LC-MS m/z (M + H) |
|---|---|---|
| 2-6 | 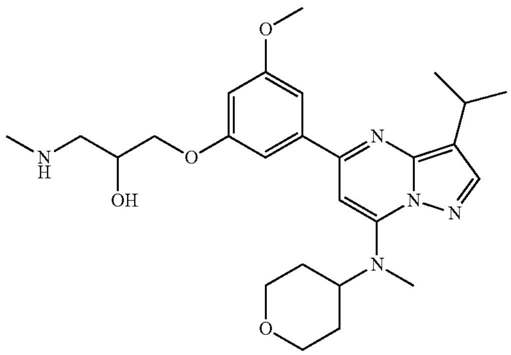 [SMILES: CNCC(O)COc1cc(OC)cc(-c2cc(N(C)C3CCOCC3)n3ncc(C(C)C)c3n2)c1] | 484.3 |
| 3-6 | 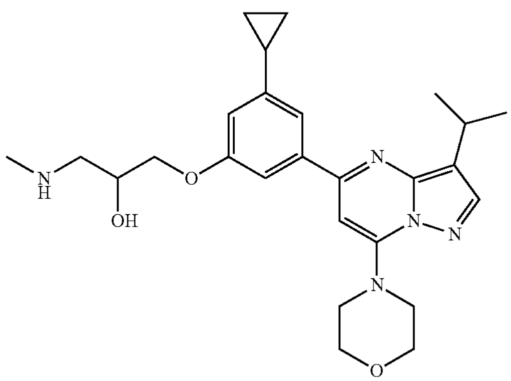 [SMILES: CNCC(O)COc1cc(-c2cc(N3CCOCC3)n3ncc(C(C)C)c3n2)cc(C2CC2)c1] | 466.3 |
| 5-6 | 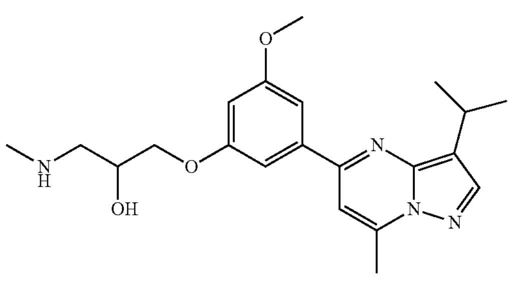 [SMILES: CNCC(O)COc1cc(OC)cc(-c2cc(C)n3ncc(C(C)C)c3n2)c1] | 385.2 |
| 6-6 | 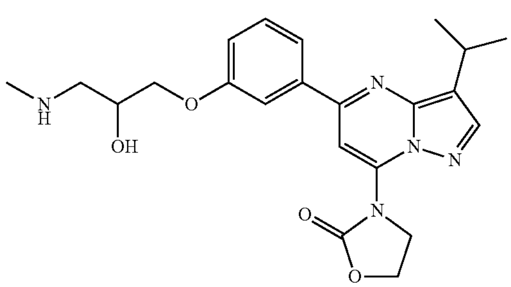 [SMILES: CNCC(O)COc1cccc(-c2cc(N3CCOC3=O)n3ncc(C(C)C)c3n2)c1] | 426.2 |

TABLE 6-continued

Exemplary Compounds

| # | Structure | LC-MS m/z (M + H) |
|---|---|---|
| 7-6 | 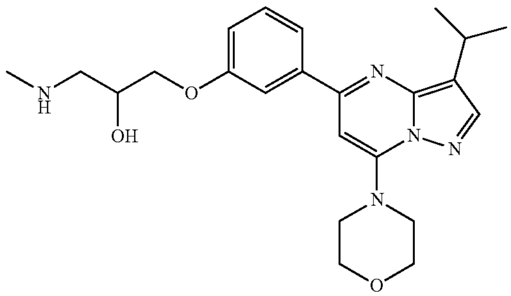 [SMILES: CNCC(O)COc1cccc(-c2cc(N3CCOCC3)n3ncc(C(C)C)c3n2)c1] | 426.3 |
| 8-6 | 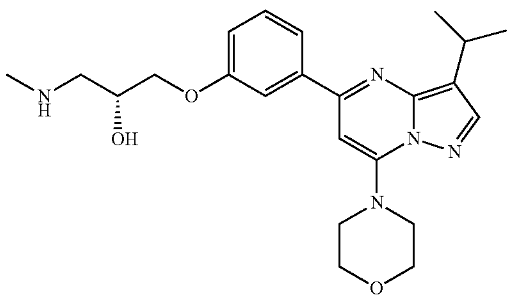 [SMILES: CNC[C@@H](O)COc1cccc(-c2cc(N3CCOCC3)n3ncc(C(C)C)c3n2)c1] | 426.2 |
| 9-6 | 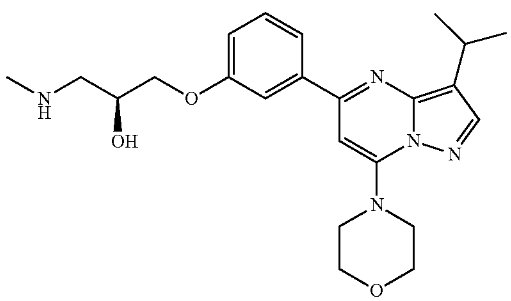 [SMILES: CNC[C@H](O)COc1cccc(-c2cc(N3CCOCC3)n3ncc(C(C)C)c3n2)c1] | 426.2 |
| 10-6 | 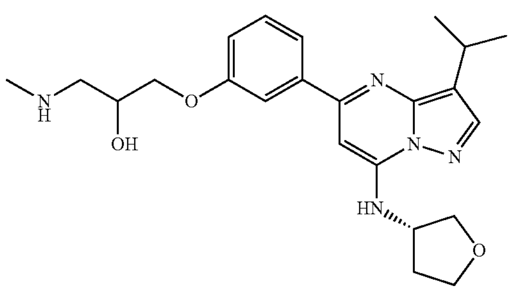 [SMILES: CNCC(O)COc1cccc(-c2cc(N[C@H]3CCOC3)n3ncc(C(C)C)c3n2)c1] | 426.3 |
| 11-6 | 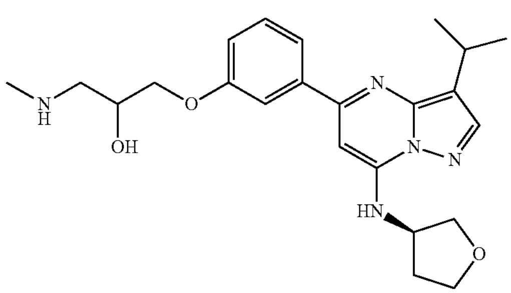 [SMILES: CNCC(O)COc1cccc(-c2cc(N[C@@H]3CCOC3)n3ncc(C(C)C)c3n2)c1] | 426.3 |

TABLE 6-continued

Exemplary Compounds

| # | Structure | LC-MS m/z (M + H) |
|---|-----------|-------------------|
| 12-6 | 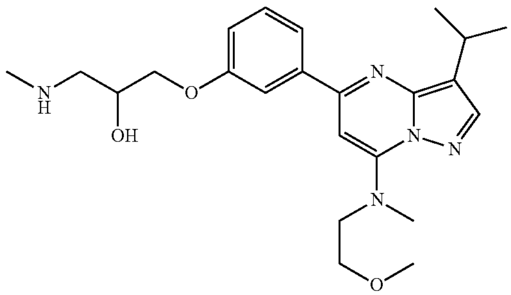 [SMILES: CNCC(O)COc1cccc(-c2cc(N(C)CCOC)n3ncc(C(C)C)c3n2)c1] | 428.3 |
| 13-6 | 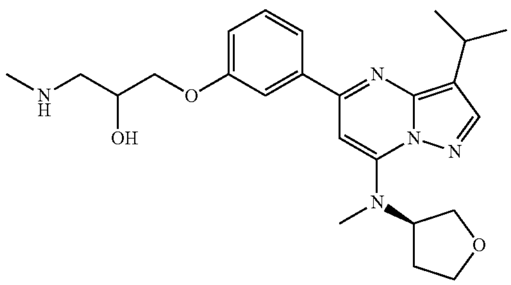 [SMILES: CNCC(O)COc1cccc(-c2cc(N(C)[C@@H]3CCOC3)n3ncc(C(C)C)c3n2)c1] | 440.3 |
| 14-6 | 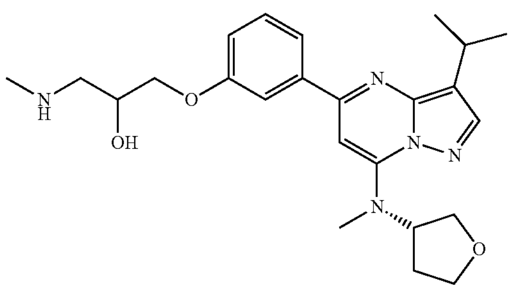 | 440.3 |
| 15-6 | 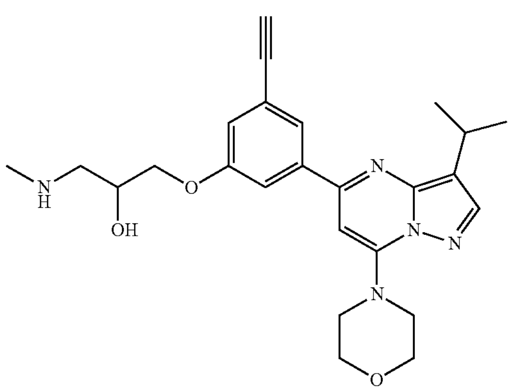 [SMILES: C#Cc1cc(OCC(O)CNC)cc(-c2cc(N3CCOCC3)n3ncc(C(C)C)c3n2)c1] | 450.3 |

TABLE 6-continued

Exemplary Compounds

| # | Structure | LC-MS m/z (M + H) |
|---|---|---|
| 16-6 | 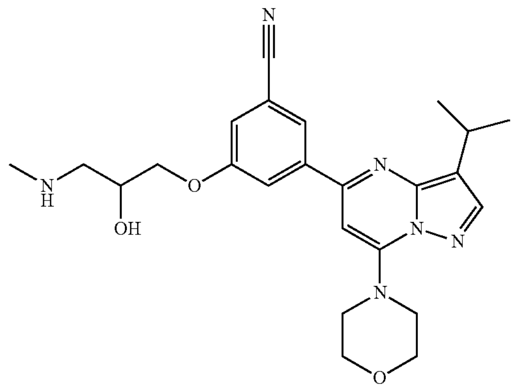 [SMILES: CNCC(O)COc1cc(C#N)cc(-c2cc(N3CCOCC3)n3ncc(C(C)C)c3n2)c1] | 451.2 |
| 17-6 | 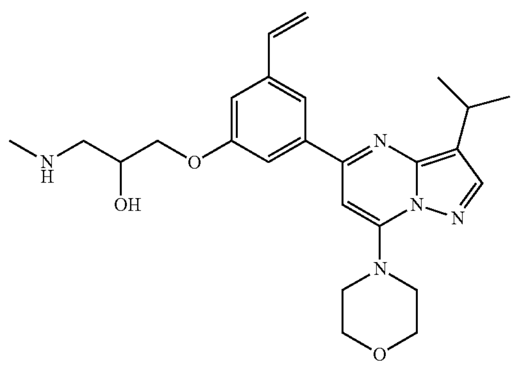 [SMILES: C=Cc1cc(OCC(O)CNC)cc(-c2cc(N3CCOCC3)n3ncc(C(C)C)c3n2)c1] | 452.3 |
| 18-6 | 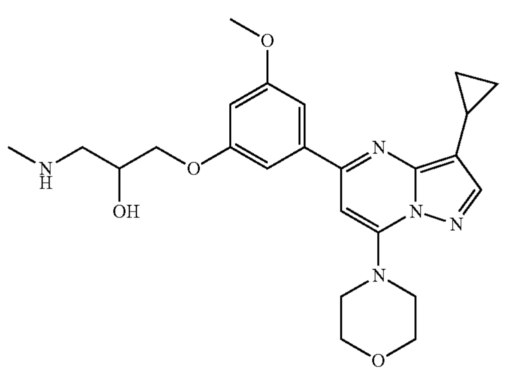 [SMILES: CNCC(O)COc1cc(OC)cc(-c2cc(N3CCOCC3)n3ncc(C4CC4)c3n2)c1] | 454.2 |
| 19-6 | 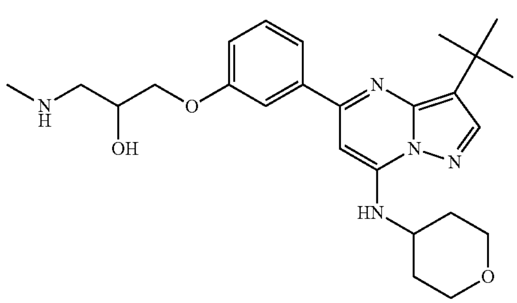 [SMILES: CNCC(O)COc1cccc(-c2cc(NC3CCOCC3)n3ncc(C(C)(C)C)c3n2)c1] | 454.3 |

TABLE 6-continued
Exemplary Compounds
| # | Structure | LC-MS m/z (M + H) |
|---|---|---|
| 20-6 | 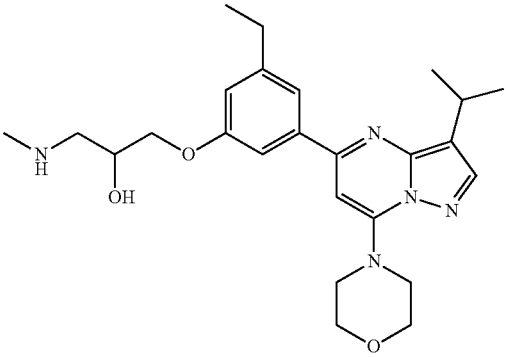 [SMILES: CCc1cc(OCC(O)CNC)cc(-c2cc(N3CCOCC3)n3ncc(C(C)C)c3n2)c1] | 454.3 |
| 21-6 | 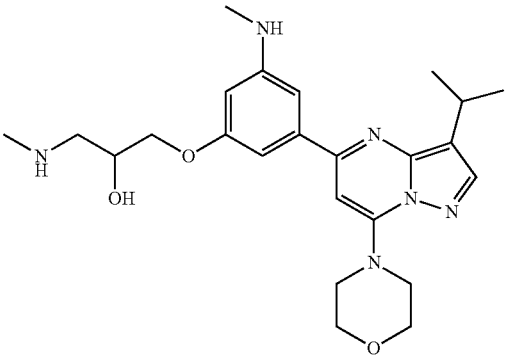 [SMILES: CNCC(O)COc1cc(NC)cc(-c2cc(N3CCOCC3)n3ncc(C(C)C)c3n2)c1] | 455.3 |
| 22-6 | 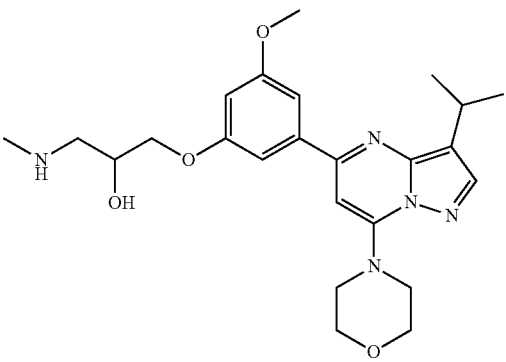 [SMILES: CNCC(O)COc1cc(OC)cc(-c2cc(N3CCOCC3)n3ncc(C(C)C)c3n2)c1] | 456.2 |
| 23-6 | 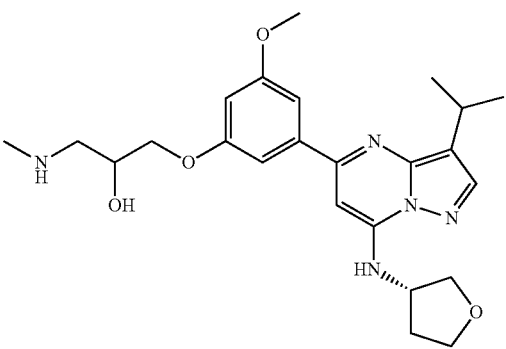 [SMILES: CNCC(O)COc1cc(OC)cc(-c2cc(N[C@H]3CCOC3)n3ncc(C(C)C)c3n2)c1] | 456.3 |

TABLE 6-continued

Exemplary Compounds

| # | Structure | LC-MS m/z (M + H) |
|---|---|---|
| 24-6 | 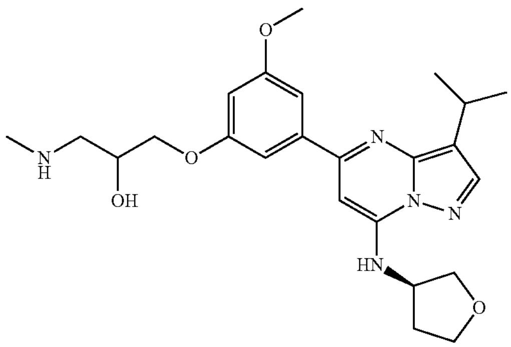 [SMILES: CNCC(O)COc1cc(OC)cc(-c2cc(N[C@@H]3CCOC3)n3ncc(C(C)C)c3n2)c1] | 456.3 |
| 25-6 | 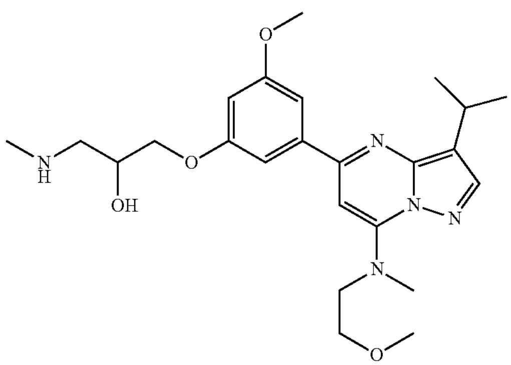 [SMILES: CNCC(O)COc1cc(OC)cc(-c2cc(N(C)CCOC)n3ncc(C(C)C)c3n2)c1] | 458.3 |
| 26-6 | 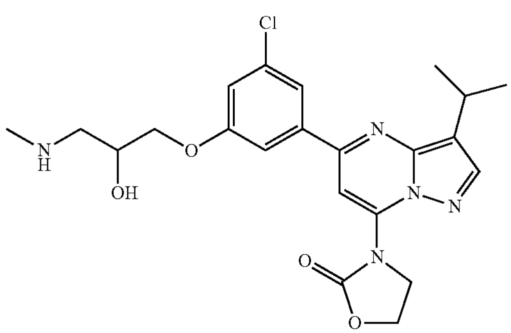 [SMILES: CNCC(O)COc1cc(Cl)cc(-c2cc(N3CCOC3=O)n3ncc(C(C)C)c3n2)c1] | 460.1 |
| 27-6 | 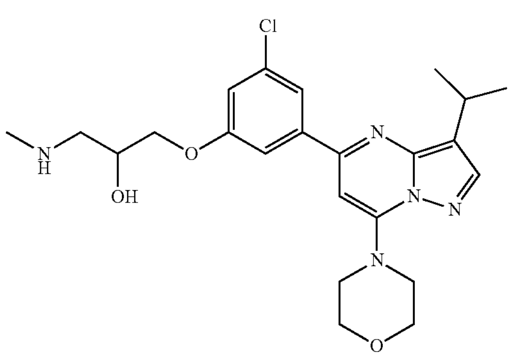 [SMILES: CNCC(O)COc1cc(Cl)cc(-c2cc(N3CCOCC3)n3ncc(C(C)C)c3n2)c1] | 460.2 |

TABLE 6-continued

Exemplary Compounds

| # | Structure | LC-MS m/z (M + H) |
|---|-----------|-------------------|
| 28-6 | 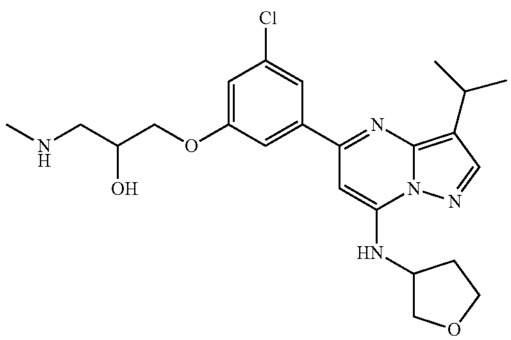 [SMILES: CNCC(O)COc1cc(Cl)cc(-c2cc(NC3CCOC3)n3ncc(C(C)C)c3n2)c1] | 460.2 |
| 29-6 | 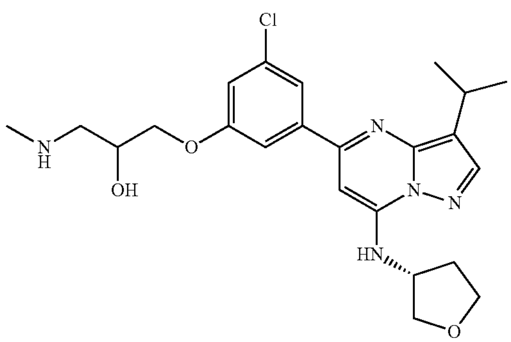 [SMILES: CNCC(O)COc1cc(Cl)cc(-c2cc(N[C@@H]3CCOC3)n3ncc(C(C)C)c3n2)c1] | 460.2 |
| 30-6 | 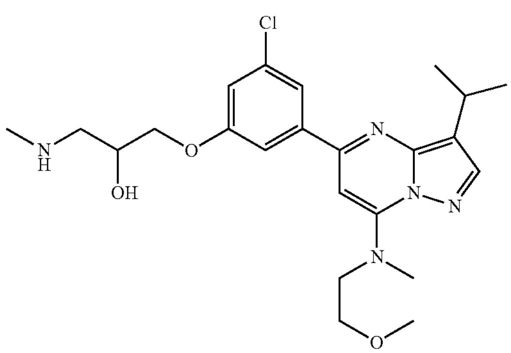 [SMILES: CNCC(O)COc1cc(Cl)cc(-c2cc(N(C)CCOC)n3ncc(C(C)C)c3n2)c1] | 462.2 |
| 31-6 | 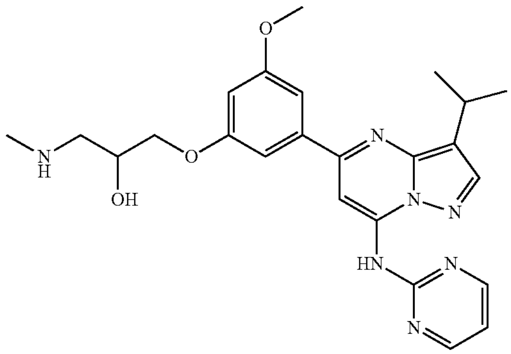 [SMILES: CNCC(O)COc1cc(OC)cc(-c2cc(Nc3ncccn3)n3ncc(C(C)C)c3n2)c1] | 464.2 |

TABLE 6-continued

Exemplary Compounds

| # | Structure | LC-MS m/z (M + H) |
|---|---|---|
| 32-6 | 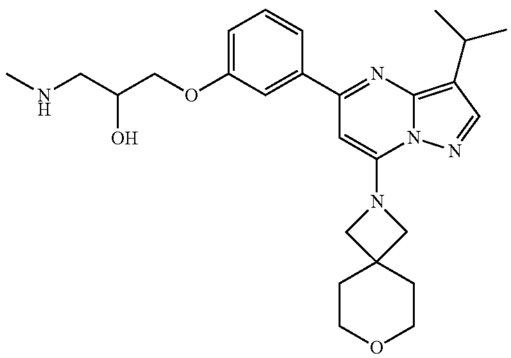 [SMILES: CNCC(O)COc1cccc(-c2cc(N3CC4(CCOCC4)C3)n3ncc(C(C)C)c3n2)c1] | 466.3 |
| 33-6 | 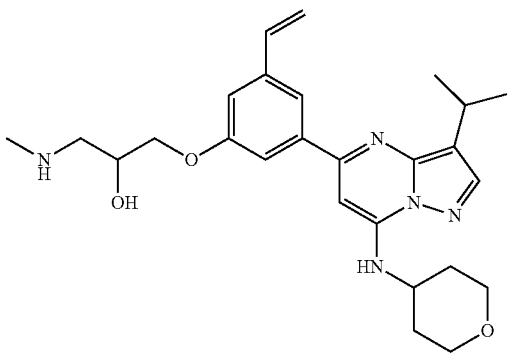 [SMILES: C=Cc1cc(OCC(O)CNC)cc(-c2cc(NC3CCOCC3)n3ncc(C(C)C)c3n2)c1] | 466.3 |
| 34-6 | 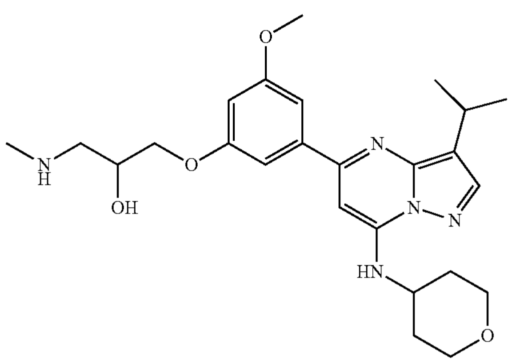 [SMILES: CNCC(O)COc1cc(OC)cc(-c2cc(NC3CCOCC3)n3ncc(C(C)C)c3n2)c1] | 470.3 |
| 35-6 | 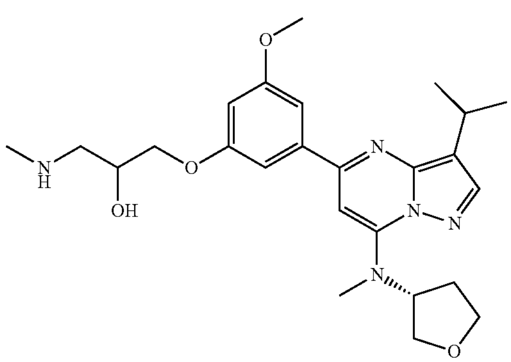 [SMILES: CNCC(O)COc1cc(OC)cc(-c2cc(N(C)[C@@H]3CCOC3)n3ncc(C(C)C)c3n2)c1] | 470.3 |

TABLE 6-continued

Exemplary Compounds

| # | Structure | LC-MS m/z (M + H) |
|---|---|---|
| 36-6 | 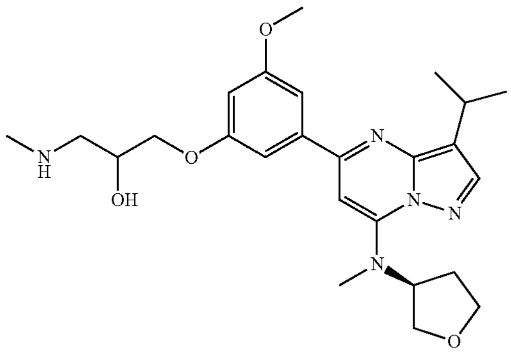 [SMILES: CNCC(O)COc1cc(OC)cc(-c2cc(N(C)[C@H]3CCOC3)n3ncc(C(C)C)c3n2)c1] | 470.3 |
| 37-6 | 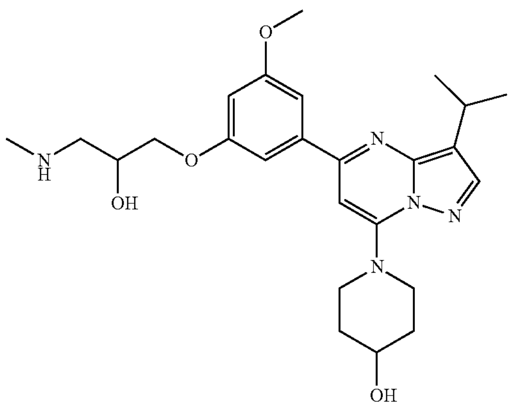 [SMILES: CNCC(O)COc1cc(OC)cc(-c2cc(N3CCC(O)CC3)n3ncc(C(C)C)c3n2)c1] | 470.3 |
| 38-6 | 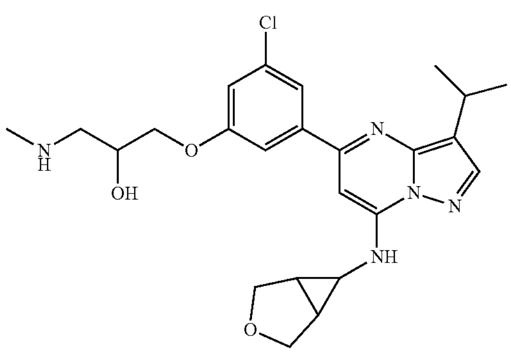 [SMILES: CNCC(O)COc1cc(Cl)cc(-c2cc(NC3C4COCC43)n3ncc(C(C)C)c3n2)c1] | 472.1 |
| 39-6 | 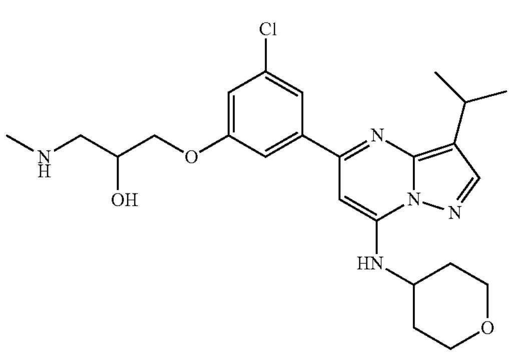 [SMILES: CNCC(O)COc1cc(Cl)cc(-c2cc(NC3CCOCC3)n3ncc(C(C)C)c3n2)c1] | 474.2 |

TABLE 6-continued
Exemplary Compounds
| # | Structure | LC-MS m/z (M + H) |
|---|---|---|
| 40-6 | 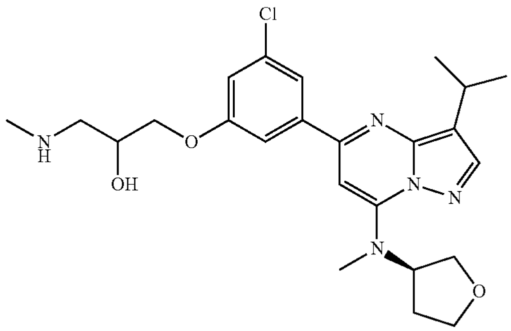 [SMILES: CNCC(O)COc1cc(Cl)cc(-c2cc(N(C)[C@@H]3CCOC3)n3ncc(C(C)C)c3n2)c1] | 474.2 |
| 41-6 | 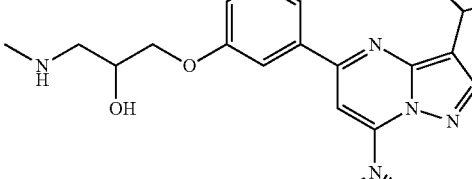 | 474.2 |
| 42-6 | 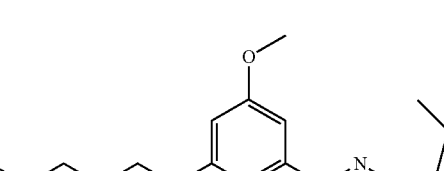 | 482.3 |
| 43-6 | 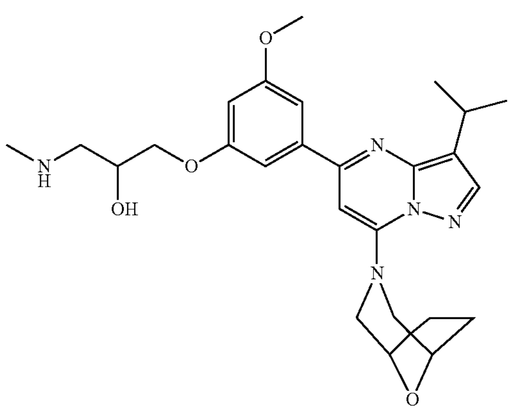 [SMILES: CNCC(O)COc1cc(OC)cc(-c2cc(N3CC4OC5CCC54C3)n3ncc(C(C)C)c3n2)c1] | 482.3 |

TABLE 6-continued
Exemplary Compounds
| # | Structure | LC-MS m/z (M + H) |
|---|---|---|
| 44-6 | 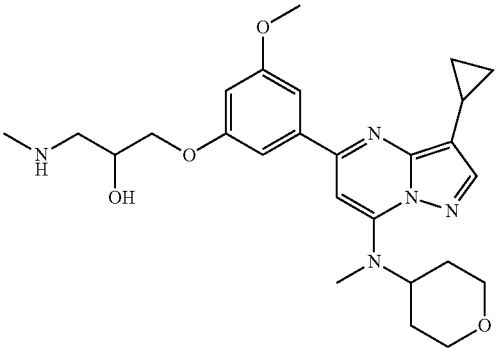 [SMILES: CNCC(O)COc1cc(OC)cc(-c2cc(N(C)C3CCOCC3)n3ncc(C4CC4)c3n2)c1] | 482.3 |
| 45-6 | 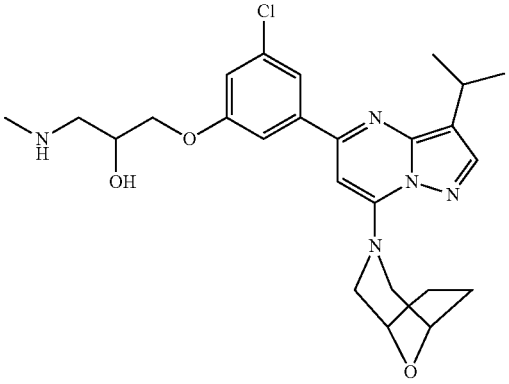 [SMILES: CNCC(O)COc1cc(Cl)cc(-c2cc(N3CC4OC5CCC54C3)n3ncc(C(C)C)c3n2)c1] | 486.3 |
| 46-6 | 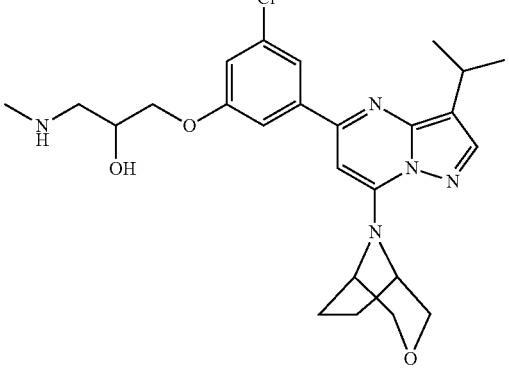 | 486.3 |
| 47-6 | 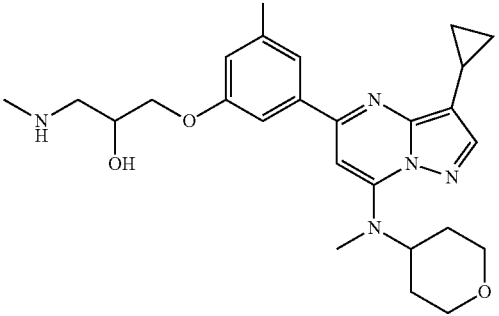 | 486.2 |

TABLE 6-continued
Exemplary Compounds
| # | Structure | LC-MS m/z (M + H) |
|---|---|---|
| 48-6 | 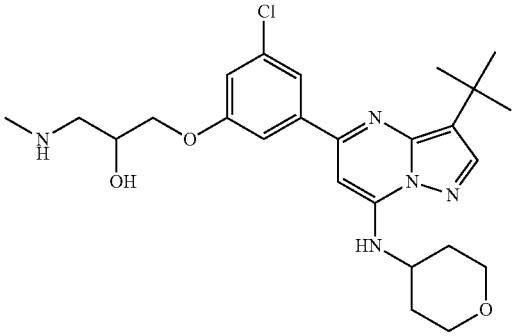 [SMILES: CNCC(O)COc1cc(Cl)cc(-c2cc(NC3CCOCC3)n3ncc(C(C)(C)C)c3n2)c1] | 488.3 |
| 49-6 | 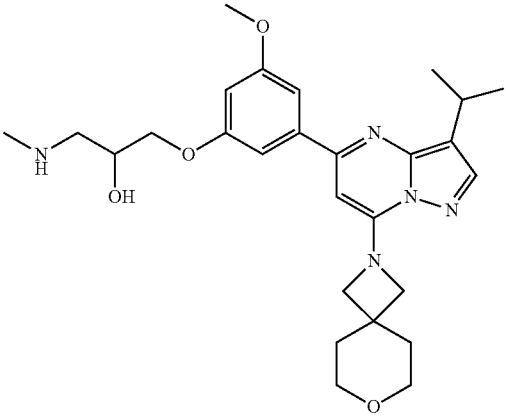 [SMILES: CNCC(O)COc1cc(OC)cc(-c2cc(N3CC4(CCOCC4)C3)n3ncc(C(C)C)c3n2)c1] | 496.3 |
| 50-6 | 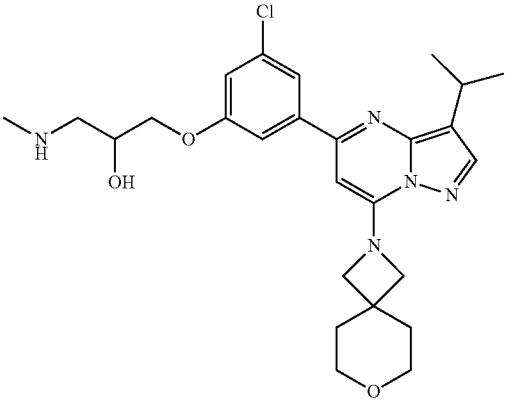 [SMILES: CNCC(O)COc1cc(Cl)cc(-c2cc(N3CC4(CCOCC4)C3)n3ncc(C(C)C)c3n2)c1] | 500.3 |
| 51-6 | 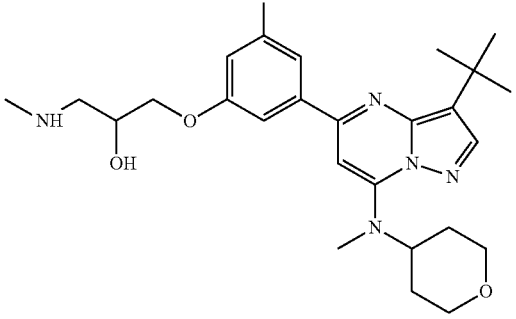 | 502.2 |

TABLE 6-continued

| # | Exemplary Compounds Structure | LC-MS m/z (M + H) |
|---|---|---|
| 52-6 | | 504.2 |
| 53-6 | | 508.2 |
| 54-6 | | 545.3 |

TABLE 7
Exemplary Compounds
| Structure | LC-MS m/z (M + H) |
|---|---|
| 1-7 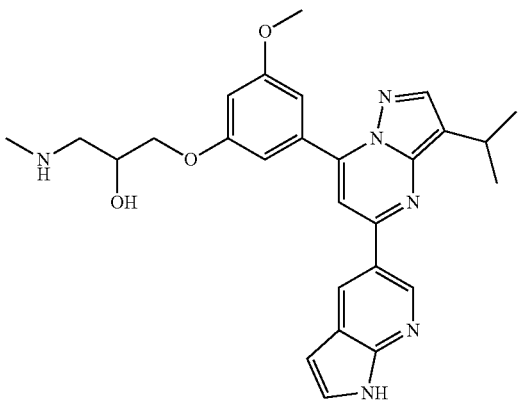 [SMILES: CNCC(O)COc1cc(OC)cc(-c2cc(-c3cnc4[nH]ccc4c3)nc3c(C(C)C)cnn23)c1] | 487.3 |
| 2-7 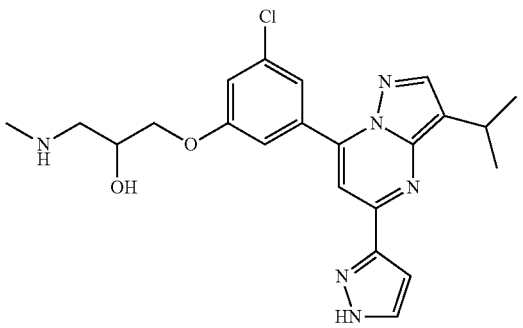 [SMILES: CNCC(O)COc1cc(Cl)cc(-c2cc(-c3cc[nH]n3)nc3c(C(C)C)cnn23)c1] | 441.2 |
| 3-7 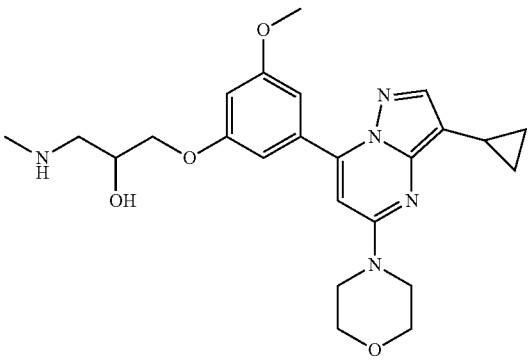 [SMILES: CNCC(O)COc1cc(OC)cc(-c2cc(N3CCOCC3)nc3c(C4CC4)cnn23)c1] | 454.2 |
| 4-7 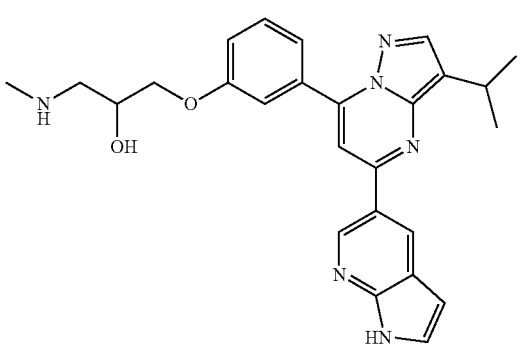 [SMILES: CNCC(O)COc1cccc(-c2cc(-c3cnc4[nH]ccc4c3)nc3c(C(C)C)cnn23)c1] | 457.2 |

In certain embodiments, a provided compound inhibits CARM1. In certain embodiments, a provided compound inhibits wild-type CARM1. In certain embodiments, a provided compound inhibits a mutant CARM1. In certain embodiments, a provided compound inhibits CARM1, e.g., as measured in an assay described herein. In certain embodiments, the CARM1 is from a human. In certain embodiments, a provided compound inhibits CARM1 at an $IC_{50}$ less than or equal to 10 µM. In certain embodiments, a provided compound inhibits CARM1 at an $IC_{50}$ less than or equal to 1 µM. In certain embodiments, a provided compound inhibits CARM1 at an $IC_{50}$ less than or equal to 0.1 µM. In certain embodiments, a provided compound inhibits CARM1 in a cell at an $EC_{50}$ less than or equal to 10 µM. In certain embodiments, a provided compound inhibits CARM1 in a cell at an $EC_{50}$ less than or equal to 1 µM. In certain embodiments, a provided compound inhibits CARM1 in a cell at an $EC_{50}$ less than or equal to 0.1 µM. In certain embodiments, a provided compound inhibits cell proliferation at an $EC_{50}$ less than or equal to 10 µM. In certain embodiments, a provided compound inhibits cell proliferation at an $EC_{50}$ less than or equal to 1 µM. In certain embodiments, a provided compound inhibits cell proliferation at an $EC_{50}$ less than or equal to 0.1 µM. In some embodiments, a provided compound is selective for CARM1 over other methyltransferases. In certain embodiments, a provided compound is at least about 10-fold selective, at least about 20-fold selective, at least about 30-fold selective, at least about 40-fold selective, at least about 50-fold selective, at least about 60-fold selective, at least about 70-fold selective, at least about 80-fold selective, at least about 90-fold selective, or at least about 100-fold selective for PRMT1 relative to one or more other methyltransferases.

It will be understood by one of ordinary skill in the art that the CARM1 can be wild-type CARM1, or any mutant or variant of CARM1.

The present disclosure provides pharmaceutical compositions comprising a compound described herein, e.g., a compound of Formula (I), or a pharmaceutically acceptable salt thereof, as described herein, and optionally a pharmaceutically acceptable excipient. It will be understood by one of ordinary skill in the art that the compounds described herein, or salts thereof, may be present in various forms, such as amorphous, hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting CARM1. In certain embodiments, the effective amount is an amount effective for treating a CARM1-mediated disorder. In certain embodiments, the effective amount is a prophylactically effective amount. In certain embodiments, the effective amount is an amount effective to prevent a CARM1-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single or multidose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one half or one third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cationexchange resins, calcium carbonate, silicates, sodium carbonate, crosslinked poly(vinylpyrrolidone) (crospovidone), sodium carboxymethyl starch (sodium starch glycolate), carboxymethyl cellulose, cross linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinylpyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinylpyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, betacarotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an antioxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogenfree water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a Bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In certain embodiments, the additional therapeutically active agent is a compound of Formula (I). In certain embodiments, the additional therapeutically active agent is not a compound of Formula (I). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of CARM1. In some embodiments, methods of treating CARM1-mediated disorder in a subject are provided which comprise administering an effective amount of a compound described herein (e.g., a compound of Formula (I), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a CARM1-mediated disorder. In certain embodiments, the subject is susceptible to a CARM1-mediated disorder.

As used herein, the term "CARM1-mediated disorder" means any disease, disorder, or other pathological condition in which CARM1 is known to play a role. Accordingly, in some embodiments, the present disclosure relates to treating or lessening the severity of one or more diseases in which CARM1 is known to play a role.

In some embodiments, the present disclosure provides a method of inhibiting CARM1 comprising contacting CARM1 with an effective amount of a compound described herein, e.g., a compound of Formula (I), or a pharmaceutically acceptable salt thereof. The CARM1 may be purified or crude, and may be present in a cell, tissue, or subject. Thus, such methods encompass both inhibition of in vitro and in vivo CARM1 activity. In certain embodiments, the method is an in vitro method, e.g., such as an assay method. It will be understood by one of ordinary skill in the art that inhibition of CARM1 does not necessarily require that all of the CARM1 be occupied by an inhibitor at once. Exemplary levels of inhibition of CARM1 include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting CARM1 activity in a subject in need thereof comprising administering to the subject an effective amount of a compound described herein (e.g., a compound of Formula (I), or a pharmaceutically acceptable salt thereof, or a pharmaceutical composition thereof.

In certain embodiments, provided is a method of modulating gene expression or activity in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, provided is a method of modulating transcription in a cell which comprises contacting a cell with an effective amount of a compound of Formula (I), or a pharmaceutically acceptable salt thereof. In certain embodiments, the cell in culture in vitro. In certain embodiments, the cell is in an animal, e.g., a human. In certain embodiments, the cell is in a subject in need of treatment.

In certain embodiments, a method is provided of selecting a therapy for a subject having a disease associated with CARM1-mediated disorder or mutation comprising the steps of determining the presence of CARM1-mediated disorder or gene mutation in the CARM1 gene or and selecting, based on the presence of CARM1-mediated disorder a gene mutation in the CARM1 gene a therapy that includes the administration of a provided compound. In certain embodiments, the disease is cancer.

In certain embodiments, a method of treatment is provided for a subject in need thereof comprising the steps of determining the presence of CARM1-mediated disorder or a gene mutation in the CARM1 gene and treating the subject in need thereof, based on the presence of a CARM1-mediated disorder or gene mutation in the CARM1 gene with a therapy that includes the administration of a provided compound. In certain embodiments, the subject is a cancer patient.

In some embodiments, a compound provided herein is useful in treating a proliferative disorder, such as cancer. For example, while not being bound to any particular mechanism, protein arginine methylation by CARM1 is a modification that has been implicated in signal transduction, gene transcription, DNA repair and mRNA splicing, among others; and overexpression of CARM1 within these pathways is often associated with various cancers. Thus, compounds which inhibit the action of PRMTs, and specifically CARM1, as provided herein, are effective in the treatment of cancer.

In some embodiments, compounds provided herein are effective in treating cancer through the inhibition of CARM1. For example, CARM1 levels have been shown to be elevated in castration-resistant prostate cancer (CRPC), as well as in aggressive breast tumors (Hong et al., *Cancer* 2004 101, 83-89; El Messaoudi et al., *Proc. Natl. Acad. Sci. U.S.A.* 2006, 103, 13351-13356; Majumder et al., *Prostate* 2006 66, 1292-1301). Thus, in some embodiments, inhibitors of CARM1, as described herein, are useful in treating cancers associated with aberrant CARM1 activity, e.g., CARM1 overexpression or aberrant protein methylation. CARM1 has also been shown to affect ERα-dependent breast cancer cell differentiation and proliferation (Al-Dhaheri et al., *Cancer Res.* 2011 71, 2118-2128), thus in some aspects CARM1 inhibitors, as described herein, are useful in treating ERα-dependent breast cancer by inhibiting cell differentiation and proliferation. In another example, CARM1 has been shown to be recruited to the promoter of E2F1 (which encodes a cell cycle regulator) as a transcriptional co-activator (Frietze et al., *Cancer Res.* 2008 68, 301-306). Thus, CARM1-mediated upregulation of E2F1 expression may contribute to cancer progression and chemoresistance as increased abundance of E2F1 triggers invasion and metastasis by activating growth receptor signaling pathways, which in turn promote an antiapoptotic tumor environment (Engelmann and Pützer, *Cancer Res* 2012 72; 571). Accordingly, in some embodiments, the inhibition of CARM1, e.g., by compounds provided herein, is useful in treating cancers associated with E2F1 upregulation. Thus, without being bound by any particular mechanism, the inhibition of CARM1, e.g., by compounds described herein, is beneficial in the treatment of cancer. CARM1 overexpression has also been demonstrated to be elevated in 75% of colorectal cancers (Kim et al., BMC Cancer, 10, 197). It has been additionally been determined that depletion of CARM1 in WNT/β-catenin dysregulated colorectal cancer suppressed anchorage independent growth (Ou et al., Mol. Cancer. Res., 2011 9, 660-670). This, in some embodiments, the inhibition of CARM1, e.g. by compounds provided herein, is useful in colorectal cancer associated with elevated CARM1 expression or dysregulated WNT/β-catenin signaling.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/ leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

CARM1 is also the most abundant PRMT expressed in skeletal muscle cells, and has been found to selectively control the pathways modulating glycogen metabolism, and associated AMPK (AMP-activated protein kinase) and p38 MAPK (mitogen-activated protein kinase) expression. See, e.g., Wang et al., Biochem (2012) 444:323-331. Thus, in some embodiments, inhibitors of CARM1, as described herein, are useful in treating metabolic disorders, e.g., for example skeletal muscle metabolic disorders, e.g., glycogen and glucose metabolic disorders. Exemplary skeletal muscle metabolic disorders include, but are not limited to, Acid Maltase Deficiency (Glycogenosis type 2; Pompe disease), Debrancher deficiency (Glycogenosis type 3), Phosphorylase deficiency (McArdle's; GSD 5), X-linked syndrome (GSD9D), Autosomal recessive syndrome (GSD9B), Tarui's disease (Glycogen storage disease VII; GSD 7), Phosphoglycerate Mutase deficiency (Glycogen storage disease X; GSDX; GSD 10), Lactate dehydrogenase A deficiency (GSD 11), Branching enzyme deficiency (GSD 4), Aldolase A (muscle) deficiency, β-Enolase deficiency, Triosephosphate isomerase (TIM) deficiency, Lafora's disease (Progressive myoclonic epilepsy 2), Glycogen storage disease (Muscle, Type 0, Phosphoglucomutase 1 Deficiency (GSD 14)), and Glycogenin Deficiency (GSD 15).

Scheme 1 shows a general synthesis route to compounds of Formula I-(i) wherein $R^{3'}$ is the same as $R^3$ as defined above or is a suitable precursor that may be converted to $R^3$. This method is based on standard palladium catalyzed coupling reactions of heteroaryl chloride intermediates of general Formula XI-(i) with appropriate intermediates. For example, in certain embodiments when L is a bond, and the heterocycle is directly attached $R^3$ by a carbon-carbon bond, standard Suzuki coupling of XI-(i) with boronic acids or ester intermediates $R^{3'}B(OH)_2$ may be implemented in the first step. The Suzuki coupling reaction of these intermediates is typically conducted in the presence of a palladium catalyst (e.g. $PdCl_2(dppf)$) and a base (e.g. potassium carbonate) in an organic solvent (e.g. toluene) at elevated temperature. In a second optional set of steps the $R^{3'}$ group as well as other groups in the molecule may be converted to the defined final substituents in Formula I-(i). In a final deprotection step the N-Boc protecting is removed by for example using an acid (e.g. HCl) in a suitable organic solvent (e.g. ethanol) to give certain corresponding embodiments of compounds of Formula I-(i). In certain embodiments when L is, —N($R^L$)—, —C(O)N($R^L$)—, or —OC(O)N($R^L$)—, —NR$^L$C(O)N($R^L$)—, Buchwald coupling of XI-(i) respectively with active; amines $R^{3'}N(R^L)H$, amides $R^{3'}C(O)N(R^L)H$, carbamates —OC(O)N($R^L$)H, or ureas —NR$^L$C(O)N($R^L$)H, may be implemented in the first step. In a second optional set of steps the $R^{3'}$ group as well as other groups in the molecule may be converted to the defined final substituents in Formula I-(i). In a final deprotection step the N-Boc protecting is removed by for example using an acid (e.g. HCl) in a suitable organic solvent (e.g. ethanol) to give certain corresponding embodiments of compounds of Formula I-(i)

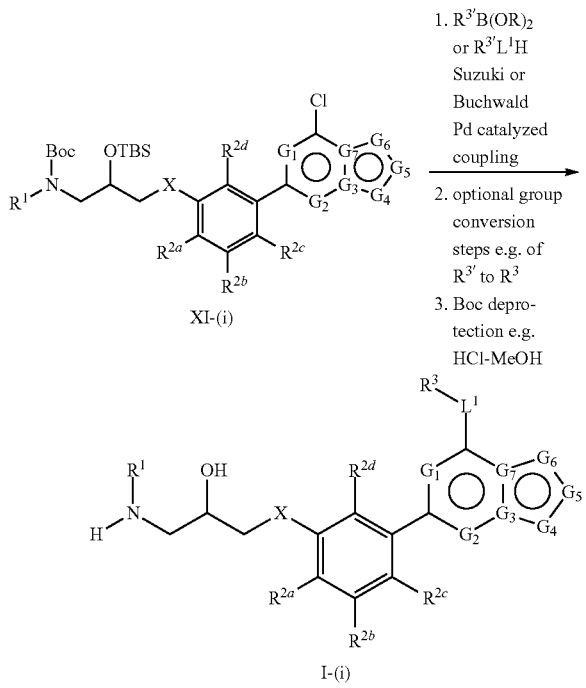

Scheme 1

Scheme 2 shows a general synthesis route to compounds of Formula I-(ii) wherein $R^{3'}$ is the same as $R^3$ as defined above or is a suitable precursor that may be converted to $R^3$. This method is analogous to the method described above using the regiosiomeric heterocyclic chloride intermediates of general Formula XI-(ii) with the identical coupling partner intermediates.

Heteroaryl chloride intermediates of general Formulas XI-(i) and XI-(ii) can be prepared from heteroaryl dichloride intermediates of general Formula X as depicted in Scheme 3. In certain embodiments the standard palladium catalyzed Suzuki coupling of X with pinacol borane intermediates of general Formula XX gives a mixture with both regioisomers XI-(i) and XI-(ii) being formed to a significant extent. In certain embodiments XI-(i) and XI-(ii) can be separated by chromatography and converted to corresponding pure isomers I-(i) and I-(ii). In certain embodiments the standard palladium catalyzed Suzuki coupling of X with pinacol borane intermediates of general Formula XX gives XI-(i) or XI-(ii) to the virtual exclusion of the other isomer.

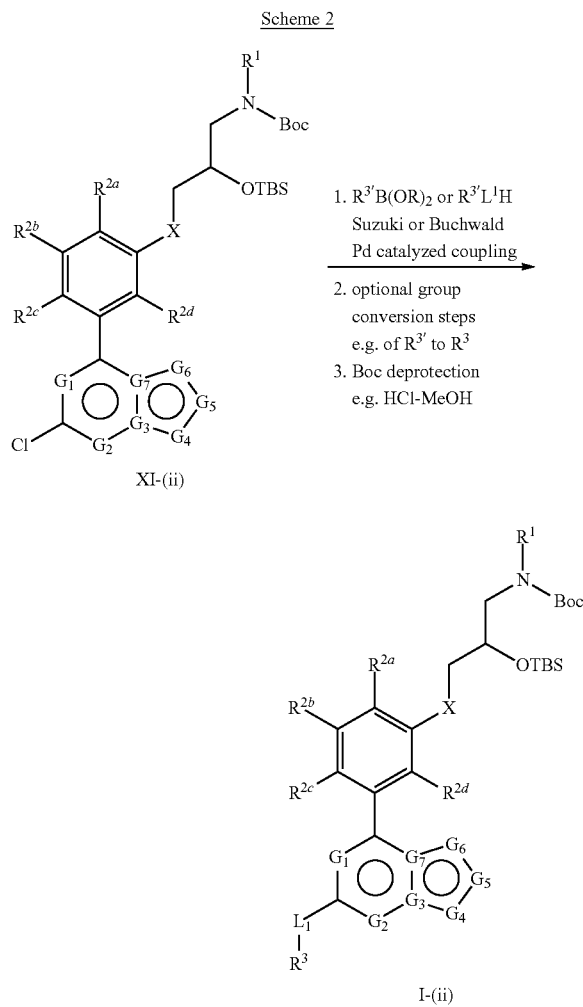

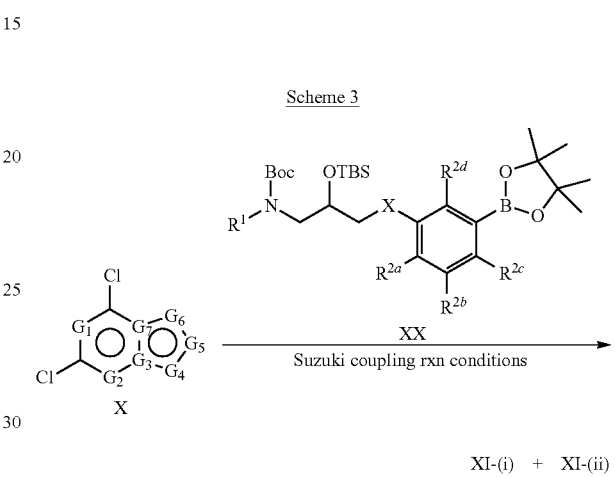

In certain embodiments wherein X in general Formulas I-(i) and I-(ii) is O, pinacol borane intermediates of general Formula XX can be prepared using standard methods as depicted in Scheme 4. Thus, in a first step 3-bromophenols of general structure XXX are treated with epibromohydrin to give epoxides XXXI. Opening of the epoxide group of intermediates XXXI in with amines of Formula $R^1NH_2$ in an organic solvent with heating as necessary followed by protection of the resulting amine with Boc-anhydride gives intermediates XXXII. TBS protection of the alcohol group in the next step using t-butyldimethylsilyltriflate gives intermediate bromides XXXIII. In a final step the Br group is converted to the pinacol borane function to give intermediates XX under standard Suzuki-Miyura conditions.

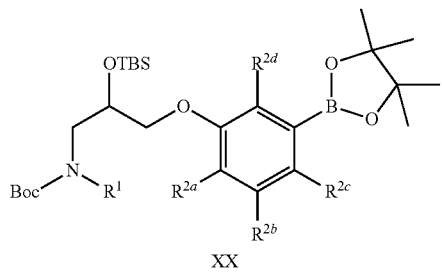 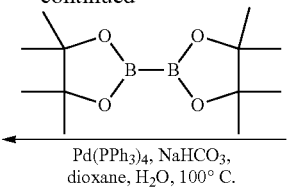 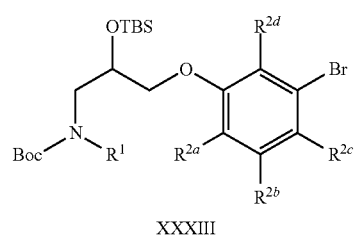

XX  XXXIII

EXAMPLES

In order that the invention described herein may be more fully understood, the following examples are set forth. It should be understood that these examples are for illustrative purposes only and are not to be construed as limiting this invention in any manner.

Synthetic Methods

The synthesis of an exemplary set of compounds of Formula (I) is provided below. These compounds are also listed in Tables 1-7, infra. Compounds provided in Table 1 have been prepared following Examples 1-5. Compounds provided in Table 2 have been prepared following Examples 6-8. Compounds provided in Table 3 have been prepared following Examples 9-11. Compounds provided in Table 4 have been prepared following Examples 12-14. Compounds provided in Table 5 have been prepared following Examples 15-21.

Compounds provided in Table 6 have been prepared following Examples 22-26. Compounds provided in Table 7 have been prepared following Example 27.

Example 1

Preparation of 4,6-dichloro-1-isopropyl-1H-pyrazolo[3,4-b]pyridine

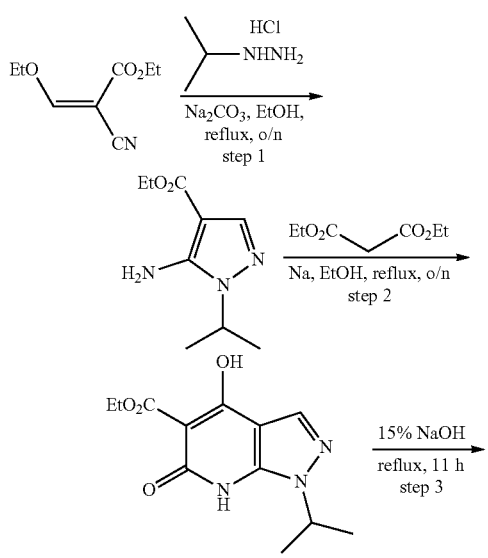

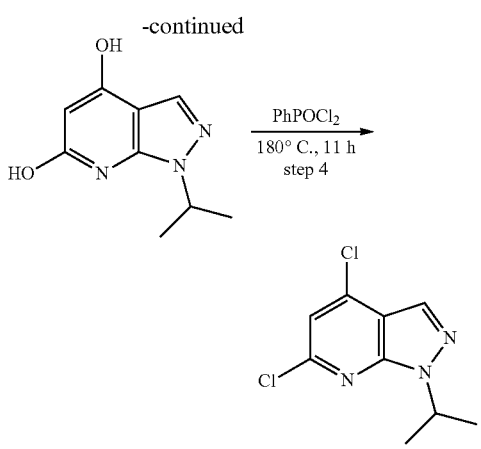

Step 1: Synthesis of ethyl 5-amino-1-isopropyl-1H-pyrazole-4-carboxylate. To a solution of (Z)-ethyl 2-cyano-3-ethoxyacrylate (30 g, 177.5 mmol) in EtOH (500 mL) were added isopropylhydrazine hydrochloride (21.5 g, 195.3 mmol) and $Na_2CO_3$ (28.2 g, 266.3 mmol). The mixture was stirred under reflux for 14 h, then cooled down to room temperature, filtered and the filtrate was concentrated, diluted with $H_2O$ (500 mL) and the mixture was extracted with EtOAc (500 mL×2). The combined organic layers were washed with brine (500 mL), dried over $Na_2SO_4$, filtered and concentrated. The residue was purified by column chromatography on silica gel (petroleum ether/EtOAc=10/1 to 5/1) to afford ethyl 5-amino-1-isopropyl-1H-pyrazole-4-carboxylate (25 g, 71% yield) as a yellow oil. ESI-LCMS (m/z): 198.3 [M+1]$^+$.

Step 2: Synthesis of ethyl 4-hydroxy-1-isopropyl-6-oxo-6,7-dihydro-1H-pyrazolo[3,4-b]pyridine-5-carboxylate. To a solution of NaOEt (freshly prepared from Na (7.9 g, 344.78 mmol) in EtOH (58 mL)), diethyl malonate (52.6 mL, 344.7 mmol) was slowly added at room temperature under nitrogen atmosphere; after the addition was completed the mixture was heated at reflux for 1 hour. Then ethyl 5-amino-1-isopropyl-1H-pyrazole-4-carboxylate (17.0 g, 86.1 mmol) was added, and the resulting mixture was further stirred under reflux for 14 h. After cooling down to room temperature the reaction mixture was concentrated under reduced pressure, the residue was diluted with $H_2O$ (500 mL) and the resulting system was extracted with EtOAc (500 mL×3). The basic aqueous phase was separated and made acidic by careful addition of concentrated HCl solution until pH=5 to render a precipitate which was collected by filtration and dried in vacuo to afford ethyl 4-hydroxy-1-isopropyl-6-oxo-6,7-dihydro-1H-pyrazolo[3,4-b]pyridine-5-carboxylate (13.0 g, 57% yield) as a yellow solid. ESI-LCMS (m/z): 266.2 [M+1]$^+$.

Step 3: Synthesis of 1-isopropyl-1H-pyrazolo[3,4-b]pyridine-4,6-diol. A solution of ethyl 4-hydroxy-1-isopropyl-6-oxo-6,7-dihydro-1H-pyrazolo[3,4-b]pyridine-5-carboxylate (16.0 g, 60.3 mmol) in 15% aqueous NaOH (160 mL) was stirred under reflux for 11 h. After cooling down to room temperature, the mixture was adjusted to pH=2 with concentrated HCl solution to give a precipitate which was collected by filtration, washed with H₂O (100 mL×2) and dried under vacuo for 2 days to afford 1-isopropyl-1H-pyrazolo[3,4-b]pyridine-4,6-diol (11.3 g, 97% yield) as a pink solid. ESI-LCMS (m/z): 194.2 [M+1]⁺.

Step 4: Synthesis of 4,6-dichloro-1-isopropyl-1H-pyrazolo[3,4-b]pyridine. A solution of 1-isopropyl-1H-pyrazolo[3,4-b]pyridine-4,6-diol (5.0 g, 25.8 mmol) in PhPOCl₂ (30 g, 155.2 mmol) was stirred at 180° C. for 11 hours. After cooling down to room temperature, the mixture was poured into crushed ice with stirring. The precipitate was collected by filtration and washed with cold H₂O (50 mL) followed by petroleum ether (100 mL×3) and dried in vacuo to afford 4,6-dichloro-1-isopropyl-1H-pyrazolo[3,4-b]pyridine (5.2 g, 88% yield) as a light yellow solid. ESI-LCMS (m/z): 230.1 [M+1]⁺.

Example 2

Preparation of ethyl 6-(3-(2-hydroxy-3-(methylamino)propoxy)phenyl)-1-isopropyl-1H-pyrazolo[3,4-b]pyridin-4-ylcarbamate

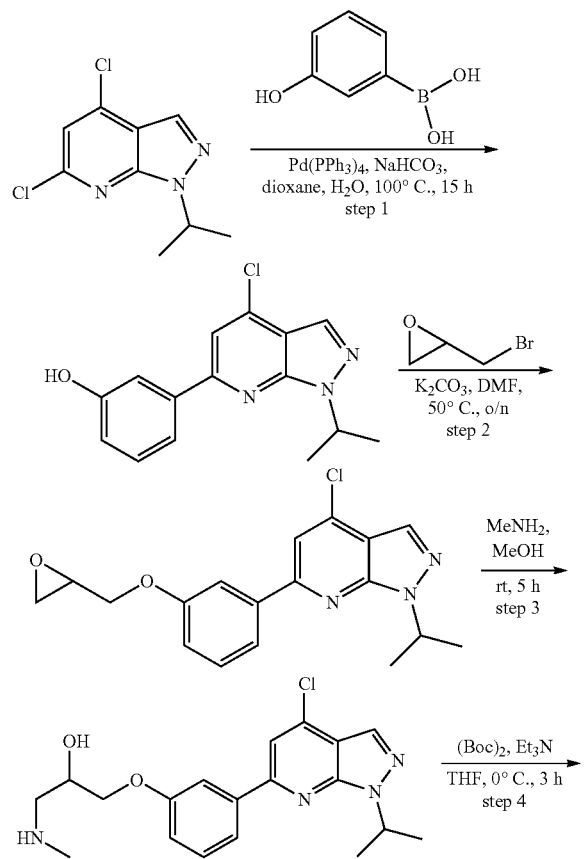

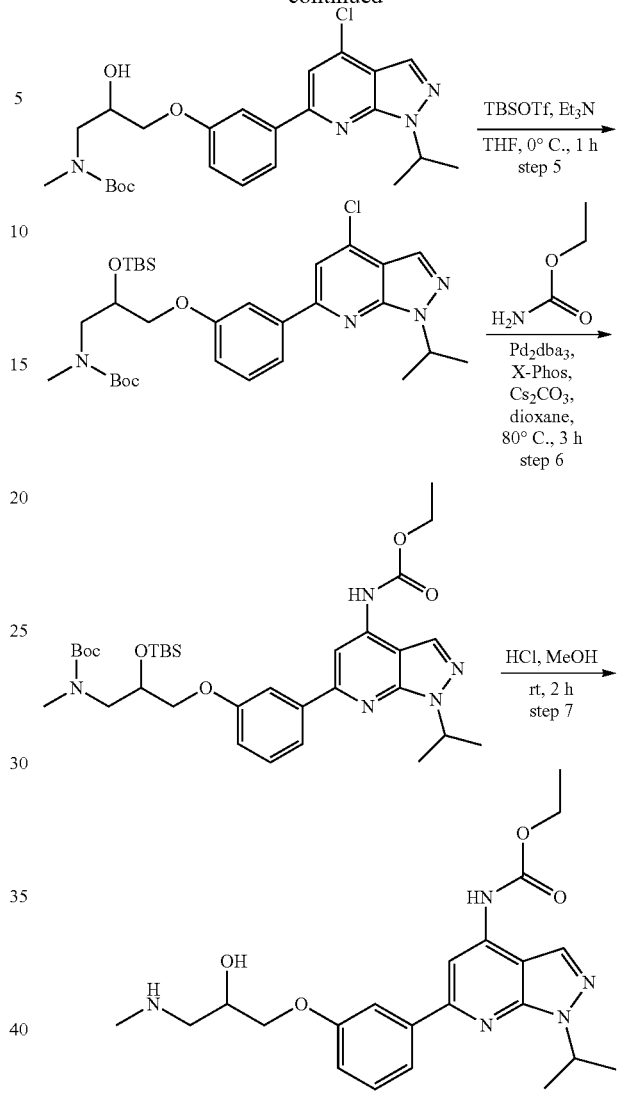

Step 1: Synthesis of 3-(4-chloro-1-isopropyl-1H-pyrazolo[3,4-b]pyridin-6-yl)phenol. A solution of 4,6-dichloro-1-isopropyl-1H-pyrazolo[3,4-b]pyridine (18 g, 78 mmol) in dioxane and H₂O (3/1, 500 mL) was treated with NaHCO₃ (26 g, 312 mmol), Pd(PPh₃)₄ (6.3 g, 5.46 mmol) and 3-hydroxyphenylboronic acid (14 g, 102 mmol). Air was removed from the system by a stream of nitrogen and then the mixture heated to 100° C. for 15 hours. After cooling down to room temperature, water (500 mL) was added and the resulting mixture was extracted with EtOAc (500 mL×2). The combined organic layers were dried over Na₂SO₄, filtered and concentrated. The residue was purified with a chromatographic column of silica gel eluted with CH₂Cl₂/MeOH=100/1 to 15/1 to give 3-(4-chloro-1-isopropyl-1H-pyrazolo[3,4-b]pyridin-6-yl)phenol (14.0 g, 63% yield). ESI-LCMS (m/z): 288.1 [M+1]⁺.

Step 2: Synthesis of 4-chloro-1-isopropyl-6-(3-(oxiran-2-ylmethoxy)phenyl)-1H-pyrazolo[3,4-b]pyridine. A solution of 3-(4-chloro-1-isopropyl-1H-pyrazolo[3,4-b]pyridin-6-yl)phenol (6 g, 20.88 mmol) in CH₃CN (500 mL) was treated with K₂CO₃ (12 g, 84 mmol) and 2-(chloromethyl)oxirane (7.68 g, 84 mmol) and the mixture was heated to 80° C. for 14 h. After cooling down to room temperature, H₂O (300 mL) was added and the mixture was extracted with EtOAc (800 mL×2). The combined organic layers were dried over Na$_2$SO$_4$, filtered and filtrate was concentrated to give 4-chloro-1-isopropyl-6-(3-(oxiran-2-ylmethoxy)phenyl)-1H-pyrazolo[3,4-b]pyridine (6.72 g, 100% yield). ESI-LCMS (m/z): 344.1 [M+1]$^+$.

Step 3: Synthesis of 1-(3-(4-chloro-1-isopropyl-1H-pyrazolo[3,4-b]pyridin-6-yl)phenoxy)-3-(methylamino)propan-2-ol. 4-Chloro-1-isopropyl-6-(3-(oxiran-2-ylmethoxy)phenyl)-1H-pyrazolo[3,4-b]pyridine (6 g, 17.4 mmol) was added to a 2N solution of CH$_3$NH$_2$ in MeOH (50 mL). The mixture was stirred at room temperature for 5 hours and then was concentrated to give 1-(3-(4-chloro-1-isopropyl-1H-pyrazolo[3,4-b]pyridin-6-yl)phenoxy)-3-(methylamino)propan-2-ol (6.5 g, 100% yield). ESI-LCMS (m/z): 375.2 [M+1]$^+$.

Step 4: Synthesis of tert-butyl 3-(3-(4-chloro-1-isopropyl-1H-pyrazolo[3,4-b]pyridin-6-yl)phenoxy)-2-hydroxypropyl(methyl)carbamate. A solution of 1-(3-(4-chloro-1-isopropyl-1H-pyrazolo[3,4-b]pyridin-6-yl)phenoxy)-3-(methylamino)propan-2-ol (6.5 g, 17.37 mmol) and Et$_3$N (7 g, 70 mmol) in THF (500 mL) stirred under nitrogen atmosphere at room temperature, was treated with Boc$_2$O (4.54 g, 20.84 mmol). The reaction mixture was further stirred at the same temperature for 1 h, the solvent was removed in vacuo, the residue dissolved in EtOAc (500 ml) and the resulting mixture was washed with saturated NH$_4$Cl solution (200 ml), H$_2$O (200 ml×2) and brine (100 mL). The organic layer was dried over Na$_2$SO$_4$, filtered and concentrated to give tert-butyl 3-(3-(4-chloro-1-isopropyl-1H-pyrazolo[3,4-b]pyridin-6-yl)phenoxy)-2-hydroxypropyl(methyl)carbamate (8.23 g, 100% yield). ESI-LCMS (m/z): 475.2 [M+1]$^+$.

Step 5: Synthesis of tert-butyl 2-(tert-butyldimethylsilyloxy)-3-(3-(4-chloro-1-isopropyl-1H-pyrazolo[3,4-b]pyridin-6-yl)phenoxy)propyl(methyl)carbamate. A solution of tert-butyl 3-(3-(4-chloro-1-isopropyl-1H-pyrazolo[3,4-b]pyridin-6-yl)phenoxy)-2-hydroxypropyl(methyl)carbamate (8.23 g, 17.37 mmol) and Et$_3$N (7 g, 70 mmol) in THF (500 mL) stirred at 0° C. under nitrogen, was treated with TBSOTf (5.5 g, 20.84 mmol). The mixture was stirred at room temperature for 1 hour, the solvent was removed in vacuo and the residue dissolved in EtOAc (500 ml). The resulting mixture was washed with saturated NH$_4$Cl solution (200 ml), H$_2$O (200 ml×2) and brine (100 mL). The organic layer was dried over Na$_2$SO$_4$, filtered and concentrated to render a residue which was purified by column chromatography on silica gel eluted with DCM/MeOH=100/1 to 50/1 to give tert-butyl 2-(tert-butyl dimethylsilyloxy)-3-(3-(4-chloro-1-isopropyl-1H-pyrazolo[3,4-b]pyridin-6-yl)phenoxy)propyl(methyl)carbamate (9.4 g, 92% yield). $^1$H NMR (500 MHz, CD$_3$OD) δ (ppm): 8.06 (s, 1H), 7.71 (t, J=1.5 Hz, 1H), 7.67 (s, 1H), 7.66 (d, J=8.0 Hz, 1H), 7.39 (t, J=8.0 Hz, 1H), 7.01 (dd, J=8.0 and 2.5 Hz, 1H), 5.36-5.31 (m, 1H), 4.33 (brs, 1H), 4.04-3.94 (m, 2H), 3.54-3.45 (m, 1H), 3.35-3.27 (m, 1H), 2.98-2.94 (m, 2H), 1.58 (d, J=6.0 Hz, 6H), 1.48-1.43 (m, 9H), 0.91 (s, 9H), 0.16-0.15 (m, 6H) ppm.

Step 6: Synthesis of (6-{3-[3-(tert-Butoxycarbonyl-methyl-amino)-2-(tert-butyl-dimethyl-silanyloxy)-propoxy]-phenyl}-1-isopropyl-1H-pyrazolo[3,4-b]pyridin-4-yl)-carbamic acid ethyl ester. To a solution of tert-butyl 2-(tert-butyldimethylsilyloxy)-3-(3-(4-chloro-1-isopropyl-1H-pyrazolo[3,4-b]pyridin-6-yl)phenoxy)propyl(methyl)carbamate (100 mg, 0.17 mmol), ethyl carbamate (62 mg, 0.69 mmol), X-Phos (8 mg, 0.015 mmol) and Cs$_2$CO$_3$ (224 mg, 0.69 mmol) in dioxane (50 mL) was added Pd$_2$dba$_3$ (5 mg, 0.0051 mmol). Air was removed from the system with a stream of nitrogen, and the reaction mixture was then heated to 80° C. for 3 hours. After cooling down to room temperature, water (50 mL) was added and the resulting mixture was extracted with EtOAc (50 mL×2). The combined organic layer was dried over Na$_2$SO$_4$, filtered and concentrated. The residue was purified by chromatographic column on silica gel (petroleum ether/EtOAc=100/1 to 10/1) to give (6-{3-[3-(tert-butoxy carbonyl-methyl-amino)-2-(tert-butyl-dimethyl-silanyloxy)-propoxyl]-phenyl}-1-isopropyl-1H-pyrazolo[3,4-b]pyridin-4-yl)-carbamic acid ethyl ester (96 mg, 89% yield). ESI-LCMS (m/z): 643.3 [M+1]$^+$.

Step 7: Synthesis of ethyl 6-(3-(2-hydroxy-3-(methylamino)propoxy)phenyl)-1-isopropyl-1H-pyrazolo[3,4-b]pyridin-4-ylcarbamate. To a solution of (6-{3-[3-(tert-butoxycarbonyl-methyl-amino)-2-(tert-butyl-dimethyl-silanyloxy)-propoxy]-phenyl}-1-isopropyl-1H-pyrazolo[3,4-b]pyridin-4-yl)-carbamic acid ethyl ester (96 mg, 0.15 mmol) in MeOH (20 mL) was added 4N HCl aqueous solution (5 mL). The resulting mixture was stirred at room temperature for 2 hours, concentrated under vacuum and the residue was purified by preparative HPLC to give ethyl 6-(3-(2-hydroxy-3-(methylamino)propoxy)phenyl)-1-isopropyl-1H-pyrazolo[3,4-b]pyridin-4-ylcarbamate (10 mg, 14% yield) as a white solid. $^1$H NMR (500 MHz, CD$_3$OD) δ (ppm): 8.30 (s, 1H), 8.19 (s, 1H), 7.74 (s, 1H), 7.69 (d, J=8.0 Hz, 1H), 7.43 (t, J=8.0 Hz, 1H), 7.10-7.07 (m, 1H), 5.40-5.35 (m, 1H), 4.36-4.30 (m, 2H), 4.19-4.15 (m, 1H), 4.11-4.08 (m, 2H), 2.92-2.88 (m, 1H), 2.83-2.79 (m, 1H), 2.51 (s, 3H), 1.61 (d, J=6.5 Hz, 6H), 1.40 (t, J=7.0 Hz, 3H) ppm; LC-MS (m/z): 428.3 [M+1]$^+$.

Example 3

Preparation of tert-butyl 2-(tert-butyldimethylsilyloxy)-3-(3-(4-chloro-1-isopropyl-1H-pyrazolo[3,4-b]pyridin-6-yl)phenoxy)propyl(methyl)carbamate

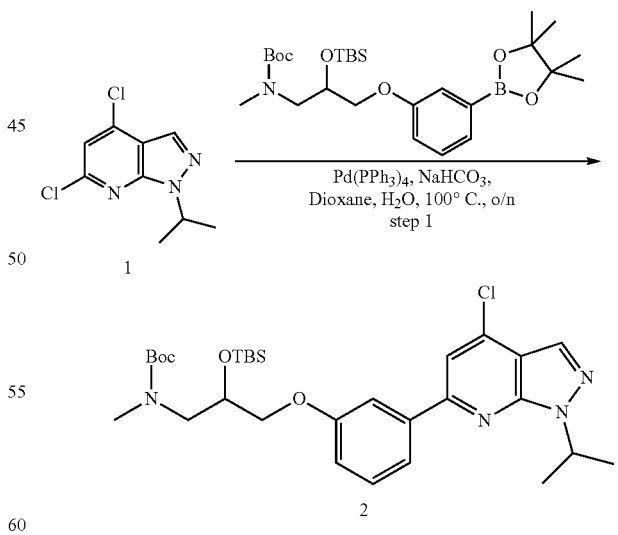

To a solution of 4,6-dichloro-1-isopropyl-1H-pyrazolo[3,4-b]pyridine (1.8 g, 7.9 mmol), tert-butyl 2-(tert-butyldimethylsilyloxy)-3-(3-(4,4,5,5-tetramethyl-1,3,2-dioxaborolan-2-yl)phenoxy)propyl(methyl)carbamate (4.9 g, 9.4 mmol) and NaHCO$_3$ (2.0 g, 23.7 mmol) in dioxane and water (32 mL, 3/1) was added Pd(PPh$_3$)$_4$ (1.8 g, 1.6 mmol).

Air was removed from the system by cycles of vacuum followed by backfilling with nitrogen (three times) then the reaction mixture was heated at 100° C. for 14 h. After cooling down to room temperature, water (30 mL) was added and the mixture was extracted with EtOAc (50 mL×2); the combined organic phase was washed with brine, dried over $Na_2SO_4$, filtered and concentrated to render a residue which was purified by column chromatography on silicagel to obtain tert-butyl2-(tert-butyldimethyl silyloxy)-3-(3-(4-chloro-1-isopropyl-1H-pyrazolo[3,4-b]pyridin-6-yl)phenoxy)propyl(methyl)carbamate (2.3 g, 50% yield) as a yellow solid. ESI-MS (m/z): 589.7 $[M+1]^+$.

Example 4

Preparation of 1-(6-(3-(2-hydroxy-3-(methylamino)propoxy)phenyl)-1-isopropyl-1H-pyrazolo[3,4-b]pyridin-4-yl)-3-(tetrahydro-2H-pyran-4-yl)urea

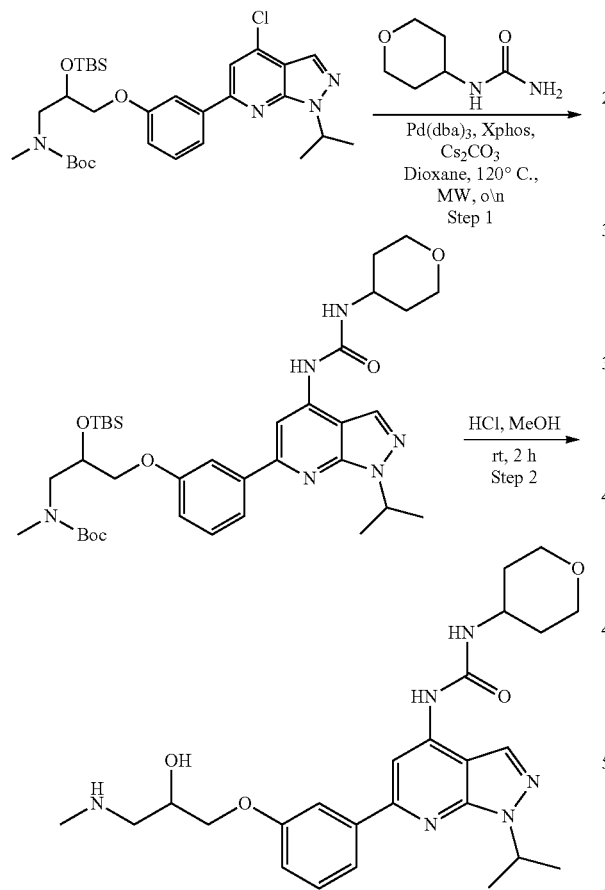

Step 1 Synthesis of tert-butyl 2-(tert-butyldimethylsilyloxy)-3-(3-(1-isopropyl-4-(3-(tetrahydro-2H-pyran-4-yl)ureido)-1H-pyrazolo[3,4-b]pyridin-6-yl)phenoxy)propyl(methyl)carbamate. To a solution of tert-butyl 2-(tert-butyldimethylsilyloxy)-3-(3-(4-chloro-1-isopropyl-1H-pyrazolo[3,4-b]pyridin-6-yl)phenoxy)propyl(methyl)carbamate (200 mg, 0.34 mmol), 1-(tetrahydro-2H-pyran-4-yl)urea (244 mg, 1.7 mmol), X-Phos (81 mg, 0.17 mmol) and $Cs_2CO_3$ (326 mg, 1 mmol) in dioxane (10 mL) was added $Pd_2(dba)_3$ (155 mg, 0.17 mmol). Air was removed from the system by cycles of vacuum followed by backfilling with nitrogen and the vial sealed, then placed in a microwave oven and irradiated at 120° C. for 30 min., cooled down to temperature, the mixture was diluted with water (10 mL) and extracted with EtOAc (10 mL×2), the combined organic phase was concentrated and the residue was purified by preparative TLC on silica gel to obtain tert-butyl 2-(tert-butyldimethylsilyloxy)-3-(3-(1-isopropyl-4-(3-(tetrahydro-2H-pyran-4-yl) ureido)-1H-pyrazolo[3,4-b]pyridin-6-yl)phenoxy)propyl(methyl)carbamate (84 mg, 35% yield) as a yellow solid. ESI-LCMS (m/z): 697.7 $[M+1]^+$.

Step 2. Synthesis of 1-(6-(3-(2-hydroxy-3-(methylamino)propoxy)phenyl)-1-isopropyl-1H-pyrazolo[3,4-b]pyridin-4-yl)-3-(tetrahydro-2H-pyran-4-yl)urea. A solution of tert-butyl 2-(tert-butyldimethylsilyloxy)-3-(3-(1-isopropyl-4-(3-(tetrahydro-2H-pyran-4-yl)ureido)-1H-pyrazolo[3,4-b]pyridin-6-yl)phenoxy)propyl(methyl)carbamate (84 mg, 0.12 mmol) in MeOH (2 mL) was treated with 5N HCl aqueous solution (2 mL) and the resulting mixture was stirred at 30° C. for 2 h, concentrated under vacuum and the residue was purified by preparative HPLC to obtain 1-(6-(3-(2-hydroxy-3-(methylamino)propoxy)phenyl)-1-isopropyl-1H-pyrazolo[3,4-b]pyridin-4-yl)-3-(tetra hydro-2H-pyran-4-yl)urea (white solid, 26 mg, 45% yield) as a formic acid salt. $^1$H NMR (500 MHz, $CD_3OD$) δ (ppm):8.58 (brs, 1H), 8.27 (s, 1H), 8.14 (s, 1H), 7.74-7.70 (m, 2H), 7.44 (t, J=8.0 Hz, 1H), 7.08 (dd, J=8.0 and 2.0 Hz, 1H), 5.40-5.32 (m, 1H), 4.33-4.29 (m, 1H), 4.20-4.10 (m, 2H), 4.01-3.95 (m, 2H), 3.93-3.87 (m, 1H), 3.60-3.52 (m, 2H), 3.35-3.30 (m, 1H), 3.25-3.19 (m, 1H), 2.79 (s, 3H), 2.02-1.98 (m, 2H), 1.65-1.55 (m, 8H) ppm; ESI-MS (m/z): 483.3 $[M+1]^+$.

Example 5

Preparation of (R)-1-amino-3-(3-(1-isopropyl-4-morpholino-1H-pyrazolo[3,4-b]pyridin-6-yl)phenoxy)propan-2-ol

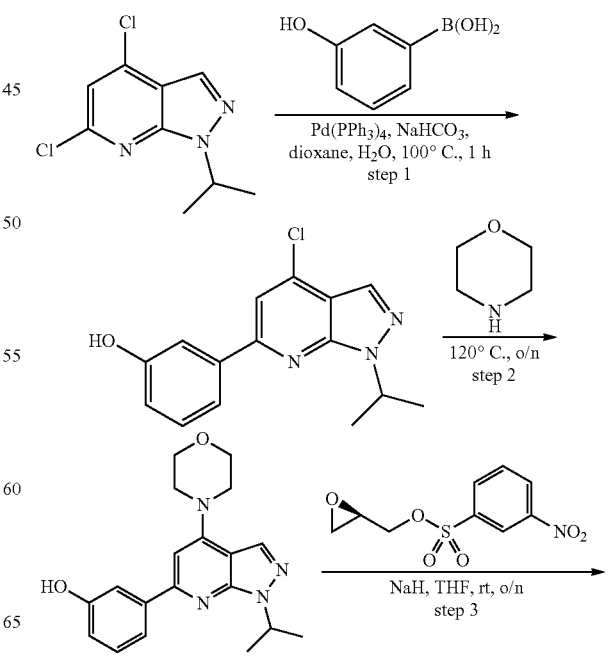

-continued

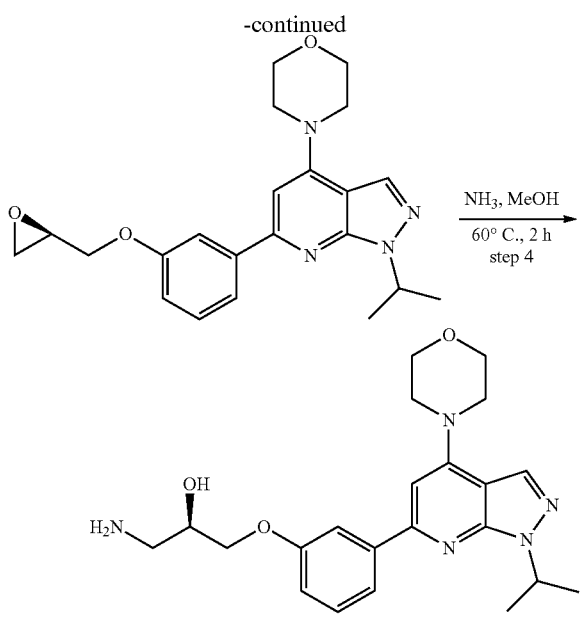

Step 1: Synthesis of 3-(4-chloro-1-isopropyl-1H-pyrazolo[3,4-b]pyridin-6-yl)phenol. A mixture of 4,6-dichloro-1-isopropyl-1H-pyrazolo[3,4-b]pyridine (5.9 g, 25.8 mmol), 3-hydroxyphenylboronic acid (3.57 g, 25.8 mmol), Pd(PPh$_3$)$_4$ (3.0 g, 2.58 mmol) and NaHCO$_3$ (4.3 g, 51.6 mmol) in 40 mL of dioxane/H$_2$O (v/v=3:1) was heated at 100° C. under N$_2$ for 1 hour. After cooling down to room temperature, water (30 mL) was added and the mixture was extracted with dichloromethane (30 mL×4). The organic phase was dried over Na$_2$SO$_4$, filtered and concentrated. The residue was purified by chromatographic column on silica gel (petroleum ether/EtOAc=5/1) to afford 3-(4-chloro-1-isopropyl-1H-pyrazolo[3,4-b]pyridin-6-yl)phenol (5.9 g, 80% yield). ESI-LCMS (m/z): 288.1 [M+1]$^+$.

Step 2: Synthesis of 3-(1-isopropyl-4-morpholino-1H-pyrazolo[3,4-b]pyridin-6-yl)phenol. A mixture of 3-(4-chloro-1-isopropyl-1H-pyrazolo[3,4-b]pyridin-6-yl)phenol (5.9 g, 20.6 mmol) and neat morpholine (20 mL) was heated at 120° C. for 14 h. The excess of morpholine was removed in vacuo and the residue dissolved in DCM (150 mL). The mixture was washed with water (150 mL×2) and brine (100 mL), the organic layer was dried over Na$_2$SO$_4$, filtered and concentrated to afford 3-(1-isopropyl-4-morpholino-1H-pyrazolo[3,4-b]pyridin-6-yl)phenol (6.9 g, 100% yield) as a white solid. ESI-LC-MS (m/z): 339.2 [M+1]$^+$.

Step 3: Synthesis of (R)-4-(1-isopropyl-6-(3-(oxiran-2-ylmethoxy)phenyl)-1H-pyrazolo[3,4-b]pyridin-4-yl)morpholine. An ice cooled solution of 3-(1-isopropyl-4-morpholino-1H-pyrazolo[3,4-b]pyridin-6-yl)phenol (50 mg, 0.15 mmol) in 3 mL of THF was treated with NaH (30 mg, 0.75 mmol) and the mixture was stirred at room temperature for 20 min. (R)-Oxiran-2-ylmethyl 3-nitrobenzenesulfonate (78 mg, 0.30 mmol) was then added and the mixture was further stirred at 45° C. for 14 h. Excess reagent was quenched with cold water, the resulting mixture was extracted with EtOAc (20 mL×3), the organic phase was dried over Na$_2$SO$_4$, filtered and concentrated to afford (R)-4-(1-isopropyl-6-(3-(oxiran-2-ylmethoxy)phenyl)-1H-pyrazolo[3,4-b]pyridin-4-yl)morpholine (60 mg, 100% yield). ESI-LCMS (m/z): 395.3 [M+1]$^+$.

Step 4: Synthesis of (R)-1-amino-3-(3-(1-isopropyl-4-morpholino-1H-pyrazolo[3,4-b]pyridin-6-yl)phenoxy)propan-2-ol. A solution of (R)-4-(1-isopropyl-6-(3-(oxiran-2-ylmethoxy)phenyl)-1H-pyrazolo[3,4-b]pyridin-4-yl)morpholine (60 mg, 0.15 mmol) in MeOH (4 mL) was treated with concentrated aqueous ammonia solution (2 mL). The mixture was heated at 60° C. for 2 hours. The volatiles were removed under vacuum and the residue was purified by preparative HPLC to give (R)-1-amino-3-(3-(1-isopropyl-4-morpholino-1H-pyrazolo[3,4-b]pyridin-6-yl)phenoxy)propan-2-ol (20 mg, 33% yield) as a solid. $^1$HNMR (500 MHz, CD$_3$OD) δ (ppm): 8.15 (s, 1H), 7.68 (t, J=2.0 Hz, 1H), 7.63 (d, J=8.0 Hz, 1H), 7.39 (t, J=8.5 Hz, 1H), 7.04 (dd, J=8.5 and 3.0 Hz, 1H), 6.87 (s, 1H), 5.40-5.30 (m, 1H), 4.12-4.05 (m, 2H), 4.02-3.98 (m, 1H), 3.92-3.88 (m, 4H), 3.68-3.64 (m, 4H), 2.95-2.90 (m, 1H), 2.84-2.75 (m, 1H), 1.56 (d, J=7.0 Hz, 6H) ppm; ESI-LC-MS (m/z): 412.3 [M+1]$^+$.

Example 6

Preparation of 4,6-dichloro-1-isopropyl-3-methyl-1H-pyrazolo[3,4-b]pyridine

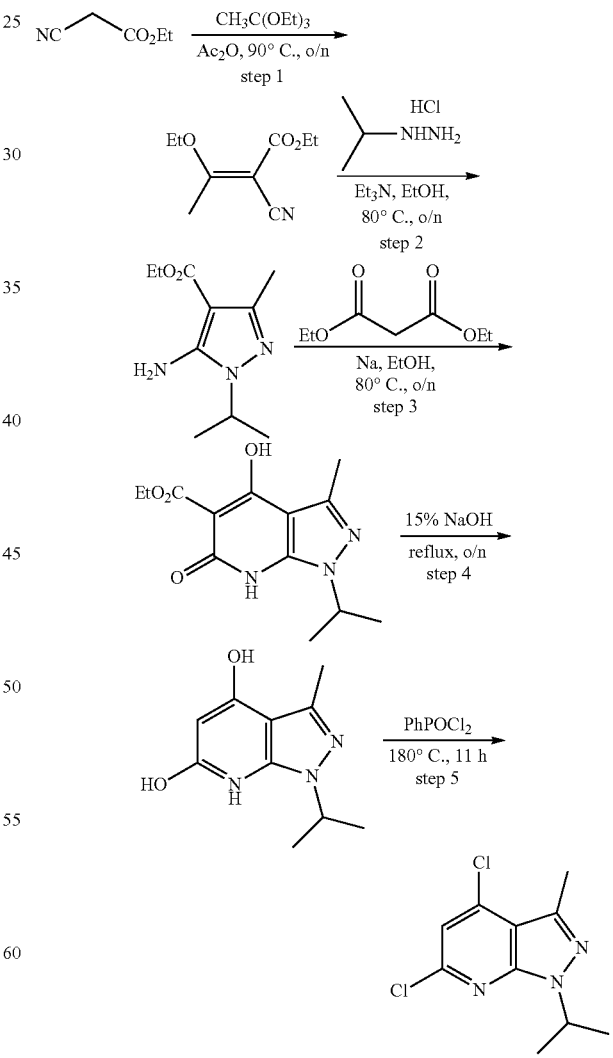

Step 1: Synthesis of 2-cyano-3-ethoxy-but-2-enoic acid ethyl ester. A solution of ethyl cyanacetate (15 mL) in Ac$_2$O (100 mL) was treated with triethyl orthoacetate (25 mL) and the mixture was stirred at 90° C. for 14 h, concentrated and cooled to 0° C. for 20 min. to render a precipitate. The resulting mixture was filtered and the white solid was collected, washed with cool petroleum ether (10 mL×2) and dried to afford the 2-cyano-3-ethoxy-but-2-enoic acid ethyl ester (5.0 g, 20% yield). 1H NMR (500 MHz, CDCl$_3$) δ (ppm): 4.30-4.21 (m, 4H), 2.61 (s, 3H), 1.43 (t, J=7.0 Hz, 3H), 1.33-1.30 (m, 3H) ppm;

Step 2: Synthesis of 5-amino-1-isopropyl-3-methyl-1H-pyrazole-4-carboxylic acid ethyl ester. To a solution of 2-cyano-3-ethoxy-but-2-enoic acid ethyl ester (22 g, 120.2 mmol) in EtOH (250 mL) was added isopropylhydrazine HCl salt (13.2 g, 120.2 mmol) and triethylamine (24.3 g, 240.4 mmol). The mixture was refluxed for 14 h, cooled down to room temperature, concentrated and diluted with H$_2$O (150 mL). The mixture was extracted with EtOAc (150 mL×2), the combined organic layers were washed with brine (500 mL), dried over Na$_2$SO$_4$ and concentrated. The residue was purified by chromatographic column on silica gel (petroleum ether/EtOAc=50/1 to 5/1) to afford 5-amino-1-isopropyl-3-methyl-1H-pyrazole-4-carboxylic acid ethyl ester (18.8 g, 74% yield). ESI-LCMS (m/z): 212.2 [M+1]$^+$.

Step 3: Synthesis of 4-Hydroxy-1-isopropyl-3-methyl-6-oxo-6,7-dihydro-1H-pyrazolo[3,4-b]pyridine-5-carboxylic acid ethyl ester. Under nitrogen atmosphere, diethyl malonate (18.60 g, 116.11 mmol) was added to a solution of NaOEt, freshly prepared from Na (3.5 g, 142.29 mmol) in EtOH (28 mL) at room temperature and the mixture was stirred at room temperature for 0.5 hour. To the mixture, 5-amino-1-isopropyl-3-methyl-1H-pyrazole-4-carboxylic acid ethyl ester (7.0 g, 33.17 mmol) was added and the system further stirred at reflux for 14 h., concentrated under reduced pressure, diluted with water (300 mL) and extracted with CH$_2$Cl$_2$ (50 mL×2). The aqueous phase was adjusted to pH=5 with 2 N HCl and the resulting white solid was collected by filtration, washed with water (50 mL×2) and dried to afford 4-hydroxy-1-isopropyl-3-methyl-6-oxo-6,7-dihydro-1H-pyrazolo[3,4-b]pyridine-5-carboxylic acid ethyl ester (5.0 g, 54% yield). ESI-LCMS (m/z): 280.2 [M+1]$^+$.

Step 4: Synthesis of 1-isopropyl-3-methyl-1H-pyrazolo[3,4-b]pyridine-4,6-diol. A solution of 4-hydroxy-1-isopropyl-3-methyl-6-oxo-6,7-dihydro-1H-pyrazolo[3,4-b]pyridine-5-carboxylic acid ethyl ester (5.0 g, 17.9 mmol) in 15% NaOH aqueous solution (50 mL) was stirred at reflux for 14 h. After cooling down to room temperature, the mixture was adjusted to pH=2 with concentrated HCl aqueous solution. The precipitate was collected by filtration, washed with H$_2$O (30 mL×2) and dried in vacuo to afford 1-isopropyl-3-methyl-1H-pyrazolo[3,4-b]pyridine-4,6-diol (4.0 g, 100% yield) as a pink solid. ESI-LCMS (m/z): 208.2 [M+1]$^+$.

Step 5: Synthesis of 4,6-dichloro-1-isopropyl-3-methyl-1H-pyrazolo[3,4-b]pyridine. A solution 1-isopropyl-3-methyl-1H-pyrazolo[3,4-b]pyridine-4,6-diol (4.0 g, 19.3 mmol) in PhPOCl$_2$ (50 mL) was stirred at 180° C. for 11 hours. After cooling down to room temperature, the mixture was poured into crushed ice and then extracted with EtOAc (80 mL×2). The combined organic layers were washed with brine (100 mL), dried over Na$_2$SO$_4$, filtered and concentrated. The residue was purified by chromatographic column on silica gel (eluted with 0% to 20% EtOAc/Petroleum) to afford 4,6-dichloro-1-isopropyl-3-methyl-1H-pyrazolo (4.0 g, 85% yield) as a light yellow solid. ESI-LCMS (m/z): 244.1 [M+1]$^+$.

Example 7

Preparation of 1-amino-3-(3-(1-isopropyl-3-methyl-4-morpholino-1H-pyrazolo[3,4-b]pyridin-6-yl)phenoxy)propan-2-ol

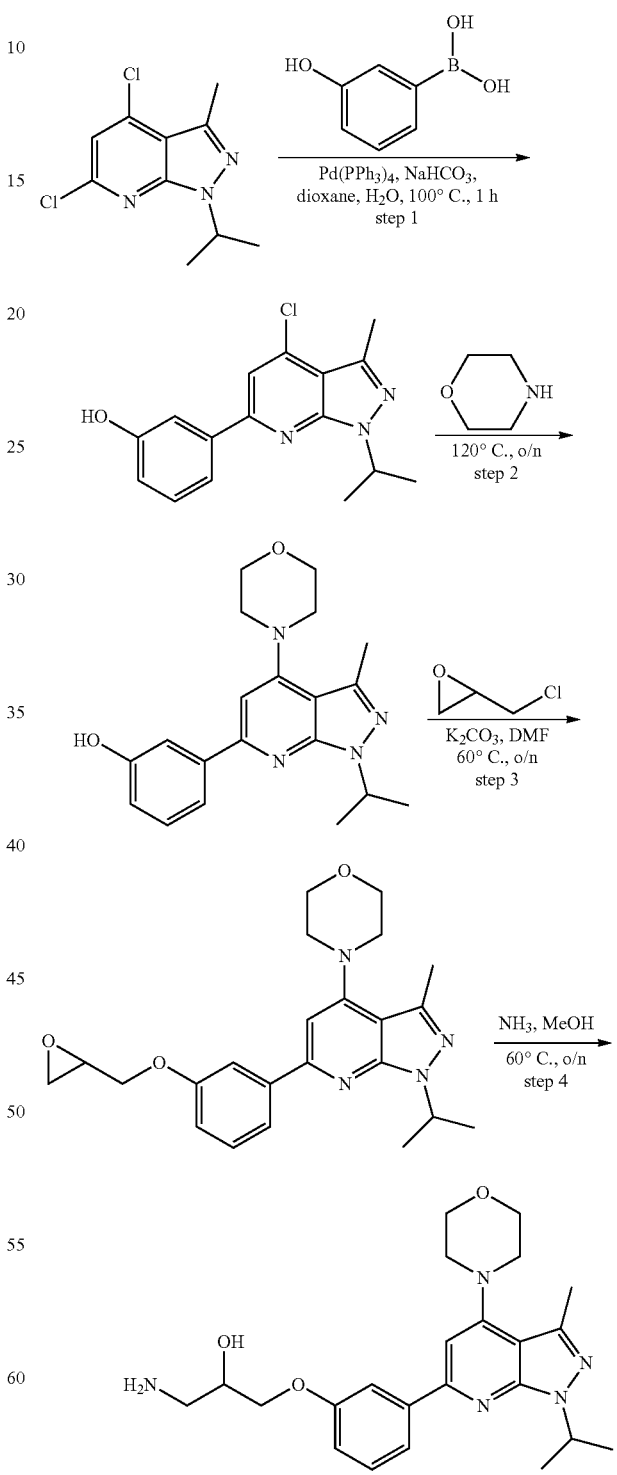

Step 1: Synthesis of 3-(4-chloro-1-isopropyl-3-methyl-1H-pyrazolo[3,4-b]pyridine-6-yl)phenol. To a solution of 4,6-dichloro-1-isopropyl-3-methyl-1H-pyrazolo[3,4-b]pyridine (450 mg, 1.85 mmol) in dioxane and water (3/1, 9 mL) was added 3-hydroxyphenyl-boronic acid (255 mg, 1.85 mmol), Pd(PPh$_3$)$_4$ (213 mg, 0.18 mmol), NaHCO$_3$ (466 mg, 5.55 mmol). The air was removed from the system by vacuum followed by filling with nitrogen for three times, then heated at 100° C. for 1 hour. After cooling down to room temperature, water (25 mL) was added, and the mixture was extracted with EtOAc (25 mL×2). The combined organic phase was dried over Na$_2$SO$_4$, filtered and concentrated. The residue was purified by preparative TLC on silica gel to obtain 3-(4-chloro-1-isopropyl-3-methyl-1H-pyrazolo[3,4-b]pyridine-6-yl)phenol (300 mg, 75% yield) as a light yellow solid. ESI-LCMS (m/z): 302.1 [M+1]$^+$.

Step 2: Synthesis of 3-(1-isopropyl-3-methyl-4-morpholino-1H-pyrazolo[3,4-b]pyridin-6-yl)phenol. A solution of 3-(4-chloro-1-isopropyl-3-methyl-1H-pyrazolo[3,4-b]pyridine-6-yl)phenol (300 mg, 0.99 mmol) in morpholine (10 mL) was heated at 120° C. for 14 h. After concentration, the residue was purified by preparative TLC on silica gel to obtain 3-(1-isopropyl-3-methyl-4-morpholino-1H-pyrazolo[3,4-b]pyridin-6-yl)phenol (300 mg, 85% yield) as a yellow solid. ESI-LCMS (m/z): 353.2 [M+1]$^+$.

Step 3: Synthesis of 4-(1-isopropyl-3-methyl-6-(3-(oxiran-2-ylmethoxy)phenyl)-1H-pyrazolo[3,4-b]pyridin-4-yl)morpholine. To a solution of 3-(1-isopropyl-3-methyl-4-morpholino-1H-pyrazolo[3,4-b]pyridine-6-yl)phenol (300 mg, 0.85 mmol) in DMF (5 mL) was added K$_2$CO$_3$ (352 mg, 2.55 mmol) and 2-(chloromethyl)oxirane (236 mg, 2.55 mmol). The mixture was heated at 60° C. for 14 h., cooled down to room temperature, diluted with water (25 mL) and the mixture was extracted with EtOAc (25 mL×2). The combined organic layers were washed with water (10 mL) and brine (10 mL), dried over Na$_2$SO$_4$, filtered and concentrated. The residue was purified by Preparative TLC on silica gel to obtain 4-(1-isopropyl-3-methyl-6-(3-(oxiran-2-ylmethoxy)phenyl)-1H-pyrazolo[3,4-b]pyridine-4-yl)morpholine (200 mg, 58% yield) as a light yellow solid. ESI-LCMS (m/z): 409.2 [M+1]$^+$.

Step 4: Synthesis of 1-amino-3-(3-(1-isopropyl-3-methyl-4-morpholino-1H-pyrazolo[3,4-b]pyridin-6-yl)phenoxy)propan-2-ol. 4-(1-Isopropyl-3-methyl-6-(3-(oxiran-2-ylmethoxy)phenyl)-1H-pyrazolo[3,4-b]pyridin-4-yl)morpholine (100 mg, 0.24 mmol) was dissolved in 7N ammonia solution in methanol (5 mL), and the mixture was heated at 60° C. for 14 h. After concentration, the residue was purified by preparative HPLC to obtain 1-amino-3-(3-(1-isopropyl-3-methyl-4-morpholino-1H-pyrazolo[3,4-b]pyridin-6-yl)phenoxy)propan-2-ol (40 mg, 38% yield) as a white solid. 1H NMR (500 MHz, CD$_3$OD) δ (ppm): 7.73-7.71 (m, 1H), 7.66 (d, J=7.5 Hz, 1H), 7.41 (t, J=8.0 Hz, 1H), 7.07 (dd, J=8.0 and 2.0 Hz, 1H), 7.00 (s, 1H), 5.33-5.28 (m, 1H), 4.10 (d, J=4.5 Hz, 2H), 4.04 (brs, 1H), 3.97-3.93 (m, 4H), 3.33-3.28 (m, 4H), 3.02-2.80 (m, 2H), 2.66 (s, 3H), 1.56 (d, J=7.0 Hz, 6H) ppm; ESI-LCMS (m/z): 426.3 [M+1]$^+$.

Example 8

Preparation of 1-(3-(3-cyclopropyl-1-isopropyl-4-(tetrahydro-2H-pyran-4-ylamino)-1H-pyrazolo[3,4-b]pyridin-6-yl)phenoxy)-3-(methylamino)propan-2-ol

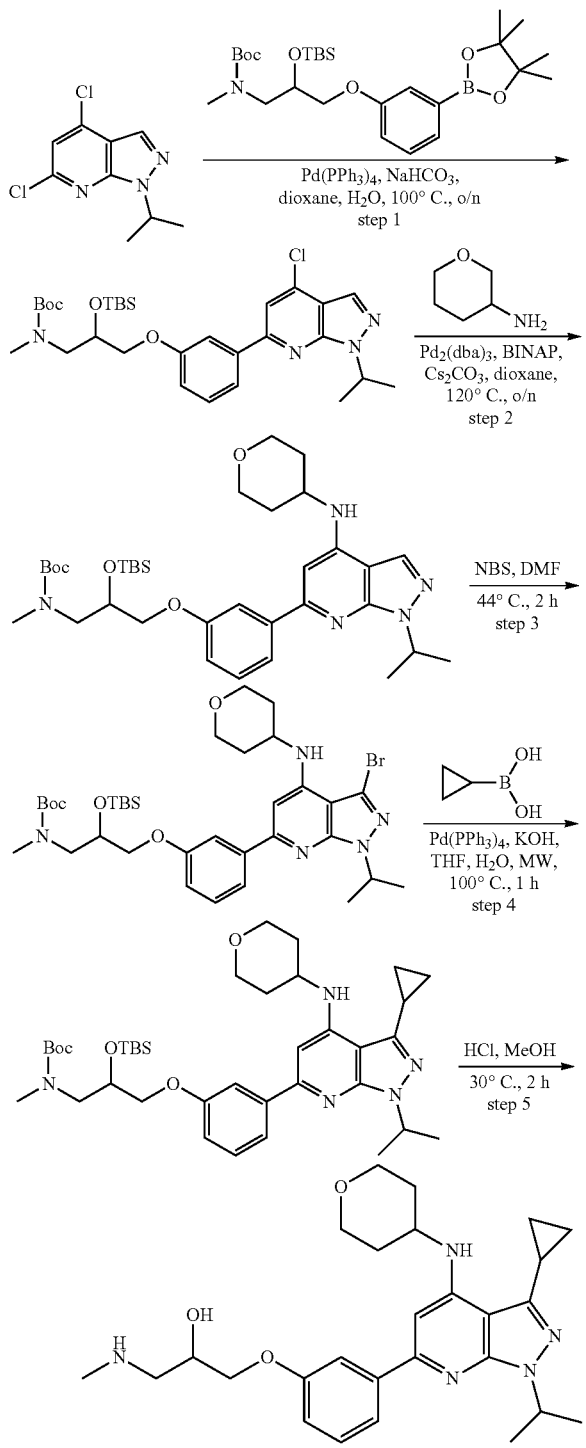

Step 1: Synthesis of tert-butyl 2-(tert-butyldimethylsilyloxy)-3-(3-(4-chloro-1-isopropyl-1H-pyrazolo[3,4-b]pyridin-6-yl)phenoxy)propyl(methyl)carbamate. To a suspension of 4,6-dichloro-1-isopropyl-1H-pyrazolo[3,4-b]pyridine (1.8 g, 7.9 mmol), tert-butyl 2-(tert-butyldimethylsilyloxy)-3-(3-(4,4,5,5-tetramethyl-1,3,2-dioxa-borolan-2-yl)phenoxy)propyl(methyl)carbamate (4.9 g, 9.4 mmol) and NaHCO$_3$ (2 g, 23.7 mmol) in dioxane and H$_2$O (3/1, 32 mL) was added Pd(PPh$_3$)$_4$ (1.8 g, 1.6 mmol). The air from the system was removed by vacuum and refilled with nitrogen for three times, then heated at 100° C. for 14 h. After cooling down to room temperature, water (50 mL) was added. The mixture was extracted with EtOAc (100 mL×2). The combined organic phase was dried over Na$_2$SO$_4$, filtered and concentrated. The residue was purified by chromatographic column on silica gel to obtain tert-butyl 2-(tert-butyldimethylsilyloxy)-3-(3-(4-chloro-1-isopropyl-1H-pyrazolo[3,4-b]pyridin-6-yl)phenoxy)propyl(methyl)carbamate (2.3 g, 50% yield) as a yellow solid. $^1$H NMR (500 MHz, CD$_3$OD) δ (ppm): 8.13 (s, 1H), 7.78-7.75 (m, 2H), 7.73 (d, J=8.0 Hz, 1H), 7.44 (t, J=8.0 Hz, 1H), 7.05 (dd, J=8.0 and 2.5 Hz, 1H), 5.42-5.36 (m, 1H), 4.41-4.33 (m, 1H), 4.12-3.98 (m, 2H), 3.60-3.48 (m, 1H), 3.40-3.33 (m, 1H), 3.00-2.97 (m, 3H), 1.63 (d, J=6.5 Hz, 6H), 1.50-1.43 (m, 9H), 0.94 (s, 9H), 0.20-0.15 (m, 6H) ppm.

Step 2: Synthesis of tert-butyl 2-(tert-butyldimethylsilyloxy)-3-(3-(1-isopropyl-4-(tetrahydro-2H-pyran-4-ylamino)-1H-pyrazolo[3,4-b]pyridin-6-yl)phenoxy)propyl(methyl)carbamate. To a suspension of tert-butyl 2-(tert-butyldimethylsilyloxy)-3-(3-(4-chloro-1-isopropyl-1H-pyrazolo[3,4-b]pyridin-6-yl)phenoxy)propyl(methyl)carbamate (2.3 g, 3.9 mmol); tetrahydro-2H-pyran-4-amine (1.9 g, 19.5 mmol); BINAP (485 mg, 0.8 mmol) and Cs$_2$CO$_3$ (3.8 g, 11.7 mmol) in dioxane (25 mL) was added Pd$_2$(dba)$_3$ (652 mg, 0.8 mmol). The system was purged with nitrogen for three times, then heated at 120° C. for 14 h. After cooling down to room temperature, water (50 mL) was added, the mixture was extracted with EtOAc (100 mL×2), the combined organic phases were dried over Na$_2$SO$_4$, filtered and concentrated. The residue was purified by chromatographic column on silica gel to obtain tert-butyl 2-(tert-butyldimethyl silyloxy)-3-(3-(1-isopropyl-4-(tetrahydro-2H-pyran-4-ylamino)-1H-pyrazolo[3,4-b]pyridine-6-yl)phenoxy)propyl(methyl)carbamate (1.5 g, 60% yield) as a yellow solid. ESI-LCMS (m/z): 654.3 [M+1]$^+$.

Step 3: Synthesis of tert-butyl 3-(3-(3-bromo-1-isopropyl-4-(tetrahydro-2H-pyran-4-ylamino)-1H-pyrazolo[3,4-b]pyridin-6-yl)phenoxy)-2-(tert-butyldimethylsilyloxy)propyl(methyl)carbamate. To a solution of tert-butyl 2-(tert-butyldimethylsilyloxy)-3-(3-(1-isopropyl-4-(tetrahydro-2H-pyran-4-ylamino)-1H-pyrazolo[3,4-b]pyridin-6-yl)phenoxy)propyl(methyl)carbamate (1.5 g, 2.3 mmol) in DMF (6 mL), NBS (450 mg, 2.5 mmol) was added while stirring at room temperature The mixture was then heated at 44° C. for 2 hours, cooled down to room temperature, diluted with EtOAc (100 mL) and the mixture was washed with water (30 mL×3) and brine (30 mL×1). The organic layer was dried over Na$_2$SO$_4$, filtered and concentrated to render a residue which was purified by chromatographic column on silica gel to obtain tert-butyl 3-(3-(3-bromo-1-isopropyl-4-(tetrahydro-2H-pyran-4-ylamino)-1H-pyrazolo[3,4-b]pyridin-6-yl)phenoxy)-2-(tert-butyldimethylsilyloxy)propyl(methyl)carbamate (1.4 g, 87% yield) as a yellow solid. ESI-MS (m/z): 732.3 [M+1]$^+$.

Step 4: Synthesis of tert-butyl 2-(tert-butyldimethylsilyloxy)-3-(3-(3-cyclopropyl-1-isopropyl-4-(tetrahydro-2H-pyran-4-ylamino)-1H-pyrazolo[3,4-b]pyridin-6-yl)phenoxy)propyl(methyl)carbamate. To a solution of tert-butyl 3-(3-(3-bromo-1-isopropyl-4-(tetrahydro-2H-pyran-4-ylamino)-1H-pyrazolo[3,4-b]pyridin-6-yl)phenoxy)-2-(tert-butyldimethylsilyloxy)propyl(methyl)carbamate (200 mg, 0.27 mmol), cyclopropylboronic acid (87 mg, 1 mmol) in THF (10 mL) and 2N aqueous KOH (2 ml) was added Pd(PPh$_3$)$_4$ (138 mg, 0.12 mmol). Air was removed from the system by cycles of vacuum followed by backfilling with nitrogen and the reaction vial sealed, placed in a microwave reactor and irradiated at 100° C. for 2 hours. Water (20 mL) was added, and the mixture was extracted with EtOAc (20 mL×2), the combined organic phases were dried over Na$_2$SO$_4$, filtered and concentrated. The residue was purified by preparative TLC on silica gel to obtain tert-butyl 2-(tert-butyldimethylsilyloxy)-3-(3-(3-cyclopropyl-1-isopropyl-4-(tetrahydro-2H-pyran-4-ylamino)-1H-pyrazolo[3,4-b]pyridin-6-yl)phenoxy)propyl(methyl)carbamate (35 mg, 19% yield) as a yellow solid. ESI-MS (m/z): 694.5 [M+1]$^+$.

Step 5: Synthesis of 1-(3-(3-cyclopropyl-1-isopropyl-4-(tetrahydro-2H-pyran-4-ylamino)-1H-pyrazolo[3,4-b]pyridin-6-yl)phenoxy)-3-(methylamino)propan-2-ol. A solution of tert-butyl 2-(tert-butyldimethylsilyloxy)-3-(3-(3-cyclopropyl-1-isopropyl-4-(tetrahydro-2H-pyran-4-ylamino)-1H-pyrazolo[3,4-b]pyridin-6-yl)phenoxy)propyl(methyl)carbamate (35 mg, 0.05 mmol) in MeOH (2 mL) was treated with 5N aqueous HCl solution (2 mL) and the resulting mixture was stirred at 30° C. for 2 hours. After concentration, the residue was purified by preparative HPLC to obtain 1-(3-(3-cyclopropyl-1-iso-propyl-4-(tetrahydro-2H-pyran-4-ylamino)-1H-pyrazolo[3,4-b]pyridin-6-yl)phenoxy)-3-(methylamino)propan-2-ol (8 mg, 33% yield) as a white solid. $^1$H NMR (500 MHz, CD$_3$OD) δ (ppm): 8.10 (s, 1H), 7.38 (d, J=10.0 Hz, 1H), 7.21-7.19 (m, 2H), 7.04-7.01 (m, 1H), 5.21-5.17 (m, 1H), 4.31-4.26 (m, 1H), 4.14-4.11 (m, 1H), 4.07-4.02 (m, 4H), 3.75-3.68 (m, 2H), 2.89-2.75 (m, 2H), 2.48 (s, 3H), 2.18-2.14 (m, 2H), 1.81-1.76 (m, 2H), 1.71-1.65 (m, 1H), 1.49 (d, J=8.5 Hz, 6H), 0.85-0.80 (m, 2H), 0.08-0.03 (m, 2H) ppm; ESI-MS (m/z): 480.3 [M+1]$^+$.

Example 9

Preparation of ethyl 6-bromo-1-isopropyl-1H-pyrazolo[3,4-b]pyridine-4-carboxylate and ethyl 6-bromo-2-isopropyl-2H-pyrazolo[3,4-b]pyridine-4-carboxylate

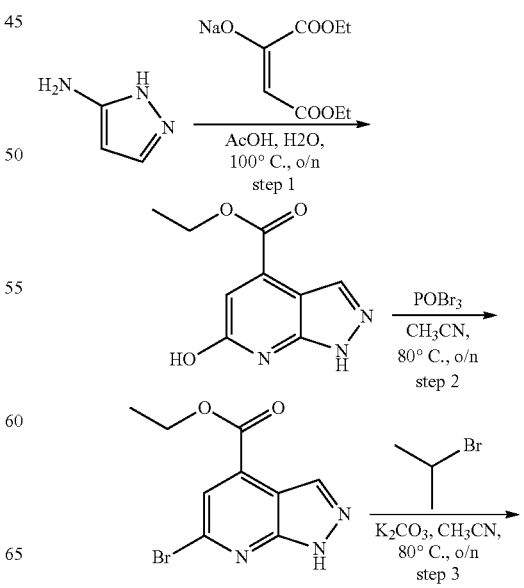

-continued

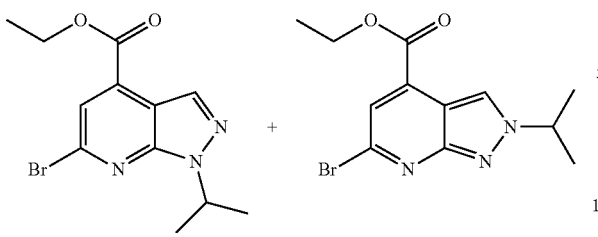

Step 1: Synthesis of ethyl 6-hydroxy-1H-pyrazolo[3,4-b]pyridine-4-carboxylate. A solution of 1H-pyrazol-5-amine (100 g, 1.2 mol) in AcOH (800 mL) was treated with a solution of sodium (E)-1,4-diethoxy-1,4-dioxobut-2-en-2-olate (250 g, 1.5 mol) in water (2400 mL). The mixture was stirred at 100° C. for 14 h, cooled down to room temperature and stirred for extra 20 min to render a precipitated. The mixture was filtered, the solid was collected and washed with water (300 mL×2) and petroleum ether (500 mL×3) to afford ethyl 6-hydroxy-1H-pyrazolo[3,4-b]pyridine-4-carboxylate (66.0 g, 26% yield). ESI-LCMS (m/z): 208.2 [M+1]$^+$.

Step 2: Synthesis of ethyl 6-bromo-1H-pyrazolo[3,4-b]pyridine-4-carboxylate. To a solution of ethyl 6-hydroxy-1H-pyrazolo[3,4-b]pyridine-4-carboxylate (40.0 g, 193 mmol) in $CH_3CN$ (200 mL) was added phosphoryl tribromide (110.0 g, 385 mmol). The mixture was stirred at 80° C. for 14 h, cooled down to room temperature, diluted with water (100 mL) and the pH adjusted to 9 by addition of saturated aqueous $Na_2CO_3$ solution (350 mL). Then the mixture was extracted with EtOAc (200 mL×2), the combined organic layers were washed with brine (300 mL×2), dried over $Na_2SO_4$ and concentrated to afford the ethyl 6-bromo-1H-pyrazolo[3,4-b]pyridine-4-carboxylate (40 g, 78% yield). ESI-LCMS (m/z): 270.0 [M+1]$^+$.

Step 3: Synthesis of ethyl 6-bromo-2-isopropyl-2H-pyrazolo[3,4-b]pyridine-4-carboxylate. A mixture of ethyl 6-bromo-1H-pyrazolo[3,4-b]pyridine-4-carboxylate (44.0 g, 0.16 mol); isopropyl bromide (40 g, 0.33 mol) and $K_2CO_3$ (34 g, 0.24 mol) in $CH_3CN$ (400 mL) was stirred at 80° C. for 14 h. After cooling down to room temperature, the mixture was filtered and the filtrate was collected and concentrated, diluted with $H_2O$ (400 mL), and extracted with EtOAc (300 mL×2). The combined organic layers were washed with brine (300 mL×2), dried over $Na_2SO_4$, filtered and concentrated. The residue was purified by chromatographic column on silica gel (petroleum ether/EtOAc=50/1 to 5/1) to afford the major isomer ethyl 6-bromo-1-isopropyl-1H-pyrazolo[3,4-b]pyridine-4-carboxylate (25.5 g, 50% yield) and the minor isomer ethyl 6-bromo-2-isopropyl-2H-pyrazolo[3,4-b]pyridine-4-carboxylate (16.5 g, 32% yield). ESI-LCMS (m/z): 312.2 [M+1]$^+$ Example 10

Preparation of N-((4,6-dimethyl-2-oxo-1,2-dihydropyridin-3-yl)methyl)-6-(3-(2-hydroxy-3-(methylamino)propoxy)phenyl)-1-isopropyl-1H-pyrazolo[3,4-b]pyridine-4-carboxamide

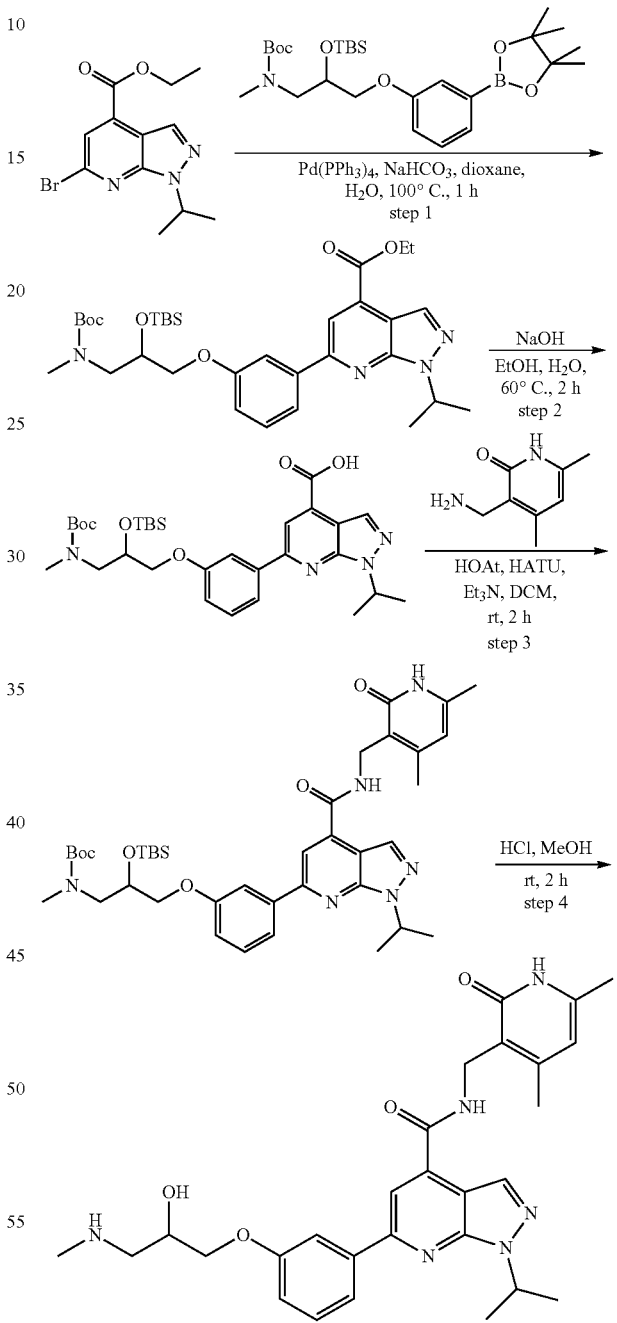

Step 1: Synthesis of ethyl 6-(3-(3-(tert-butoxycarbonyl)methyl)amino)-2-(tert-butyldimethylsilyloxy)propoxy)phenyl)-1-isopropyl-1H-pyrazolo[3,4-b]pyridine-4-carboxylate. To a solution of tert-butyl 2-(tert-butyldimethylsilyloxy)-3-(3-(4,4,5,5-tetramethyl-1,3,2-dioxaborolan-2-yl)phenoxy)propyl(methyl)carbamate above (4.0 g, 6.33 mmol), ethyl 6-bromo-1-isopropyl-1H- pyrazolo[3,4-b]pyridine-4-carboxylate (2.0 g, 6.33 mmol) and NaHCO₃ (1.6 g, 18.99 mmol) in dioxane (15 mL) and H₂O (5 mL), Pd(PPh3)4 (728 mg, 0.63 mmol) was added. The system was purged with nitrogen stream and then heated at 100° C. for 1 hour, cooled down to room temperature, diluted with H₂O (50 mL), extracted with EtOAc (50 mL×2), and the combined organic layers were dried over Na₂SO₄, filtered and concentrated. The residue was purified by chromatographic column on silica gel (petroleum ether/EtOAc=50/1 to 10/1) to afford ethyl 6-(3-(3-(tert-butoxycarbonyl(methyl)amino)-2-(tert-butyl-dimethylsilyloxy)propoxy)phenyl)-1-isopropyl-1H-pyrazolo[3,4-b]pyridine-4-carboxylate (2.5 g, 63% yield). ESI-LCMS (m/z): 627.3 [M+1]⁺, 649.3 [M+Na]⁺.

Step 2: Synthesis of 6-(3-(3-(tert-butoxycarbonyl(methyl)amino)-2-(tert-butyl dimethylsilyloxy)propoxy)phenyl)-1-isopropyl-1H-pyrazolo[3,4-b]pyridine-4-carboxylic acid. A solution of ethyl 6-(3-(3-(tert-butoxycarbonyl(methyl)amino)-2-(tert-butyl-di methylsilyloxy)propoxy)phenyl)-1-isopropyl-1H-pyrazolo[3,4-b]pyridine-4-carboxylate (2.5 g, 3.99 mmol) in EtOH (20 mL) was treated with aqueous NaOH solution (3N, 4.0 mL), and the resulting solution was heated to 60° C. for 2 hours. After cooling down to room temperature, the mixture was concentrated and treated with 2N HCl to adjust pH to 5.0. The white solid was collected and dried to afford 6-(3-(3-(tert-butoxycarbonyl(methyl)amino)-2-(tert-butyldimethylsilyloxy)propoxy)phenyl)-1-isopropyl-1H-pyrazolo[3,4-b]pyridine-4-carboxylic acid (2.0 g, 84% yield). ESI-LCMS (m/z): 621.3 [M+Na]⁺

Step 3: Synthesis of tert-butyl 2-(tert-butyldimethylsilyloxy)-3-(3-(4-((4,6-di methyl-2-oxo-2,3-dihydropyridin-3-yl)methylcarbamoyl)-1-isopropyl-1H-pyrazolo[3,4-b]pyridin-6-yl)phenoxy)propyl)methyl)carbamate. A mixture of 6-(3-(3-(tert-butoxycarbonyl(methyl)amino)-2-(tert-butyldimethyl silyloxy)propoxy)phenyl)-1-isopropyl-1H-pyrazolo[3,4-b]pyridine-4-carboxylic acid (150 mg, 0.25 mmol); 3-(aminomethyl)-4,6-dimethylpyridin-2(3H)-one (38 mg, 0.25 mmol); HOBT (68 mg, 0.50 mmol); HATU (190 mg, 0.50 mmol) and Et₃N (50 mg, 0.50 mmol) in dichloromethane (5 mL) was stirred at room temperature for 2 hours; diluted with DCM (30 mL), washed with saturated NH4Cl aqueous solution (20 mL), water (20 mL) and brine (20 mL). The organic phase was dried over Na₂SO₄, filtered and concentrated to get tert-butyl 2-(tert-butyldimethylsilyloxy)-3-(3-(4-((4,6-dimethyl-2-oxo-2,3-dihydropyridin-3-yl)methylcarbamoyl)-1-isopropyl-1H-pyrazolo[3,4-b]pyridin-6-yl)phenoxy)propyl(methyl)carbamate (190 mg, crude), which was used directly for next step without further purification. ESI-LCMS (m/z): 733.3 [M+H]⁺

Step 4: Synthesis of N-((4,6-dimethyl-2-oxo-2,3-dihydropyridin-3-yl)methyl)-6-(3-(2-hydroxy-3-(methylamino)propoxy)phenyl)-1-isopropyl-1H-pyrazolo[3,4-b]pyridine-4-carboxamide. To a solution of tert-butyl 2-(tert-butyldimethylsilyloxy)-3-(3-(4-((4,6-di methyl-2-oxo-2,3-dihydropyridin-3-yl)methylcarbamoyl)-1-isopropyl-1H-pyrazolo[3,4-b]pyridin-6-yl)phenoxy)propyl(methyl) carbamate (190 mg, crude from previous step) in MeOH (2 mL) was added 5N HCl aqueous solution (2 mL). The resulting solution was stirred at room temperature for 2 hours. After concentration, the residue was purified by preparative HPLC to afford N-((4,6-dimethyl-2-oxo-2,3-dihydropyridin-3-yl)methyl)-6-(3-(2-hydroxy-3-(methylamino)propoxy)phenyl)-1-isopropyl-1H-pyrazolo[3,4-b]pyridine-4-carboxamide (51 mg, 39% yield, two steps). 1H NMR (500 MHz, CD₃OD) δ (ppm): 8.36 (s, 1H), 8.05 (s, 1H), 7.85 (d, J=2.0 Hz, 1H), 7.82 (d, J=7.5 Hz, 1H), 7.45 (t, J=7.5 Hz, 1H), 7.10 (dd, J₁=8.0 Hz, J₂=2.0 Hz, 1H), 6.15 (s, 1H), 5.47-5.42 (m, 1H), 4.61 (s, 2H), 4.16-4.10 (m, 3H), 2.91-2.88 (m, 1H), 2.83-2.79 (m, 1H), 2.51 (s, 3H), 2.45 (s, 3H), 2.28 (s, 3H), 1.63 (d, J=7.0 Hz, 6H). ESI-LCMS (m/z): 519.2 [M+H]⁺

Example 11

Preparation of 6-(3-(3-amino-2-hydroxypropoxy)phenyl)-N-((4,6-dimethyl-2-oxo-1,2-dihydropyridin-3-yl)methyl)-2-isopropyl-2H-pyrazolo[3,4-b]pyridine-4-carboxamide

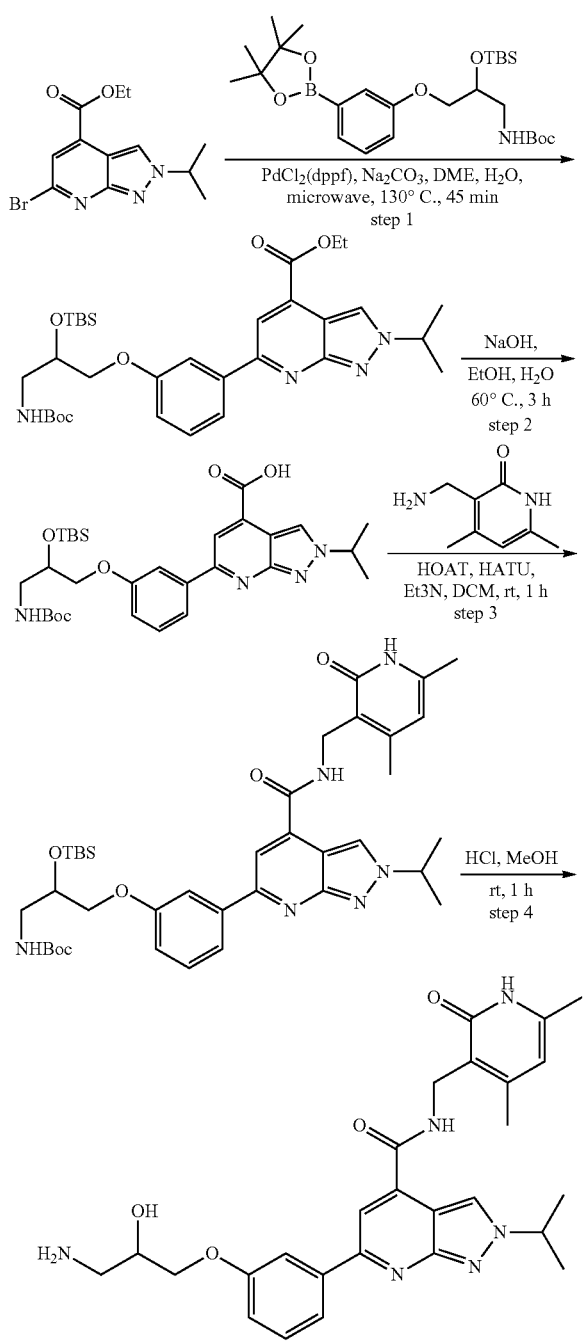

Step 1: Synthesis of ethyl 6-(3-(3-(tert-butoxycarbonylamino)-2-(tert-butyl-dimethylsilyloxy)propoxy)phenyl)-2-isopropyl-2H-pyrazolo[3,4-b]pyridine-4-carboxylate. A solution of ethyl 6-bromo-2-isopropyl-2H-pyrazolo[3,4-b]pyridine-4-carboxylate (310 mg, 1 mmol); tert-butyl 2-(tert-butyl dimethylsilyloxy)-3-(3-(4,4,5,5-tetramethyl-1,3,2-dioxaborolan-2-yl)phenoxy)propylcarbamate (610 mg, 1.2 mmol) and $Na_2CO_3$ (210 mg, 2 mmol) in DME and water (3/1, 4 mL) was treated with $PdCl_2(dppf)$ (82 mg, 0.1 mmol). Air was removed from the reaction vial by cycles of vacuum followed by backfilling with nitrogen and then the vial was sealed, placed in a microwave reactor and irradiated for 45 min at 130° C. After cooling down, water (15 mL) was added, the mixture was extracted with EtOAc (20 mL×2), the combined organic layers were washed with brine (25 mL×2), dried over $Na_2SO_4$ and concentrated. The residue was purified by preparative TLC on silica gel developed with DCM/EtOAc/MeOH=15/4/1 to afford ethyl 6-(3-(3-(tert-butoxy carbonyl amino)-2-(tert-butyldimethylsilyloxy)propoxy)phenyl)-2-isopropyl-2H-pyrazolo[3,4-b]pyridine-4-carboxylate (474 mg, 77% yield). ESI LCMS (m/z): 613.4 $[M+1]^+$.

Step 2: Synthesis of 6-(3-(3-(tert-butoxycarbonylamino)-2-(tert-butyldimethyl-silyloxy)propoxy)phenyl)-2-isopropyl-2H-pyrazolo[3,4-b]pyridine-4-carboxylic acid. A solution of ethyl 6-(3-(3-(tert-butoxycarbonylamino)-2-(tert-butyldimethyl-silyloxy)propoxy)phenyl)-2-isopropyl-2H-pyrazolo[3,4-b]pyridine-4-carboxylate (474 mg, 0.77 mmol) in EtOH and water (5/1, 30 mL) was treated with NaOH (124 mg, 3 mmol) and the mixture was heated at 60° C. for 2 hours. The solvent was removed in vacuo, the residue was treated with 2N HCl aqueous solution until pH=4.0, then the mixture was extracted with $CH_2Cl_2$ (15 mL×2), the combined organic layers were washed with brine (25 mL×2), dried over $Na_2SO_4$ filtered and concentrated to afford 6-(3-(3-(tert-butoxycarbonylamino)-2-(tert-butyldimethylsilyloxy)propoxy)phenyl)-2-isopropyl-2H-pyrazolo[3,4-b]pyridine-4-carboxylic acid (300 mg, 66% yield). ESI-LCMS (m/z): 585 $[M+1]^+$.

Step 3: Synthesis of tert-butyl 2-(tert-butyldimethylsilyloxy)-3-(3-(4-((4,6-dimethyl-2-oxo-1,2-dihydropyridin-3-yl)methylcarbamoyl)-2-isopropyl-2H-pyrazolo[3, 4-b]pyridin-6-yl)phenoxy)propylcarbamate. A mixture of 6-(3-(3-(tert-butoxycarbonylamino)-2-(tert-butyldimethylsilyloxy)propoxy)phenyl)-2-isopropyl-2H-pyrazolo[3,4-b]pyridine-4-carboxylic acid (300 mg, 0.5 mmol); 3-(aminomethyl)-4,6-dimethylpyridin-2(1H)-one (152 mg, 1 mmol); HATU (296 mg, 0.77 mmol; HOBt (105 mg, 0.77 mmol) and $Et_3N$ (78 mg, 0.77 mmol) in $CH_2Cl_2$ (30 mL) was stirred at room temperature for 1 hour. The mixture was diluted with $CH_2Cl_2$ (20 mL), washed with water (20 mL×3) and brine (20 mL). The combined organic layer was dried over $Na_2SO_4$, filtered and concentrated. The residue was purified by column chromatography on silica gel (DCM/MeOH=100/1 to 10/1) to afford the tert-butyl 2-(tert-butyldimethylsilyloxy)-3-(3-(4-((4,6-dimethyl-2-oxo-1,2-dihydropyridin-3-yl)methylcarbamoyl)-2-isopropyl-2H-pyrazolo[3,4-b]pyridin-6-yl)phenoxy)propylcarbamate (150 mg, 41% yield). ESI-LCMS (m/z): 719 $[M+1]^+$.

Step 4: Synthesis of 6-(3-(3-amino-2-hydroxypropoxy)phenyl)-N-((4,6-dimethyl-2-oxo-1,2-dihydropyridin-3-yl)methyl)-2-isopropyl-2H-pyrazolo[3,4-b]pyridine-4-carboxamide. A solution of tert-butyl 2-(tert-butyldimethylsilyloxy)-3-(3-(4-((4,6-dimethyl-2-oxo-1,2-dihydropyridin-3-yl)methylcarbamoyl)-2-isopropyl-2H-pyrazolo[3,4-b]pyridin-6-yl)phenoxy)propylcarbamate (150 mg, 0.2 mmol) in MeOH (2 mL) was treated with 2N HCl solution in MeOH (4 mL). The mixture was stirred for 1 hour at room temperature, concentrated under vacuum and the residue was purified by preparative HPLC to afford 6-(3-(3-amino-2-hydroxypropoxy)phenyl)-N-((4,6-dimethyl-2-oxo-1,2-dihydro-pyridin-3-yl)methyl)-2-isopropyl-2H-pyrazolo[3,4-b]pyridine-4-carboxamide (12 mg, 11% yield). $^1H$ NMR (500 MHz, $CD_3OD$) δ (ppm): 8.59 (s, 1H), 8.00 (s, 1H), 7.79 (s, 1H), 7.74 (d, J=8.0 Hz, 1H), 7.41 (t, J=7.5 Hz, 1H), 7.08 (d, J=8.0 Hz, 1H), 6.12 (s, 1H), 4.93-4.87 (m, 1H), 4.57 (s, 2H), 4.10-4.07 (m, 2H), 4.05-3.99 (m, 1H), 3.00-2.90 (m, 1H), 2.85-2.80 (m, 1H), 2.41 (s, 3H), 2.24 (s, 3H), 1.69 (d, J=6.0 Hz, 6H) ppm; ESI-LCMS (m/z): 505.3 $[M+1]^+$.

Example 12

Preparation of 1-(3-(1-isopropyl-4-(1H-pyrrolo[2,3-b]pyridin-5-yl)-1H pyrazolo[3,4-b]pyridin-6-yl)-5-methoxyphenoxy)-3-(methylamino)propan-2-ol

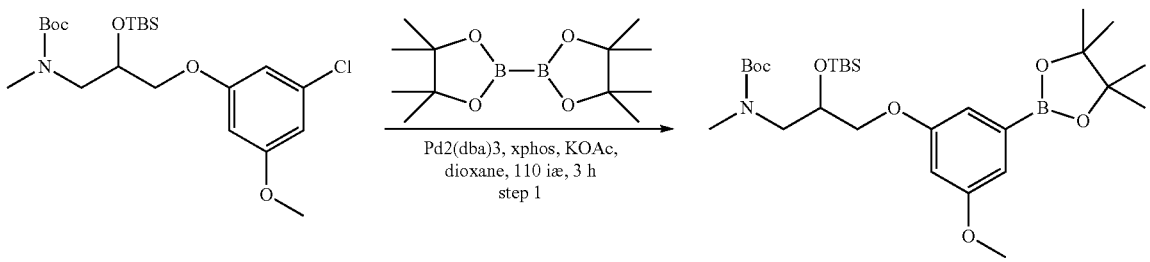

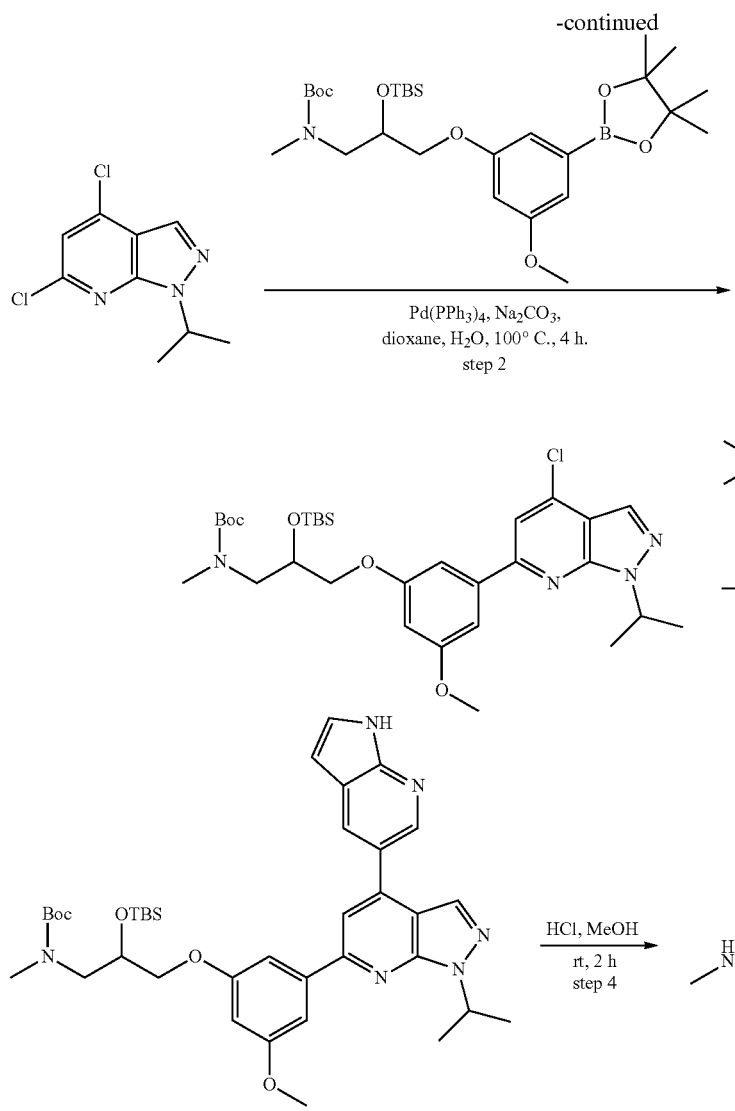

Step 1: Synthesis of tert-butyl 2-(tert-butyldimethylsilyloxy)-3-(3-methoxy-5-(4,4,5,5-tetramethyl-1,3,2-dioxaborolan-2-yl)phenoxy)propyl)methyl)carbamate. A mixture of tert-butyl 2-(tert-butyldimethylsilyloxy)-3-(3-chloro-5-methoxyphenoxy)propyl(methyl)carbamate (2.8 g, 6.1 mmol); 4,4,4',4',5,5,5',5'-octamethyl-2,2'-bi(1,3,2-dioxaborolane) (3.1 g, 12.2 mmol); Pd$_2$(dba)$_3$ (428 mg, 0.61 mmol); XPhos (290 mg, 0.61 mmol) and KOAc (1.8 g, 18.3 mmol) in 50 mL of dioxane was heated at 110° C. under N$_2$ for 3 h. Then 50 mL of water was added and the mixture extracted with EtOAc (50 mL×3), the combined organic layers were dried over Na$_2$SO$_4$, filtered and concentrated. The residue was purified by chromatographic column on silica gel (petroleum ether/EtOAc=10/1) to afford tert-butyl 2-(tert-butyldimethyl silyloxy)-3-(3-methoxy-5-(4,4,5,5-tetramethyl-1,3,2-dioxaborolan-2-yl)phenoxy)propyl(methyl) carbamate (4.2 g, 72% yield). ESI-LCMS (m/z): 574.3 [M+23]$^+$.

Step 2: 2-(tert-butyldimethylsilyloxy)-3-(3-(4-chloro-1-isopropyl-1H-pyrazolo[3,4-b]pyridin-6-yl)-5-methoxyphenoxy)propyl(methyl)carbamate. A mixture of 4,6-dichloro-1-isopropyl-1H-pyrazolo[3,4-b]pyridine (1.08 g, 4.72 mmol); tert-butyl 2-(tert-butyldimethylsilyloxy)-3-(3-methoxy-5-(4,4,5,5-tetra-methyl-1,3,2-dioxaborolan-2-yl) phenoxy)propyl(methyl)carbamate (4.42 g, 8.02 mmol); Pd(PPh$_3$)$_4$ (545 mg, 0.47 mmol) and Na$_2$CO$_3$ (1.5 g, 14.2 mmol) in 50 mL of dioxane/H$_2$O (v/v=10:1) was heated at 100° C. under N$_2$ for 14 h. LCMS indicated product formed. Water (100 mL) was added and the mixture was extracted with EtOAc (50 mL×3), the combined organic phases were washed with brine (50 mL), dried over Na$_2$SO$_4$, filtered and concentrated. The residue was purified by chromatographic column on silica gel (petroleum ether/EtOAc=10/1) to afford 2-(tert-butyldimethyl-silyloxy)-3-(3-(4-chloro-1-isopropyl-1H-pyrazolo[3,4-b]pyridine-6-yl)-5-methoxy-phenoxy)propyl(methyl)carbamate (2.8 g, 93% yield). ESI-LCMS (m/z): 619.3 [M+1]$^+$.

Step 3: Synthesis of tert-butyl 2-(tert-butyldimethylsilyloxy)-3-(3-(1-isopropyl-4-(1H-pyrrolo[2,3-b]pyridin-5-yl)-1H-pyrazolo[3,4-b]pyridin-6-yl)-5-methoxy-phenoxy)propyl)methyl)carbamate. A mixture of tert-butyl 2-(tert-butyldimethylsilyloxy)-3-(3-(7-chloro-3-isopropyl-pyrazolo[1,5-a]pyrimidin-5-yl)-5-methoxyphenoxy)propyl(methyl) carbamate (150 mg, 0.24 mmol); 5-(4,4,5,5-tetramethyl-1, 3,2-dioxaborolan-2-yl)-1H-pyrrolo[2,3-b]pyridine (118 mg, 0.48 mmol); Pd(PPh₃)₄ (28 mg, 0.024 mmol) and Na₂CO₃ (78 mg, 0.73 mmol) in 11 mL of dioxane/H₂O (v/v=10:1) was heated at 100° C. under N₂ for 14 h. After cooling down to room temperature, water (30 mL) was added and the mixture was extracted with EtOAc (30 mL×3). The organic phase was concentrated and the residue was purified by preparative TLC on silica gel (CH₂Cl₂/MeOH=20:1) to afford tert-butyl 2-(tert-butyldimethylsilyloxy)-3-(3-(1-isopropyl-4-(1H-pyrrolo[2,3-b]pyridin-5-yl)-1H-pyrazolo[3,4-b]pyridin-6-yl)-5-methoxyphenoxy)propyl(methyl)carbamate (200 mg, >100% yield). ESI-LCMS (m/z): 701.3 [M+1]⁺.

Step 4: Synthesis of 1-(3-(1-isopropyl-4-(1H-pyrrolo[2,3-b]pyridin-5-yl)-1H-pyrazolo[3,4-b]pyridin-6-yl)-5-methoxyphenoxy)-3-(methylamino)propan-2-ol. A solution of tert-butyl 2-(tert-butyldimethylsilyloxy)-3-(3-(1-isopropyl-4-(1H-pyrrolo[2,3-b]pyridin-5-yl)-1H-pyrazolo[3,4-b]pyridin-6-yl)-5-methoxy-phenoxy)propyl(methyl)carbamate (200 mg, from previous step) in 2 mL of MeOH was treated with 6N HCl aqueous solution (2 mL) and the mixture was stirred at room temperature for 2 hours. The solvent was removed under vacuum and the residue was purified by preparative HPLC to afford 1-(3-(1-isopropyl-4-(1H-pyrrolo[2,3-b]pyridin-5-yl)-1H-pyrazolo[3,4-b]pyridin-6-yl)-5-methoxyphenoxy)-3-(methylamino)propan-2-ol (42 mg, 35% yield for two steps) as a white solid. ¹H NMR (500 MHz, CD₃OD) δ (ppm): 8.74 (d, J=2.0 Hz, 1H), 8.55 (d, J=2.0 Hz, 1H), 8.29 (s, 1H), 7.85 (s, 1H), 7.55 (d, J=3.5 Hz, 1H), 7.45 (d, J=2.5 Hz, 2H), 6.69 (t, J=1.5 Hz, 2H), 5.50-5.45 (m, 1H), 4.32-4.29 (m, 1H), 4.20-4.12 (m, 2H), 3.92 (s, 3H), 3.31-3.19 (m, 2H), 2.79 (s, 3H), 1.66 (d, J=6.5 Hz, 6H) ppm; LC-MS (m/z): 487.2 [M+1]⁺.

Example 13

Preparation of 1-(3-chloro-5-(1-isopropyl-4-(tetrahydro-2H-pyran-4-yl-amino)-1H-pyrazolo[3,4-b]pyridin-6-yl)phenoxy)-3-(methylamino)propan-2-ol

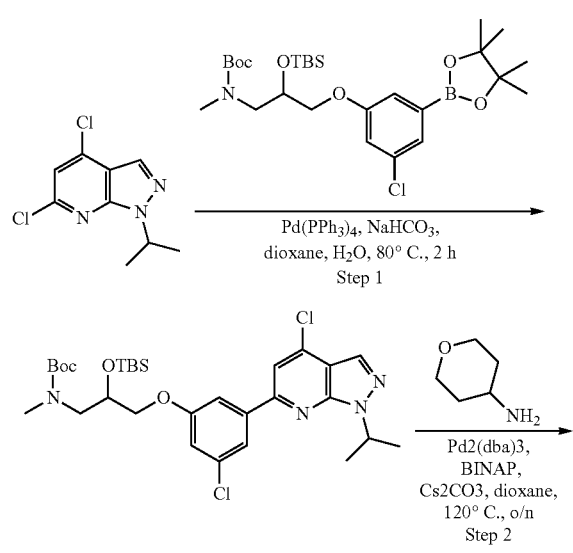

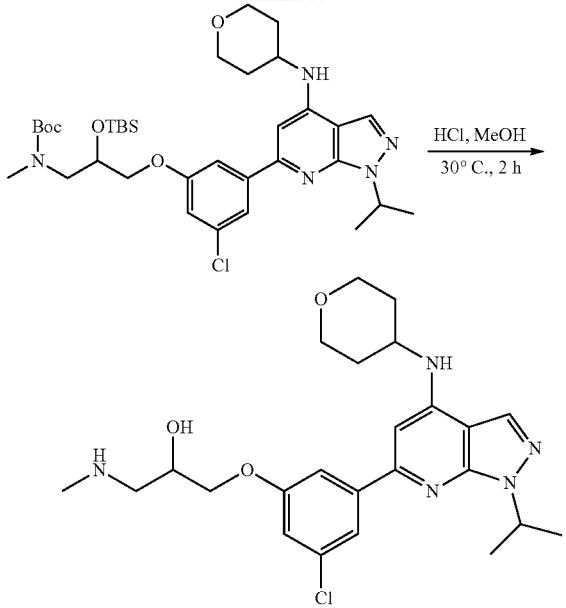

Step 1: Synthesis of tert-butyl 2-(tert-butyldimethylsilyloxy)-3-(3-chloro-5-(4-chloro-1-isopropyl-1H-pyrazolo[3,4-b]pyridin-6-yl)phenoxy)propyl(methyl)carbamate: To a solution of 4,6-dichloro-1-isopropyl-1H-pyrazolo[3,4-b]pyridine (67 mg, 0.29 mmol); tert-butyl 2-(tert-butyldimethylsilyloxy)-3-(3-chloro-5-(4,4,5,5-tetramethyl-1,3,2-dioxaborolan-2-yl)phenoxy)propyl(methyl)carbamate (195 mg, 0.35 mmol) and NaHCO₃ (73 mg, 0.87 mmol) in dioxane and water (3/1, 12 mL) was added Pd(PPh₃)₄ (69 mg, 0.06 mmol). The vial was purged with nitrogen for three times, then heated at 80° C. for 2 hours, cooled down to room temperature and the mixture was diluted with water (20 mL) and extracted with EtOAc (20 mL×2). The combined organic phases were concentrated and the residue was purified by preparative TLC on silica gel to obtain tert-butyl 2-(tert-butyldimethylsilyloxy)-3-(3-chloro-5-(4-chloro-1-isopropyl-1H-pyrazolo[3,4-b]pyridin-6-yl)phenoxy)propyl (methyl)carbamate (140 mg, 47% yield) as a yellow solid. ¹H NMR (500 MHz, CD₃OD) δ (ppm): 8.14 (s, 1H), 7.79 (s, 1H), 7.77 (d, J=2.0 Hz, 1H), 7.67-7.64 (m, 1H), 7.07 (s, 1H), 5.41-5.35 (m, 1H), 4.39-4.31 (m, 1H), 4.10-4.06 (m, 1H), 4.05-3.96 (m, 1H), 3.55-3.45 (m, 1H), 3.39-3.33 (m, 1H), 3.00-2.97 (m, 3H), 1.62 (d, J=7.0 Hz, 6H), 1.50-1.43 (m, 9H), 0.95-0.90 (m, 9H), 0.19-0.10 (m, 6H).

Step 2: Synthesis of tert-butyl 2-(tert-butyldimethylsilyloxy)-3-(3-chloro-5-(1-isopropyl-4-(tetrahydro-2H-pyran-4-ylamino)-1H-pyrazolo[3,4-b]pyridin-6-yl)phenoxy)propyl(methyl)carbamate. To a solution of tert-butyl 2-(tert-butyldimethylsilyloxy)-3-(3-chloro-5-(4-chloro-1-isopropyl-1H-pyrazolo[3,4-b]pyridin-6-yl)phenoxy)propyl (methyl)carbamate (130 mg, 0.21 mmol); tetrahydro-2H-pyran-4-amine (85 mg, 0.84 mmol); BINAP (37 mg, 0.06 mmol) and Cs₂CO₃ (205 mg, 0.63 mmol) in dioxane (10 mL) was added Pd₂(dba)₃ (49 mg, 0.06 mmol). The vial was purged with nitrogen for three times, then heated at 120° C. for 14 h. Water (10 mL) was added, the mixture was extracted with EtOAc (20 mL×2), the combined organic phases were dried over Na₂SO₄, filtered and concentrated. The residue was purified by preparative TLC on silica gel to obtain tert-butyl 2-(tert-butyldimethylsilyloxy)-3-(3-chloro-5-(1-isopropyl-4-(tetrahydro-2H-pyran-4-ylamino)-1H- pyrazolo[3,4-b]pyridin-6-yl)phenoxy)propyl(methyl)carbamate (110 mg, 71% yield) as a yellow solid. $^1$H NMR (500 MHz, CD$_3$OD) δ (ppm): 8.13 (s, 1H), 7.62-7.59 (m, 1H), 7.52-7.49 (m, 1H), 7.02-7.00 (m, 1H), 6.66 (s, 1H), 5.30-5.21 (m, 1H), 4.40-4.31 (m, 1H), 4.10-3.90 (m, 5H), 3.68-3.61 (m, 1H), 3.57-3.45 (m, 1H), 3.40-3.33 (m, 1H), 3.00-2.97 (m, 3H), 2.15-2.05 (m, 2H), 1.76-1.65 (m, 2H), 1.55 (d, J=8.5 Hz, 6H), 1.46 (s, 9H), 0.90 (s, 9H), 0.16 (s, 3H), 0.15 (s, 3H) ppm.

Step 3: Synthesis of 1-(3-chloro-5-(1-isopropyl-4-(tetrahydro-2H-pyran-4-yl-amino)-1H-pyrazolo[3,4-b]pyridin-6-yl)phenoxy)-3-(methylamino)propan-2ol. A solution of tert-butyl 2-(tert-butyldimethylsilyloxy)-3-(3-chloro-5-(1-isopropyl-4-(tetrahydro-2H-pyran-4-ylamino)-1H-pyrazolo[3,4-b]pyridin-6-yl)phenoxy)propyl(methyl)carbamate (110 mg, 0.21 mmol) in MeOH (2 mL) was treated with 5N HCl aqueous solution (2 mL) and the mixture stirred at 30° C. for 2 hours; concentrated under vacuo and the resulting residue was purified by preparative HPLC to obtain 1-(3-chloro-5-(1-isopropyl-4-(tetrahydro-2H-pyran-4-yl-amino)-1H-pyrazolo[3,4-b]pyridin-6-yl)phenoxy)-3-(methylamino)propan-2-ol (white solid, 49 mg, 65% yield) as formic acid salt. $^1$H NMR (500 MHz, CD$_3$OD) δ (ppm): 8.56 (brs, 1H), 8.15 (s, 1H), 7.64-7.63 (m, 1H), 7.58-7.57 (m, 1H), 7.10-7.09 (m, 1H), 6.67 (s, 1H), 5.29-5.23 (m, 1H), 4.30-4.27 (m, 1H), 4.17-4.11 (m, 2H), 4.05-3.96 (m, 3H), 3.68-3.62 (m, 2H), 3.30-3.27 (m, 1H), 3.22-3.17 (m, 1H), 2.77 (s, 3H), 2.09-2.06 (m, 2H), 1.75-1.65 (m, 2H), 1.56 (d, J=8.0 Hz, 6H) ppm; ESI-LCMS (m/z): 474.2 [M+1]$^+$.

Example 14

Preparation of 1-(3-(1-isopropyl-4-(pyrimidin-5-ylamino)-1H-pyrazolo[3,4-b]pyridin-6-yl)-5-methoxyphenoxy)-3-(methylamino)propan-2-ol

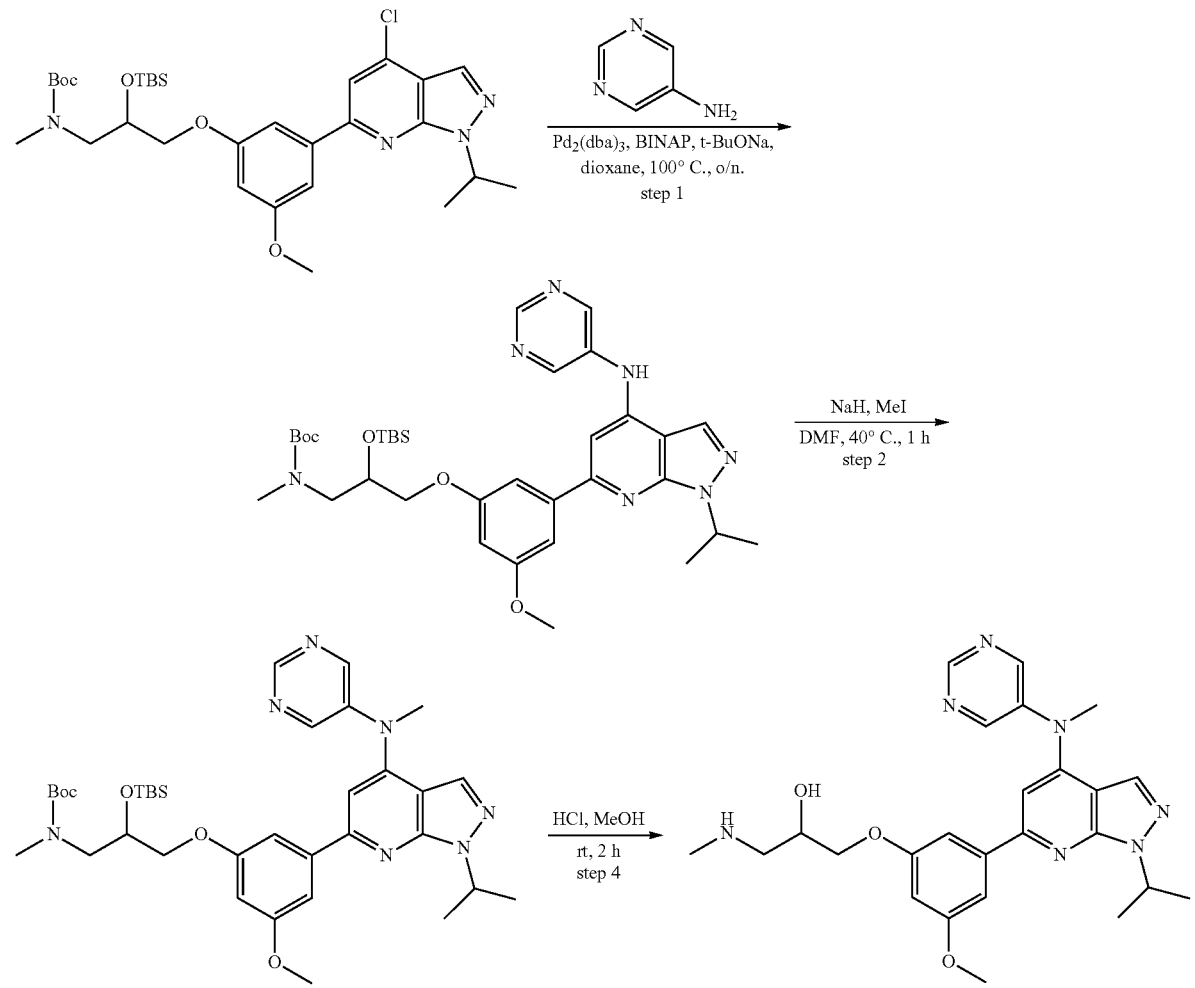

Step 1: Synthesis of tert-butyl 2-(tert-butyldimethylsilyloxy)-3-(3-(1-isopropyl-4-(pyrimidin-5-ylamino)-1H-pyrazolo[3,4-b]pyridin-6-yl)-5-methoxyphenoxy)propyl(methyl)carbamate. A mixture of tert-butyl 2-(tert-butyldimethylsilyloxy)-3-(3-(7-chloro-3-isopropyl-pyrazolo[1,5-a]pyrimidin-5-yl)-5-methoxyphenoxy)-propyl (methyl)-carbamate (600 mg, 0.97 mmol); pyrimidin-5-amine (139 mg, 1.46 mmol); Pd$_2$(dba)$_3$ (136 mg, 0.194 mmol); BINAP (121 mg, 0.19 mmol) and NaOt-Bu (286 mg, 2.31 mmol) in 15 mL of dioxane was heated at 100° C. under N$_2$ for 14 h. After cooling down to room temperature, water (30 mL) was added and the mixture was extracted with EtOAc (30 mL×3). The organic phase was concentrated and the residue was purified by preparative TLC on silica gel developed with DCM/MeOH=20:1 to afford 2-(tert-butyldimethylsilyloxy)-3-(3-(1-isopropyl-4-(pyrimidin-5-ylamino)-1H-pyrazolo[3,4-b]pyridin-6-yl)-5-methoxyphenoxy)propyl(methyl)carbamate (190 mg, 29% yield) as a pale yellow solid. ESI-LCMS (m/z): 678.3 [M+1]+.

Step 2: Synthesis of tert-butyl 2-(tert-butyldimethylsilyloxy)-3-(3-(1-isopropyl-4-(methyl(pyrimidin-5-yl)amino)-1H-pyrazolo[3,4-b]pyridin-6-yl)-5-methoxy phenoxy)propyl(methyl)carbamate. A solution of 2-(tert-butyldimethylsilyloxy)-3-(3-(1-isopropyl-4-(pyrimidin-5-ylamino)-1H-pyrazolo[3,4-b]pyridin-6-yl)-5-methoxyphenoxy)propyl(methyl)carbamate (190 mg, 0.28 mmol) in 5 mL of DMF was treated with NaH (210 mg, 1.40 mmol) and the mixture stirred at room temperature for 20 minutes. Then MeI (114 mg, 2.8 mmol) was added and the system was further stirred at 40° C. for 1 hour. The mixture was quenched with cold water, extracted with EtOAc (20 mL×3), the combined organic phases were dried over Na$_2$SO$_4$, filtered and concentrated. The residue was purified by preparative TLC on silica gel developed with DCM/MeOH=20:1 to afford tert-butyl 2-(tert-butyldimethylsilyloxy)-3-(3-(1-isopropyl-4-(methyl (pyrimidin-5-yl)amino)-1H-pyrazolo[3,4-b]pyridin-6-yl)-5-methoxyphenoxy)propyl(methyl)carbamate (105 mg, yield 53% yield) as a pale yellow solid. ESI-LCMS (m/z): 692.3 [M+1]+.

Step 3: Synthesis of 1-(3-(1-isopropyl-4-(pyrimidin-5-ylamino)-1H-pyrazolo[3,4-b]pyridin-6-yl)-5-methoxyphenoxy)-3-(methylamino)propan-2-ol. To a solution of tert-butyl 2-(tert-butyldimethylsilyloxy)-3-(3-(1-isopropyl-4-(methyl (pyrimidin-5-yl)amino)-1H-pyrazolo[3,4-b]pyridin-6-yl)-5-methoxyphenoxy)propyl(methyl)carbamate (105 mg) in 2 mL of MeOH was added 6N HCl aqueous solution (2 mL) and the mixture was stirred at room temperature for 2 hours. The solvent was removed under vacuum and the residue was purified by preparative HPLC to afford 1-(3-(1-isopropyl-4-(pyrimidin-5-ylamino)-1H-pyrazolo[3,4-b]pyridin-6-yl)-5-methoxyphenoxy)-3-(methylamino)propan-2-ol (55 mg, formic acid salt, 75% yield) as a white solid. $^1$H NMR (500 MHz, CD$_3$OD) δ (ppm): 9.12 (s, 1H), 8.86 (s, 2H), 8.60 (brs, 1H), 7.28 (d, J=11.0 Hz, 2H), 7.04 (s, 1H), 6.70 (s, 1H), 6.67 (t, J=2.0 Hz, 1H), 5.40-5.30 (m, 1H), 4.35-4.30 (m, 1H), 4.20-4.09 (m, 2H), 3.89 (s, 3H), 3.68 (s, 3H), 3.22-3.19 (m, 2H), 2.79 (s, 3H), 1.54 (d, J=6.5 Hz, 6H) ppm; LC-MS (m/z): 478.2[M+1]+.

Example 15

Preparation of 6-[3-(3-methylamino-2-hydroxy-propoxy)-phenyl]-1-isopropyl-4-morpholin-4-yl-1H-pyrazolo[3,4-b]pyridine-5-carboxylic acid ethyl ester

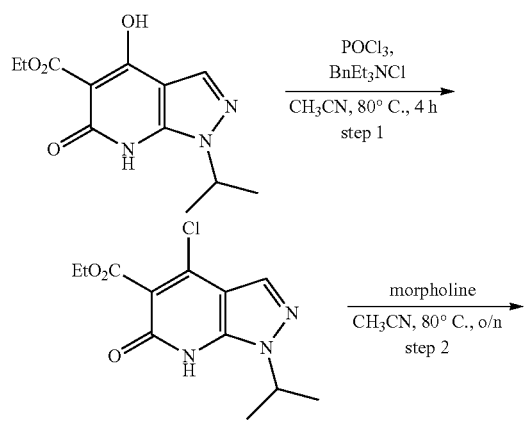

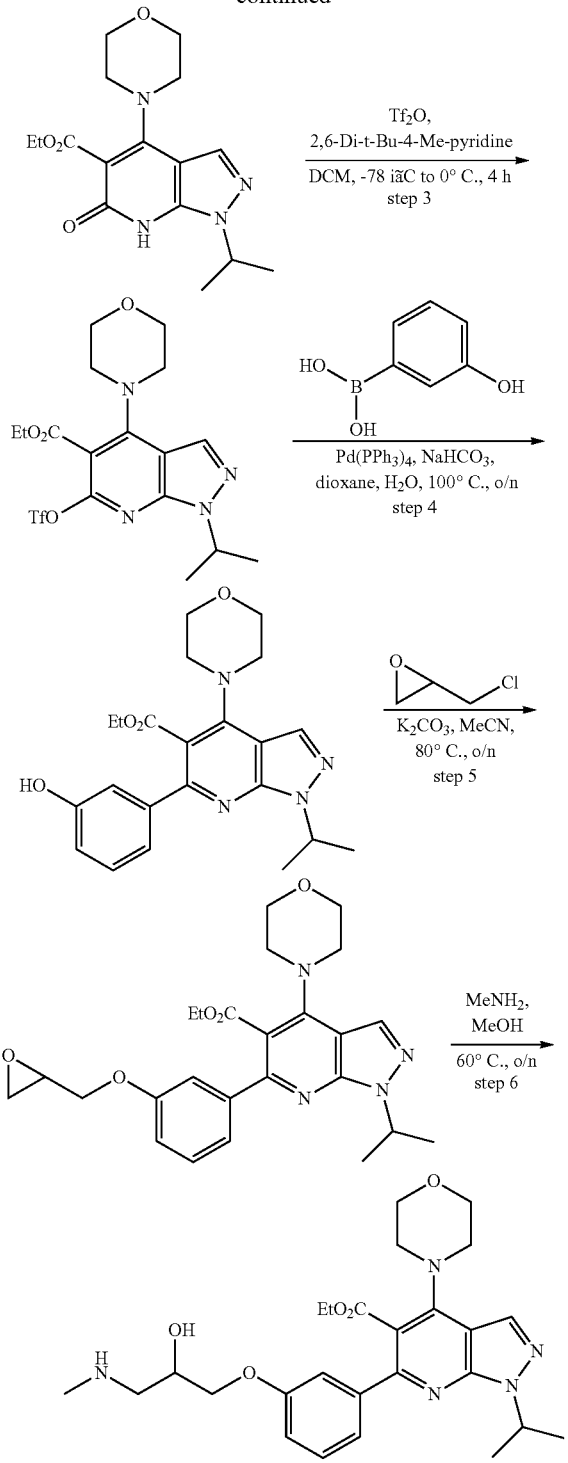

Step 1: Synthesis of 4-Chloro-1-isopropyl-6-oxo-6,7-dihydro-1H-pyrazolo[3,4-b]pyridine-5-carboxylic acid ethyl ester. A solution of 4-hydroxy-1-isopropyl-6-oxo-6,7-dihydro-1H-pyrazolo[3,4-b]pyridine-5-carboxylic acid ethyl ester (5.0 g, 18.87 mmol) in CH$_3$CN (150 mL) was treated with POCl$_3$ (13.0 g, 84.90 mmol) and BnEt$_3$NCl (17.0 g, 75.47 mmol) and the mixture was heated to 80° C. for 4 h. After cooling down to room temperature, water (200 mL) was added dropwise and the mixture was further stirred for 20 min., extracted with EtOAc (150 mL×3), the combined organic layers were washed with brine, dried over Na₂SO₄, filtered and concentrated. The resulting residue was purified by passage through a column of silica gel (petroleum ether/EtOAc=100/1 to 10/1) to give 4-Chloro-1-isopropyl-6-oxo-6,7-dihydro-1H-pyrazolo[3,4-b]pyridine-5-carboxylic acid ethyl ester (3.0 g, 57% yield). ESI-LCMS (m/z): 284.1 [M+1]⁺.

Step 2: Synthesis of 1-Isopropyl-4-morpholin-4-yl-6-oxo-6,7-dihydro-1H-pyrazolo[3,4-b]pyridine-5-carboxylic acid ethyl ester. A solution of 4-chloro-1-isopropyl-6-oxo-6,7-dihydro-1H-pyrazolo[3,4-b]pyridine-5-carboxylic acid ethyl ester (800 mg, 2.83 mmol) in CH₃CN (80 mL) was treated with neat morpholine (738 mg, 8.48 mmol). The mixture was heated to 80° C. for 14 h and concentrated under high vacuum, diluted with water (50 mL) and the mixture was extracted with EtOAc (50 mL×2). The organic layers were combined, washed with brine and dried over Na₂SO₄, filtration and concentrated. The resulting residue was purified by chromatographic column on silica gel (petroleum ether/EtOAC=4/1) to give 1-Isopropyl-4-morpholin-4-yl-6-oxo-6,7-dihydro-1H-pyrazolo[3,4-b]pyridine-5-carboxylic acid ethyl ester (800 mg, 85% yield). ESI-LCMS (m/z): 335.2 [M+1]⁺.

Step 3: Synthesis of 1-Isopropyl-4-morpholin-4-yl-6-trifluoromethanesulfonyloxy-1H-pyrazolo[3,4-b]pyridine-5-carboxylic acid ethyl ester. A solution of 1-isopropyl-4-morpholin-4-yl-6-oxo-6,7-dihydro-1H-pyrazolo[3,4-b]pyridine-5-carboxylic acid ethyl ester (800 mg, 2.40 mmol) and 2,6-di-tert-butyl-4-methylpyridine (740 mg, 3.60 mmol) in DCM (40 mL) stirred –78° C. under nitrogen atmosphere, was treated with slow addition of Tf₂O (1.2 g, 4.32 mmol) dissolved in DCM (40 mL). The mixture was stirred at –78° C. for 15 minutes, warmed to 0° C. and stirred at that temperature for 4 hours. Saturated NaHCO₃ aqueous solution (50 mL) was added to the mixture, the organic layer was separated and washed with water (50 mL) and 10% HCl solution (50 mL), dried over Na₂SO₄ filtered and concentrated to give 1-isopropyl-4-morpholin-4-yl-6-trifluoromethane sulfonyloxy-1H-pyrazolo[3,4-b]pyridine-5-carboxylic acid ethyl ester (1.1 g, 100% yield). ESI-LCMS (m/z): 467.1 [M+1]⁺.

Step 4: Synthesis of 6-(3-Hydroxy-phenyl)-1-isopropyl-4-morpholin-4-yl-1H-pyrazolo[3,4-b]pyridine-5-carboxylic acid ethyl ester. To a solution of 1-isopropyl-4-morpholin-4-yl-6-trifluoromethanesulfonyloxy-1H-pyrazolo[3,4-b]pyridine-5-carboxylic acid ethyl ester (1.1 g, 2.4 mmol) in dioxane and H₂O (4/1, 25 mL) was added NaHCO₃ (300 mg, 3.6 mmol), Pd(PPh₃)₄ (150 mg, 0.12 mmol) and 3-hydroxyphenylboronic acid (330 mg, 2.4 mmol). The system was purged with N₂ and the mixture was stirred at 100° C. for 14 h, cooled down to room temperature, diluted with water (50 mL) and extracted with EtOAc (50 mL×2). The organic layers were combined, dried over Na₂SO₄, filtered and concentrated and the residue was purified by preparative TLC on silica gel developed with petroleum ether/EtOAc=10/15 to give 6-(3-Hydroxy-phenyl)-1-isopropyl-4-morpholin-4-yl-1H-pyrazolo[3,4-b]pyridine-5-carboxylic acid ethyl ester (800 mg, 81% yield). ESI-LCMS (m/z): 411.2 [M+1]⁺.

Step 5: Synthesis of 1-Isopropyl-4-morpholin-4-yl-6-(3-oxiranylmethoxy-phenyl)-1H-pyrazolo[3,4-b]pyridine-5-carboxylic acid ethyl ester. A solution of 6-(3-Hydroxy-phenyl)-1-isopropyl-4-morpholin-4-yl-1H-pyrazolo[3,4-b]pyridine-5-carboxylic acid ethyl ester (150 mg, 0.37 mmol) and 2-(chloromethyl)oxirane (100 mg, 1.09 mmol) in CH₃CN (5 mL) was treated with K₂CO₃ (76 mg, 0.55 mmol) and the mixture heated to 80° C. for 14 h.; cooled down to room temperature, diluted with H₂O (20 mL) and the mixture was extracted with EtOAc (20 mL×2). The combined organic layers were dried over Na₂SO₄ filtered and concentrated to give 1-isopropyl-4-morpholin-4-yl-6-(3-oxiranylmethoxy-phenyl)-1H-pyrazolo[3,4-b]pyridine-5-carboxylic acid ethyl ester (170 mg, 100% yield). ESI-LCMS (m/z): 467.3 [M+1]⁺.

Step 6: Synthesis of 6-[3-(3-methylamino-2-hydroxy-propoxy)-phenyl]-1-isopropyl-4-morpholin-4-yl-1H-pyrazolo[3,4-b]pyridine-5-carboxylic acid ethyl ester. 1-Isopropyl-4-morpholin-4-yl-6-(3-oxiranylmethoxy-phenyl)-1H-pyrazolo[3,4-b]pyridine-5-carboxylic acid ethyl ester (170 mg, 0.36 mmol) was dissolved in a 2N CH₃NH₂ solution in MeOH, (10 mL) and then stirred at 60° C. for 14 h. The mixture was concentrated and the residue was purified by preparative HPLC to give 6-[3-(3-amino-2-hydroxy-propoxy)-phenyl]-1-isopropyl-4-morpholin-4-yl-1H-pyrazolo[3,4-b]pyridine-5-carboxylic acid ethyl ester (70 mg, 51% yield) as a white solid. 1H NMR (500 MHz, CD₃OD) δ (ppm): 8.14 (s, 1H), 7.24 (t, J=8.0 Hz, 1H), 6.97 (t, J=2.0 Hz, 1H), 6.93 (dd, J=8.0 and 1.5 Hz, 2H), 5.18-5.12 (m, 1H), 4.04-3.96 (m, 1H), 3.92-3.84 (m, 4H), 3.74-3.70 (m, 4H), 3.50-3.46 (m, 4H), 2.71-2.59 (m, 2H), 2.33 (s, 3H), 1.41 (d, J=7.0 Hz, 6H), 0.82 (t, J=7.0 Hz, 3H) ppm; ESI-LCMS (m/z): 498.3 [M+1]⁺.

Example 16

Preparation of 6-[3-(2-Hydroxy-3-methylamino-propoxy)-phenyl]-1-isopropyl-3-methyl-4-(tetrahydro-pyran-4-ylamino)-1H-pyrazolo[3,4-b]pyridine-5-carboxylic acid dimethylamide

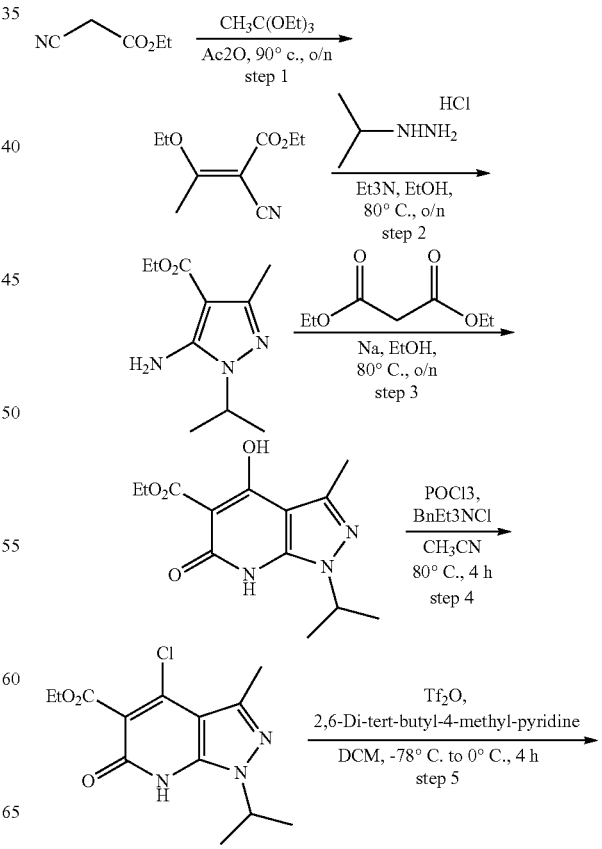

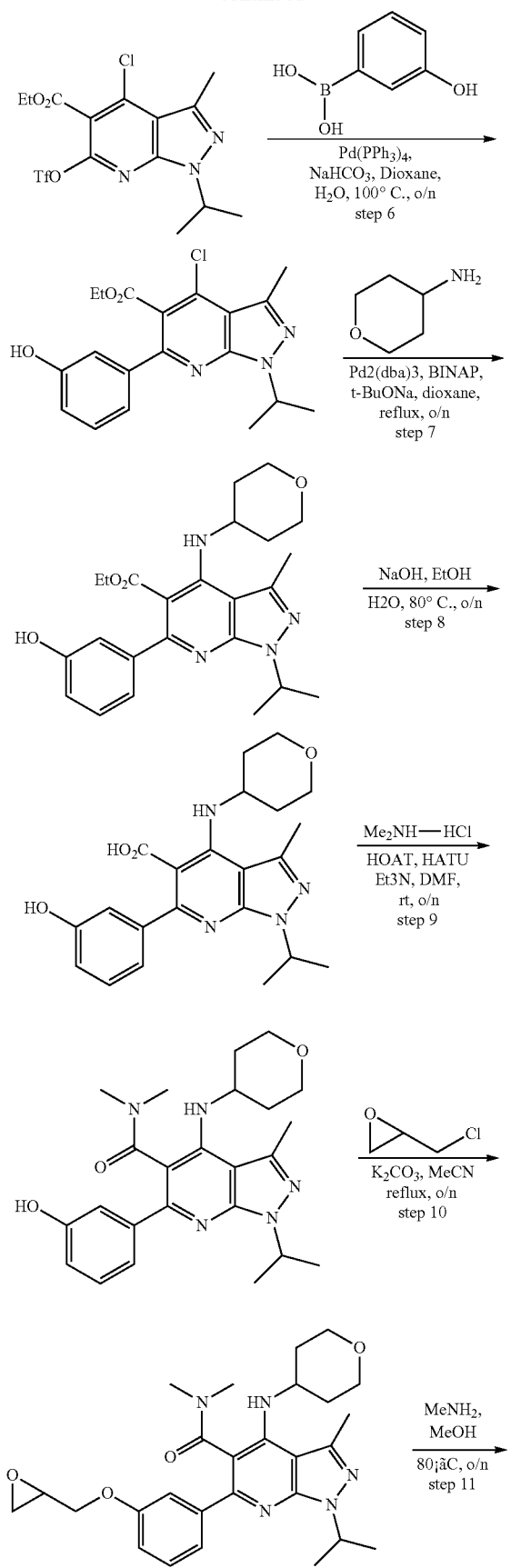

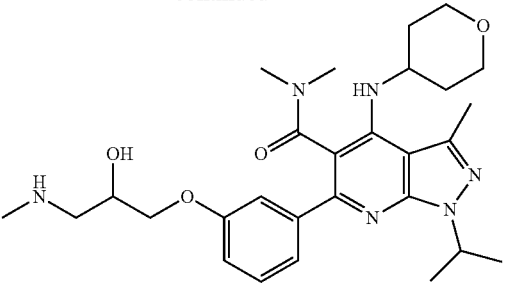

Step 1: Synthesis of 2-cyano-3-ethoxy-but-2-enoic acid ethyl ester. A solution of ethyl cyanacetate (15 mL) in Ac$_2$O (100 mL) was treated with neat triethyl orthoacetate (25 mL) and the mixture stirred at 90° C. for 14 h, concentrated under vacuum and cooled to 0° C. for 20 min. to render a white precipitate which was collected by filtration, washed with cooled petroleum ether (10 mL×2) and dried to afford 2-cyano-3-ethoxy-but-2-enoic acid ethyl ester (5.0 g, 20% yield). 1H NMR (500 MHz, CDCl$_3$) δ (ppm): 4.30-4.21 (m, 4H), 2.61 (s, 3H), 1.43 (t, J=7.0 Hz, 3H), 1.33-1.30 (m, 3H) ppm;

Step 2: Synthesis of 5-amino-1-isopropyl-3-methyl-1H-pyrazole-4-carboxylic acid ethyl ester. To a solution of 2-cyano-3-ethoxy-but-2-enoic acid ethyl ester (22 g, 120.2 mmol) in EtOH (250 mL) was added isopropylhydrazine HCl salt (13.2 g, 120.2 mmol) and triethylamine (24.3 g, 240.4 mmol). The mixture was refluxed for 14 h. After cooling down, the mixture was concentrated and diluted with H$_2$O (150 mL), extracted with EtOAc (150 mL×2), the combined organic layers were washed with brine (500 mL), dried over Na$_2$SO$_4$ and concentrated. The residue was purified by chromatographic column on silica gel (petroleum ether/EtOAc=50/1 to 5/1) to afford 5-amino-1-isopropyl-3-methyl-1H-pyrazole-4-carboxylic acid ethyl ester (18.8 g, 74% yield). ESI-LCMS (m/z): 212.2 [M+1]$^+$.

Step 3: Synthesis of 4-Hydroxy-1-isopropyl-3-methyl-6-oxo-6,7-dihydro-1H-pyrazolo[3,4-b]pyridine-5-carboxylic acid ethyl ester. A freshly prepared solution of NaOEt, (made from Na (3.5 g, 142.29 mmol) in EtOH (28 mL)) was treated with neat diethyl malonate (18.60 g, 116.11 mmol) under nitrogen atmosphere and the mixture was stirred at room temperature for 0.5 hour. Then 5-amino-1-isopropyl-3-methyl-1H-pyrazole-4-carboxylic acid ethyl ester (7.0 g, 33.17 mmol) was added and the system further stirred at reflux for 14 h, cooled down to room temperature, concentrated under reduced pressure, diluted with water (300 mL) and the mixture was extracted with CH$_2$Cl$_2$ (50 mL×2). The aqueous phase was adjusted to pH=5 with 2 N HCl to render a white precipitate which was collected by filtration, washed with water (50 mL×2) and dried to afford 4-hydroxy-1-isopropyl-3-methyl-6-oxo-6,7-dihydro-1H-pyrazolo[3,4-b]pyridine-5-carboxylic acid ethyl ester (5.0 g, 54% yield). ESI-LCMS (m/z): 280.2 [M+1]$^+$.

Step 4: Synthesis of 4-chloro-1-isopropyl-3-methyl-6-oxo-6,7-dihydro-1H-pyrazolo[3,4-b]pyridine-5-carboxylic acid ethyl ester. To a solution of 4-hydroxy-1-isopropyl-3-methyl-6-oxo-6,7-dihydro-1H-pyrazolo[3,4-b]pyridine-5-carboxylic acid ethyl ester (5.0 g, 17.92 mmol) in CH$_3$CN (150 mL) was added POCl$_3$ (12.26 g, 80.64 mmol) and Bn Et$_3$NCl (16.27 g, 71.68 mmol). The mixture was heated to 80° C. for 4 h, cooled down to room temperature, quenched with slow addition of cold water, then diluted with excess water (200 mL) and further stirred for 20 min. The mixture was extracted with EtOAc (150 mL×3), the combined organic layers were dried over Na$_2$SO$_4$, filtered and concentrated and the residue purified with chromatographic column of silica gel (petroleum ether/EtOAc=20/1 to 4/1) to give 4-chloro-1-isopropyl-3-methyl-6-oxo-6,7-dihydro-1H-pyrazolo[3,4-b]pyridine-5-carboxylic acid ethyl ester (1.6 g, 30% yield). ESI-LCMS (m/z): 298.1 [M+1]$^+$.

Step 5: Synthesis of 4-Chloro-1-isopropyl-3-methyl-6-trifluoromethane-sulfonyloxy-1H-pyrazolo[3,4-b]pyridine-5-carboxylic acid ethyl ester. A solution of 4-chloro-1-isopropyl-3-methyl-6-oxo-6,7-dihydro-1H-pyrazolo[3,4-b]pyridine-5-carboxylic acid ethyl ester (1.6 g, 5.39 mmol) and 2,6-di-tert-butyl-4-methylpyridine (1.66 g, 8.08 mmol) in dichloromethane (25 mL) was cooled to −78° C. and treated with slow addition of a solution of Tf$_2$O (2.57 g, 8.62 mmol) in DCM (10 mL). The mixture was stirred for 15 minutes at −78° C., then warmed to 0° C. and further stirred for 4 h at the same temperature, and finally quenched with saturated NaHCO$_3$ aqueous solution (50 mL). The organic layer was separated, washed with water (50 mL) and 10% HCl solution (50 mL), dried over Na$_2$SO$_4$, filtered and concentrated to give 4-chloro-1-isopropyl-3-methyl-6-trifluoro methane-sulfonyloxy-1H-pyrazolo[3,4-b]pyridine-5-carboxylic acid ethyl ester (1.84 g, crude, used directly). ESI-LCMS (m/z): 430.0 [M+1]$^+$.

Step 6: Synthesis of 4-Chloro-6-(3-hydroxy-phenyl)-1-isopropyl-3-methyl-1H-pyrazolo[3,4-b]pyridine-5-carboxylic acid ethyl ester. To a solution of 4-chloro-1-isopropyl-3-methyl-6-trifluoromethane-sulfonyloxy-1H-pyrazolo[3,4-b]pyridine-5-carboxylic acid ethyl ester (1.84 g, from previous step) in dioxane and H$_2$O (4/1, 50 mL) was added NaHCO$_3$ (680 mg, 8.08 mmol), Pd(PPh3)4 (100 mg, 0.08 mmol) and 3-hydroxyphenylboronic acid (743 mg, 5.39 mmol). The system was purged with nitrogen and stirred at 100° C. for 14 h., cooled down to room temperature, and diluted with water (50 mL). The resulting mixture was extracted with EtOAc (50 mL×2), the combined organic layers were dried over Na$_2$SO$_4$, filtered and concentrated. The residue was purified by column chromatography on silica gel (petroleum ether/EtOAc=100/1 to 20/1) to give 4-chloro-6-(3-hydroxy-phenyl)-1-isopropyl-3-methyl-1H-pyrazolo[3,4-b]pyridine-5-carboxylic acid ethyl ester (800 mg, 40% yield, two steps). ESI-LCMS (m/z): 374.1 [M+1]$^+$.

Step 7: Synthesis of 6-(3-hydroxy-phenyl)-1-isopropyl-3-methyl-4-(tetrahydro-pyran-4-ylamino)-1H-pyrazolo[3,4-b]pyridine-5-carboxylic acid ethyl ester. To a solution of 4-chloro-6-(3-hydroxy-phenyl)-1-isopropyl-3-methyl-1H-pyrazolo[3,4-b]pyridine-5-carboxylic acid ethyl ester (800 mg, 2.14 mmol) in dioxane (50 mL) was added t-BuONa (411 mg, 4.29 mmol); tris(dibenzylideneacetone)-dipalladium (100 mg, 0.11 mmol), racemic BINAP (100 mg, 0.16 mmol) and tetrahydro-2H-pyran-4-amine (433 mg, 4.29 mmol). The system was purged with nitrogen and the mixture stirred at 100° C. for 14 h. After cooling down to room temperature, water (50 mL) was added. The resulting mixture was extracted with EtOAc (50 mL×2), the combined organic layers were dried over Na$_2$SO$_4$, filtered and concentrated. The residue was purified by column chromatography on silica gel (petroleum ether/EtOAc=100/1 to 10/1) to give 6-(3-hydroxy-phenyl)-1-isopropyl-3-methyl-4-(tetrahydro-pyran-4-ylamino)-1H-pyrazolo[3,4-b]pyridine-5-carboxylic acid ethyl ester (120 mg, 21% yield). ESI-LCMS (m/z): 439.2 [M+1]$^+$.

Step 8: Synthesis of 6-(3-Hydroxy-phenyl)-1-isopropyl-3-methyl-4-(tetrahydro-pyran-4-ylamino)-1H-pyrazolo[3,4-b]pyridine-5-carboxylic acid. A solution of 6-(3-hydroxy-phenyl)-1-isopropyl-3-methyl-4-(tetrahydro-pyran-4-ylamino)-1H-pyrazolo[3,4-b]pyridine-5-carboxylic acid ethyl ester (120 mg, 0.27 mmol) in EtOH and H$_2$O (10/1, 5 mL) was treated with NaOH (44 mg, 1.09 mmol) and the mixture was heated to 80° C. for 14 h, concentrated in vacuo and to the residue a 2N aqueous HCl solution was added slowly until pH=5. Finally the mixture was concentrated and stored under high vacuum to give crude 6-(3-Hydroxy-phenyl)-1-isopropyl-3-methyl-4-(tetrahydro-pyran-4-ylamino)-1H-pyrazolo[3,4-b]pyridine-5-carboxylic acid which was used without any further purification. ESI-LCMS (m/z): 411.2 [M+1]$^+$.

Step 9: Synthesis of 6-(3-Hydroxy-phenyl)-1-isopropyl-3-methyl-4-(tetrahydro-pyran-4-ylamino)-1H-pyrazolo[3,4-b]pyridine-5-carboxylic acid Dimethylamide. To a solution of 6-(3-Hydroxy-phenyl)-1-isopropyl-3-methyl-4-(tetrahydro-pyran-4-ylamino)-1H-pyrazolo[3,4-b]pyridine-5-carboxylic acid (0.27 mmol) in DMF (5 mL) was added N,N-dimethylamine HCl salt (100 mg, 1.2 mmol), triethylamine (138 mg, 1.37 mmol), 1-Hydroxy-7-azabenzotriazole (HOBt, 38 mg, 0.274 mmol) and (dimethylamino)-N,N-dimethyl(3H-[1,2,3]triazolo[4,5-b]pyridin-3-yloxy)methan iminium hexafluorophosphate (HATU, 104 mg, 0.274 mmol). The mixture was heated to 45° C. for 14 h, cooled down to room temperature, diluted with water (20 mL) and extracted with EtOAc (10 mL×2). The combined organic layers were dried over Na$_2$SO$_4$, filtered and concentrated. The residue was purified by preparative TLC on silica gel developed with DCM/MeOH=15:1 to give 6-(3-hydroxy-phenyl)-1-isopropyl-3-methyl-4-(tetrahydro-pyran-4-ylamino)-1H-pyrazolo[3,4-b]pyridine-5-carboxylic acid dimethylamide (65 mg, 54% yield, two steps). ESI-LCMS (m/z): 438.3 [M+1]$^+$.

Step 10: Synthesis of 1-isopropyl-3-methyl-6-(3-oxiranylmethoxy-phenyl)-4-(tetrahydro-pyran-4-ylamino)-1H-pyrazolo[3,4-b]pyridine-5-carboxylic acid dimethylamide. To a solution of 6-(3-hydroxy-phenyl)-1-isopropyl-3-methyl-4-(tetrahydro-pyran-4-ylamino)-1H-pyrazolo[3,4-b]pyridine-5-carboxylic acid dimethylamide (65 mg, 0.14 mmol) in CH$_3$CN (5 mL) was added K$_2$CO$_3$ (62 mg, 0.447 mmol) and 2-(chloromethyl)oxirane (137 mg, 1.49 mmol). The mixture was heated to 80° C. for 14 h. After cooling down to room temperature, H$_2$O (20 mL) was added and the mixture was extracted with EtOAc (20 mL×2). The combined organic layers were dried over Na$_2$SO$_4$ and filtered and concentrated to give 1-isopropyl-3-methyl-6-(3-oxiranylmethoxy-phenyl)-4-(tetrahydro-pyran-4-ylamino)-1H-pyrazolo[3,4-b]pyridine-5-carboxylic acid dimethylamide (74 mg, 100% yield). ESI-LCMS (m/z): 494.3 [M+1]$^+$.

Step 11: Synthesis of 6-[3-(2-hydroxy-3-methylamino-propoxy)-phenyl]-1-isopropyl-3-methyl-4-(tetrahydro-pyran-4-ylamino)-1H-pyrazolo[3,4-b]pyridine-5-carboxylic acid dimethylamide. 1-Isopropyl-3-methyl-6-(3-oxiranylmethoxy-phenyl)-4-(tetrahydro-pyran-4-ylamino)-1H-pyrazolo[3,4-b]pyridine-5-carboxylic acid dimethylamide (74 mg) was dissolved in a 2N CH$_3$NH$_2$ solution in MeOH (5 mL) and the mixture was stirred at 60° C. for 14 h., concentrated and the residue was purified by preparative HPLC to give 6-[3-(2-hydroxy-3-methylamino-propoxy)-phenyl]-1-isopropyl-3-methyl-4-(tetra hydro-pyran-4-ylamino)-1H-pyrazolo[3,4-b]pyridine-5-carboxylic acid dimethyl amide (45 mg yield 57% yield) as a white solid. 1H NMR (500 MHz, MeOD) δ (ppm): 7.38 (t, J=7.5 Hz, 1H), 7.30-7.20 (m, 2H), 7.07 (d, J=8.0 Hz, 1H), 5.21-5.15 (m, 1H), 4.22-4.16 (brs, 1H), 4.10-3.96 (m, 4H), 3.82-3.75 (m, 1H), 3.49-3.40 (m, 2H), 3.05-2.90 (m, 2H), 2.85 (s, 3H), 2.75 (s, 3H), 2.66 (s, 3H), 2.59 (s, 3H), 2.05-1.90 (m, 2H), 1.75-1.55 (m, 2H), 1.53 (d, J=6.5 Hz, 3H), 1.49 (d, J=6.5 Hz, 3H) ppm; LC-MS (m/z): 525.3 [M+1]+.

Example 17

Preparation of 4,6-dichloro-1-isopropyl-1H-pyrazolo[3,4-d]pyrimidine

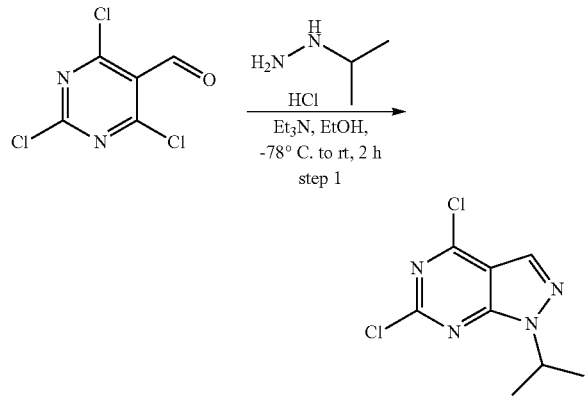

A solution of 2,4,6-trichloropyrimidine-5-carbaldehyde (1.0 g, 4.7 mmol) and isopropylhydrazine hydrochloride (522 mg, 4.7 mmol) in ethanol (10 mL) stirred at −78° C. was treated with slow addition of triethylamine (1.42 g, 14.0 mmol). Then the mixture was warmed up to room temperature and stirred for 5 h., concentrated under vacuum at room temperature, diluted with water (10 mL) and extracted with EtOAc (20 ml mL×2). The combined organic layers were washed with brine (20 mL), dried over Na$_2$SO$_4$, filtered and concentrated to give 4,6-dichloro-1-isopropyl-1H-pyrazolo[3,4-d]pyrimidine (946 mg, 87% yield) which was used directly without further purification. ESI-LCMS (m/z): 231.1 [M+1]+.

Example 18

Preparation of 1-{3-[1-tert-Butyl-4-(tetrahydro-pyran-4-ylamino)-1H-pyrazolo[3,4-d]pyrimidin-6-yl]-phenoxy}-3-methylamino-propan-2-ol

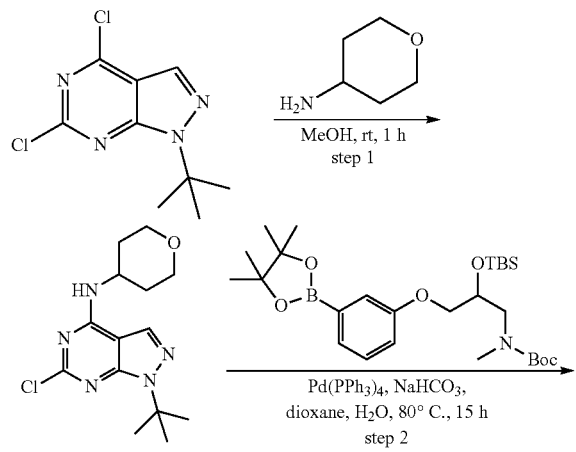

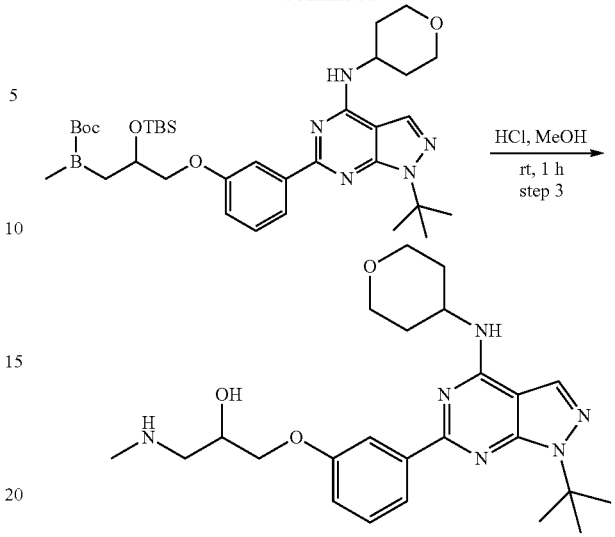

Step 1: Synthesis of 1-tert-butyl-6-chloro-N-(tetrahydro-2H-pyran-4-yl)-1H-pyrazolo[3,4-d]pyrimidin-4-amine. To a solution of 1-tert-butyl-4,6-dichloro-1H-pyrazolo[3,4-d]pyrimidine (180 mg, 0.7 mmol) in MeOH (10 mL) was added tetrahydro-2H-pyran-4-amine (89 mg, 0.8 mmol). The mixture was stirred at room temperature for 1 h., diluted with water (50 mL) and extracted with EtOAc (100 mL×2). The combined organic layers were dried over Na$_2$SO$_4$, filtered and concentrated. The residue was purified by column chromatography on silica gel (petroleum ether/EtOAc=100/1 to 10/1) to give 1-tert-butyl-6-chloro-N-(tetrahydro-2H-pyran-4-yl)-1H-pyrazolo[3,4-d]pyrimidin-4-amine (195 mg, 85% yield). ESI-LCMS (m/z): 310.2 [M+1]+.

Step 2: Synthesis of tert-butyl 3-(3-(1-tert-butyl-4-(tetrahydro-2H-pyran-4-ylamino)-1H-pyrazolo[3,4-d]pyrimidin-6-yl)phenoxy)-2-(tert-butyldimethyl-silyloxy)propyl (methyl)carbamate. To a solution of 1-tert-butyl-6-chloro-N-(tetrahydro-2H-pyran-4-yl)-1H-pyrazolo[3,4-d]pyrimidin-4-amine (190 mg, 0.6 mmol); tert-butyl 2-(tert-butyldimethylsilyloxy)-3-(3-(4,4,5,5-tetramethyl-1,3,2-dioxaborolan-2-yl)phenoxy)propyl(methyl)carbamate (384 mg, 0.7 mmol) and NaHCO$_3$ (99 mg, 1.18 mmol) in dioxane and H$_2$O (3/1, 12 mL) was added Pd(PPh$_3$)$_4$ (7 mg, 0.005 mmol). The system was purged with nitrogen three times and then heated at 80° C. for 15 hours. After cooling down to room temperature the reaction mixture was diluted with H$_2$O (100 mL) and extracted with EtOAc (100 mL×2). The combined organic layers were dried over Na$_2$SO$_4$, filtered and concentrated and the resulting residue was purified by column chromatography on silica gel (petroleum ether/EtOAc=100/1 to 10/1) to give (2-(tert-Butyl-dimethyl-silanyloxy)-3-{3-[1-tert-butyl-4-(tetrahydro-pyran-4-ylamino)-1H-pyrazolo[3,4-d]pyrimidin-6-yl]-phenoxy}-propyl)-methyl-carbamic acid tert-butyl ester (126 mg, 30% yield). ESI-LCMS (m/z): 670.0 [M+1]+.

Step 3: Synthesis of 1-(3-(1-tert-butyl-4-(tetrahydro-2H-pyran-4-ylamino)-1H-pyrazolo[3,4-d]pyrimidin-6-yl)phenoxy)-3-(methylamino)propan-2-ol. A solution of tert-butyl 3-(3-(1-tert-butyl-4-(tetrahydro-2H-pyran-4-ylamino)-1H-pyrazolo[3,4-d]pyrimidin-6-yl)phenoxy)-2-(tert-butyldimethylsilyloxy)propyl(methyl)carbamate (126 mg, 0.18 mmol) in MeOH (20 mL) was treated with 4N HCl aqueous solution (5 mL) and the mixture was stirred at room temperature for 2 h., concentrated, and the resulting residue was purified by preparative HPLC to give 1-(3-(1-tert-butyl-4-(tetrahydro-2H-pyran-4-ylamino)-1H-pyrazolo[3,4-d]pyrimidin-6-yl)phenoxy)-3-(methylamino)propan-2-ol (white solid, 28 mg, 33% yield) as formic acid salt. 1H NMR (500 MHz, CD$_3$OD) δ (ppm): 8.60 (brs, 1H), 8.12-8.08 (m, 2H), 7.99 (s, 1H), 7.38 (t, J=10.0 Hz, 1H), 7.06 (dd, J=10.5 and 3.0 Hz, 1H), 4.55-4.48 (m, 1H), 4.30-4.25 (m, 1H), 4.15-4.03 (m, 4H), 3.67-3.60 (m, 2H), 3.30-3.24 (m, 1H), 3.17-3.11 (m, 1H), 2.73 (s, 1H), 2.14-2.10 (m, 2H), 1.84 (s, 9H), 1.80-1.69 (m, 2H) ppm; ESI-LCMS (m/z): 455.4 [M+1]$^+$.

Example 19

Preparation of 1-(3-(1-isopropyl-4-morpholino-1H-pyrazolo[3,4-d]pyrimidin-6-yl)-5-methoxyphenoxy)-3-(methylamino)propan-2-ol

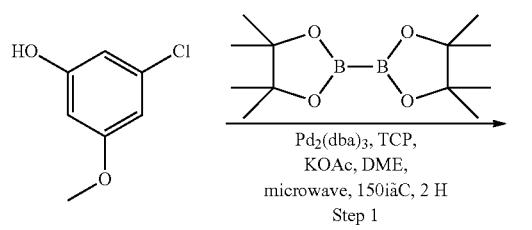

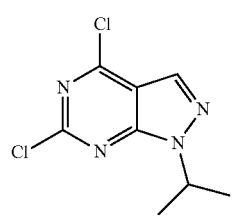

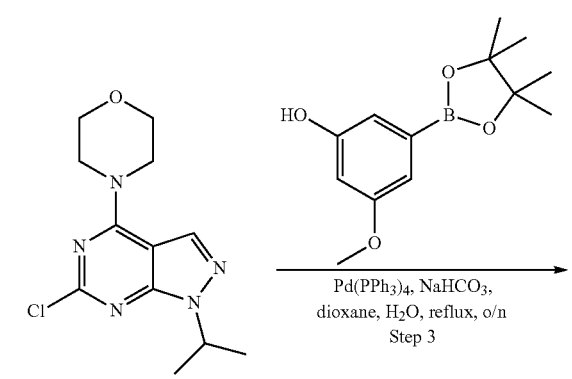

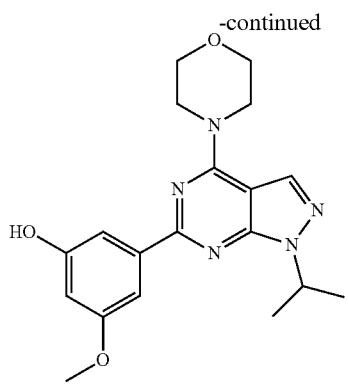

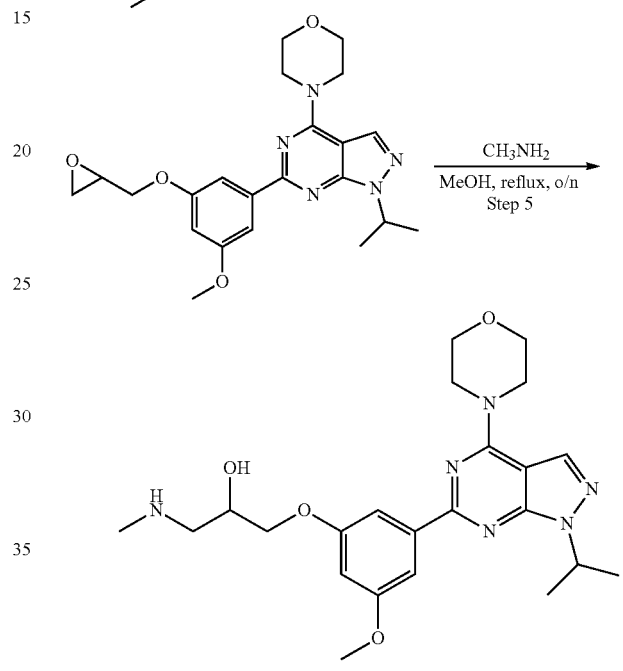

Step 1: Synthesis of 3-methoxy-5-(4,4,5,5-tetramethyl-1,3,2-dioxaborolan-2-yl)phenol. To a solution of 3-chloro-5-methoxyphenol (100 mg, 0.63 mmol) in DME (3 mL) was added KOAc (93 mg, 0.076 mmol); Pd$_2$(dba)$_3$ (20 mg) and TCP (21 mg, 0.076 mmol). The system was purged with nitrogen stream and the vial sealed, placed in a microwave reactor and the mixture irradiated at 150° C. for 2 h. After cooling down to room temperature, water (10 mL) and EtOAc (10 mL) were added, the organic layer was separated and dried over Na$_2$SO$_4$, filtered and concentrated. The residue was purified with preparative TLC on silica gel (petroleum ether/EtOAc=2/1) to give 3-methoxy-5-(4,4,5,5-tetramethyl-1,3,2-dioxaborolan-2-yl)phenol (120 mg, 76% yield). $^1$H NMR (500 MHz, CDCl$_3$) δ (ppm): 6.91 (d, J=2.0 Hz 1H), 6.85 (d, J=2.0 Hz, 1H), 6.85 (t, J=2.0 Hz, 1H), 3.80 (s, 3H), 1.33 (s, 9H) ppm.

Step 2: Synthesis of 4-(6-chloro-1-isopropyl-1H-pyrazolo[3,4-d]pyrimidin-4-yl)morpholine. To a solution of 4,6-dichloro-1-isopropyl-1H-pyrazolo[3,4-d]pyrimidine (300 mg, 1.30 mmol) in EtOH (5 mL) was added Et$_3$N (198 mg, 1.96 mmol) and morpholine (125 mg, 1.44 mmol). The mixture was heated to 80° C. for 14 h., cooled down to room temperature, concentrated and the residue was purified with preparative TLC on silica gel developed with petroleum ether/EtOAc=2/1 to give 4-(6-chloro-1-isopropyl-1H-pyrazolo[3,4-d]pyrimidin-4-yl)morpholine (300 mg, 82% yield). ESI-LCMS (m/z): 282.3 [M+1]$^+$.

Step 3: Synthesis of 3-(1-isopropyl-4-morpholino-1H-pyrazolo[3,4-d]pyrimidin-6-yl)-5-methoxyphenol. A mixture of 4-(6-chloro-1-isopropyl-1H-pyrazolo[3,4-d]pyrimidin-4-yl)morpholine (135 mg, 0.48 mmol) in dioxane and H$_2$O (4/1, 15 mL); NaHCO$_3$ (61 mg, 0.72 mmol); Pd(PPh$_3$)$_4$ (30 mg) and 3-methoxy-5-(4,4,5,5-tetramethyl-1,3,2-dioxaborolan-2-yl)phenol (120 mg, 0.48 mmol) was heated to 100° C. for 14 h under N$_2$ atmosphere, cooled down to room temperature, diluted with water (30 mL) and extracted with EtOAc (20 mL). The organic layer was separated and dried over Na$_2$SO$_4$, filtered and concentrated. The resulting residue was purified with preparative TLC on silica gel (petroleum ether/EtOAc=10/15) to give 3-(1-isopropyl-4-morpholino-1H-pyrazolo[3,4-d]pyrimidin-6-yl)-5-methoxyphenol (110 mg, 62% yield). ESI-LCMS (m/z): 370.3 [M+1]$^+$.

Step 4: Synthesis of 4-(1-isopropyl-6-(3-methoxy-5-(oxiran-2-ylmethoxy)phenyl)-1H-pyrazolo[3,4-d]pyrimidin-4-yl)morpholine. A solution of 3-(1-isopropyl-4-morpholino-1H-pyrazolo[3,4-d]pyrimidin-6-yl)-5-methoxyphenol (110 mg, 0.29 mmol) in CH$_3$CN (5 mL) was treated with K$_2$CO$_3$ (62 mg, 0.45 mmol) and 2-(chloromethyl)oxirane (137 mg, 1.49 mmol) and the mixture was stirred at 80° C. for 14 h., cooled down to room temperature, concentrated and the residue was purified with preparative TLC on silica gel (petroleum ether/EtOAc=1/1) to give 4-(1-isopropyl-6-(3-methoxy-5-(oxiran-2-ylmethoxy)phenyl)-1H-pyrazolo[3,4-d]pyrimidin-4-yl)morpholine (65 mg, 51% yield). ESI-LCMS (m/z): 426.3 [M+1]$^+$.

Step 5: Synthesis of 1-(3-(1-isopropyl-4-morpholino-1H-pyrazolo[3,4-d]pyrimidin-6-yl)-5-methoxyphenoxy)-3-(methylamino)propan-2-ol. A solution of 4-(1-isopropyl-6-(3-methoxy-5-(oxiran-2-ylmethoxy)phenyl)-1H-pyrazolo[3,4-d]pyrimidin-4-yl)morpholine (65 mg, 0.15 mmol) in 2N methylamine solution in MeOH (10 mL) was stirred at 60° C. for 14 h. The mixture was concentrated and the residue was purified by preparative HPLC to give 1-(3-(1-isopropyl-4-morpholino-1H-pyrazolo[3,4-d]pyrimidin-6-yl)-5-methoxy-phenoxy)-3-(methylamino)propan-2-ol (15 mg, 21% yield) as a white solid. $^1$H NMR (500 MHz, CD$_3$OD) δ (ppm): 8.20 (s, 1H), 7.68 (dd, J=2.5 and 5.5 Hz, 2H), 6.67 (t, J=4.5 Hz, 1H), 5.35-5.25 (m, 1H), 4.21-4.15 (m, 1H), 4.12-4.05 (m, 6H), 3.92-3.86 (m, 7H), 23.00-2.83 (m, 2H), 2.55 (s, 3H), 1.58 (d, J=6.5 Hz, 6H) ppm; ESI-LCMS (m/z): 457.4 [M+1]$^+$.

Example 20

Preparation of 4,6-dichloro-1-cyclopropyl-1H-pyrazolo[3,4-d]pyrimidine

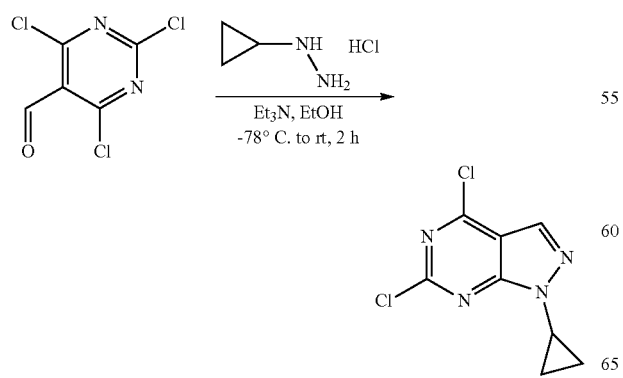

A solution of cyclopropylhydrazine hydrochloride (1.2 g, 7.5 mmol) in EtOH (20 ml) was slowly added to a solution of 2,4,6-trichloropyrimidine-5-carbaldehyde (1.43 g, 6.8 mmol) and Et$_3$N (2.8 ml, 20.4 mmol) in EtOH (20 ml) stirred at −78° C. The resulting mixture was then warmed to room temperature and further stirred at the same temperature for 10 min. EtOAc (150 ml) was added, and the organic layer was washed with water (100 mL×2) and brine (100 ml); dried over Na$_2$SO$_4$, filtered and concentrated. The residue was purified by chromatographic column on silica gel (petroleum ether/EtOAc=15/1) to give 4,6-dichloro-1-cyclopropyl-1H-pyrazolo[3,4-d]pyrimidine (1.1 g, 48% yield). ESI-LCMS (m/z): 229.1 [M+1]$^+$.

Example 21

Preparation of 1-(3-(4-((1S,5R)-3-oxa-8-aza-bicyclo[3.2.1]octan-8-yl)-1-cyclopropyl-1H-pyrazolo[3,4-d]pyrimidin-6-yl)phenoxy)-3-(methylamino)propan-2-ol

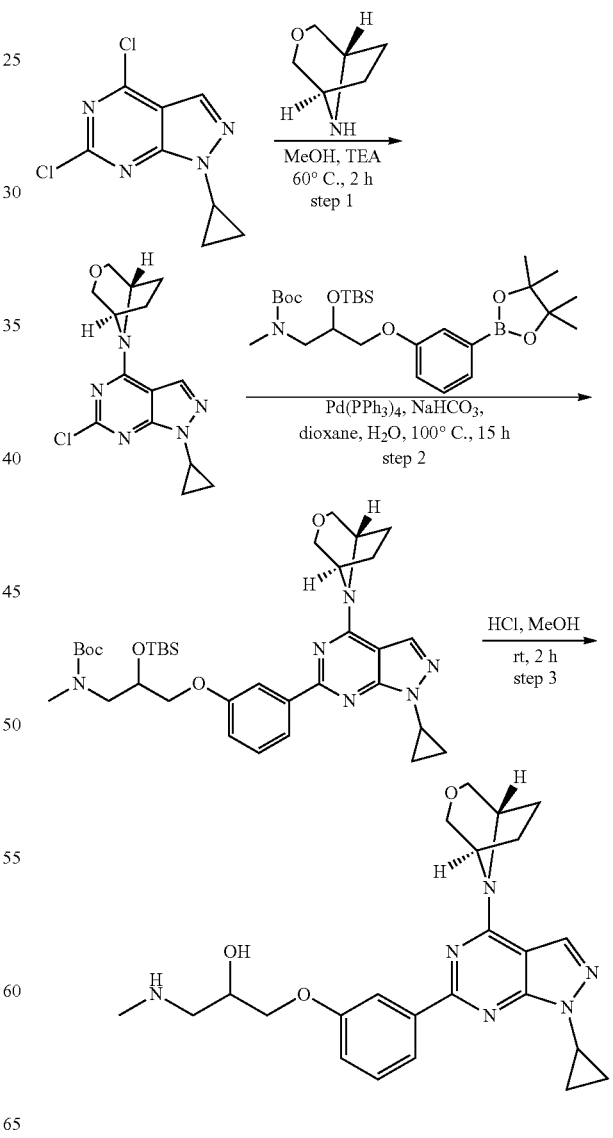

Step 1: Synthesis of (1S,5R)-8-(6-chloro-1-cyclopropyl-1H-pyrazolo[3,4-d]pyrimidin-4-yl)-3-oxa-8-aza-bicyclo

[3.2.1]octane. To a solution of 4,6-dichloro-1-cyclopropyl-1H-pyrazolo[3,4-d]pyrimidine (400 mg, 1.7 mmol) and triethylamine (340 mg, 3.4 mmol) in MeOH (50 mL) at room temperature was added (1S,5R)-3-oxa-8-aza-bicyclo[3.2.1]octane (236 mg, 2.1 mmol) and the mixture was heated at 60° C. for 2 hours. The solvent was removed in vacuo, and the residue was purified by chromatographic column on silica gel (petroleum ether/EtOAc=100/1 to 10/1) to give (1S,5R)-8-(6-chloro-1-cyclopropyl-1H-pyrazolo[3,4-d]pyrimidin-4-yl)-3-oxa-8-aza-bicyclo[3.2.1]octane (426 mg, 80% yield). ESI-LCMS (m/z): 306.2 [M+1]$^+$.

Step 2: Synthesis of tert-butyl 3-(3-(4-((1S,5R)-3-oxa-8-aza-bicyclo[3.2.1]octan-8-yl)-1-cyclopropyl-1H-pyrazolo[3,4-d]pyrimidin-6-yl)phenoxy)-2-(tert-butyldimethylsilyloxy)propyl)methyl)carbamate. A suspension of (1S,5R)-8-(6-chloro-1-cyclopropyl-1H-pyrazolo[3,4-d]pyrimidin-4-yl)-3-oxa-8-aza-bicyclo[3.2.1]octane (180 mg, 0.59 mmol); tert-butyl 2-(tert-butyldimethylsilyloxy)-3-(3-(4,4,5,5-tetramethyl-1,3,2-dioxaborolan-2-yl)phenoxy)propyl(methyl)carbamate (369 mg, 0.7 mmol); Pd(PPh$_3$)$_4$ (7 mg, 0.005 mmol) and NaHCO$_3$ (99 mg, 1.18 mmol) in degassed dioxane/H$_2$O mixture (3/1, 100 mL) was heated at 80° C. for 3 h. under nitrogen atmosphere, cooled down to room temperature, diluted with H$_2$O (100 mL) and extracted with EtOAc (100 mL×2). The combined organic layers were dried over Na$_2$SO$_4$, filtered and concentrated. The residue was purified by chromatographic column on silica gel (petroleum ether/EtOAc=100/1 to 10/1) to give tert-butyl 3-(3-(4-((1S,5R)-3-oxa-8-aza-bicyclo[3.2.1]octan-8-yl)-1-cyclopropyl-1H-pyrazolo[3,4-d]pyrimidin-6-yl)phenoxy)-2-(tert-butyldimethylsilyloxy)propyl(methyl)carbamate (280 mg, 71% yield). ESI-LCMS (m/z): 665.3 [M+1]$^+$.

Step 3: Synthesis of 1-(3-(4-((1S,5R)-3-oxa-8-aza-bicyclo[3.2.1]octan-8-yl)-1-cyclopropyl-1H-pyrazolo[3,4-d]pyrimidin-6-yl)phenoxy)-3-(methylamino)propan-2-ol. A solution of tert-butyl 3-(3-(4-((1S,5R)-3-oxa-8-aza-bicyclo[3.2.1]octan-8-yl)-1-cyclopropyl-1H-pyrazolo[3,4-d]pyrimidin-6-yl)phenoxy)-2-(tert-butyldimethyl-silyloxy)propyl(methyl)carbamate (180 mg, 0.27 mmol) in MeOH (20 mL) was treated with 4N HCl aqueous solution (5 mL), and the mixture stirred at room temperature for 2 h., concentrated and the residue purified by preparative HPLC to give 1-(3-(4-((1S,5R)-3-oxa-8-aza-bicyclo[3.2.1]octan-8-yl)-1-cyclopropyl-1H-pyrazolo[3,4-d]pyrimidin-6-yl)phenoxy)-3-(methylamino)propan-2-ol (white solid, 31 mg, 23% yield) as formic acid salt. $^1$H NMR (500 MHz, CDCl$_3$) δ (ppm): 8.52 (brs, 1H), 8.11 (d, J=7.0 Hz, 1H), 8.03 (s, 1H), 7.76 (s, 1H), 7.34 (t, J=8.0 Hz, 1H), 6.99-6.95 (m, 1H), 4.50 (brs, 1H), 4.21-4.16 (m, 1H), 4.10-4.06 (m, 1H), 4.00-3.95 (m, 1H), 3.86 (d, J=10.5 Hz, 2H), 3.74 (d, J=10.5 Hz, 2H), 3.60-3.10 (m, 4H), 2.75 (s, 3H), 2.25-2.18 (m, 2H), 2.14-2.11 (m, 2H), 1.39-1.34 (m, 2H), 1.17-1.13 (m, 2H) ppm; ESI-LCMS (m/z): 451.2 [M+1]$^+$.

Example 22

Preparation of 5,7-dichloro-3-isopropylpyrazolo[1,5-a]pyrimidine

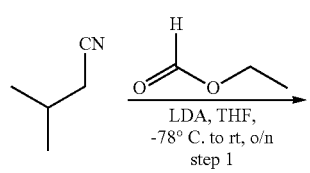

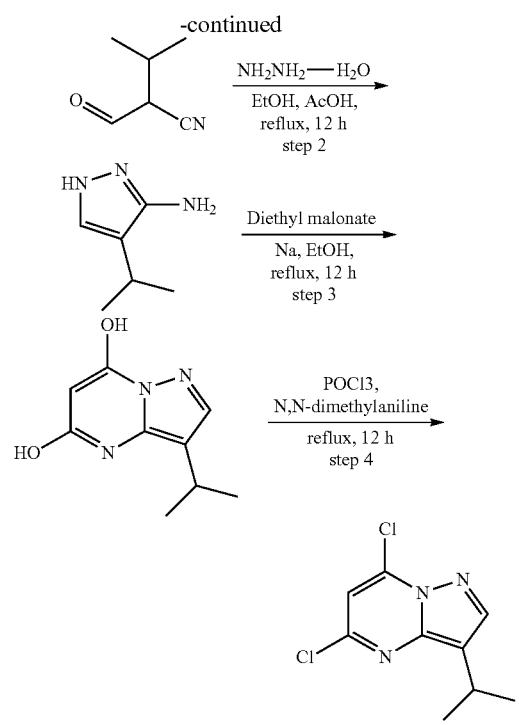

Step 1: Synthesis of 2-formyl-3-methylbutanenitrile. Isovaleronitrile (20 g, 240 mmol) was added slowly to the solution of LDA (264 mmol) in THF (232 ml) at −78° C.; after being stirred for 20 min. at same temperature ethyl formate (22 mL, 277 mmol) in THF (100 mL) was added dropwise at −78° C. over 30 minutes. The resulting mixture was stirred for 45 minutes at this temperature and then allowed to warm to room temperature and further stirred for 14 h. Water (50 mL) was added, the mixture was concentrated in vacuo, pH was adjusted to 3 with 1N aqueous HCl solution and extracted with ethyl acetate (100 mL×3). The combined organic phases were dried over MgSO$_4$, filtered and concentrated to give the 2-formyl-3-methylbutanenitrile (22 g, 84% yield).

Step 2: Synthesis of 4-isopropyl-1H-pyrazol-3-amine. A solution of 2-formyl-3-methyl-butanenitrile (11.1 g, 100.0 mmol) in ethanol (250 mL) was treated with hydrazine hydrate (8.2 mL, 144.0 mmol) followed by acetic acid (10.8 mL, 188.2 mmol). The reaction mixture was heated under reflux for 16 h. monitoring reaction progress by LCMS. The mixture was concentrated in vacuo to approximately one third the original volume, diluted with saturated aqueous sodium bicarbonate (150 mL) and the product was extracted with dichloromethane (150 mL×3). The combined organic phases were washed with brine, dried over MgSO$_4$ and concentrated to yield the 4-isopropyl-1H-pyrazol-3-amine (12 g, 96% yield). ESI-LCMS (m/z): 126.2 [M+1]$^+$.

Step 3: Synthesis of 3-isopropylpyrazolo[1,5-a]pyrimidine-5,7-diol. 4-Isopropyl-1H-pyrazol-3-amine (5.0 g, 40.0 mmol) followed by diethyl malonate (6.50 ml, 43.1 mmol) were added to a solution of NaOEt freshly prepared by dissolving sodium (0.98 g, 42.8 mmol) in ethanol (100 mL). The resulting mixture was heated under reflux for 12 hours, cooled down to room temperature, concentrated and diluted with water (60 mL); pH was adjusted to 3 with aqueous 2N HCl solution to render a precipitate which was collected by filtration, washed with water (50 mL×3) and dried under vacuum to give the 3-isopropylpyrazolo[1,5-a]pyrimidine-5,7-diol (6.6 g, 85% yield) as off-white solid. ESI-LCMS (m/z): 194.3[M+1]⁺.

Step 4: Synthesis of 5,7-dichloro-3-isopropylpyrazolo[1,5-a]pyrimidine. 3-Isopropyl-5,7-dihydroxypyrazolo[1,5-a]pyrimidine (4.83 g, 25.0 mmol) and N,N-dimethylaniline (0.30 g, 2.50 mmol) were suspended in neat phosphorous oxychloride (38.1 mL, 0.41 mol) and the mixture heated under reflux for 12 hours. The excess POCl$_3$ was removed in vacuo, the residue poured onto ice (50 g) and the product was extracted with dichloromethane (50 mL×3). The combined organic phases were washed with brine, dried over MgSO$_4$ and concentrated. The residue was purified by chromatographic column on silica gel (petroleum ether/EtOAc=10/1) to give 5,7-dichloro-3-isopropylpyrazolo[1,5-a]pyrimidine (4.86 g, 86% yield) as a yellow solid. ESI-LCMS (m/z): 229.9 [M+1]⁺.

Example 23

Preparation of 1-(3-(3-isopropyl-7-(1H-pyrrolo[2,3-b]pyridin-5-yl)pyrazolo[1,5-a]pyrimidin-5-yl)-5-methoxyphenoxy)-3-(methylamino)propan-2-ol Step 1: Synthesis of tert-butyl 2-(tert-butyldimethylsilyloxy)-3-(3-(7-chloro-3-isopropylpyrazolo[1,5-a]pyrimidin-5-yl)-5-methoxyphenoxy)propyl(methyl)carbamate. A mixture of 5,7-dichloro-3-isopropylpyrazolo[1,5-a]pyrimidine (1.0 g, 4.34 mmol); tert-butyl2-(tert-butyldimethylsilyloxy)-3-(3-methoxy-5-(4,4,5,5-tetramethyl-1,3,2-dioxaborolan-2-yl)phenoxy)propyl(methyl)carbamate (2.39 g, 4.34 mmol); Pd(PPh$_3$)$_4$ (500 mg, 0.434 mmol) and NaHCO$_3$ (1.09 g, 13.0 mmol) in degassed dioxane and water (3/1, 12 mL) was stirred at 100° C. for 1 h under nitrogen atmosphere, cooled down to room temperature, diluted with water (30 mL) and the mixture was extracted with EtOAc (30 mL×2). The combined organic phases were washed with brine (30 mL), dried over Na$_2$SO$_4$, filtered and concentrated. The residue was purified by silica gel chromatography to obtain tert-butyl 2-(tert-butyldimethylsilyloxy)-3-(3-(7-chloro-3-isopropylpyrazolo[1,5-a]pyrimidin-5-yl)-5-methoxyphenoxy)propyl(methyl)carbamate (light yellow oil, 1.6 g, 59% yield) as major regioiosmer along with the minor regioisomer tert-butyl 2-(tert-butyldimethyl silyloxy)-3-(3-(5-chloro-3-isopropyl-pyrazolo[1,5-a]pyrimidin-7-yl)-5-methoxyphenoxy)propyl(methyl)carbamate (379 mg, 14% yield). ESI-LCMS (m/z): 619 [M+1]⁺.

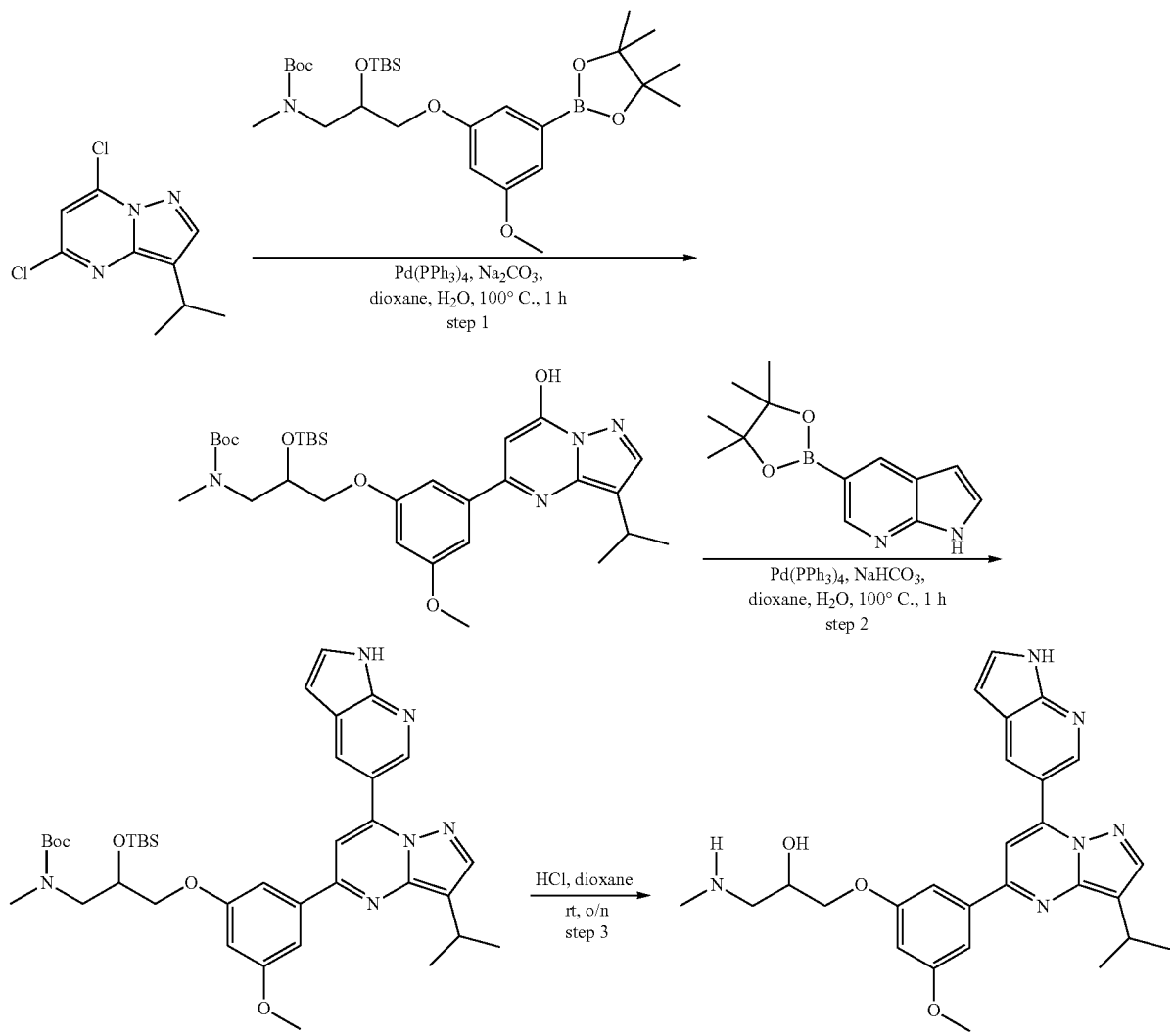

Step 2: Synthesis of tert-butyl 2-(tert-butyldimethylsilyloxy)-3-(3-(3-isopropyl-7-(1H-pyrrolo[2,3-b]pyridin-5-yl)pyrazolo[1,5-a]pyrimidin-5-yl)-5-methoxy-phenoxy)propyl(methyl)carbamate. To a suspension of tert-butyl 2-(tert-butyldimethylsilyloxy)-3-(3-(7-chloro-3-iso-propylpyrazolo[1,5-a]pyrimidin-5-yl)-5-methoxyphenoxy)propyl(methyl)carbamate (300 mg, 0.48 mmol); 5-(4,4,5,5-tetramethyl-1,3,2-dioxaborolan-2-yl)-1H-pyrrolo[2,3-b]pyridine (118 mg, 0.48 mmol) and NaHCO$_3$ (120 mg, 1.44 mmol) in degassed dioxane and water (3/1, 12 mL) was added Pd(PPh$_3$)$_4$ (55 mg, 0.048 mmol). The system was purged with nitrogen for three times, then heated at 100° C. for 1 hour. After cooling down to room temperature, water (20 mL) was added. The mixture was extracted with EtOAc (25 mL×2), the combined organic layer were dried over Na$_2$SO$_4$, filtered and concentrated. The residue was purified by preparative TLC on silica gel to obtain tert-butyl 2-(tert-butyldimethylsilyloxy)-3-(3-(3-isopropyl-7-(1H-pyrrolo[2,3-b]pyridin-5-yl)pyrazolo[1,5-a]pyrimidin-5-yl)-5-methoxyphenoxy)propyl(methyl)carbamate (130 mg, 38% yield) as a yellow solid. ESI-LCMS (m/z): 701.3 [M+1]$^+$.

Step 3: Synthesis of 1-(3-(3-isopropyl-7-(1H-pyrrolo[2,3-b]pyridin-5-yl)pyrazolo[1,5-a]pyrimidin-5-yl)-5-methoxyphenoxy)-3-(methylamino)propan-2-ol. tert-Butyl 2-(tert-butyldimethylsilyloxy)-3-(3-(3-isopropyl-7-(1H-pyrrolo[2,3-b]pyridin-5-yl)pyrazolo[1,5-a]pyrimidin-5-yl)-5-methoxyphenoxy)propyl(methyl)carbamate (130 mg, 0.18 mmol) was dissolved in 2N HCl solution in dioxane, (5 mL), and the mixture was stirred at room temperature for 14 h., concentrated and the residue was purified by preparative HPLC to obtain 1-(3-(3-isopropyl-7-(1H-pyrrolo[2,3-b]pyridin-5-yl)pyrazolo[1,5-a]pyrimidin-5-yl)-5-methoxyphenoxy)-3-(methyl-amino)propan-2-ol (20 mg, 22% yield) as a yellow solid. $^1$H NMR (500 MHz, CD$_3$OD) δ (ppm): 8.94 (s, 1H), 8.83 (d, J=3.5 Hz, 1H), 8.09 (d, J=2.0 Hz, 1H) 7.62-7.55 (m, 2H), 7.48 (s, 2H), 6.73-6.68 (m, 2H), 4.32-4.28 (m, 1H), 4.20-4.11 (m, 2H), 3.92-3.91 (m, 3H) 3.50-3.44 (m, 1H), 3.26-3.21 (m, 1H), 2.79 (s, 3H), 1.49 (d, J=6.5 Hz, 6H) ppm; ESI-LCMS (m/z): 487.3 [M+1]$^+$.

Example 24

Preparation of 5-chloro-3-isopropyl-N-methyl-N-(tetrahydro-2H-pyran-4-yl)pyrazolo[1,5-a]pyrimidin-7-amine

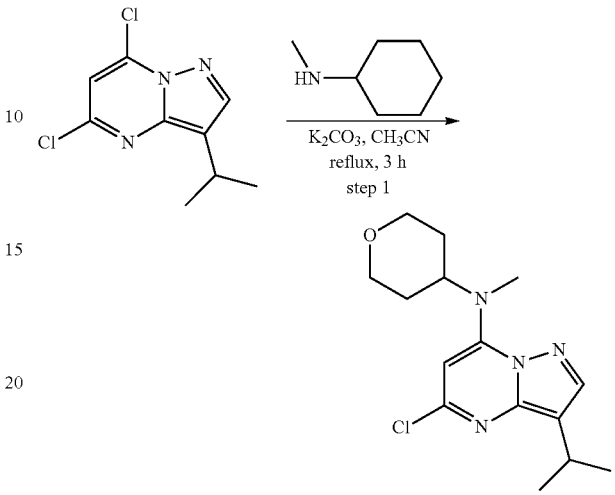

Step 1: Synthesis of 5-chloro-3-isopropyl-N-methyl-N-(tetrahydro-2H-pyran-4-yl) pyrazolo[1,5-a]pyrimidin-7-amine. A mixture of 5,7-dichloro-3-isopropylpyrazolo[1,5-a]pyrimidine (687 mg, 3.0 mmol), N-methyl-tetrahydro-2H-pyran-4-amine (414 mg, 3.6 mmol), and K$_2$CO$_3$ (828 mg, 6.0 mmol) in 10 mL of acetonitrile was heated at reflux under N$_2$ for 2 h., diluted with water (10 mL) and the mixture was extracted with EtOAc (15 mL×3). The combined organic phases were dried over Na$_2$SO$_4$, filtered and concentrated. The residue was purified by preparative TLC on silica gel (petroleum ether/EtOAc=3/1) to afford 5-chloro-3-isopropyl-N-methyl-N-(tetrahydro-2H-pyran-4-yl)pyrazolo[1,5-a]pyrimidin-7-amine (813 mg, 88% yield) as yellow solid. ESI-LCMS (m/z): 309.1 [M+1]$^+$.

Example 25

Preparation of 1-(3-(3-isopropyl-7-(methyl(tetrahydro-2H-pyran-4-yl)amino)-pyrazolo[1,5-a]pyrimidin-5-yl)-5-methoxyphenoxy)-3-(methylamino)propan-2-ol

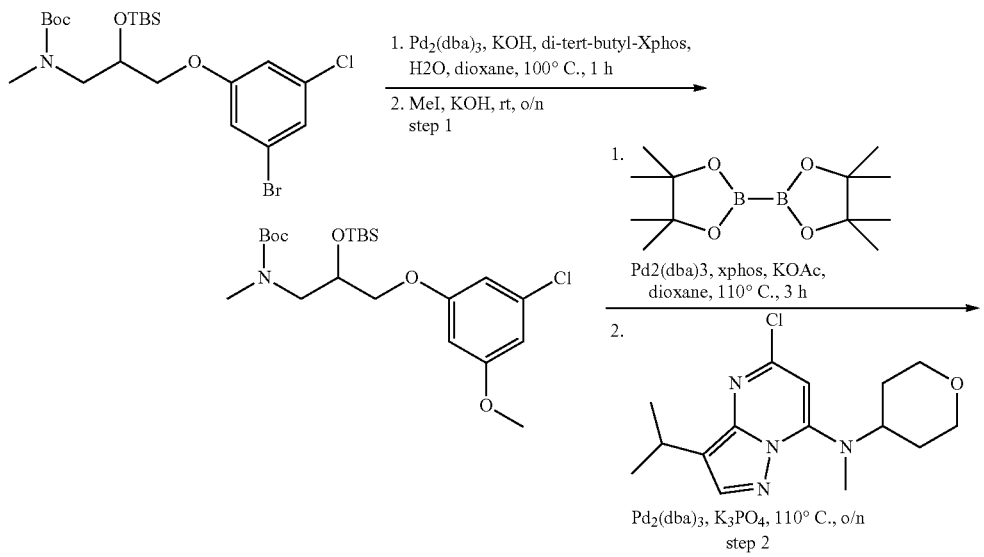

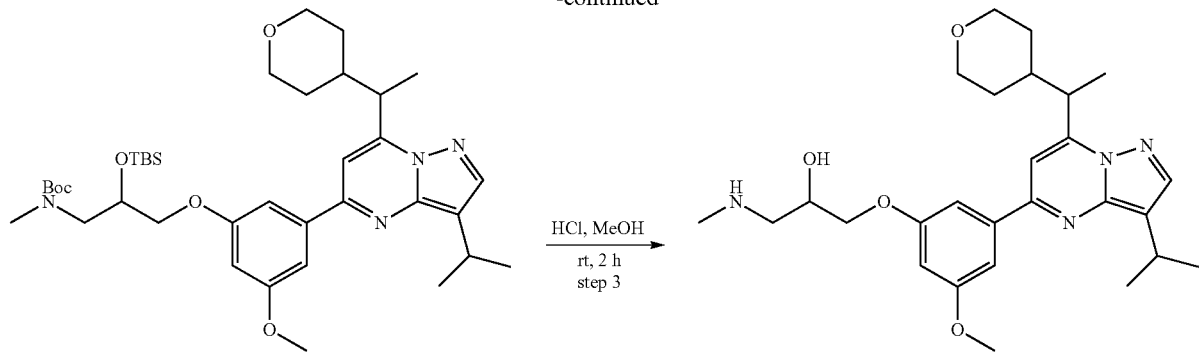

Step 1: Synthesis of tert-butyl 2-(tert-butyldimethylsilyloxy)-3-(3-chloro-5-methoxyphenoxy)propyl(methyl)carbamate. A mixture of tert-butyl 3-(3-bromo-5-chlorophenoxy)-2-(tert-butyldimethyl-silyloxy)propyl(methyl) carbamate (4.8 g, 9.47 mmol); $Pd_2(dba)_3$ (330 mg, 0.47 mmol); di-tert-butyl(2',4',6'-triisopropylbiphenyl-2-yl)phosphine (425 mg, 0.75 mmol) and KOH (1.17 g, 20.8 mmol) in 35 mL of degassed dioxane/$H_2O$ (v/v=6/1) was heated at 100° C. for 1 hour. After cooling down to room temperature, MeI (4.04 g, 28.4 mmol) was added and the mixture was stirred at room temperature for 14 h., diluted with water (40 mL), extracted with EtOAc (50 mL×3) and the combined organic layer were dried over $Na_2SO_4$, filtered and concentrated. The residue was purified by chromatographic column on silica gel to give tert-butyl 2-(tert-butyldimethylsilyloxy)-3-(3-chloro-5-methoxyphenoxy)propyl(methyl)carbamate (3.6 g, 83% yield). ESI-LCMS (m/z): 360.3 [M−100]+.

Step 2: Synthesis of tert-butyl 2-(tert-butyldimethylsilyloxy)-3-(3-(3-isopropyl-7-(methyl(tetrahydro-2H-pyran-4-yl)amino)pyrazolo[1,5-a]pyrimidin-5-yl)-5-methoxyphenoxy)propyl(methyl)carbamate. A mixture of tert-butyl 2-(tert-butyldimethylsilyloxy)-3-(3-chloro-5-methoxyphenoxy)propyl(methyl)carbamate (500 mg, 1.09 mmol); 4,4,4',4',5,5,5',5'-octamethyl-2,2'-bi(1,3,2-dioxaborolane) (554 mg, 2.18 mmol); $Pd_2(dba)_3$ (77 mg, 0.109 mmol); X-Phos (36 mg, 0.11 mmol) and KOAc (320 mg, 3.27 mmol) in 20 mL of degassed dioxane was heated at 100° C. for 4 hours. Then 5-chloro-3-isopropyl-N-methyl-N-(tetra-hydro-2H-pyran-4-yl)pyrazolo[1,5-a]pyrimidin-7-amine (200 mg, 0.65 mmol), $Pd_2(dba)_3$ (77 mg, 0.10 mmol) and $K_3PO_4$ (870 mg, 3.27 mmol) were added at the same temperature. The mixture was further stirred at 100° C. for 14 h., cooled down to room temperature, diluted with water (50 mL) and extracted with EtOAc (50 mL×3). The combined organic layer were dried over $Na_2SO_4$, filtered and concentrated. The residue was purified by Preparative TLC on silica gel to give tert-butyl 2-(tert-butyldimethylsilyloxy)-3-(3-(3-isopropyl-7-(methyl(tetrahydro-2H-pyran-4-yl)amino)pyrazolo[1,5-a]pyrimidin-5-yl)-5-methoxy phenoxy)propyl(methyl)carbamate (150 mg, 33% yield). ESI-LCMS (m/z): 698.4 [M+1]+.

Step 3: Synthesis of 1-(3-(3-isopropyl-7-(methyl(tetrahydro-2H-pyran-4-yl)amino)pyrazolo[1,5-a]pyrimidin-5-yl)-5-methoxyphenoxy)-3-(methylamino)propan-2-ol. A solution of tert-butyl 2-(tert-butyldimethylsilyloxy)-3-(3-(3-isopropyl-7-(methyl(tetrahydro-2H-pyran-4-yl)amino)pyrazolo[1,5-a]pyrimidin-5-yl)-5-methoxy-phenoxy)propyl (methyl)carbamate (150 mg, 0.21 mmol) in MeOH (5 mL) was treated with 6N HCl aqueous solution (3 mL). The mixture was stirred at room temperature for 2 h., the volatiles were removed under vacuum and the residue was purified by preparative HPLC to afford 1-(3-(3-isopropyl-7-(methyl(tetrahydro-2H-pyran-4-yl)amino) pyrazolo[1,5-a]pyrimidin-5-yl)-5-methoxyphenoxy)-3-(methylamino) propan-2-ol (55 mg, 53% yield) as a white solid. 1HNMR (400 MHz, $CD_3OD$) δ (ppm): 7.94 (s, 1H), 7.27-7.25 (m, 2H), 6.65 (d, J=1.2 Hz, 1H), 6.57 (d, J=1.6 Hz, 1H), 5.20-5.11 (m, 1H), 4.15-4.10 (m, 1H), 4.08-4.00 (m, 4H), 3.87 (s, 3H), 3.52-3.45 (m, 2H), 3.40-3.32 (m, 1H), 3.15-3.12 (m, 3H), 2.85-2.70 (m, 2H), 2.45 (s, 3H), 2.10-1.98 (m, 2H), 1.85-1.80 (m, 2H), 1.41 (d, J=6.8 Hz, 6H) ppm; LC-MS (m/z): 484.3 [M+1]+.

Example 26

Preparation of 1-(3-cyclopropyl-5-(3-isopropyl-7-morpholinopyrazolo[1,5-a]pyrimidin-5-yl)phenoxy)-3-(methylamino)propan-2-ol

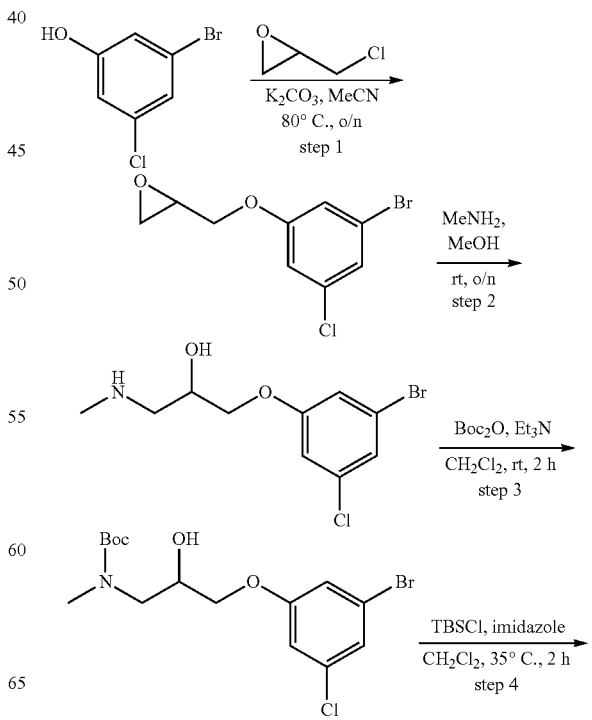

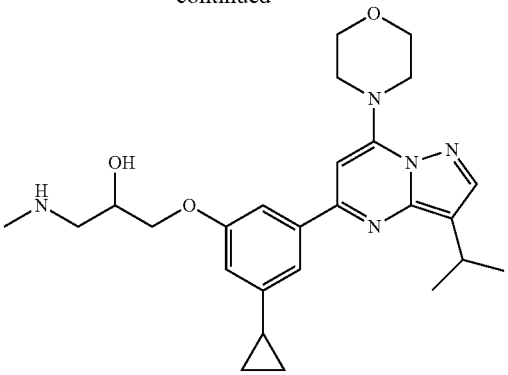
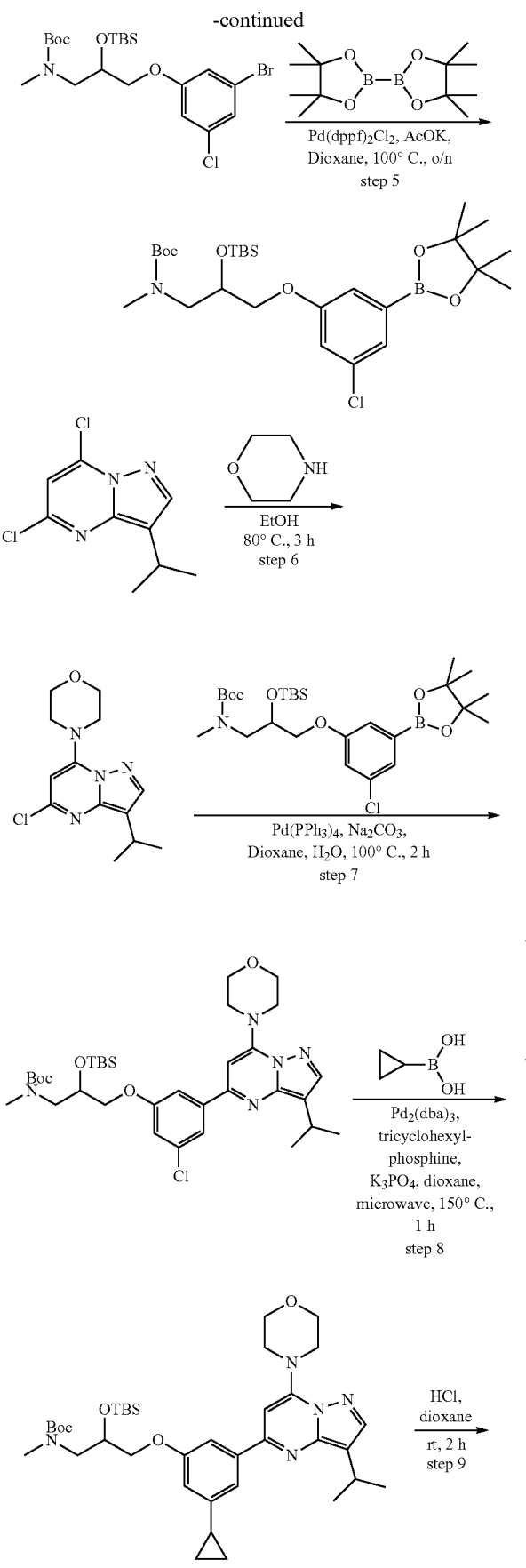

Step 1: Synthesis of 2-((3-bromo-5-chlorophenoxy)methyl)oxirane. A solution of 3-bromo-5-chlorophenol (50 g, 243.9 mmol) in MeCN (300 mL) was treated with 2-(chloromethyl)oxirane (251 mmol) followed by K$_2$CO$_3$ (100.9 g, 0.73 mol) and the mixture was stirred at 80° C. for 14 h. The precipitate solid was filtered off and washed with EtOAc (100 mL×2) and the combined filtrates were concentrated in vacuo to obtain 2-((3-bromo-5-chlorophenoxy)methyl)oxirane (73 g, crude) as pale yellow oil, which was used directly in next step without further purification.

Step 2: Synthesis of 1-(3-bromo-5-chlorophenoxy)-3-(methylamino)propan-2-ol. 2-((3-bromo-5-chlorophenoxy)methyl)oxirane (73 g, crude, from previous step) was dissolved in 2N MeNH$_2$ solution in MeOH, (180 mL), and the solution was stirred at room temperature for 14 h. and the concentrated under vacuum to afford 1-(3-bromo-5-chlorophenoxy)-3-(methylamino)propan-2-ol (90 g, crude) as pale yellow oil, which was used directly in next step without further purification. ESI-LCMS (m/z): 294.0 [M+1]$^+$.

Step 3: Synthesis of tert-butyl 3-(3-bromo-5-chlorophenoxy)-2-hydroxypropyl(methyl)carbamate. To a solution of 1-(3-bromo-5-chlorophenoxy)-3- (methylamino)propan-2-ol (90 g) and triethylamine (116 mL, 0.88 mol) in dichloromethane (500 mL) was treated with (Boc)$_2$O (76.51 g, 0.35 mol), added portionwise during 30 minutes at room temperature. The resulting solution was further stirred at room temperature for 2 h, and then washed consecutively with saturated NH$_4$Cl aqueous solution (150 mL×2), water (150 mL×1) and brine (150 mL×1). The organic phase was separated, dried over Na$_2$SO$_4$, filtered and concentrated. The residue was purified by chromatographic column on silica gel (CH$_2$Cl$_2$/MeOH=30/1) to afford tert-butyl 3-(3-bromo-5-chlorophenoxy)-2-hydroxypropyl(methyl)carbamate (50 g, 52% yield for two steps) as white solid. ESI-LCMS (m/z): 338.0 [M−55]$^+$.

Step 4: Synthesis of tert-butyl 3-(3-bromo-5-chlorophenoxy)-2-(tert-butyl-dimethylsilyloxy)propyl(methyl)carbamate. A solution of tert-butyl 3-(3-bromo-5-chlorophenoxy)-2-hydroxypropyl(methyl)carbamate (20 g, 50.8 mmol) and imidazole (4.28 g, 62.9 mmol) in dichloromethane (200 mL) at room temperature was treated with TBSCl (9.44 g, 62.6 mmol) and the resulting mixture was stirred at 35° C. for 14 h. The reaction mixture was then washed with water (200 mL) and brine (200 mL), the organic phase was separated, dried over Na$_2$SO$_4$, filtered and concentrated. The residue was purified by chromatographic column on silica gel (petroleum ether/EtOAc=60/1) to obtain tert-butyl 3-(3-bromo-5-chlorophenoxy)-2-(tert-butyl-dimethylsilyloxy)propyl(methyl)carbamate (22.0 g, 88% yield) as pale yellow oil. ESI-LCMS (m/z): 530.2 [M+23]$^+$.

Step 5: Synthesis of tert-butyl 2-(tert-butyldimethylsilyloxy)-3-(3-chloro-5-(4,4,5,5-tetramethyl-1,3,2-dioxaborolan-2-yl)phenoxy)propyl(methyl)carbamate. To a suspension of tert-butyl 3-(3-bromo-5-chlorophenoxy)-2-(tert-butyl-dimethyl-silyloxy)propyl(methyl)carbamate (10 g, 19.72 mmol); 4,4,4',4',5,5,5',5'-octamethyl-2,2'-bi(1,3,2-dioxaborolane) (6.01 g, 23.67 mmol); and KOAc (5.8 g, 59.17 mmol) in degassed 1,4-dioxane (200 mL) at room temperature was added PdCl$_2$(dppf) (803 mg, 0.986 mmol). The system was purged with nitrogen three times, then heated 100° C. for 14 h., cooled down to room temperature, the precipitate was filtered off and washed with dioxane (100 mL). The filtrate was concentrated and the residue was purified by chromatographic column on silica gel (petroleum ether/EtOAc=25/1) to afford the tert-butyl 2-(tert-butyldimethylsilyloxy)-3-(3-chloro-5-(4,4,5,5-tetramethyl-1,3,2-dioxaborolan-2-yl)phenoxy)propyl(methyl)carbamate (11.9 g, >100% yield) as pale yellow oil. ESI-LCMS (m/z): 578 [M+23]$^+$.

Step 6: Synthesis of 4-(5-chloro-3-isopropylpyrazolo[1,5-a]pyrimidin-7-yl)morpholine. A solution of 5,7-dichloro-3-isopropylpyrazolo[1,5-a]pyrimidine (1 g, 4.37 mmol) and morpholine (751 mg, 8.73 mmol) in EtOH (20 mL) were heated at 80° C. for 3 h. The mixture was concentrated under high vacuum to obtain 4-(5-chloro-3-isopropylpyrazolo[1,5-a]pyrimidin-7-yl)morpholine (1.5 g, >100% yield), which was used directly without further purification. ESI-LCMS (m/z): 281.1 [M+1]$^+$.

Step 7: Synthesis of tert-butyl 2-(tert-butyldimethylsilyloxy)-3-(3-chloro-5-(3-isopropyl-7-morpholinopyrazolo[1,5-a]pyrimidin-5-yl)phenoxy)propyl(methyl)carbamate. A suspension of 4-(5-chloro-3-isopropylpyrazolo[1,5-a]pyrimidin-7-yl)morpholine (1.1 g, 4.21 mmol); tert-butyl 2-(tert-butyldimethylsilyloxy)-3-(3-chloro-5-(4, 4, 5, 5-tetramethy 1,1,3,2-dioxaborolan-2-yl)phenoxy)propyl (methyl)carbamate (3.51 g, 6.32 mmol) and Na$_2$CO$_3$ (1.34 g, 12.64 mmol) in degassed dioxane and water (3:1, 60 mL) was treated with Pd(PPh$_3$)$_4$ (244 mg, 0.21 mmol). The system was purged with nitrogen three times, then heated at 100° C. for 2 h., cooled down to room temperature, filtered through a pad of silica gel which was washed with EtOAc (50 mL×2), the combined filtrates were concentrated and the resulting residue was purified by chromatographic column on silica gel (petroleum ether/EtOAc=50/1 to 5/1) to afford tert-butyl 2-(tert-butyldimethyl-silyloxy)-3-(3-chloro-5-(3-isopropyl-7-morpholino pyrazolo[1,5-a]pyrimidin-5-yl)phenoxy)propyl(methyl)carbamate (2.2 g, 85% yield). ESI-LCMS (m/z): 674.3 [M+1]$^+$.

Step 8: Synthesis of tert-butyl 2-(tert-butyldimethylsilyloxy)-3-(3-cyclopropyl-5-(3-isopropyl-7-morpholinopyrazolo[1,5-a]pyrimidin-5-yl)phenoxy)propyl(methyl)-carbamate. To a suspension of tert-butyl 2-(tert-butyldimethylsilyloxy)-3-(3-chloro-5-(3-isopropyl-7-morpholinopyrazolo[1,5-a]pyrimidin-5-yl)phenoxy)propyl (methyl)carbamate (150 mg, 0.22 mmol); cyclopropylboronic acid (23 mg, 0.27 mmol); K$_3$PO$_4$·3 H$_2$O (118 mg, 0.45 mmol) and tricyclohexylphosphine (6 mg, 0.022 mmol) in degassed dioxane (5 mL) was added Pd$_2$(dba)$_3$ (21 mg, 0.022 mmol) under nitrogen atmosphere. Then, the sealed vial was heated with microwave at 150° C. for 1 hour. The reaction mixture was filtered and the filtrate was concentrated. The residue was purified by chromatographic column on silica gel (EtOAc/petroleum ether=1:1 to 3:1) to obtain tert-butyl 2-(tert-butyldimethylsilyloxy)-3-(3-cyclopropyl-5-(3-isopropyl-7-morpholinopyrazolo[1,5-a]pyrimidin-5-yl)phenoxy)propyl(methyl)carbamate (130 mg, 86% yield) as a brown solid. ESI-LCMS (m/z): 680.5 [M+1]$^+$.

Step 9: Synthesis of 1-(3-cyclopropyl-5-(3-isopropyl-7-morpholinopyrazolo[1,5-a]pyrimidin-5-yl)phenoxy)-3-(methylamino)propan-2-ol. tert-Butyl 2-(tert-butyldimethylsilyloxy)-3-(3-cyclopropyl-5-(3-isopropyl-7-morpholinopyrazolo[1,5-a]pyrimidin-5-yl)phenoxy)propyl (methyl)carbamate (130 mg, 0.19 mmol) was treated with 2N HCl solution in dioxane, (5 mL) and the mixture was stirred at room temperature for 2 hours. The solvent was removed in vacuo and the residue was purified by preparative HPLC to obtain 1-(3-cyclopropyl-5-(3-isopropyl-7-morpholinopyrazolo[1,5-a]pyrimidin-5-yl)phenoxy)-3-(methyl amino)propan-2-ol (80 mg, 90% yield) as formic acid salt. $^1$H NMR (500 MHz, CD$_3$OD) δ (ppm): 8.56 (s, 1H), 7.99 (s, 1H), 7.52 (s, 1H), 7.48 (s, 1H), 6.80 (s, 1H), 6.70 (s, 1H), 4.32-4.25 (m, 1H), 4.17-4.08 (m, 2H), 4.00-3.94 (m, 4H), 3.80-3.74 (m, 4H), 3.42-3.36 (m, 1H), 3.31-3.18 (m, 1H), 2.78 (s, 3H), 2.07-2.02 (m, 1H), 1.43 (d, J=6.5 Hz, 6H), 1.07-1.02 (m, 2H), 0.82-0.78 (m, 2H) ppm; ESI-LCMS (m/z): 466.3 [M+1]$^+$.

Example 27

Preparation of 1-(3-(3-isopropyl-5-(1H-pyrrolo[2,3-b]pyridin-5-yl)pyrazolo[1,5-a]pyrimidin-7-yl)-5-methoxyphenoxy)-3-(methylamino)propan-2-ol

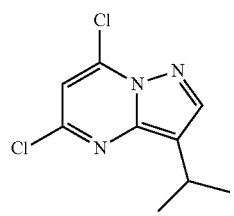
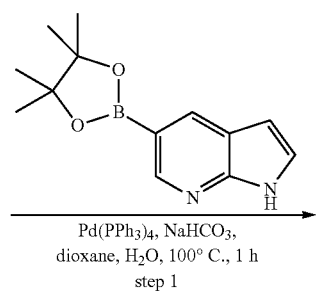

Pd(PPh$_3$)$_4$, NaHCO$_3$,
dioxane, H$_2$O, 100° C., 1 h step 1

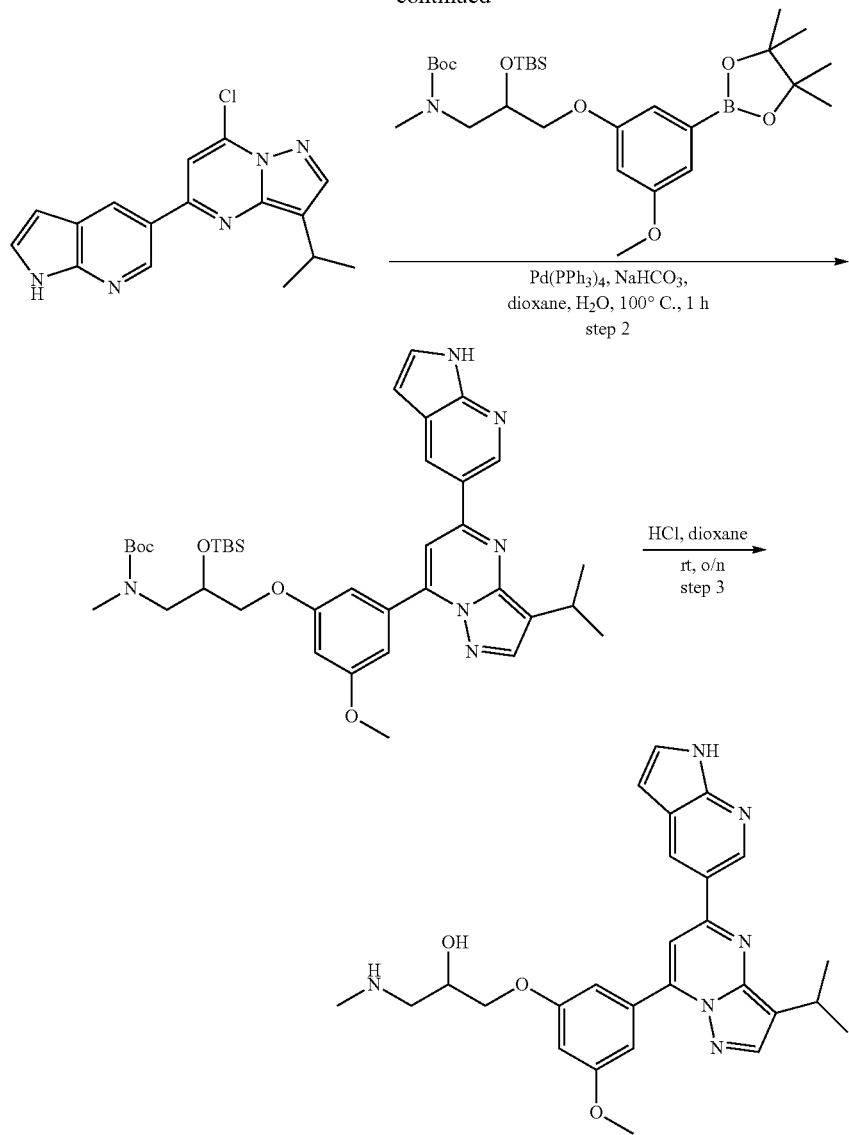

Step 1: Synthesis of 7-chloro-3-isopropyl-5-(1H-pyrrolo[2,3-b]pyridin-5-yl)pyrazolo[1,5-a]pyrimidine. To a suspension of 5,7-dichloro-3-isopropylpyrazolo[1,5-a]pyrimidine (280 mg, 1.2 mmol); 5-(4,4,5,5-tetramethyl-1,3,2-dioxaborolan-2-yl)-1H-pyrrolo[2,3-b]pyridine (297 mg, 1.2 mmol) and NaHCO$_3$ (302 mg, 3.6 mmol) in degassed dioxane and water (3/1, 12 mL) was added Pd(PPh$_3$)$_4$ (138 mg, 0.12 mmol); the system was purged with nitrogen for 3 times, then heated at 100° C. for 1 h., cooled down to room temperature, diluted with water (20 mL) and the mixture extracted with EtOAc (25 mL×2). The combined organic layers were dried over Na$_2$SO$_4$, filtered and concentrated. Two regioisomer 7-chloro-3-isopropyl-5-(1H-pyrrolo[2,3-b]pyridin-5-yl)pyrazolo[1,5-a]pyrimidine and 5-chloro-3-isopropyl-7-(1H-pyrrolo[2,3-b]pyridin-5-yl)pyrazolo[1,5-a]pyrimidine were found form LCMS. The crude product was purified by preparative TLC on silica gel to obtain 7-chloro-3-isopropyl-5-(1H-pyrrolo[2,3-b]pyridin-5-yl)pyrazolo[1,5-a]pyrimidine (150 mg, 48% yield) as the major isomer. ESI-LCMS (m/z): 312.1 [M+1]$^+$.

Step 2: Synthesis of (2-(tert-Butyl-dimethyl-silanyloxy)-3-{3-[3-isopropyl-5-(1H-pyrrolo[2,3-b]pyridin-5-yl)-pyrazolo[1,5-a]pyrimidin-7-yl]-5-methoxy-phenoxyl}-propyl)-methyl-carbamic acid tert-butyl ester. To a suspension of 7-chloro-3-isopropyl-5-(1H-pyrrolo[2,3-b]pyridin-5-yl)pyrazolo[1,5-a]pyrimidine (150 mg, 0.48 mmol), {2-(tert-Butyl-dimethyl-silanyloxy)-3-[3-methoxy-5-(4,4,5,5-tetramethyl-[1,3,2]dioxaborolan-2-yl)-phenoxy]-propyl}-methyl-carbamic acid tert-butyl ester (264 mg, 0.48 mmol) and NaHCO$_3$ (121 mg, 1.44 mmol) in degassed dioxane and water (3/1, 12 mL) was added Pd(PPh$_3$)$_4$ (55 mg, 0.048 mmol); the system was purged with nitrogen three times and heated at 100° C. for 1 h. After cooling down to room temperature, water (20 mL) was added, the mixture was extracted with EtOAc (25 mL×2), the combined organic layer were dried over Na$_2$SO$_4$, filtered and concentrated. The residue was purified by preparative TLC on silica gel to obtain (2-(tert-Butyl-dimethyl-silanyloxy)-3-{3-[3-isopropyl-5-(1H-pyrrolo[2,3-h]pyridine-5-yl)-pyrazolo[1,5-a]pyrimidin-7-yl]-5-methoxy-phenoxy}-propyl)-methyl-carbamic acid tert-butyl ester (150 mg, 44% yield) as a yellow solid. ESI-LCMS (m/z): 701.3 [M+1]$^+$.

Step 3: Synthesis of 1-(3-(3-isopropyl-5-(1H-pyrrolo[2,3-b]pyridin-5-yl)pyrazolo[1,5-a]pyrimidin-7-yl)-5-methoxyphenoxy)-3-(methylamino)propan-2-ol. tert-Butyl 2-(tert-butyldimethylsilyloxy)-3-(3-(3-isopropyl-5-(1H-pyrrolo[2,3-b]pyridin-5-yl)pyrazolo[1,5-a]pyrimidin-7-yl)-5-methoxyphenoxy)propyl(methyl)carbamate (150 mg, 0.21 mmol) was dissolved in 2N HCl solution in dioxane, (5 mL), and the mixture was stirred at room temperature for 14 h. After concentration, the residue was purified by preparative HPLC to obtain 1-(3-(3-isopropyl-5-(1H-pyrrolo[2,3-b]pyridin-5-yl)pyrazolo[1,5-a]pyrimidin-7-yl)-5-methoxyphenoxy)-3-(methyl-amino)propan-2-ol (76 mg, 67% yield) as formic acid salt. $^1$H NMR (500 MHz, CD$_3$OD) δ (ppm): 9.12 (s, 1H), 8.83 (s, 1H), 8.56 (brs, 1H), 8.03 (s, 1H), 7.58 (s, 1H), 7.48 (d, J=3.0 Hz, 1H), 7.28 (s, 1H), 7.25 (s, 1H), 6.78 (s, 1H), 6.64 (d, J=3.0 Hz, 1H), 4.31-4.26 (m, 1H), 4.15-4.09 (m, 1H), 3.89 (s, 1H), 3.50-3.43 (m, 1H), 3.31-3.16 (m, 2H), 2.76 (s, 3H), 1.49 (d, J=7.0 Hz, 6H) ppm; ESI-LCMS (m/z): 487.3 [M+1]$^+$.

Biological Assays

General Materials

S-adenosylmethionine (SAM), S-adenosylhomocysteine (SAH), bicine, Tween20, dimethylsulfoxide (DMSO), bovine skin gelatin (BSG), sodium butyrate and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates

Peptide representative of human histone H3 residues 16-30 was synthesized with an N-terminal linker-affinity tag motif and a C-terminal amide cap by 21$^{St}$ Century Biochemicals. The peptide was purified by high-performance liquid chromatography (HPLC) to greater than 95% purity and confirmed by liquid chromatography mass spectrometry (LC-MS). The sequence was Biot-Ahx-PRKQLAT-KAARKSAP-amide and contained a monomethylated arginine at position 26 (SEQ ID NO.:1).

Molecular Biology

Human CARM1 (PRMT4) (NM_199141.1) transcript clone was amplified from an HEK 293 cDNA library, incorporating a flanking 5' sequence encoding a FLAG tag (MDYKDDDDK) (SEQ ID NO.:2) fused directly to Ala 2 of CARM1 and 3' sequence encoding a hexa His sequence (EGHHHHHH) (SEQ ID NO.:3) fused directly to Ser 608. The gene sequence encoding isoform1 containing a deletion of amino acids 539-561 was amplified subsequently and subcloned into pFastBacMam (Viva Biotech).

Protein Expression

Recombinant baculovirus were generated according to Bac-to-Bac kit instructions (Life Technologies). Protein over-expression was accomplished by infecting exponentially growing HEK 293F cell culture at 1.3×10$^6$ cell/ml with virus (MOI=10) in the presence of 8 mM sodium butyrate. Infections were carried out at 37° C. for 48 hours, harvested by centrifugation, and stored at −80° C. for purification.

Protein Purification

Expressed full-length human Flag- and His-tagged CARM1 protein was purified from cell paste by anti-flag M2 affinity chromatography with resin equilibrated with buffer containing 20 mM Tris, 150 mM NaCl, 5% glycerol, pH 7.8. Column was washed with 500 mM NaCl in buffer A and Flag-CARM1-His was eluted with 200 ug/ml FLAG peptide in buffer A. Pooled fractions were dialyzed in 20 mM Tris, 150 mM NaCl, 5% glycerol and 1 mM DTT, pH 7.8. The purity of recovered protein was 94.

Predicted Translations

```
Flag-CARM1-His
                              (SEQ ID NO.: 4)
MDYKDDDDKAAAAAAVGPGAGGAGSAVPGGAGPCATVSVFPGARLLTIGD

ANGEIQRHAEQQALRLEVRAGPDSAGIALYSHEDVCVFKCSVSRETECSR

VGKQSFIITLGCNSVLIQFATPNDFCSFYNILKTCRGHTLERSVFSERTE

ESSAVQYFQFYGYLSQQQNMMQDYVRTGTYQRAILQNHTDFKDKIVLDVG

CGSGILSFFAAQAGARKIYAVEASTMAQHAEVLVKSNNLTDRIVVIPGKV

EEVSLPEQVDIIISEPMGYMLFNERMLESYLHAKKYLKPSGNMFPTIGDV

HLAPFTDEQLYMEQFTKANFWYQPSFHGVDLSALRGAAVDEYFRQPVVDT

FDIRILMAKSVKYTVNFLEAKEGDLHRIEIPFKFHMLHSGLVHGLAFWFD

VAFIGSIMTVWLSTAPTEPLTHWYQVRCLFQSPLFAKAGDTLSGTCLLIA

NKRQSYDISIVAQVDQTGSKSSNLLDLKNPFFRYTGTTPSPPPGSHYTSP

SENMWNTGSTYNLSSGMAVAGMPTAYDLSSVIASGSSVGHNNLIPLGSSG

AQGSGGGSTSAHYAVNSQFTMGGPAISMASPMSIPTNTMHYGSEGHHHHH

H
```

General Procedure for CARM1 Enzyme Assays on Peptide Substrates

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of CARM1, was added to columns 11, 12, 23, 24, rows I-P for the minimum signal control. A cocktail (40 ul) containing the CARM1 enzyme was added by Multidrop Combi (Thermo-Fisher). The compounds were allowed to incubate with CARM1 for 30 min at room temperature, then a cocktail (10 ul) containing $^3$H-SAM and peptide was added to initiate the reaction (final volume=51 ul). The final concentrations of the components were as follows: CARM1 was 0.25 nM, $^3$H-SAM was 30 nM, peptide was 250 nM, SAH in the minimum signal control wells was 1 mM, and the DMSO concentration was 2%. The assays were stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% inhibition calculation $$\% \, inh = 100 - \left(\frac{dpm_{cmpd} - dpm_{min}}{dpm_{max} - dpm_{min}}\right) \times 100$$

where dpm=disintegrations per minute, cmpd=signal in assay well, and min and max are the respective minimum and maximum signal controls.

Parameter IC50 Fit $$Y = \text{Bottom} + \frac{(\text{Top} - \text{Bottom})}{\left(1 + \left(\frac{X}{IC_{50}}\right)\text{Hill Coefficient}\right)}$$

where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

RKO Methylation Assay

RKO adherent cells were purchased from ATCC (American Type Culture Collection), Manassas, Va., USA. DMEM/Glutamax medium, penicillin-streptomycin, heat inactivated fetal bovine serum, 0.05% trypsin and D-PBS were purchased from Life Technologies, Grand Island, N.Y., USA. Odyssey blocking buffer, 800CW goat anti-rabbit IgG (H+L) antibody, and Licor Odyssey infrared scanner were purchased from Licor Biosciences, Lincoln, Nebr., USA. Asymmetric di-methyl PABP1 antibody was purchased from Cell Signaling Technology, Danvers, Mass., USA. Methanol was purchased from VWR, Franklin, Mass., USA. 10% Tween 20 was purchased from KPL, Inc., Gaithersburg, Md., USA. Paraformaldehyde (PFA) was purchased from EM Sciences. DRAQ5 was purchased from Biostatus Limited, Leicestershire, UK.

RKO adherent cells were maintained in growth medium (DMEM/Glutamax medium supplemented with 10% v/v heat inactivated fetal bovine serum and 100 units/mL penicillin-streptomycin) and cultured at 37° C. under 5% $CO_2$ Cell treatment, In Cell Western (ICW) for detection of asymmetric di-methyl PABP1 and DNA content: RKO cells were seeded in assay medium at a concentration of 30,000 cells per mL to a poly-D-lysine coated 384 well culture plate (BD Biosciences 356697) with 50 μL per well. Compound (100 nL) from a 96-well source plate was added directly to 384 well cell plate. Plates were incubated at 37° C., 5% $CO_2$ for 48 hours. After two days of incubation, plates were brought to room temperature outside of the incubator for ten minutes and blotted on paper towels to remove cell media. Cells were fixed for 20 minutes at room temperature by adding 50 ul of 8% PFA followed by aspiration of supernatant with the Biotek EL406 plate washer. Cells were then permeabilized by addition of 50 μL of ice cold 100% methanol directly to each well and incubated for 30 min at room temperature. After 30 min, plates were transferred to a Biotek EL406 plate washer and washed 2 times with 100 μL per well of wash buffer (1×PBS). Next 60 μL per well of Odyssey blocking buffer (Odyssey Buffer with 0.1% Tween 20 (v/v)) were added to each plate and incubated 1 hour at room temperature. Blocking buffer was removed and 20 μL per well of primary antibody was added (asymmetric-methyl PABP1) diluted 1:400 in Odyssey buffer with 0.1% Tween 20 (v/v)) and plates were incubated overnight (16 hours) at 4° C. Plates were washed 5 times with 100 μL per well of wash buffer. Next 20 μL per well of secondary antibody was added (1:800 800CW goat anti-rabbit IgG (H+L) antibody, 1:2000 DRAQ5 in Odyssey buffer with 0.1% Tween 20 (v/v)) and incubated for 1 hour at room temperature. The plates were washed 5 times with 100 μL per well wash buffer then 2 times with 100 μL per well of water. Plates were allowed to dry at room temperature then imaged on the Licor Odyssey machine which measures integrated intensity at 700 nm and 800 nm wavelengths. Both 700 and 800 channels were scanned.

Calculations. First, the ratio for each well was determined by:

$$\left(\frac{\text{asymmetric } di\text{-methyl } PABP1 \text{ 800 nm value}}{DRAQ5 \text{ 700 nm value}}\right)$$

Each plate included fourteen control wells of DMSO only treatment (minimum inhibition) as well as fourteen control wells for maximum inhibition treated with 20 μM of a reference compound. The average of the ratio values for each control type was calculated and used to determine the percent activation for each test well in the plate. Reference compound was serially diluted three-fold in DMSO for a total of nine test concentrations, beginning at 20 μM.

Percent inhibition was determined and $IC_{50}$ curves were generated using triplicate wells per concentration of compound.

$$\text{Percent Inhibition} = 100 - \left(\left(\frac{(\text{Minimum Inhibition Ratio}) - (\text{Individual Test Sample Ratio})}{(\text{Minimum Inhibition Ratio}) - (\text{Maximum Inhibition Ratio})}\right) * 100\right)$$

TABLE 8

| Biochemical potencies | |
|---|---|
| Compound | Biochem $IC_{50}$ |
| 1-1 | B |
| 2-1 | A |
| 3-1 | A |
| 4-1 | C |
| 5-1 | B |
| 6-1 | B |
| 7-1 | B |
| 8-1 | B |
| 9-1 | B |
| 10-1 | B |
| 11-1 | B |
| 12-1 | B |
| 13-1 | A |
| 14-1 | B |
| 15-1 | B |
| 16-1 | B |
| 17-1 | B |
| 18-1 | B |
| 19-1 | B |
| 20-1 | A |
| 21-1 | B |
| 22-1 | A |
| 23-1 | B |
| 24-1 | B |
| 25-1 | D |
| 26-1 | A |
| 27-1 | A |
| 28-1 | B |
| 29-1 | D |

TABLE 8-continued

Biochemical potencies

| Compound | Biochem IC$_{50}$ |
|---|---|
| 30-1 | A |
| 31-1 | A |
| 32-1 | A |
| 33-1 | B |
| 34-1 | B |
| 35-1 | B |
| 36-1 | A |
| 37-1 | D |
| 38-1 | A |
| 39-1 | B |
| 40-1 | B |
| 41-1 | A |
| 42-1 | A |
| 43-1 | B |
| 44-1 | B |
| 45-1 | A |
| 46-1 | A |
| 47-1 | B |
| 48-1 | A |
| 49-1 | B |
| 50-1 | A |
| 51-1 | A |
| 52-1 | A |
| 53-1 | A |
| 54-1 | B |
| 55-1 | A |
| 56-1 | B |
| 57-1 | B |
| 58-1 | B |
| 59-1 | B |
| 60-1 | B |
| 61-1 | B |
| 62-1 | B |
| 63-1 | B |
| 64-1 | A |
| 65-1 | B |
| 66-1 | B |

Classification codes for biochemical potencies:
A: IC$_{50}$ < 0.1 uM
B: 0.1 uM ≤ IC$_{50}$ < 1 uM
C: 1 uM ≤ IC$_{50}$ < 3 uM
D: 3 uM ≤ IC$_{50}$ < 10 uM
E: 10 uM < IC$_{50}$

TABLE 9

Cellular potencies

| Compound | Cellular IC$_{50}$ |
|---|---|
| 28-1 | C |
| 29-1 | C |
| 34-1 | C |
| 40-1 | B |
| 46-1 | C |
| 3-4 | C |
| 4-4 | C |
| 13-4 | C |
| 17-4 | C |
| 18-6 | B |
| 3-7 | C |

Classification codes for cellular potencies:
A: IC$_{50}$ < 5 uM
B: 5 uM ≤ IC$_{50}$ < 10 uM
C: 10 uM ≤ IC$_{50}$ < 20 uM

Other Embodiments

The foregoing has been a description of certain nonlimiting embodiments of the invention. Those of ordinary skill in the art will appreciate that various changes and modifications to this description may be made without departing from the spirit or scope of the present invention, as defined in the following claims.

---

What is claimed is:

1. A compound of Formula (I):

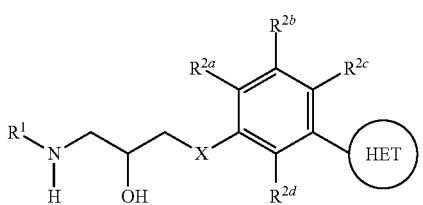

(I)

or a pharmaceutically acceptable salt thereof;

wherein:

X is —O—, —S—, or —CH$_2$—;

R$^1$ is hydrogen or optionally substituted C$_{1-4}$ aliphatic;

each of R$^{2a}$, R$^{2b}$, R$^{2c}$, and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring;

Ring HET is an optionally substituted 6,5-bicyclic heteroaryl ring system comprising 2 to 5 nitrogen atoms, inclusive, wherein the point of attachment is provided on the 6-membered ring of the 6,5-bicyclic heteroaryl ring system, and wherein the 6-membered ring is further substituted with a group of formula -$L^1$-$R^3$;

$L^1$ is a bond, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(=$NR^L$)—, —C(=$NNR^L$)—, —C(=$NOR^L$)—, —C(=N $R^L$)N ($R^L$)—, —$NR^L$C(=$NR^L$)—, —C(S)—, —C(S)N ($R^L$)—, —$NR^L$C(S)—, —S(O)—, —OS(O)$_2$—, —S(O)$_2$O—, —SO$_2$—, —N($R^L$)SO$_2$—, —SO$_2$N ($R^L$)—, —N($R^L$)SO$_2$N($R^L$)—, or an optionally substituted $C_{1-10}$ saturated or unsaturated hydrocarbon chain, wherein one or more moieties selected from the group consisting of —O—, —N($R^L$)—, —S—, —C(O)—, —C(O)O—, —C(O)S—, —C(O)N($R^L$)—, —C(O)N ($R^L$)N($R^L$)—, —OC(O)—, —OC(O)N($R^L$)—, —$NR^L$C(O)—, —$NR^L$C(O)N($R^L$)—, —$NR^L$C(O)N ($R^L$)N($R^L$)—, —$NR^L$C(O)O—, —SC(O)—, —C(=$NR^L$)—, —C(=$NNR^L$)—, —C(=$NOR^L$)—, —C(=$NR^L$)N($R^L$)—, —$NR^L$C(=$NR^L$)—, —C(S)—, —C(S)N($R^L$)—, —$NR^L$C(S)—, —S(O)—, —OS(O)$_2$—, —S(O)$_2$O—, —SO$_2$—, —N($R^L$)SO$_2$—, —SO$_2$N($R^L$)—, and —N($R^L$)SO$_2$N($R^L$)— is optionally and independently present between two carbon atoms of the hydrocarbon chain, and optionally and independently present at one or both ends of the hydrocarbon chain;

each $R^L$ is independently hydrogen, optionally substituted alkyl, or a nitrogen protecting group, or $R^L$ and $R^3$ taken together form an optionally substituted heterocyclyl or optionally substituted heteroaryl ring; and $R^3$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided when $R^3$ is hydrogen, then $L^1$ is not a bond.

2. The compound of claim 1, wherein X is —O—.

3. The compound of claim 1, wherein X is —S— or —CH$_2$—.

4. The compound of claim 1, wherein the Ring HET is of the formula:

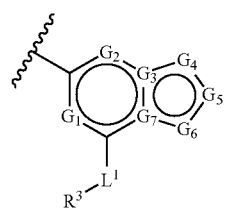

(i)

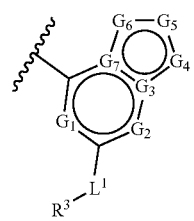

(ii)

wherein:
$G_1$ is C—$R^7$ or N;
$G_2$ is or N;
$G_3$ and $G_7$ are each independently C or N;
$G_4$ is C—$R^4$, N, or N—$R^{4N}$;
$G_5$ is C—$R^5$, N, or N—$R^{5N}$;
$G_6$ is C—$R^6$, N, or N—$R^{6N}$;
provided at least two and not more than five instances of $G_1$, $G_2$, $G_3$, $G_4$, $G_5$, $G_6$, and $G_7$ is nitrogen;

each instance of $R^{4N}$, $R^{5N}$, and $R^{6N}$ is independently hydrogen, —C(=O)R', —C(=O)OR', —C(=O)N(R')$_2$, —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^4$, $R^5$, $R^6$, and $R^7$ is independently hydrogen, halo, —CN, —NO$_2$, —C(=O)R', —C(=O)OR', —C(=O)N(R')$_2$, —N(R')$_2$, —OR', —SR', —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, or optionally substituted heteroaryl; and each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring.

5. The compound of claim 4, wherein Ring HET is selected from the group consisting of:

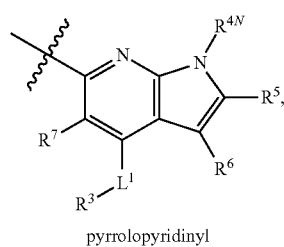

(i-a)

pyrrolopyridinyl

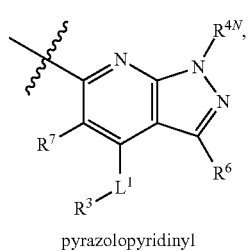
pyrazolopyridinyl (i-b)
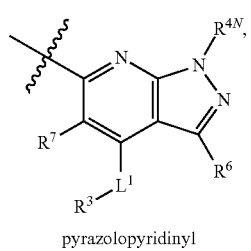
pyrazolopyridinyl (i-c)
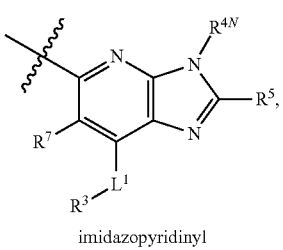
imidazopyridinyl (i-d)
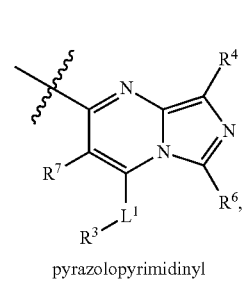
pyrazolopyrimidinyl (i-e)
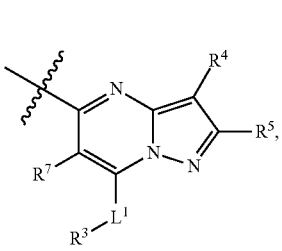
pyrazolopyrimidinyl (i-f)
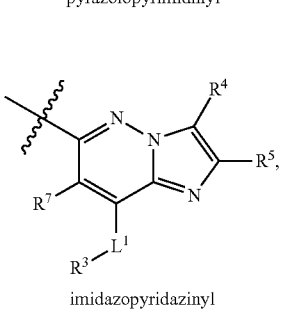
imidazopyridazinyl (i-g)
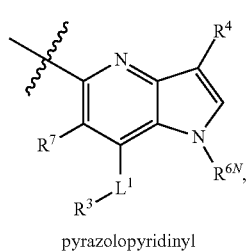
pyrazolopyridinyl (i-h)
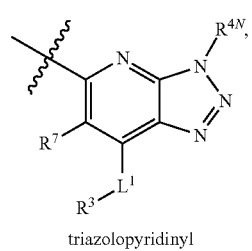
triazolopyridinyl (i-i)
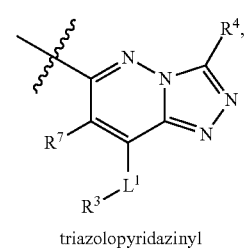
triazolopyridazinyl (i-j)
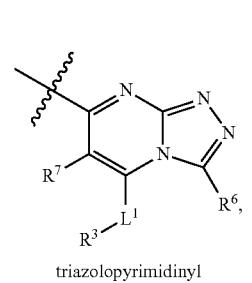
triazolopyrimidinyl (i-k)
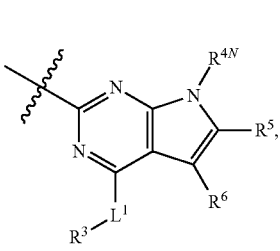
pyrazolopyrimidinyl (i-l)
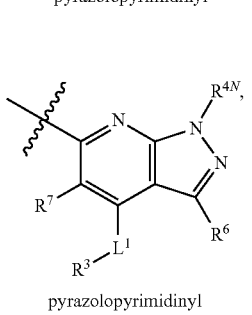
pyrazolopyrimidinyl (i-m)

-continued
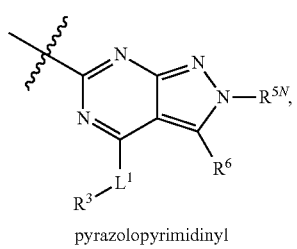
pyrazolopyrimidinyl (i-n)
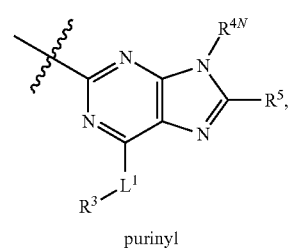
purinyl (i-o)
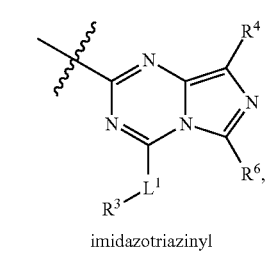
imidazotriazinyl (i-p)
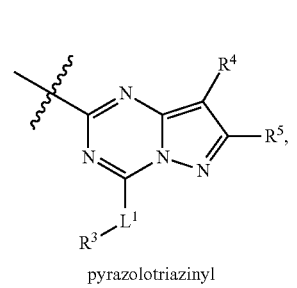
pyrazolotriazinyl (i-q)
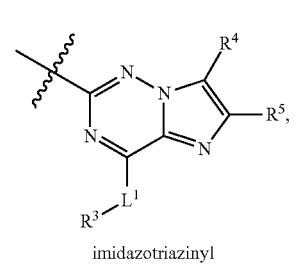
imidazotriazinyl (i-r)
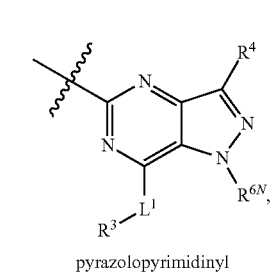
pyrazolopyrimidinyl (i-s)
-continued
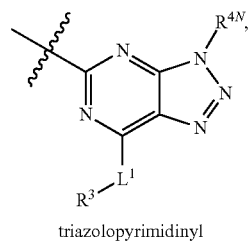
triazolopyrimidinyl (i-t)
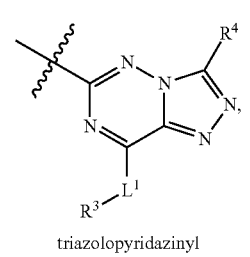
triazolopyridazinyl (i-u)
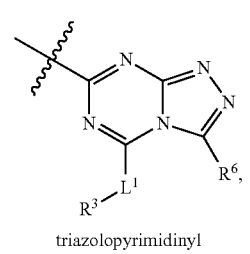
triazolopyrimidinyl (i-v)
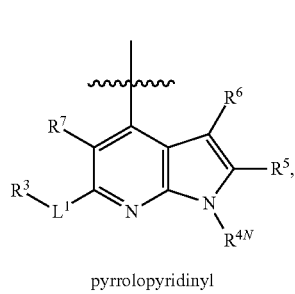
pyrrolopyridinyl (ii-a)
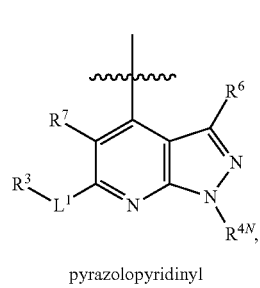
pyrazolopyridinyl (ii-b)
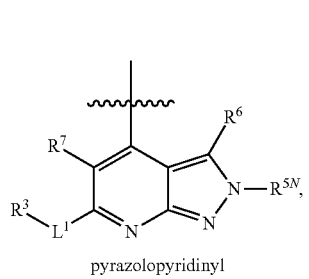
pyrazolopyridinyl (ii-c)

(ii-d)
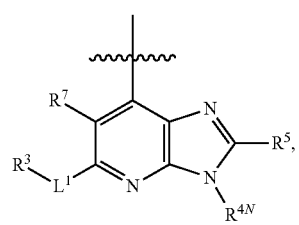
imidazopyridinyl
(ii-e)
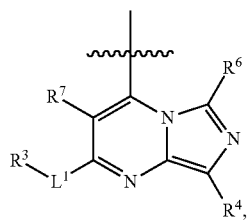
pyrazolopyrimidinyl
(ii-f)
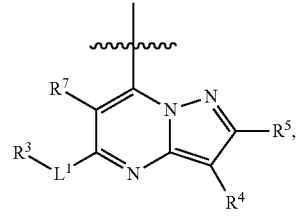
pyrazolopyrimidinyl
(ii-g)
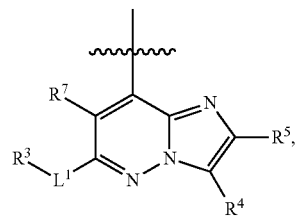
imidazopyridazinyl
(ii-h)
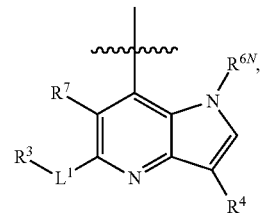
pyrazolopyridinyl
(ii-i)
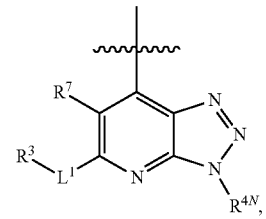
triazolopyridinyl
(ii-j)
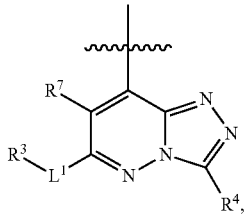
triazolopyridazinyl
(ii-k)
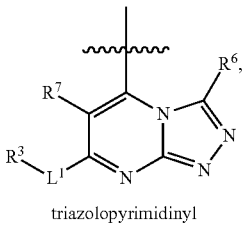
triazolopyrimidinyl
(ii-l)
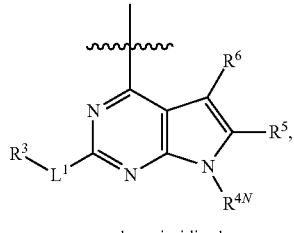
pyrrolopyrimidinyl
(ii-m)
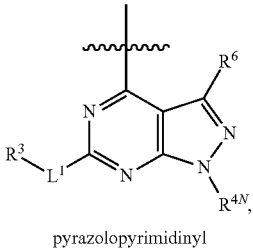
pyrazolopyrimidinyl
(ii-n)
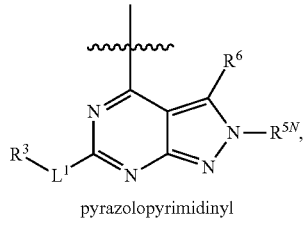
pyrazolopyrimidinyl
(ii-o)
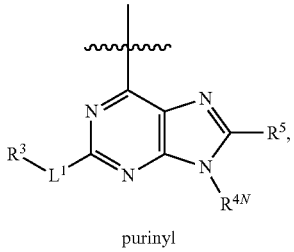
purinyl (ii-p)
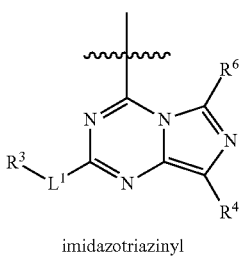
imidazotriazinyl (ii-q)
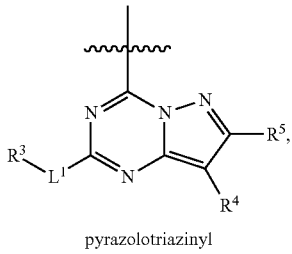
pyrazolotriazinyl (ii-r)
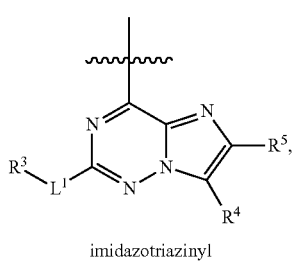
imidazotriazinyl (ii-s)
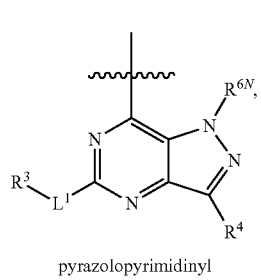
pyrazolopyrimidinyl (ii-t)
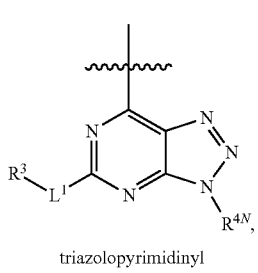
triazolopyrimidinyl (ii-u)
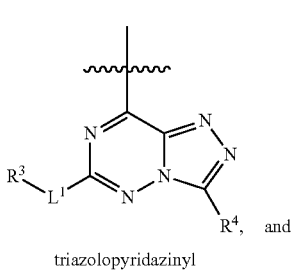
triazolopyridazinyl (ii-v)
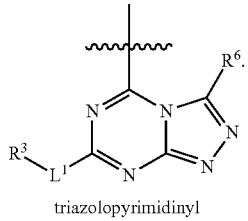
triazolopyrimidinyl 6. The compound of claim 4, wherein the compound is of Formula (I-j):

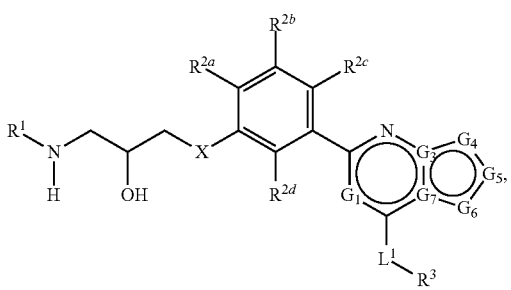
(I-j)

or a pharmaceutically acceptable salt thereof.

7. The compound of claim 4, wherein the compound is of Formula (I-q):

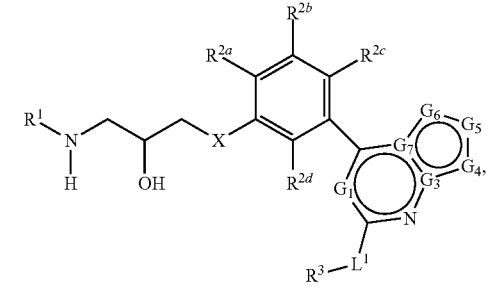
(I-q)

or a pharmaceutically acceptable salt thereof.

8. The compound of claim 4, wherein at least one instance of $R^{4N}$, $R^{5N}$, and $R^{6N}$ is optionally substituted $C_3$carbocyclyl or optionally substituted $C_{1-4}$alkyl.

9. The compound of claim 4, wherein at least one instance of $R^4$, $R^5$, $R^6$, and $R^7$ is hydrogen, optionally substituted $C_{1-4}$alkyl, optionally substituted $C_3$carbocyclyl, —CN, —C(=O)R', —C(=O)OR', or —C(=O)N(R')$_2$.

10. The compound of claim 1, wherein $L^1$ is a bond, —N($R^L$)—, —NR$^L$C(O)O—, —NR$^L$C(O)N($R^L$)—, —N($R^L$SO$_2$N($R^L$)—, —NR$^L$—(CH$_2$)$_x$—C(O)O—, —NR$^L$—(CH$_2$)$_x$—O—, —NR$^L$C(O)N($R^L$)—, —NR$^L$—(CH$_2$)$_x$—, —(CH$_2$)$_x$—NR$^L$—, —NR$^L$C(O)O(CH$_2$)$_x$—, —NR$^L$C(O)NR$^L$(CH$_2$)$_x$—, or —NR$^L$(CH$_2$)$_x$NR$^L$C(O)—, and x is 1, 2, 3, 4, 5, 6, 7, 8, 9, or 10.

11. The compound of claim 1, wherein $R^3$ is an optionally substituted monocyclic or bicyclic heterocyclyl, or an optionally substituted monocyclic or bicyclic heteroaryl.

12. The compound of claim 1, wherein $R^3$ is selected from the group consisting of:

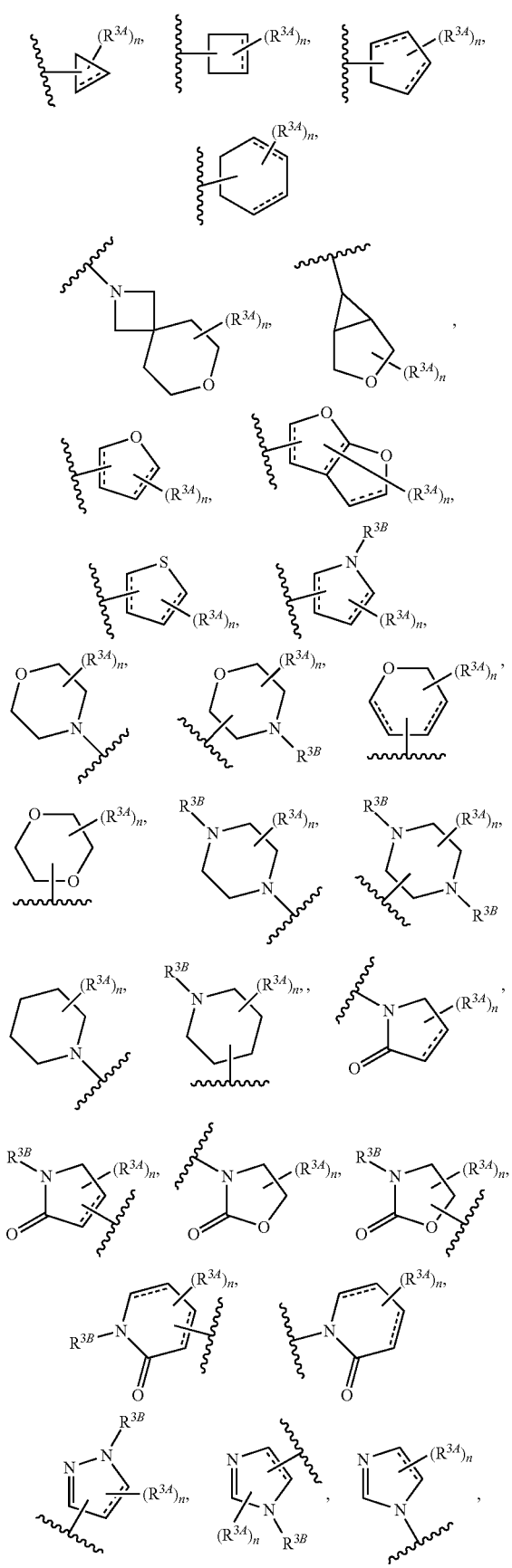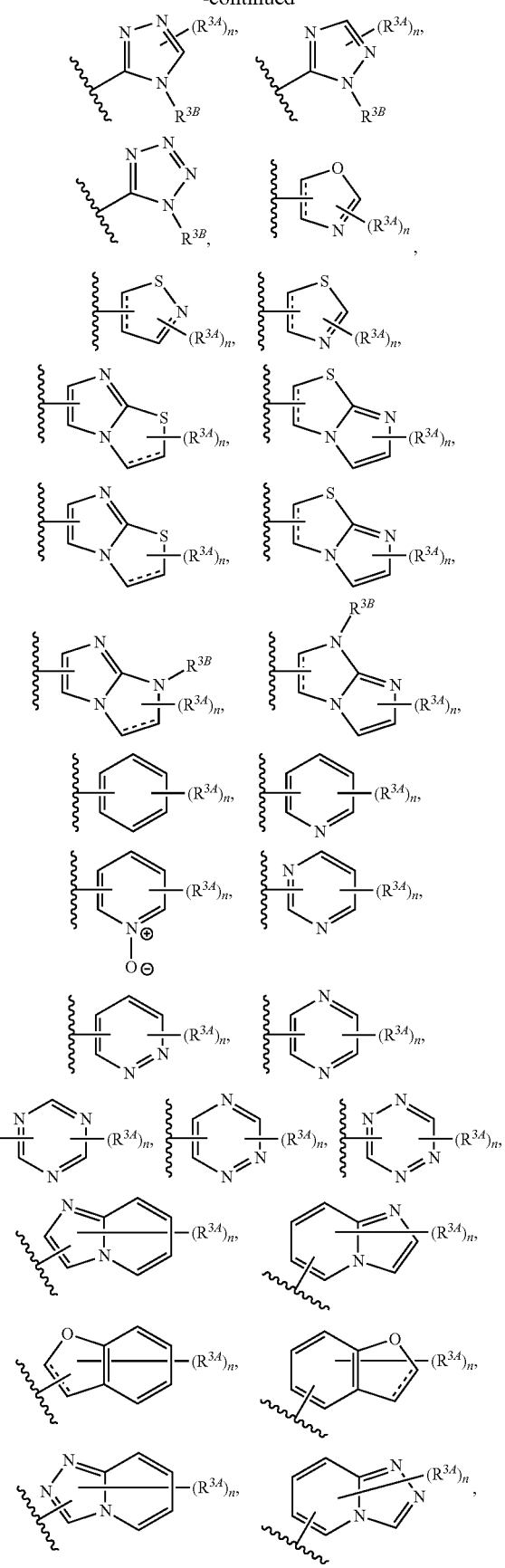

-continued

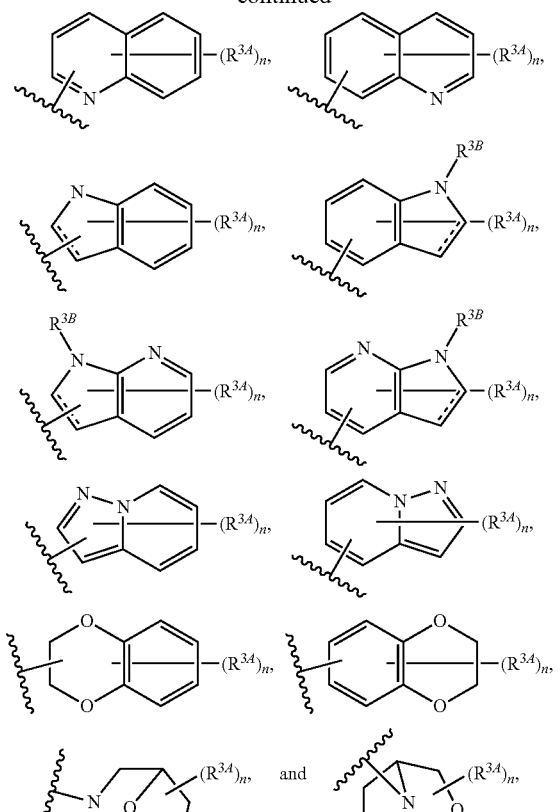

wherein:
each instance of ═ independently represents a single or double bond;
n is 0, 1, 2, or 3;
each instance of $R^{3A}$ is independently hydroxyl, substituted hydroxyl, thiol, substituted thiol, amino, substituted amino, carbonyl, sulfonyl, sulfinyl, —CN, —NO$_2$, halogen, or optionally substituted alkyl, or two $R^{3A}$ groups are joined to form an optionally substituted carbocyclic, optionally substituted heterocyclic, optionally substituted aryl, or optionally substituted heteroaryl ring, or $R^{3A}$ and $R^{3B}$ groups are joined to form an optionally substituted carbocyclic, optionally substituted heterocyclic, optionally substituted aryl, or optionally substituted heteroaryl ring; and
$R^{3B}$ is hydrogen, optionally substituted alkyl, or a nitrogen protecting group.

13. The compound of claim 1, wherein $R^1$ is hydrogen, methyl, ethyl, n-propyl, isopropyl, or cyclopropyl.

14. The compound of claim 1, wherein each of $R^{2a}$, $R^{2c}$, and $R^{2d}$ is hydrogen.

15. The compound of claim 1, wherein $R^{2b}$ is —F, —Cl, —Br, —I, —CN, optionally substituted $C_{1-4}$ alkyl, optionally substituted $C_{3-5}$ carbocyclyl, or —OR$^{A2}$, wherein $R^{A2}$ is optionally substituted $C_{1-4}$ alkyl, or optionally substituted $C_{3-5}$ carbocyclyl.

16. The compound of claim 1, wherein the compound is selected from the group consisting of:

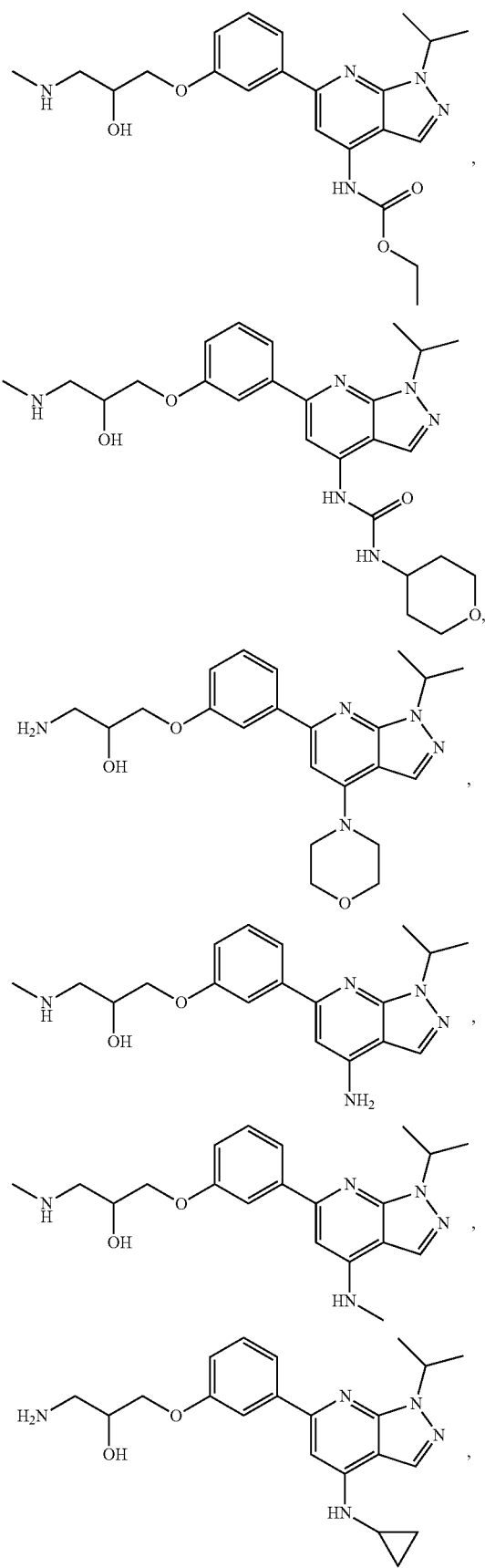

251
-continued
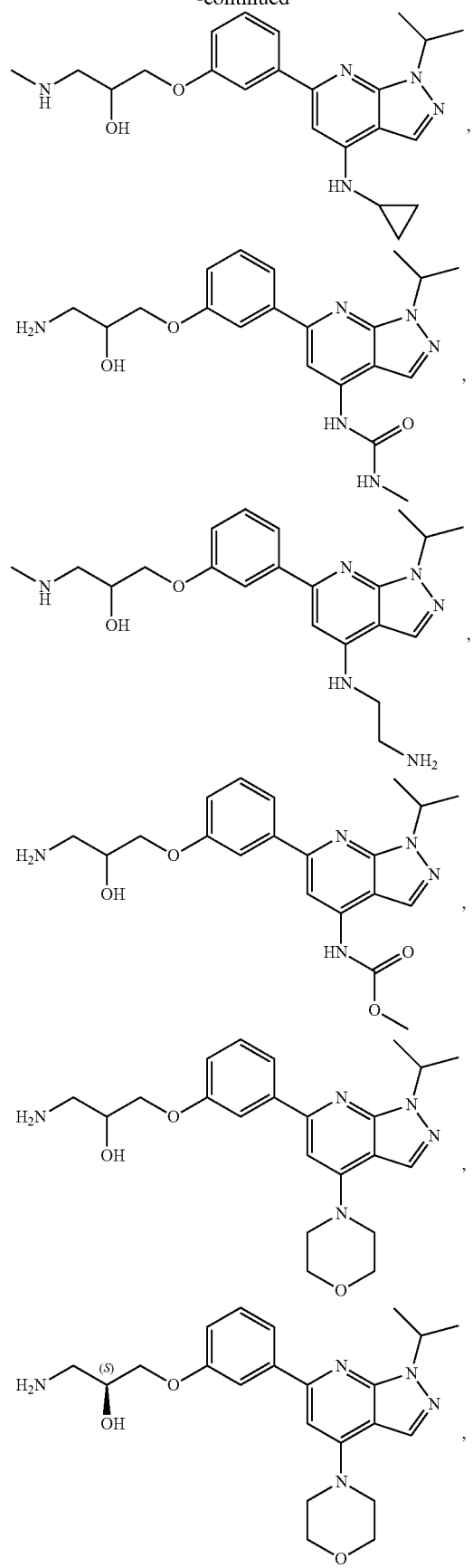
252
-continued
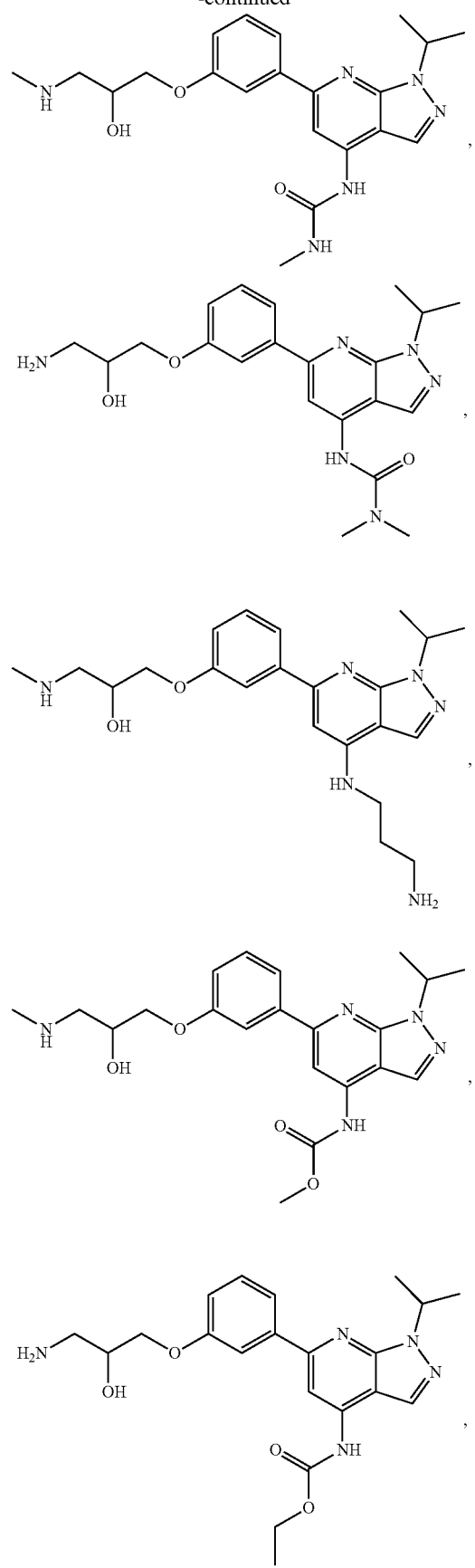

253
-continued
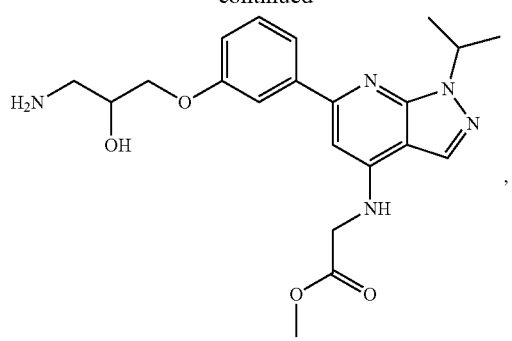
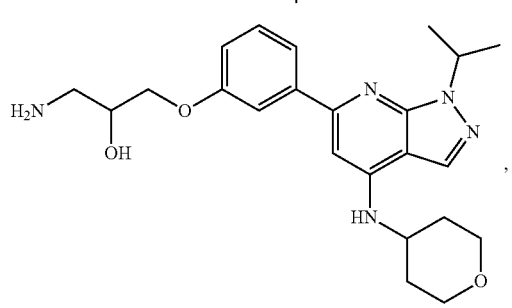
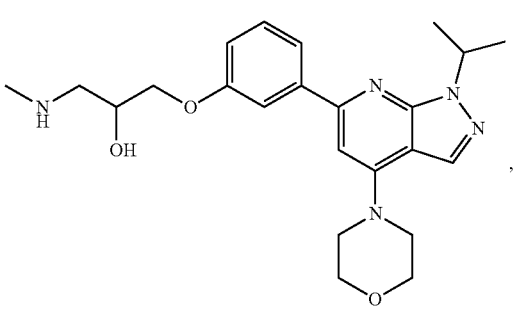
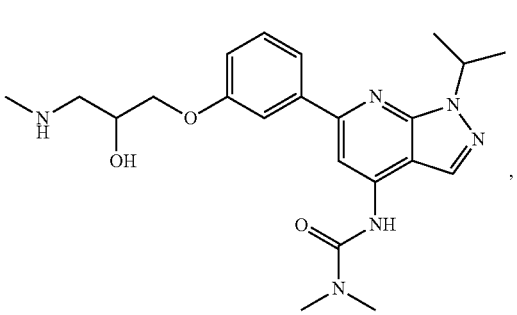
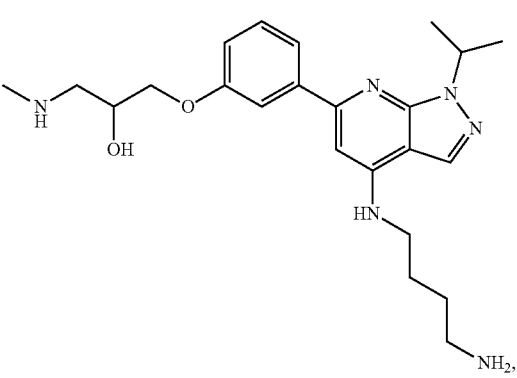
254
-continued
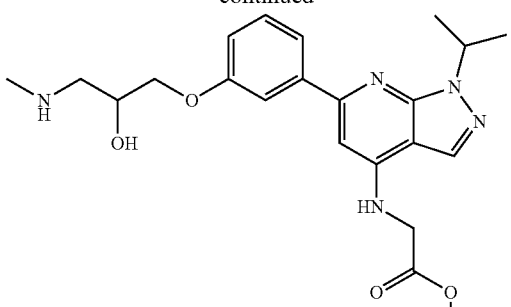
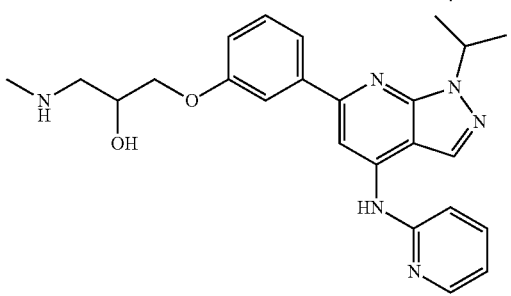
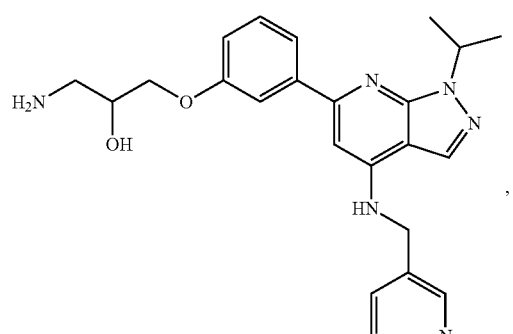
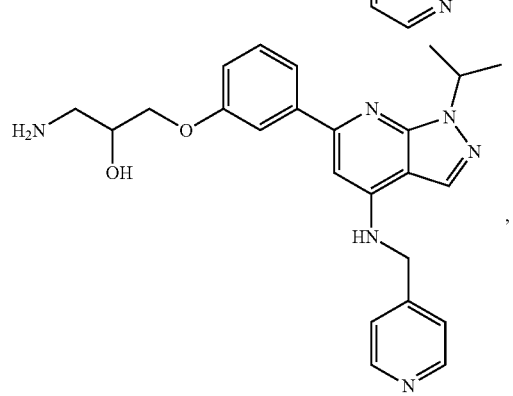
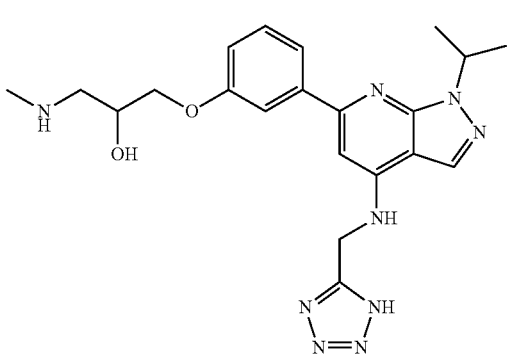

255
-continued
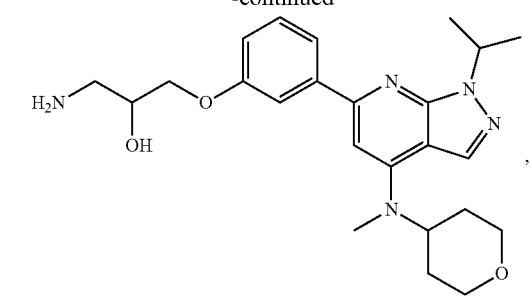
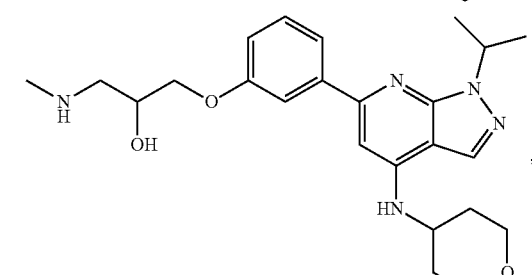
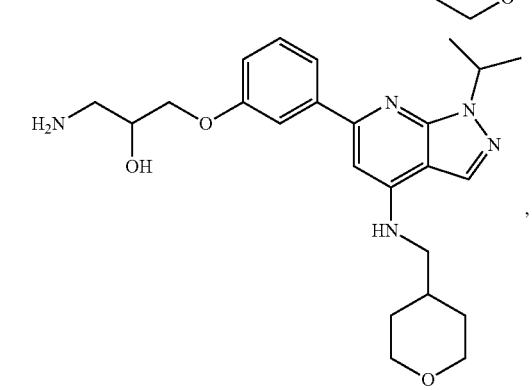
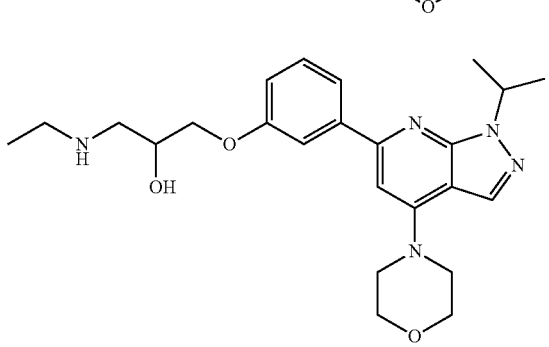
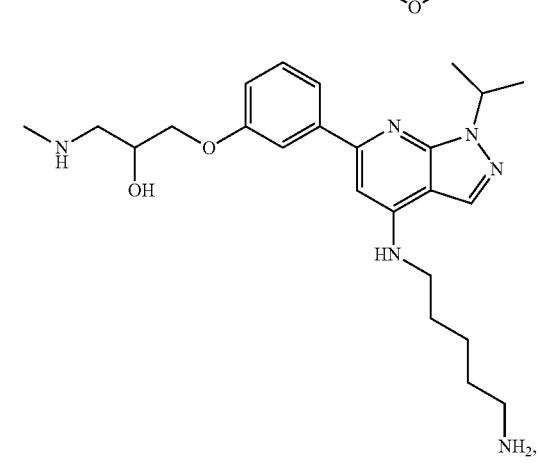
256
-continued
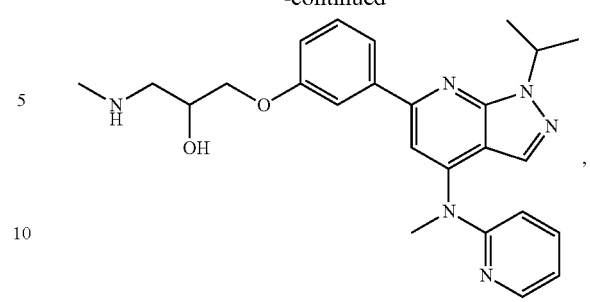
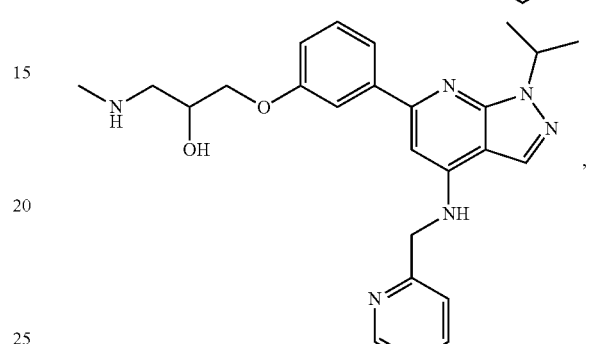
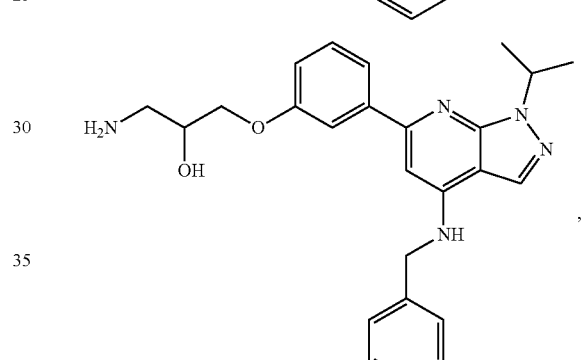
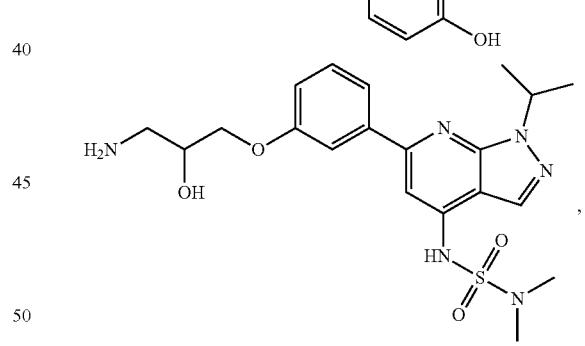
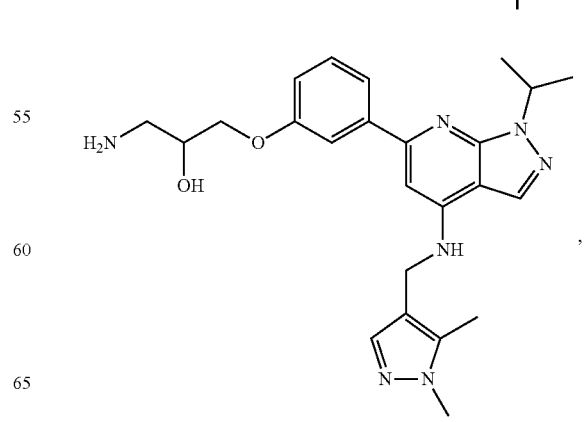

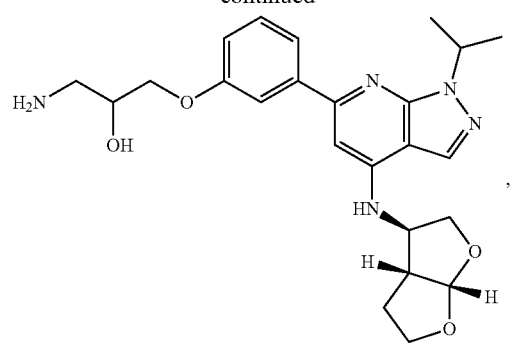
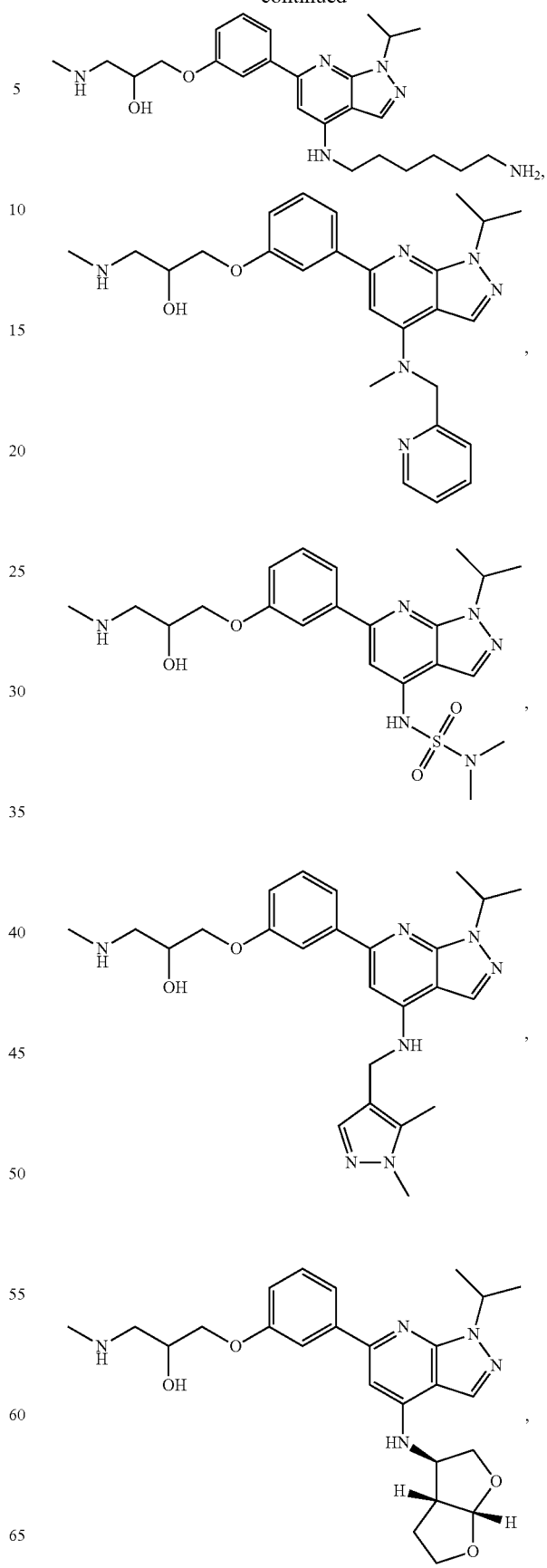

259
-continued
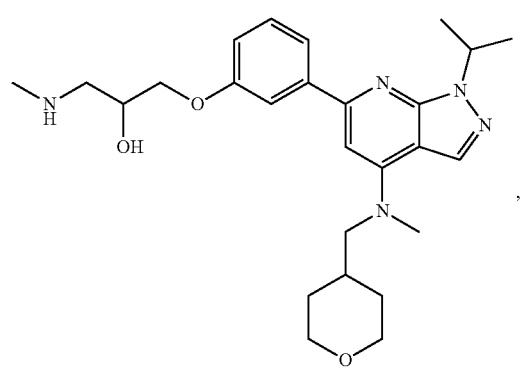
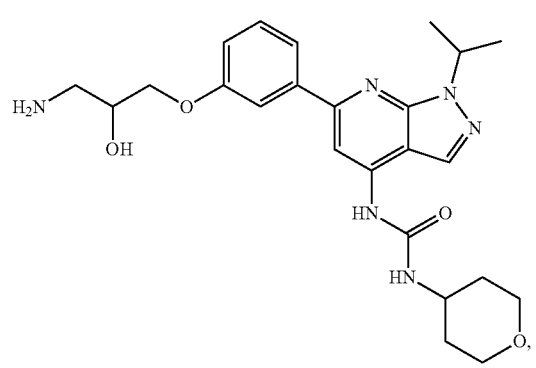
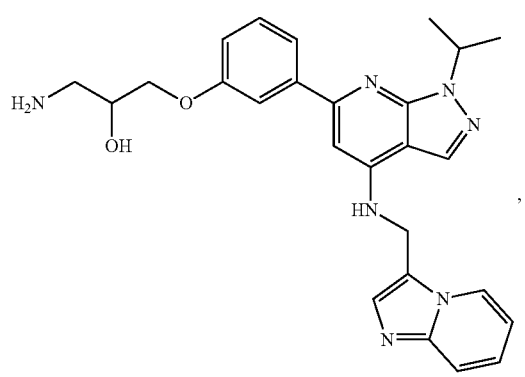
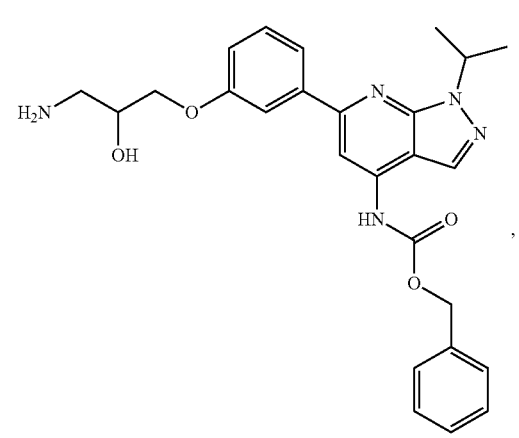
260
-continued
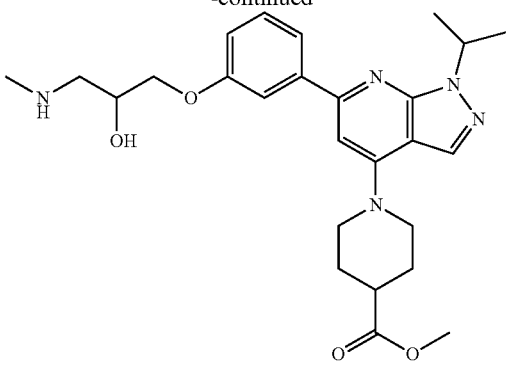
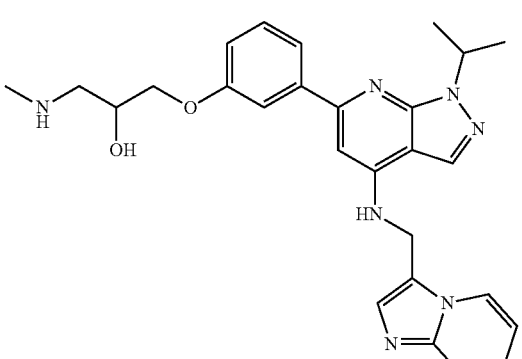
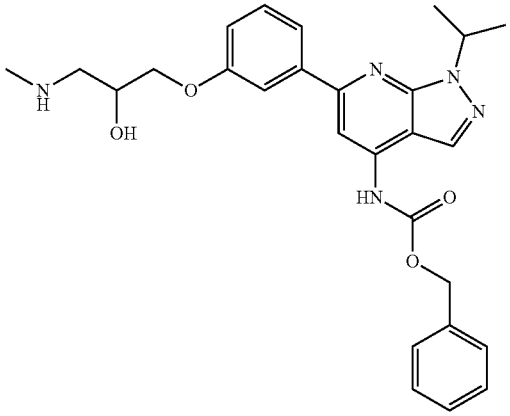
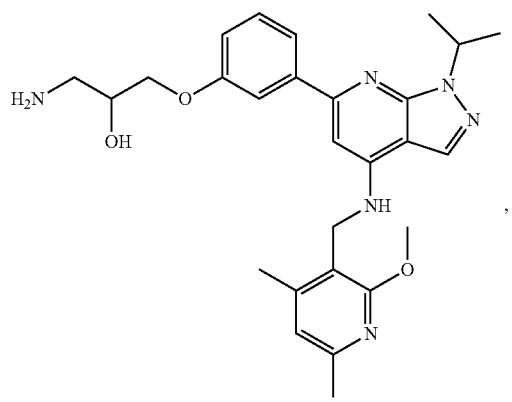

261
-continued
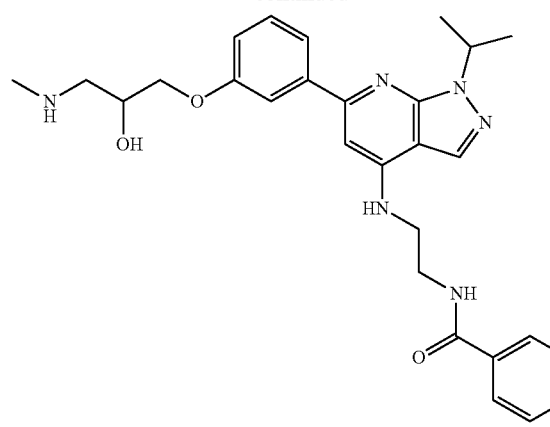
262
-continued
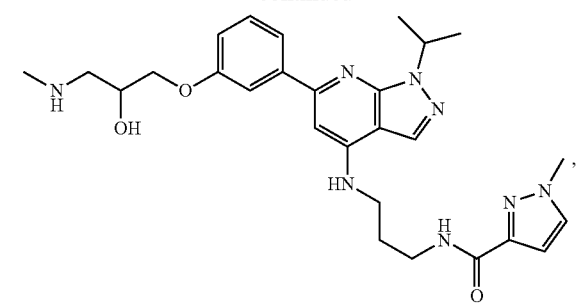
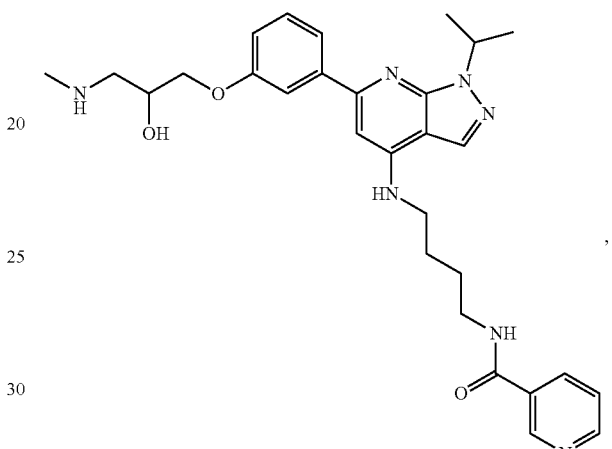
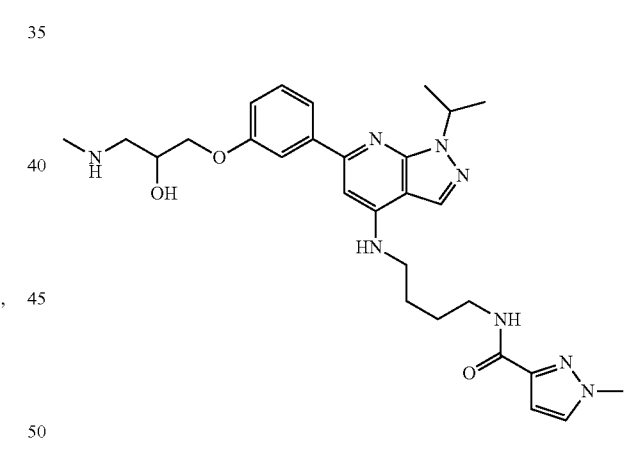
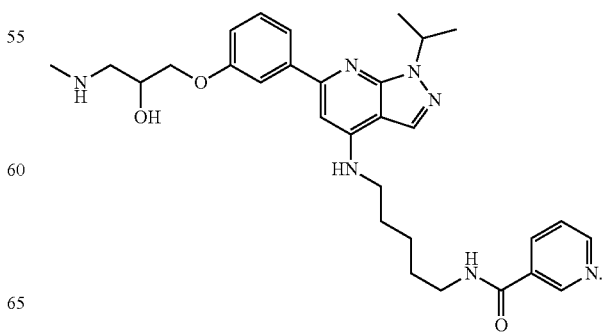

263
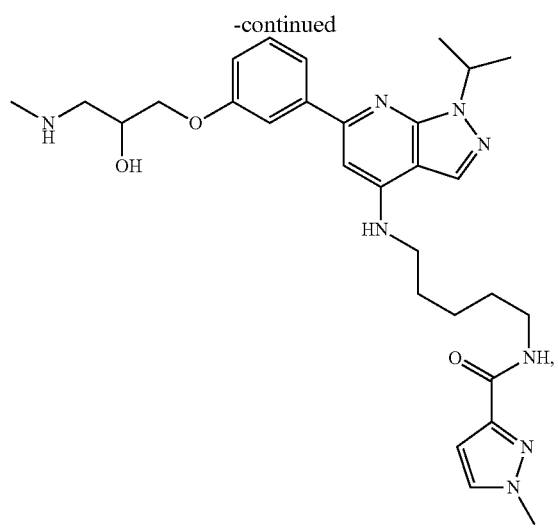
,
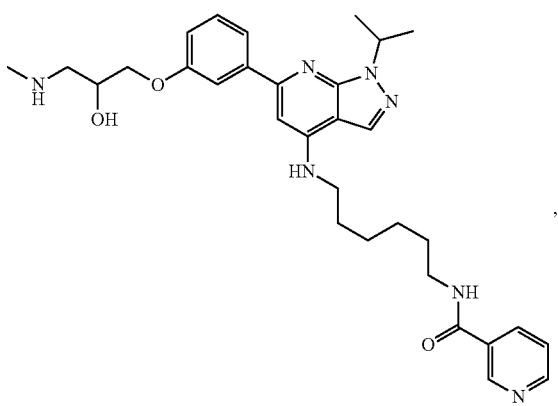
,
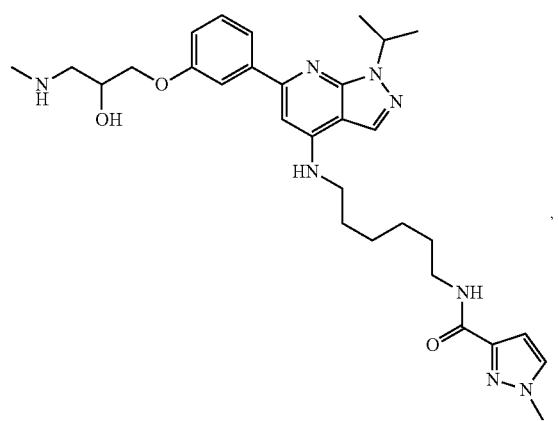
,
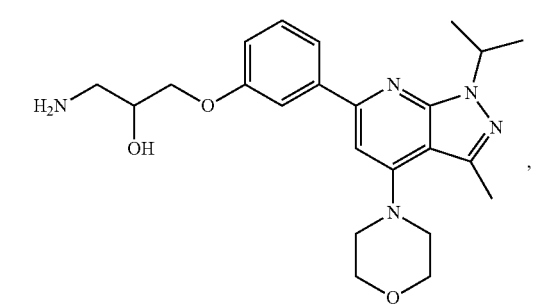
,
264
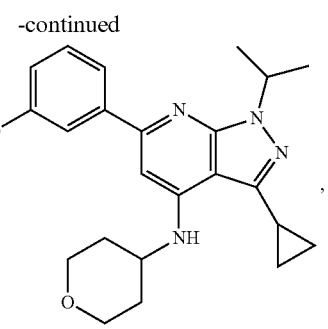
,
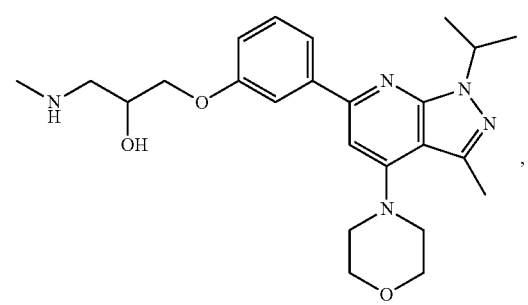
,
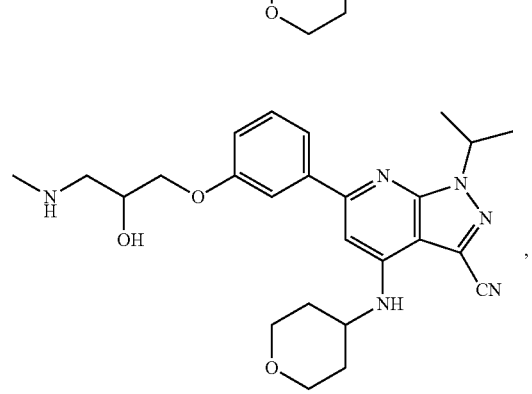
,
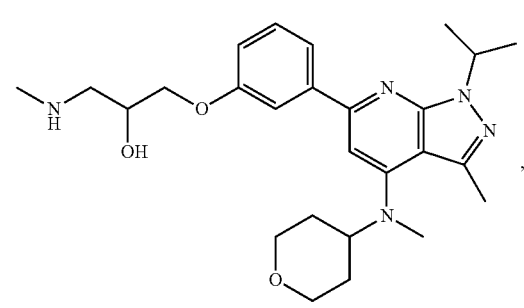
, 265 -continued
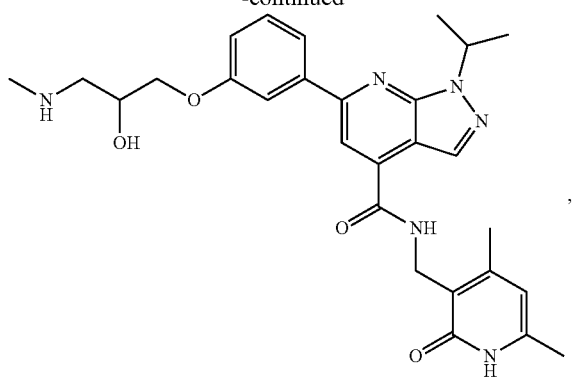
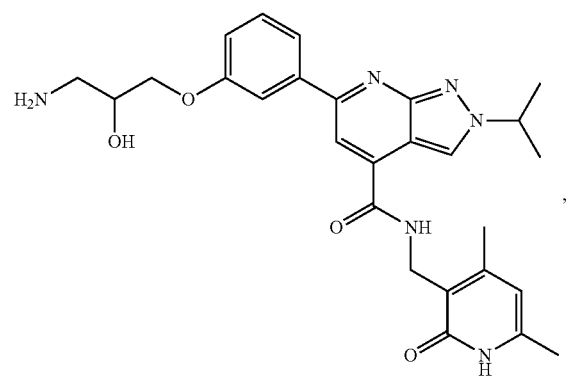
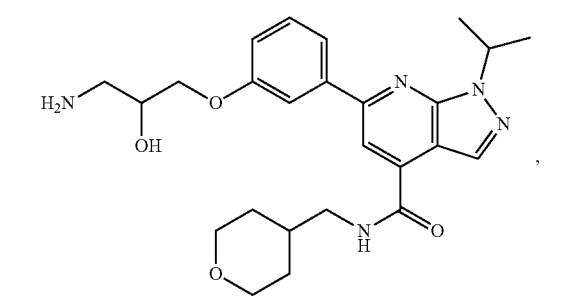
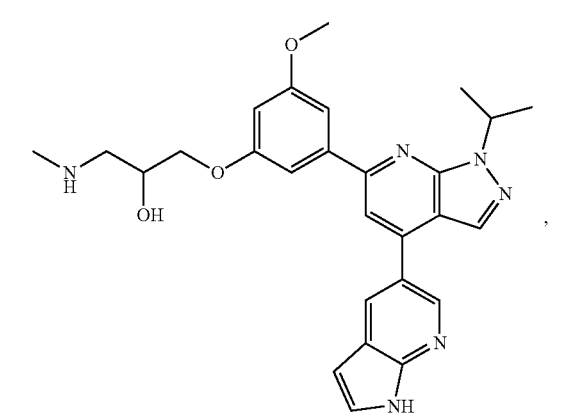
266 -continued
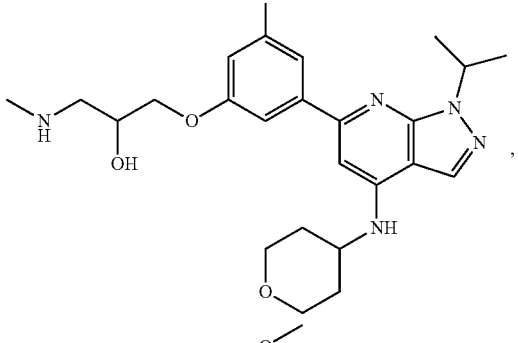
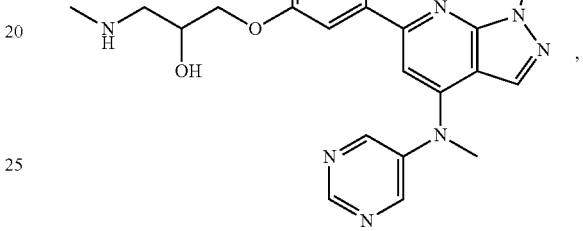
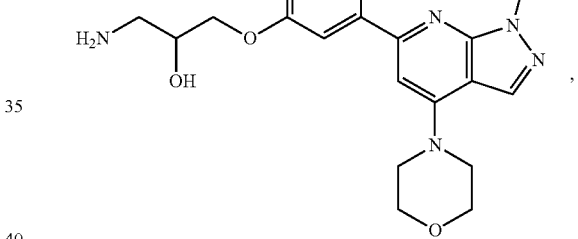
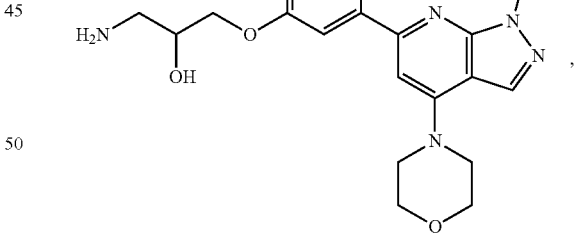
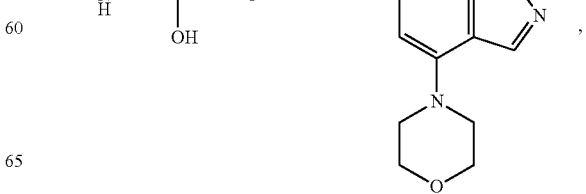

267
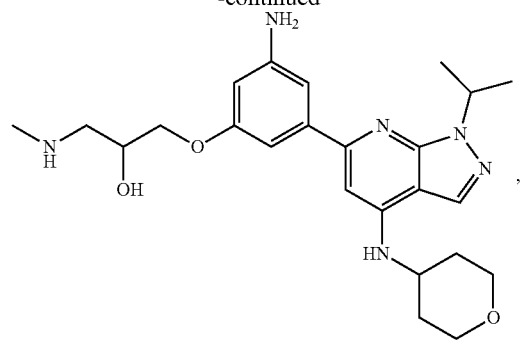
,
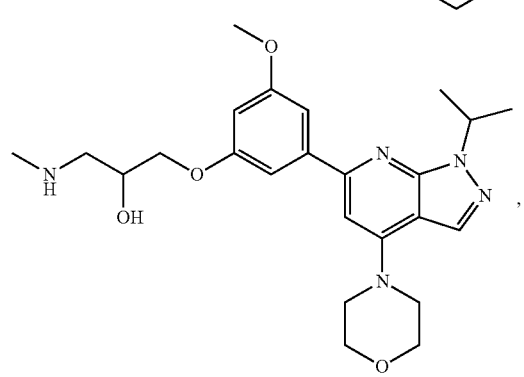
,
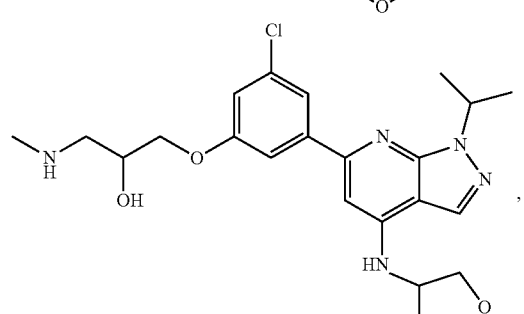
,
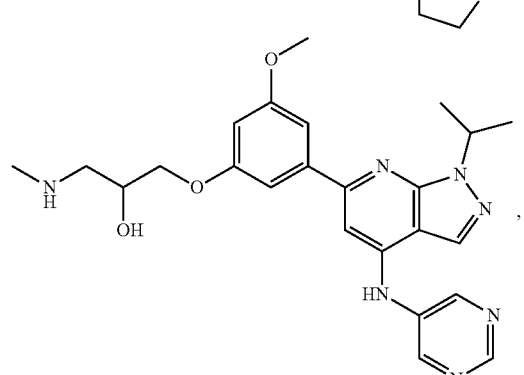
,
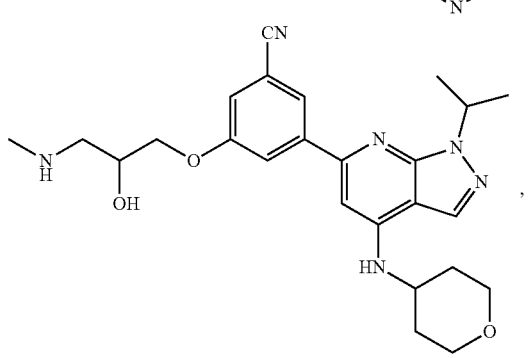
,
268
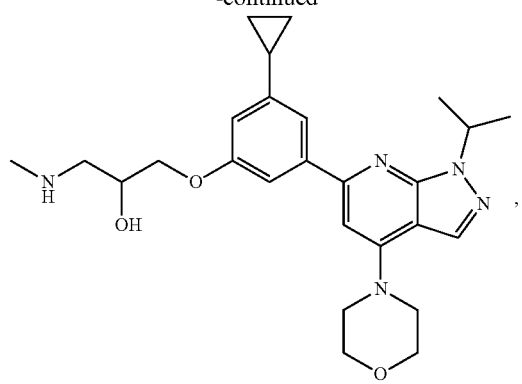
,
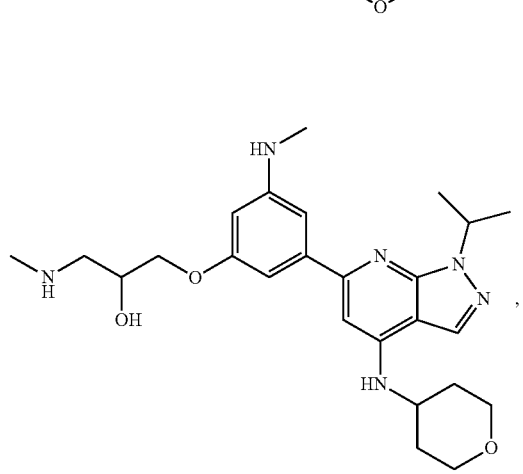
,
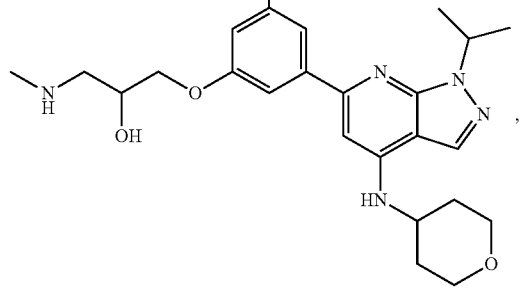
,
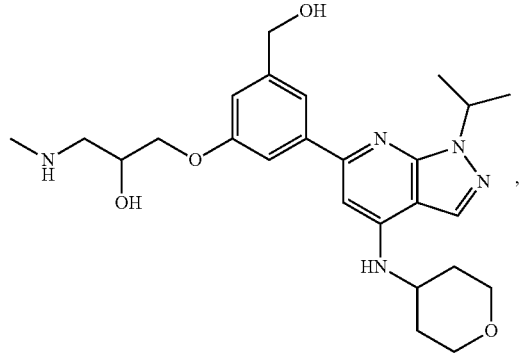
,

269
-continued
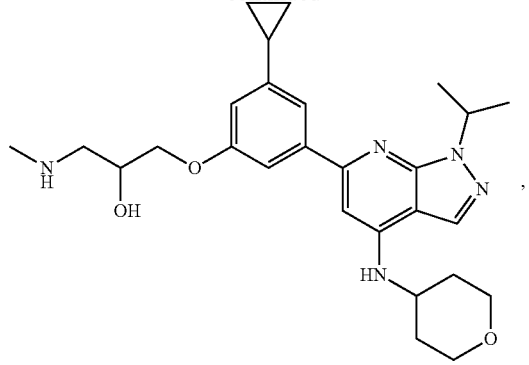
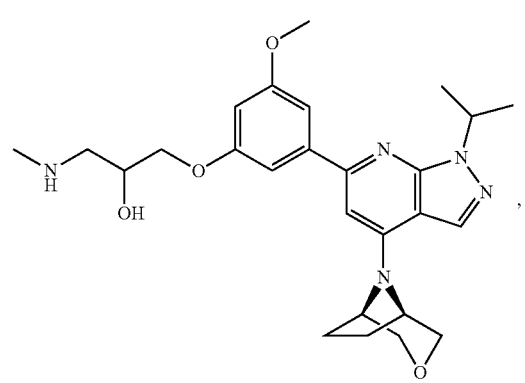
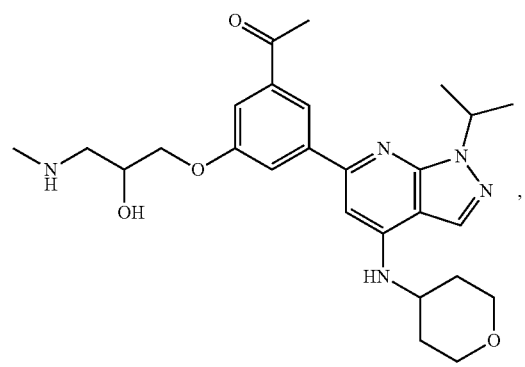
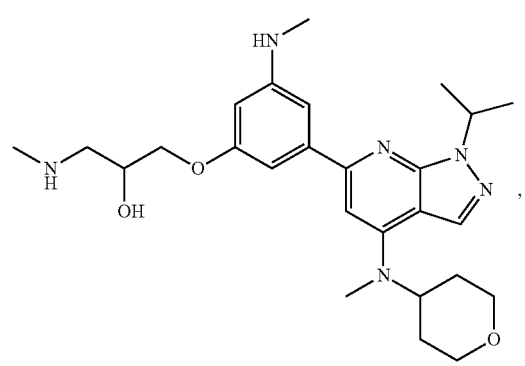
270
-continued
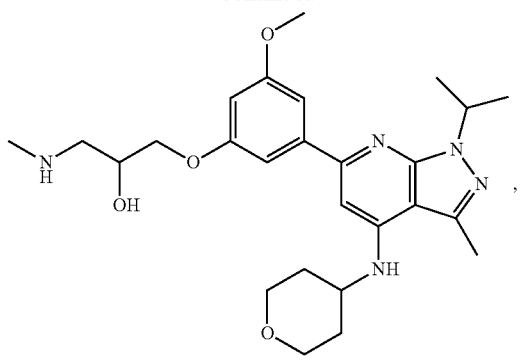
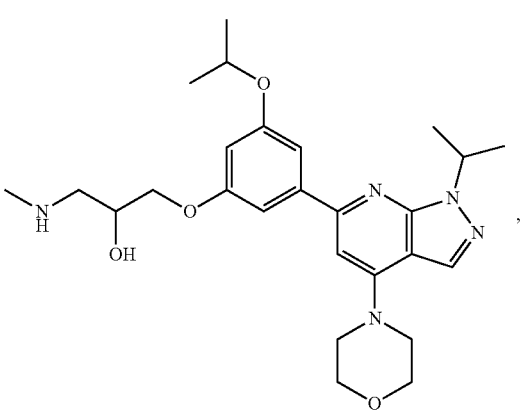
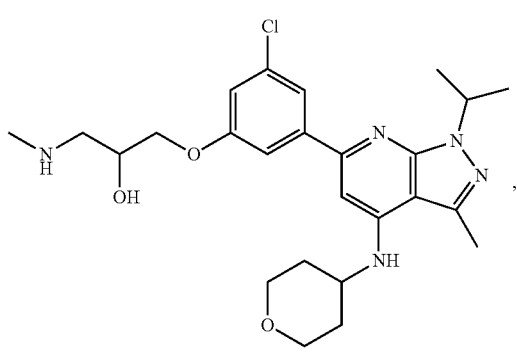
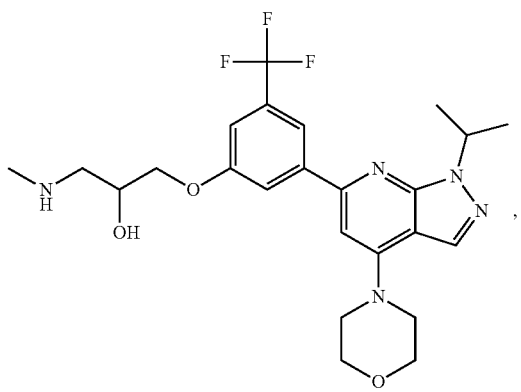

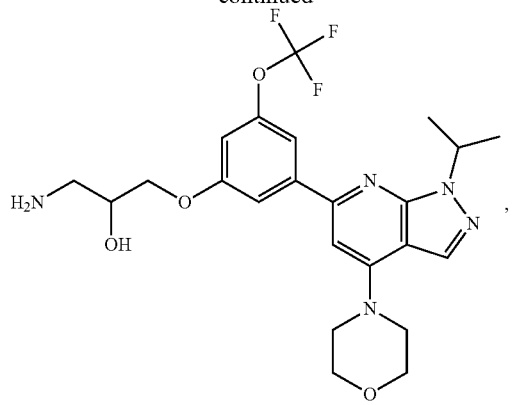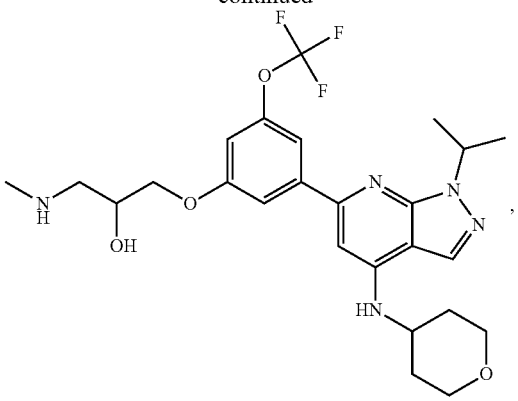

-continued
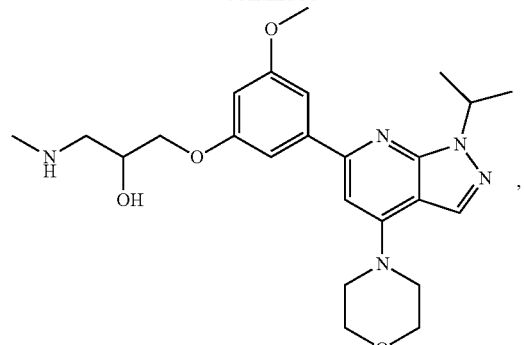
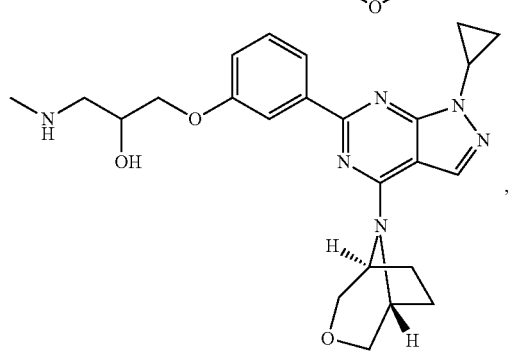
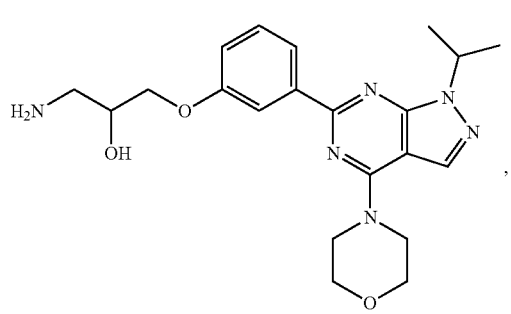
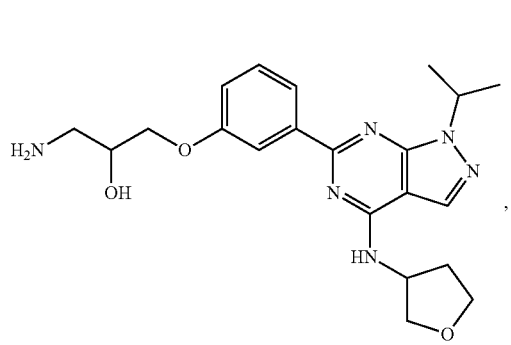
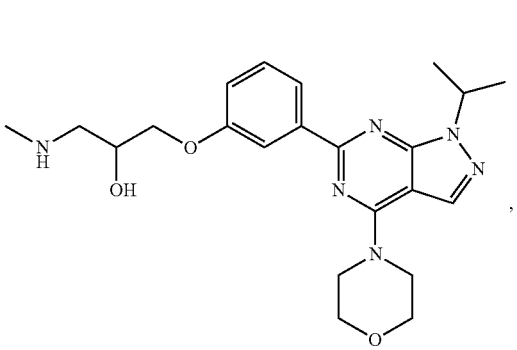
-continued
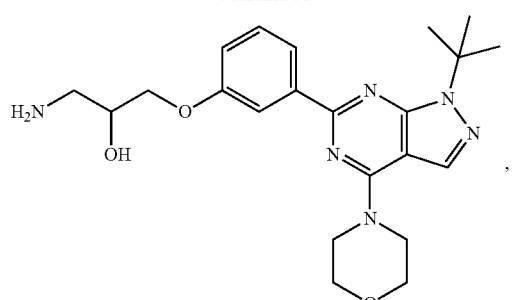
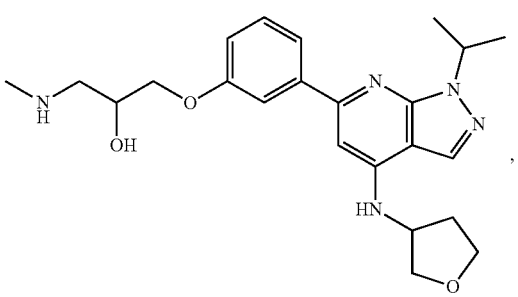
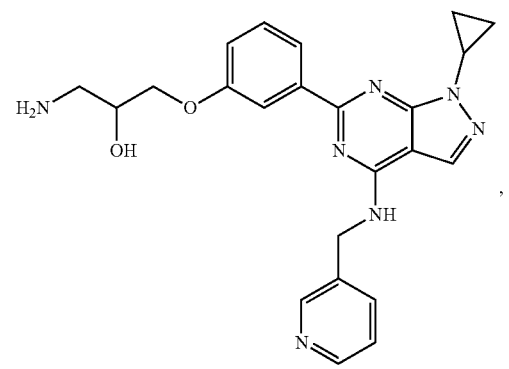
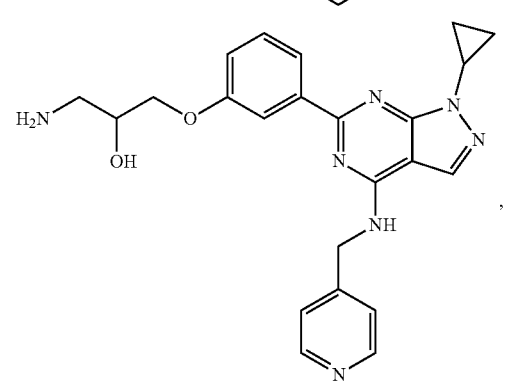
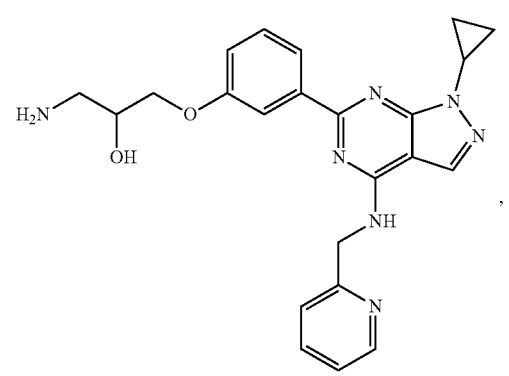

275
-continued
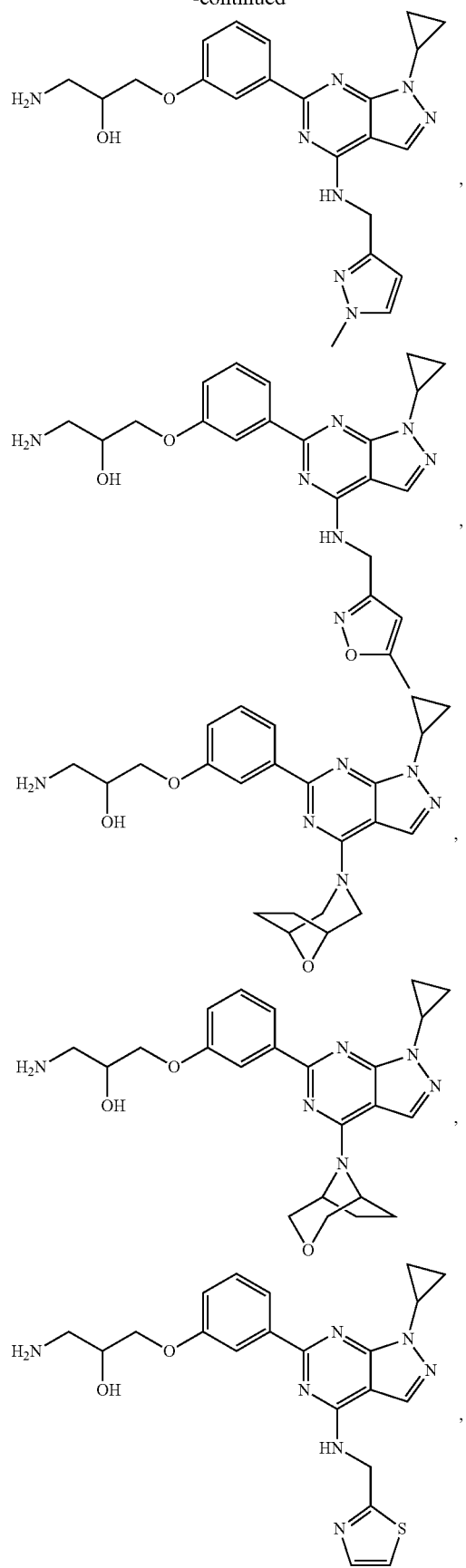
276
-continued
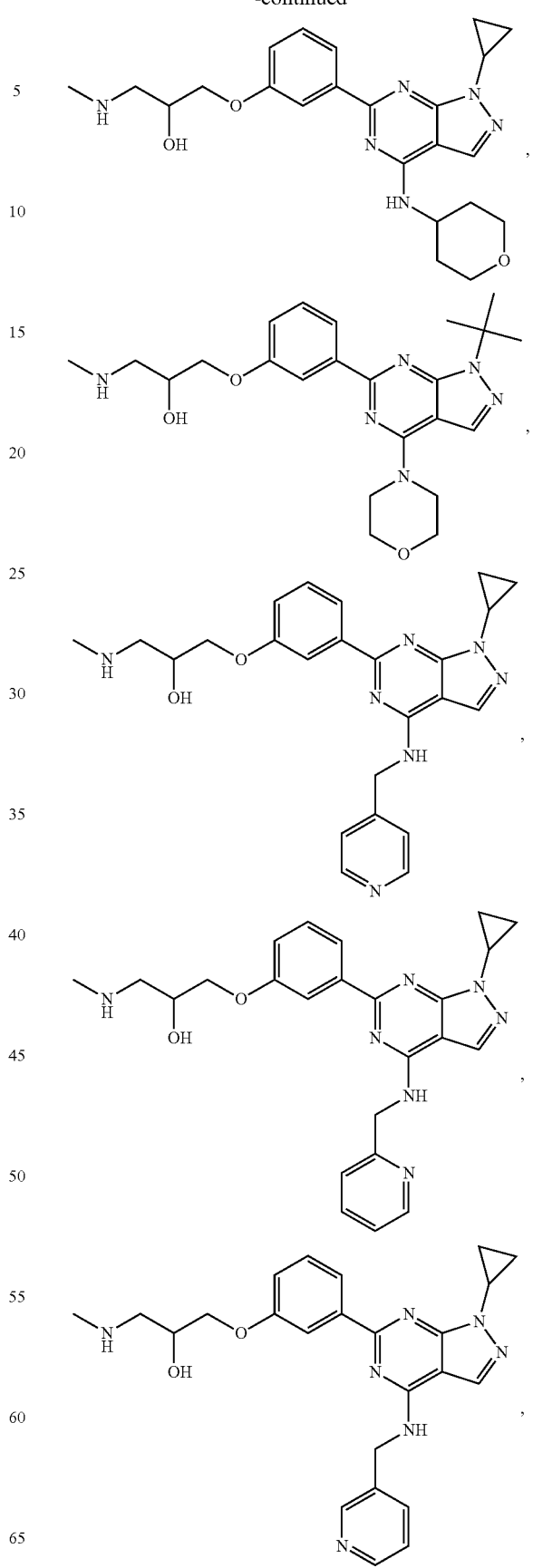

277
-continued
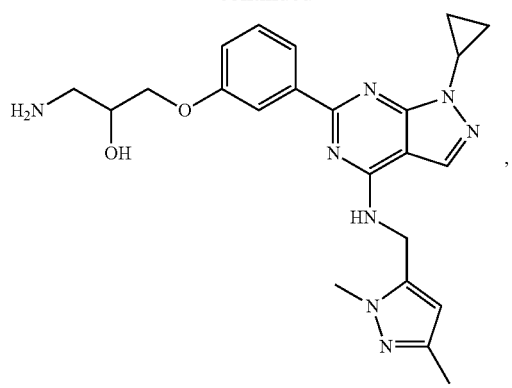
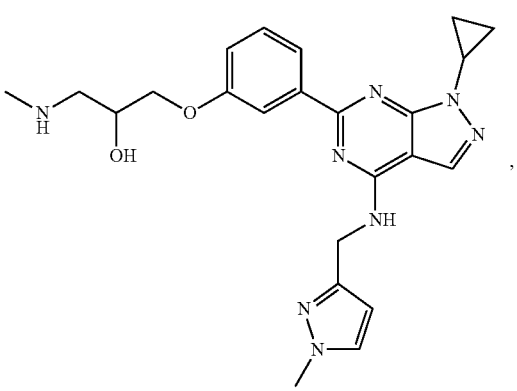
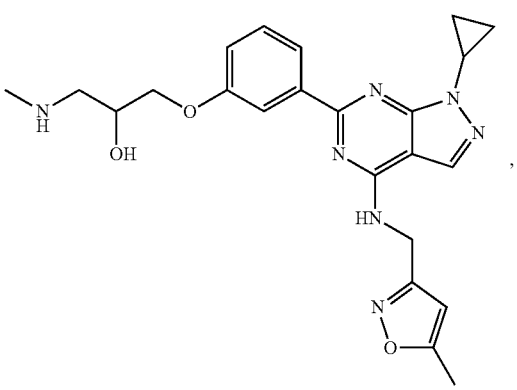
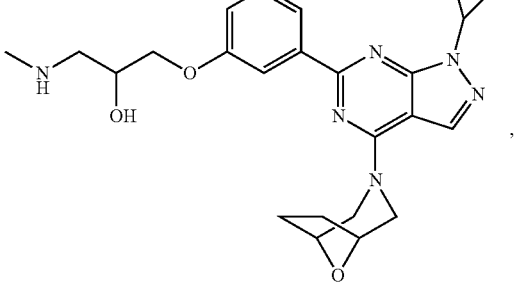
278
-continued
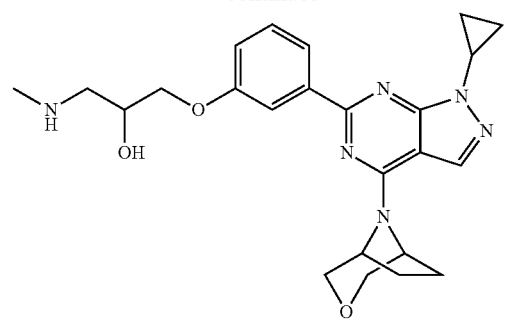
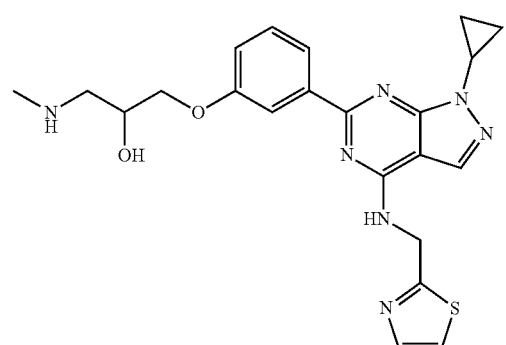
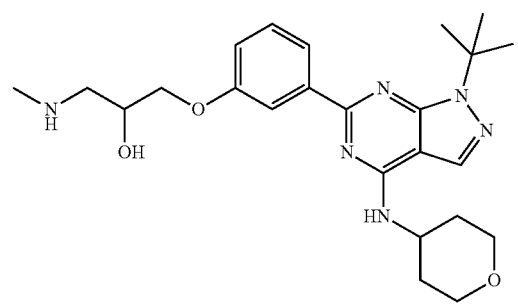
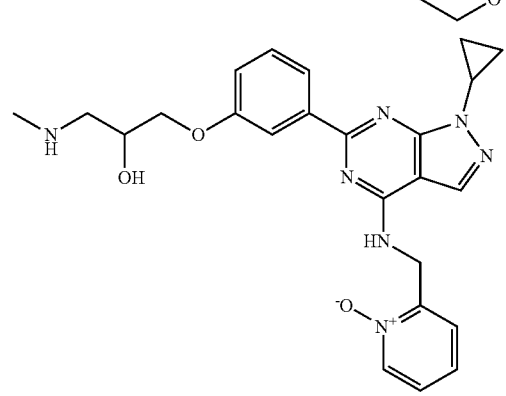
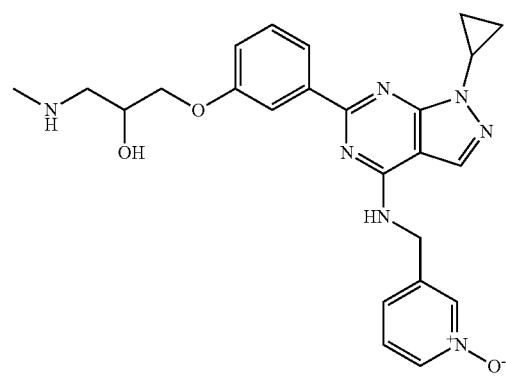

279
-continued
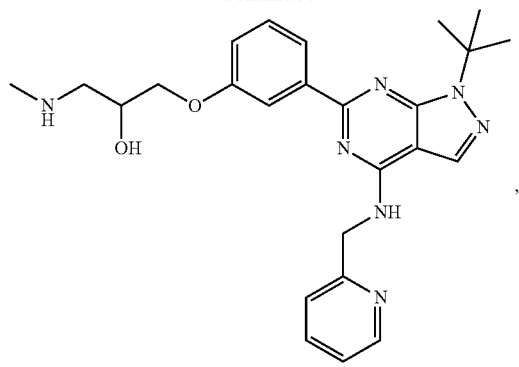
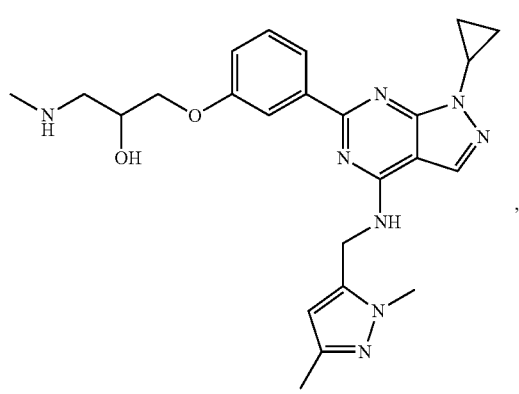
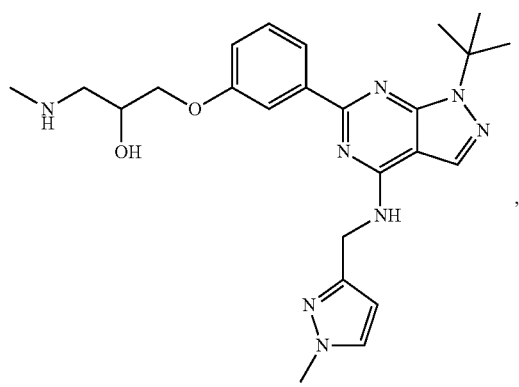
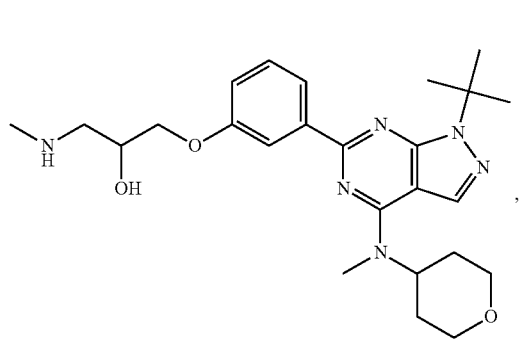
280
-continued
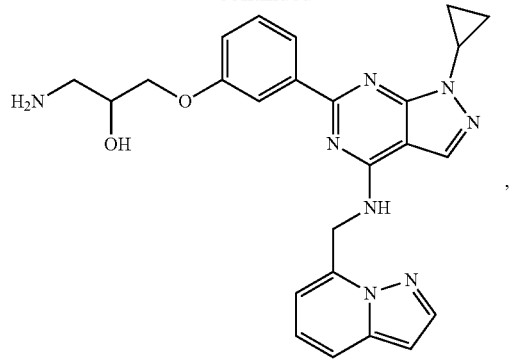
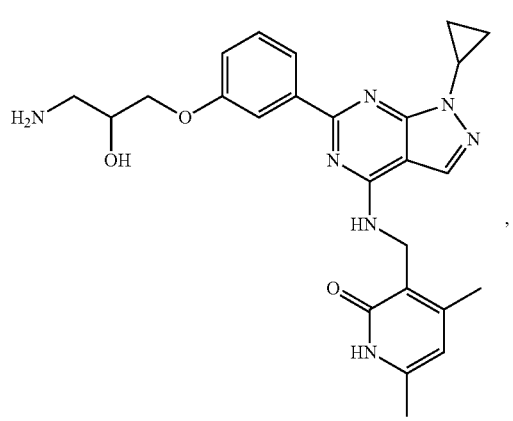
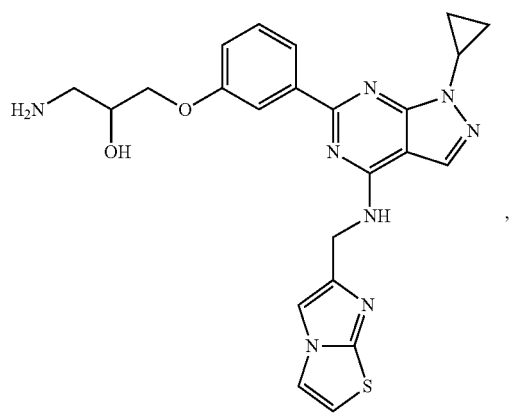
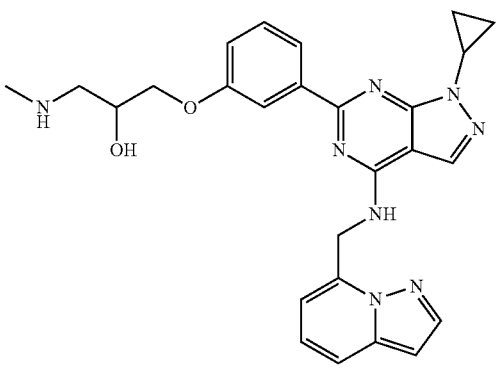

281
-continued
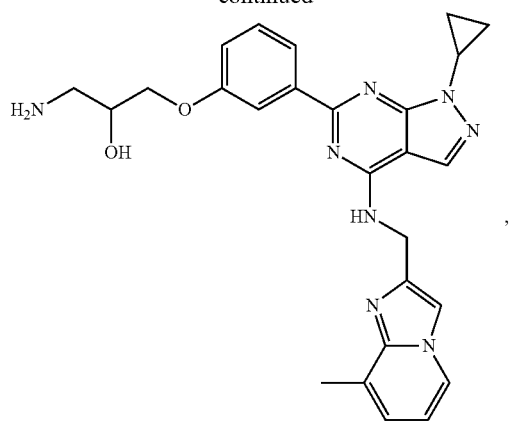
,
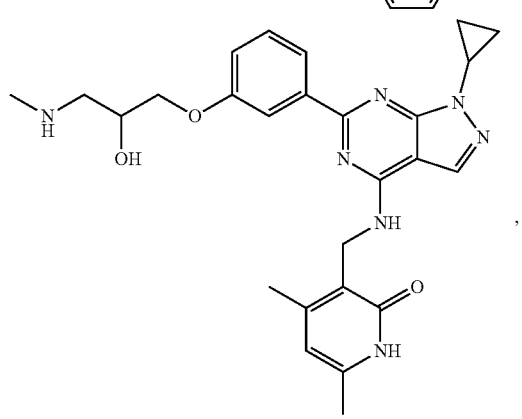
,
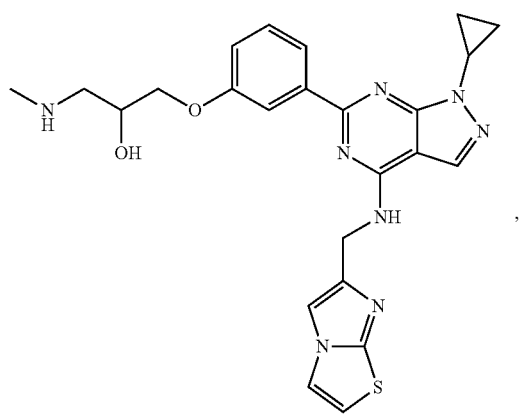
,
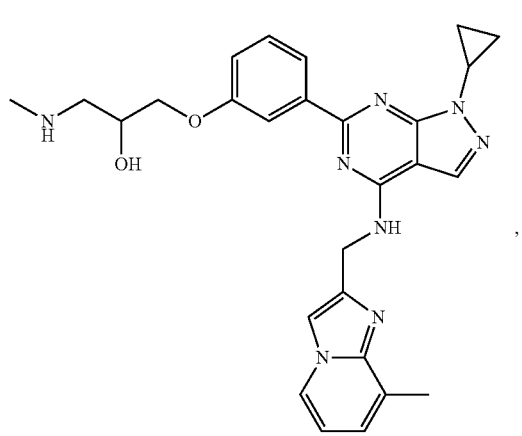
,
282
-continued
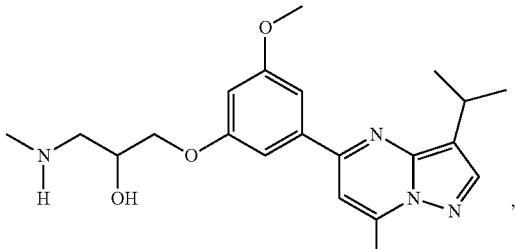
,
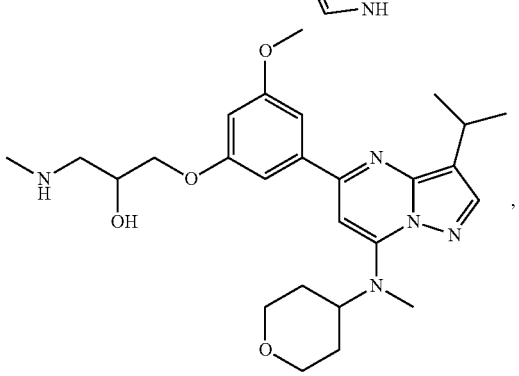
,
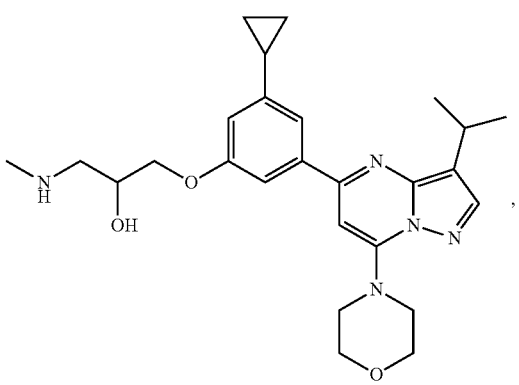
,
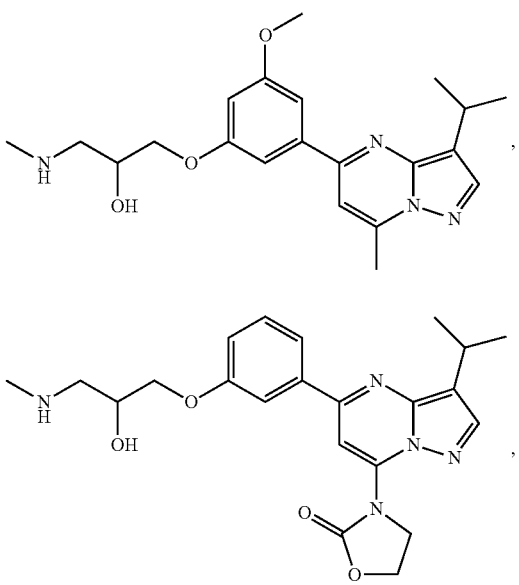
, 283
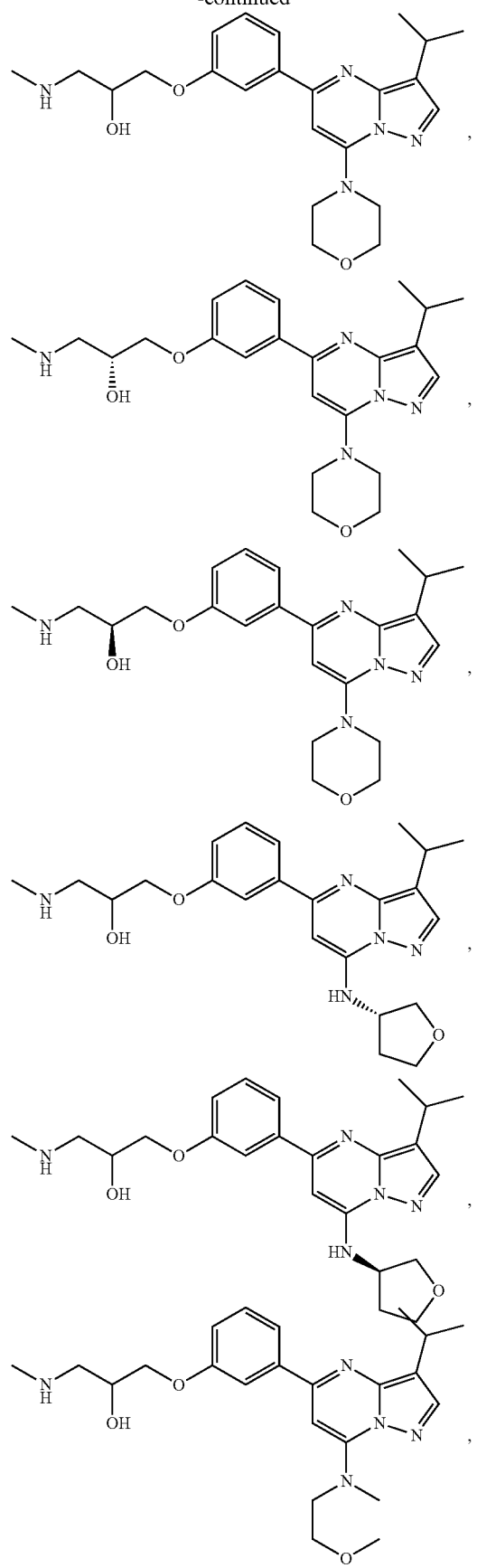
284
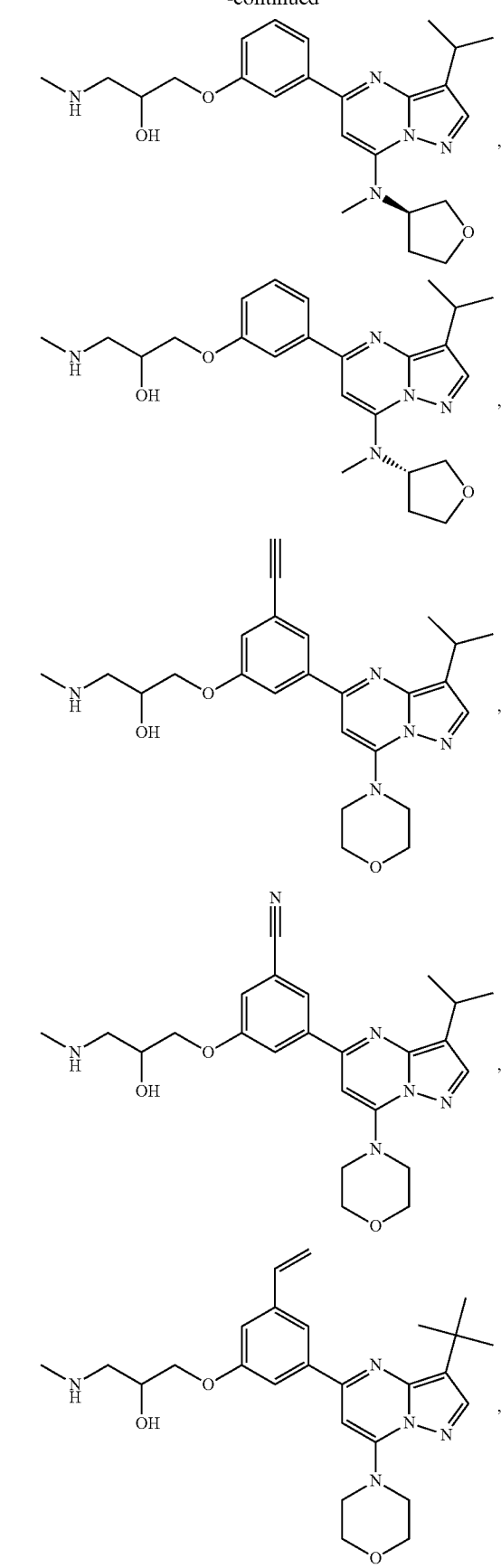

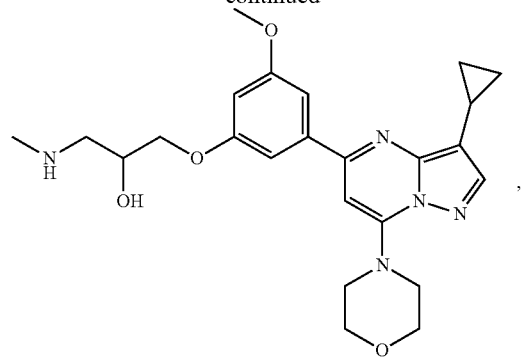
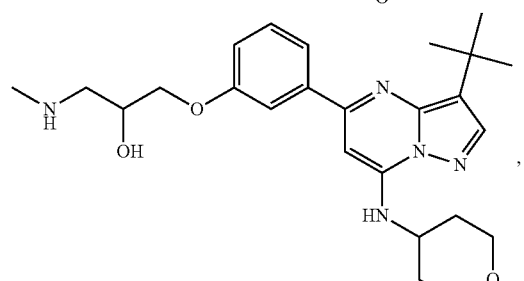
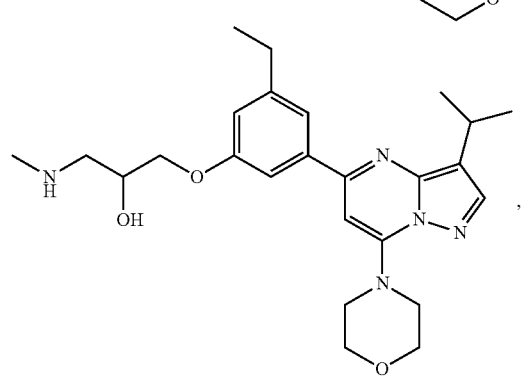
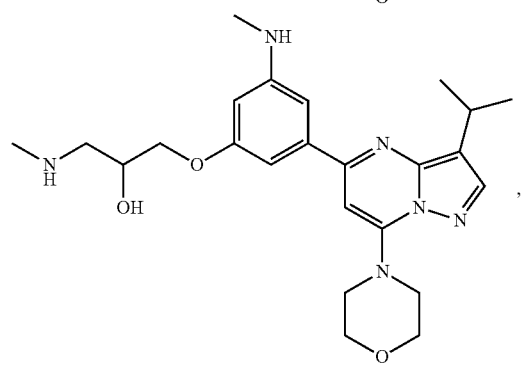
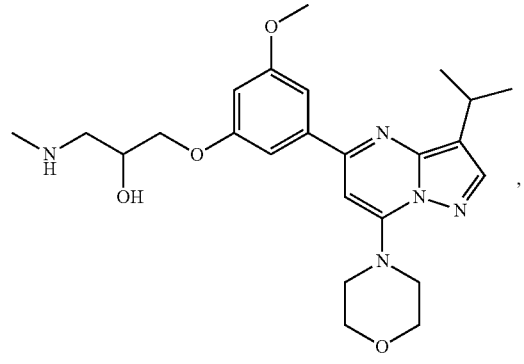
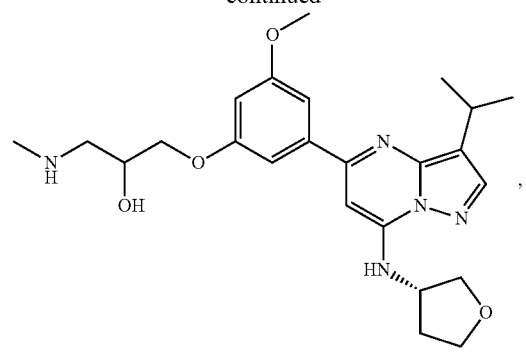
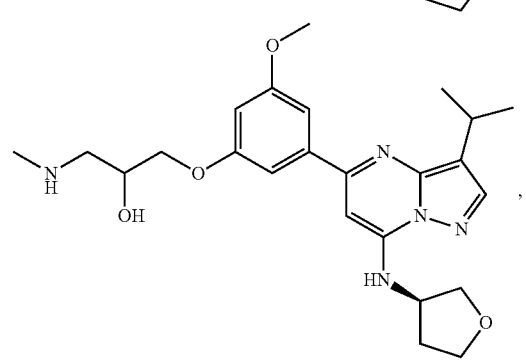
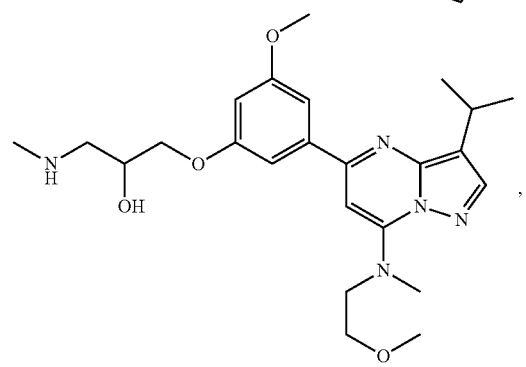
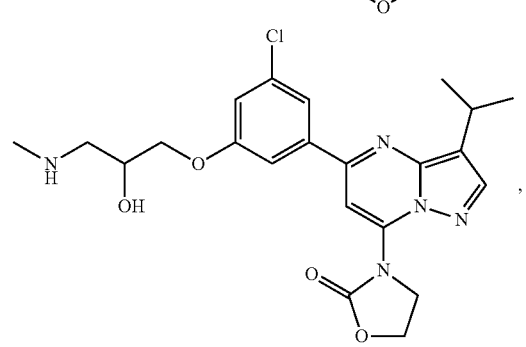
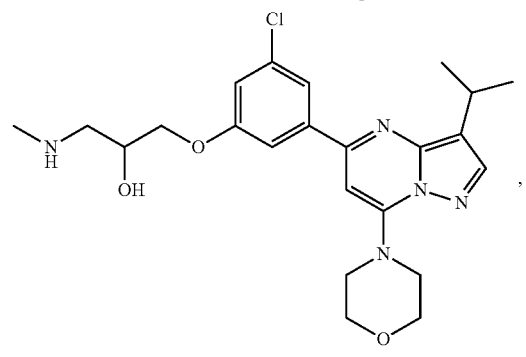

287
-continued
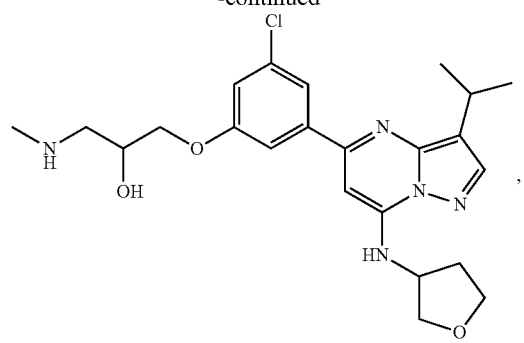,
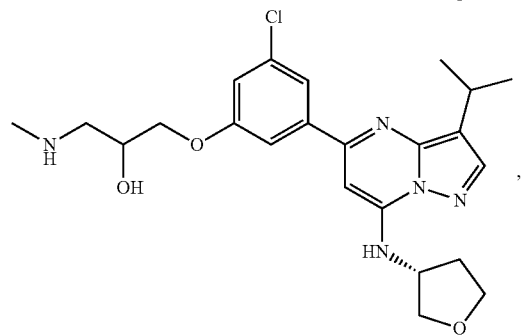,
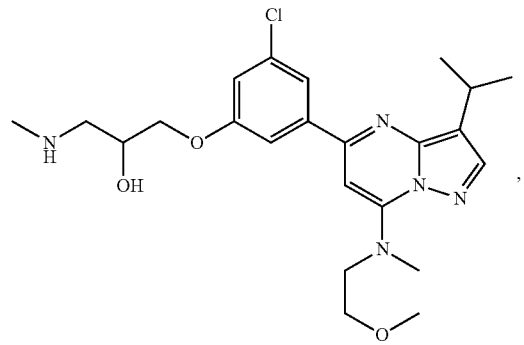,
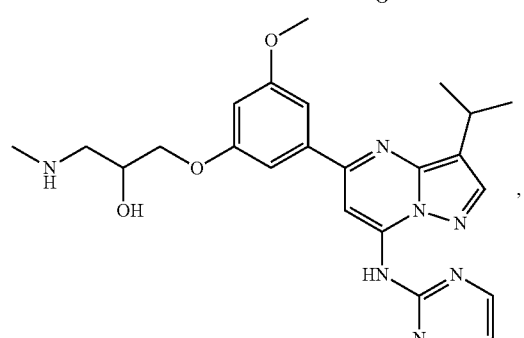,
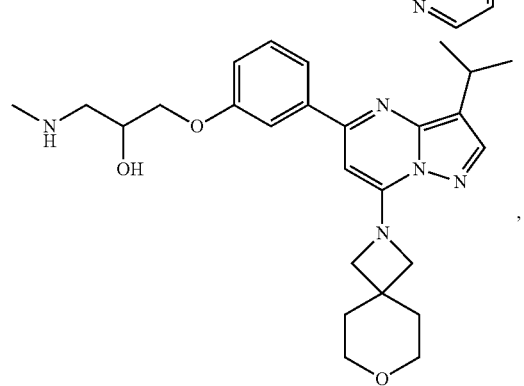,
288
-continued
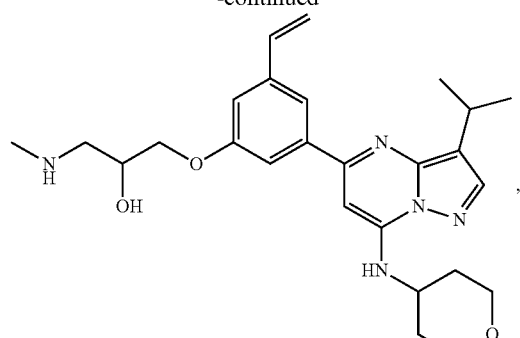,
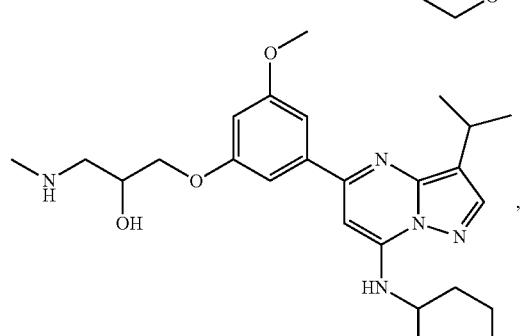,
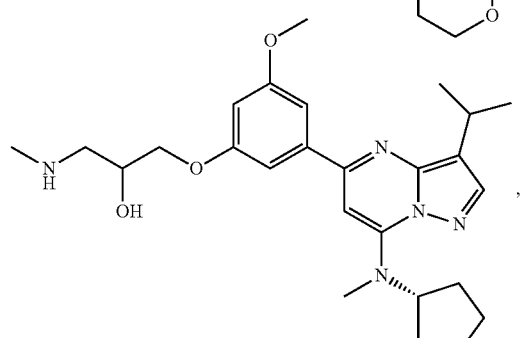,
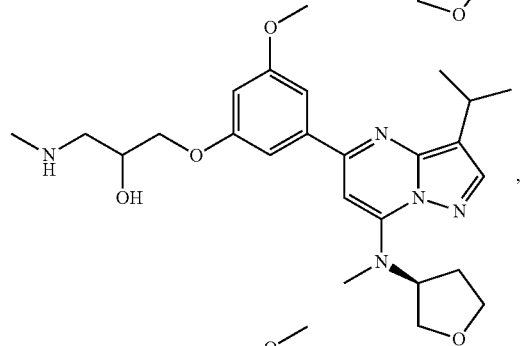,
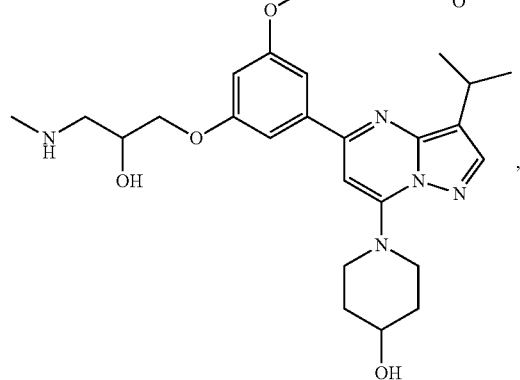,

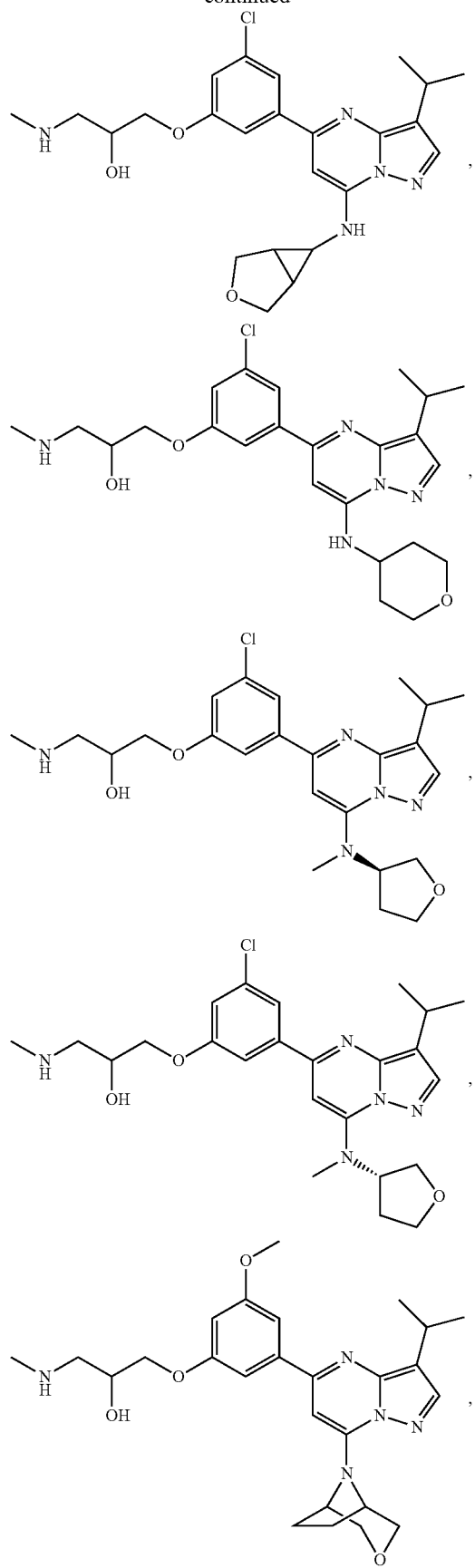
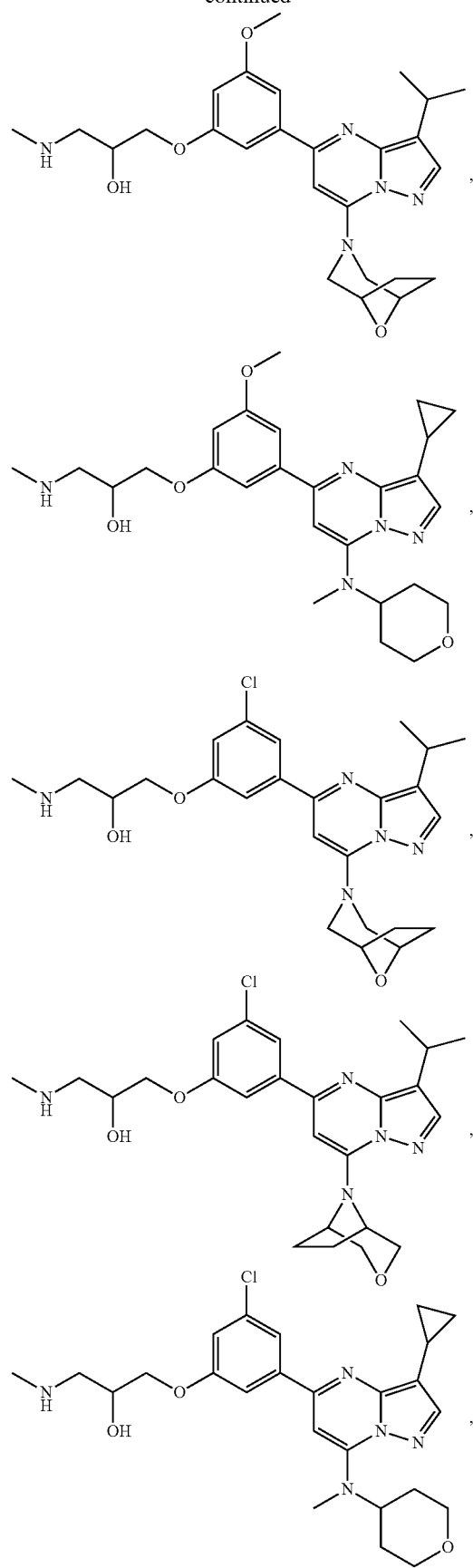

-continued
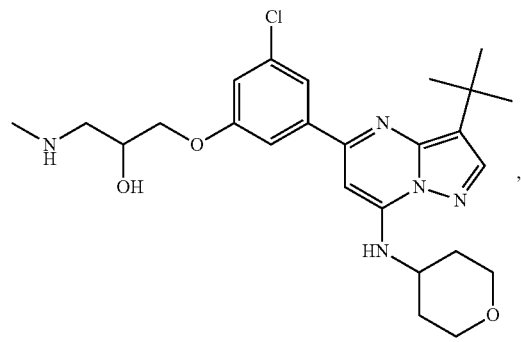
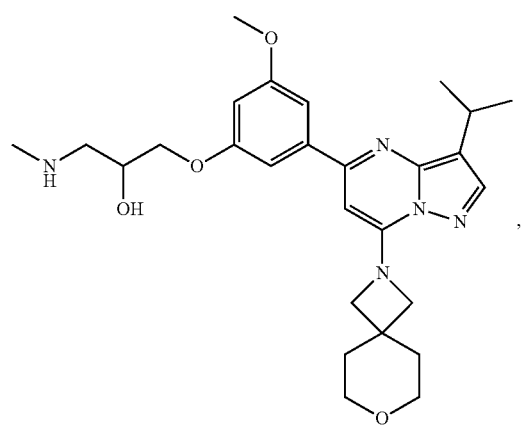
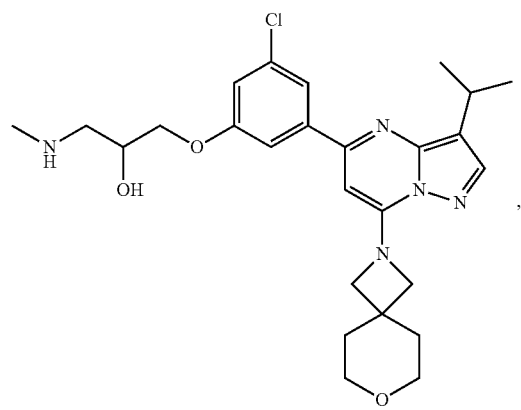
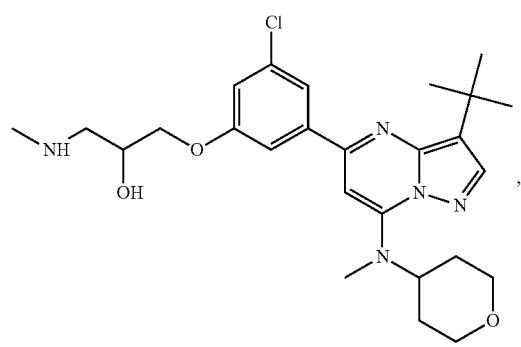
-continued
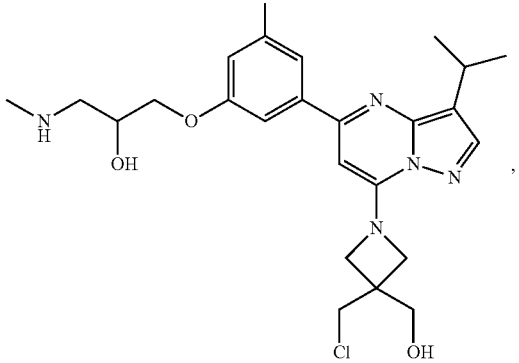
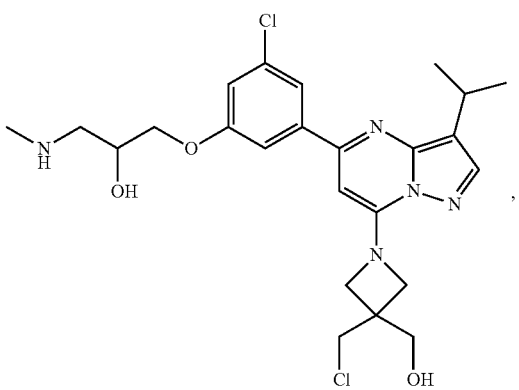
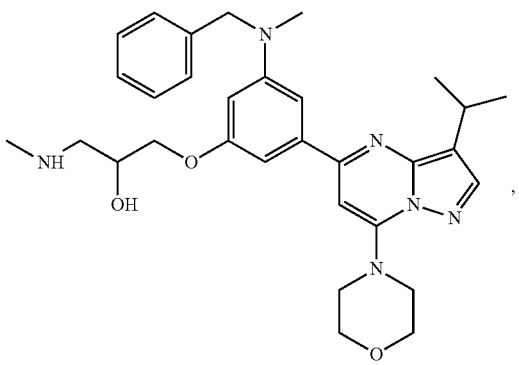
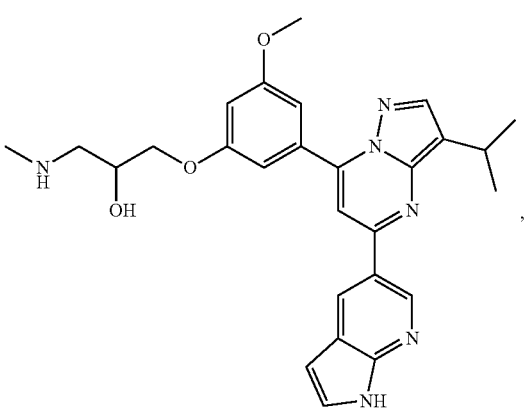

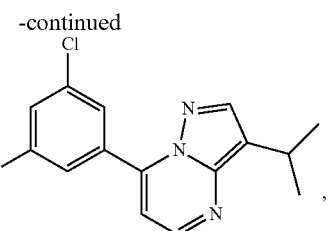

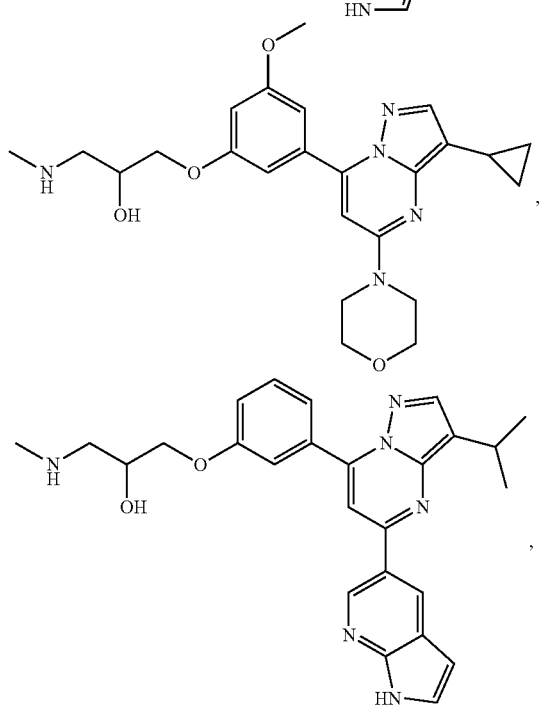

and pharmaceutically acceptable salts thereof.

17. A pharmaceutical composition comprising a compound of claim 1, or a pharmaceutically acceptable salt thereof, and a pharmaceutically acceptable excipient.

18. A kit or packaged pharmaceutical comprising a compound of claim 1, or a pharmaceutically acceptable salt thereof, and instructions for use thereof.

19. A method of treating a CARM1-mediated disorder, comprising administering to a subject in need thereof an effective amount of a compound of claim 1, or a pharmaceutically acceptable salt thereof.

20. The method of claim 19, wherein the disorder is a proliferative disorder or a metabolic disorder.

21. The method of claim 20, wherein the disorder is a proliferative disorder, and wherein the proliferative disorder is cancer.

22. The method of claim 21, wherein the cancer is associated with E2F1 upregulation or associated with aberrant CARM1 activity.

23. The method of claim 21, wherein the cancer is breast cancer, prostate cancer, or colorectal cancer.

24. The method of claim 21, wherein the cancer is ERα-dependent breast cancer, castration-resistant prostate cancer, or colorectal cancer associated with dysregulated WNT/β-catenin signaling.

25. A pharmaceutical composition comprising a compound of claim 16, or a pharmaceutically acceptable salt thereof, and a pharmaceutically acceptable excipient.

26. A kit or packaged pharmaceutical comprising a compound of claim 16, or a pharmaceutically acceptable salt thereof, and instructions for use thereof.

27. A compound of Formula (I):

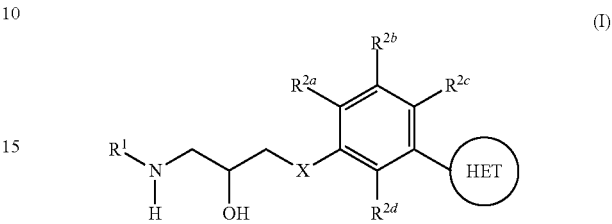

or a pharmaceutically acceptable salt thereof;
wherein:
X is —O—, —S—, or —CH$_2$—;
R$^1$ is hydrogen or optionally substituted C$_{1-4}$ aliphatic;
each of R$^{2a}$, R$^{2b}$, R$^{2c}$ and R$^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of R$^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{A2}$ groups attached to the same nitrogen atom are joined to form an optionally substituted heterocyclyl or optionally substituted heteroaryl ring;

Ring HET is an optionally substituted 6,5-bicyclic heteroaryl ring system comprising 2 to 5 nitrogen atoms, inclusive, wherein the point of attachment is provided on the 6-membered ring of the 6,5-bicyclic heteroaryl ring system, and wherein the 6-membered ring is further substituted with a group of formula -L$^1$-R$^3$;

L$^1$ is a bond, —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=N R$^L$)—, —N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, —N(R$^L$)SO$_2$N(R$^L$)—, or an optionally substituted C$_{1-10}$ saturated or unsaturated hydrocarbon chain, wherein one or more moieties selected from the group consisting of —O—, —N(R$^L$)—, —S—, —C(O)—, —C(O)O—, —C(O)S—, —C(O)N(R$^L$)—, —C(O)N(R$^L$)N(R$^L$)—, —OC(O)—, —OC(O)N(R$^L$)—, —NR$^L$C(O)—, —NR$^L$C(O)N(R$^L$)—, —NR$^L$C(O)N(R$^L$)N(R$^L$)—, —NR$^L$C(O)O—, —SC(O)—, —C(=NR$^L$)—, —C(=NNR$^L$)—, —C(=NOR$^L$)—, —C(=NR$^L$)N(R$^L$)—, —NR$^L$C(=NR$^L$)—, —C(S)—, —C(S)N(R$^L$)—, —NR$^L$C(S)—, —S(O)—, —OS(O)$_2$—, —S(O)$_2$O—, —SO$_2$—, —N(R$^L$)SO$_2$—, —SO$_2$N(R$^L$)—, and —N(R$^L$)SO$_2$N(R$^L$)— is optionally and independently present between two carbon atoms of the hydrocarbon chain, and optionally and independently present at one or both ends of the hydrocarbon chain;

each $R^L$ is independently hydrogen, optionally substituted alkyl, or a nitrogen protecting group, or $R^L$ and $R^3$ taken together form an optionally substituted heterocyclyl or optionally substituted heteroaryl ring; and $R^3$ is optionally substituted alkyl, optionally substituted alkenyl, optionally substituted alkynyl, optionally substituted carbocyclyl, optionally substituted heterocyclyl, optionally substituted aryl, or optionally substituted heteroaryl.

28. A compound of Formula (I):

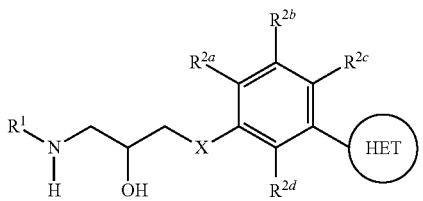

or a pharmaceutically acceptable salt thereof;
wherein:

X is —O—, —S—, or —CH$_2$—;

$R^1$ is hydrogen or optionally substituted $C_{1-4}$ aliphatic;

each of $R^{2a}$, $R^{2b}$, $R^{2c}$, and $R^{2d}$ is independently hydrogen, halogen, —CN, —NO$_2$, —C(=O)R$^{A2}$, —C(=O)OR$^{A2}$, —C(=O)N(R$^{A2}$)$_2$, —OR$^{A2}$, —SR$^{A2}$, —N(R$^{A2}$)$_2$, —S(=O)R$^{A2}$, —S(=O)$_2$R$^{A2}$, optionally substituted alkyl, optionally substituted alkenyl, optionally substituted alkynyl, optionally substituted carbocyclyl, optionally substituted heterocyclyl, wherein each instance of $R^{A2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{A2}$ groups attached to the same nitrogen atom are joined to form an optionally substituted heterocyclyl or optionally substituted heteroaryl ring;

Ring HET is selected from the group consisting of:

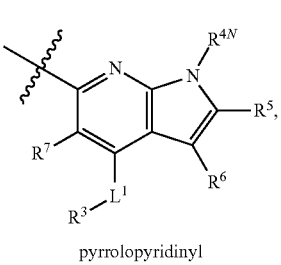

pyrrolopyridinyl

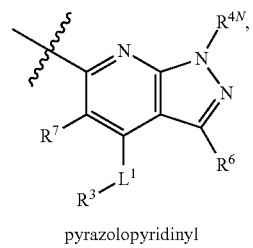

pyrazolopyridinyl

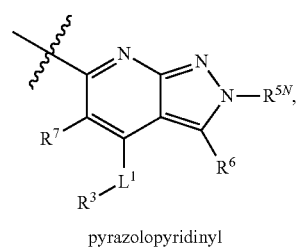

pyrazolopyridinyl

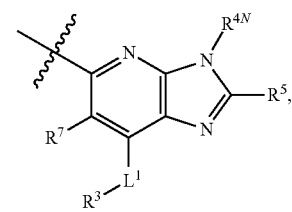

imidazopyridinyl

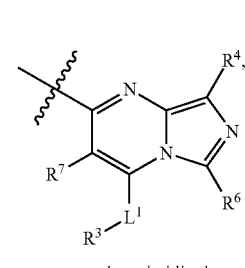

pyrazolopyrimidinyl

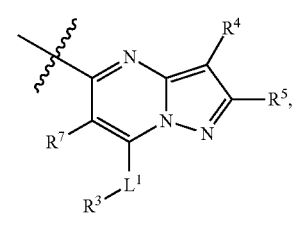

pyrazolopyrimidinyl

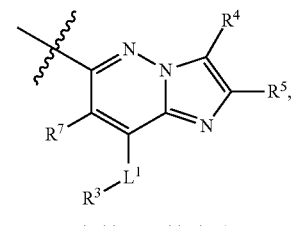

imidazopyridazinyl

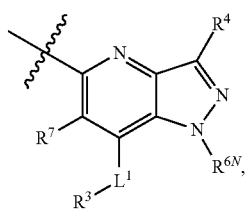
pyrazolopyridinyl (i-h)
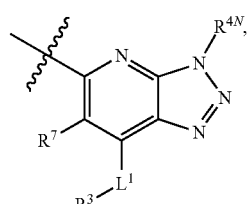
triazolopyridinyl (i-i)
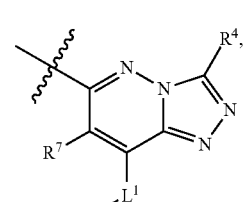
triazolopyridazinyl (i-j)
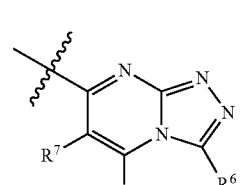
triazolopyrimidinyl (i-k)
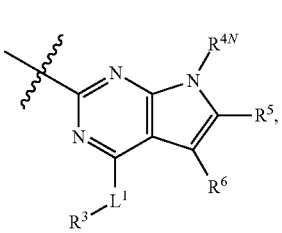
pyrrolopyrimidinyl (i-l)
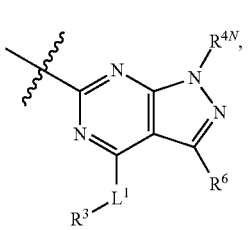
pyrazolopyrimidinyl (i-m)
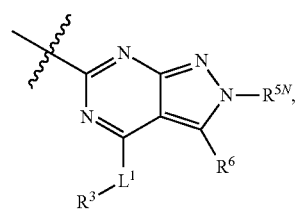
pyrazolopyrimidinyl (i-n)
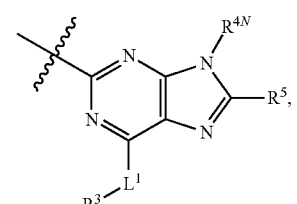
purinyl (i-o)
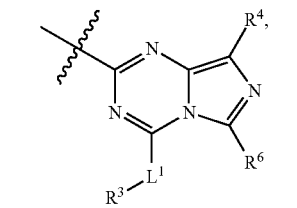
imidazotriazinyl (i-p)
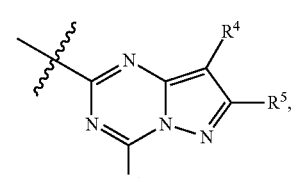
pyrazolotriazinyl (i-q)
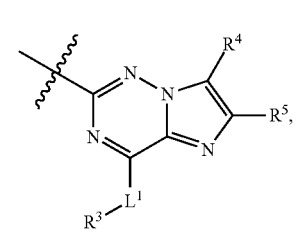
imidazotriazinyl (i-r)
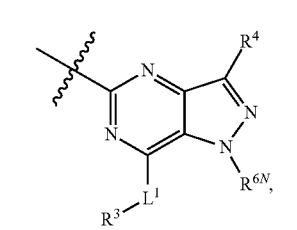
pyrazolopyrimidinyl (i-s)

-continued
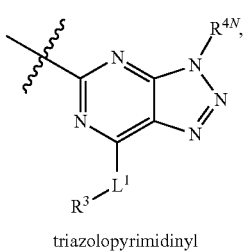
triazolopyrimidinyl
(i-t)
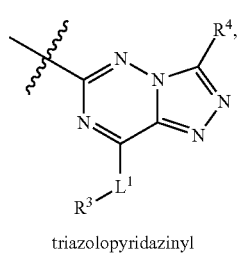
triazolopyridazinyl
(i-u)
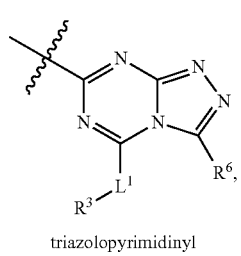
triazolopyrimidinyl
(i-v)
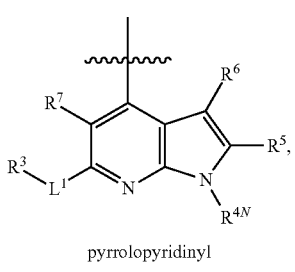
pyrrolopyridinyl
(ii-a)
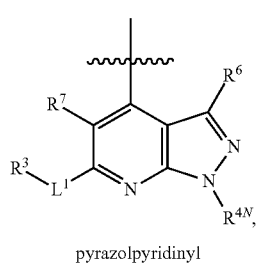
pyrazolpyridinyl
(ii-b)
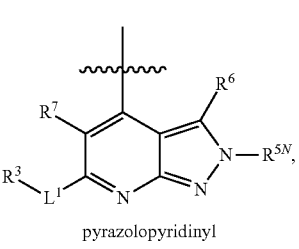
pyrazolopyridinyl
(ii-c)
-continued
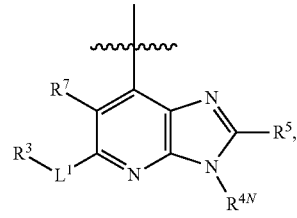
imidazopyridinyl
(ii-d)
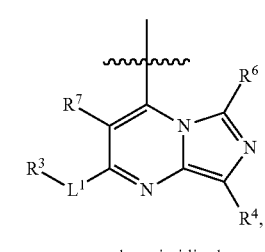
pyrazolopyrimidinyl
(ii-e)
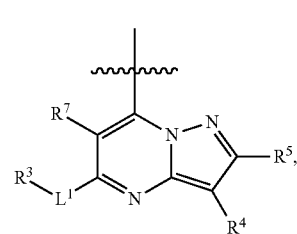
pyrazolopyrimidinyl
(ii-f)
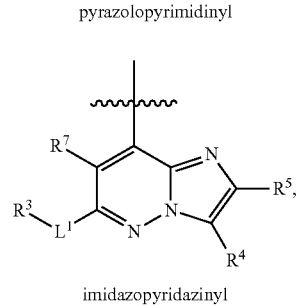
imidazopyridazinyl
(ii-g)
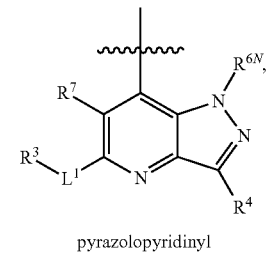
pyrazolopyridinyl
(ii-h)
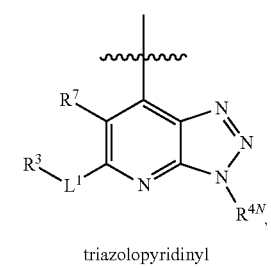
triazolopyridinyl
(ii-i)

-continued
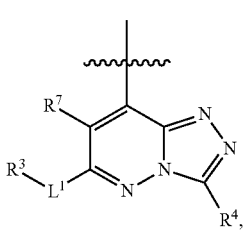
triazolopyridazinyl
(ii-j)
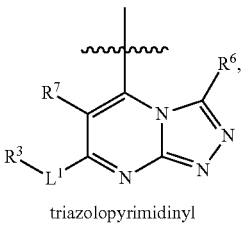
triazolopyrimidinyl
(ii-k)
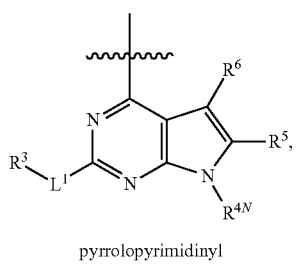
pyrrolopyrimidinyl
(ii-l)
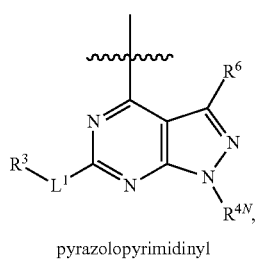
pyrazolopyrimidinyl
(ii-m)
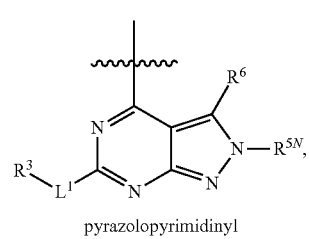
pyrazolopyrimidinyl
(ii-n)
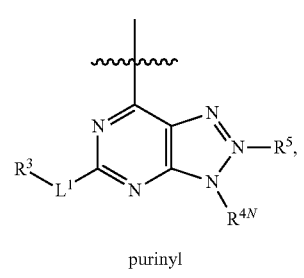
purinyl
(ii-o)
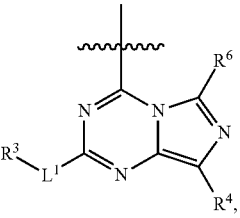
imidazotriazinyl
(ii-p)
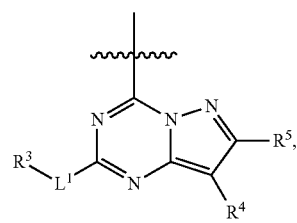
pyrazolotriazinyl
(ii-q)
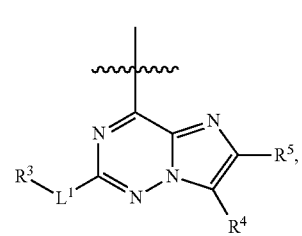
imidazotriazinyl
(ii-r)
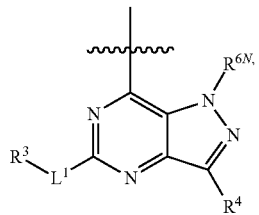
pyrazolopyrimidinyl
(ii-s)
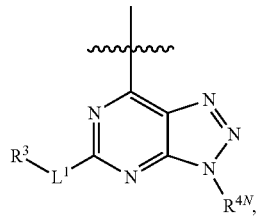
triazolopyrimidinyl
(ii-t)
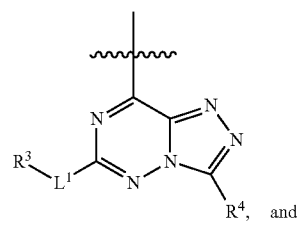
triazolopyridazinyl, and
(ii-u)

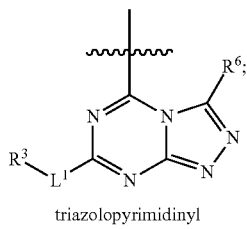

triazolopyrimidinyl (ii-v)

$L^1$ is a bond, —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(=$NR^L$)—, —C(=$NNR^L$)—, —C(=$NOR^L$)—, —C(=N $R^L$)N($R^L$)—, —$NR^L$C(=$NR^L$)—, —C(S)—, —C(S)N($R^L$)—, —$NR^L$C(S)—, —S(O)—, —OS(O)$_2$—, —S(O)$_2$O—, —SO$_2$—, —N($R^L$)SO$_2$—, —SO$_2$N($R^L$)—, —N($R^L$)SO$_2$N($R^L$)—, or an optionally substituted $C_{1-10}$ saturated or unsaturated hydrocarbon chain, wherein one or more moieties selected from the group consisting of —O—, —N($R^L$)—, —S—, —C(O)—, —C(O)O—, —C(O)S—, —C(O)N($R^L$)—, —C(O)N($R^L$)N($R^L$)—, —OC(O)—, —OC(O)N ($R^L$)—, —$NR^L$C(O)—, —$NR^L$C(O)N($R^L$)—, —$NR^L$C(O)N($R^L$)N($R^L$)—, —$NR^L$C(O)O—, —SC(O)—, —C(=$NR^L$)—, —C(=$NNR^L$)—, —C(=$NOR^L$)—, —C(=$NR^L$)N($R^L$)—, —$NR^L$C(=$NR^L$)—, —C(S)—, —C(S)N($R^L$)—, —$NR^L$C(S)—, —S(O)—, —OS(O)$_2$—, —S(O)$_2$O—, —SO$_2$—, —N($R^L$)SO$_2$—, —SO$_2$N($R^L$)—, and —N($R^L$)SO$_2$N($R^L$)— is optionally and independently present between two carbon atoms of the hydrocarbon chain, and optionally and independently present at one or both ends of the hydrocarbon chain;

each $R^L$ is independently hydrogen, optionally substituted alkyl, or a nitrogen protecting group, or $R^L$ and $R^3$ taken together form an optionally substituted heterocyclyl or optionally substituted heteroaryl ring;

$R^3$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided when $R^3$ is hydrogen, then $L^1$ is not a bond;

each instance of $R^{4N}$, $R^{5N}$, and $R^{6N}$ is independently hydrogen, —C(=O)R', —C(=O)OR', —C(=O)N(R')$_2$, —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^4$, $R^5$, $R^6$, and $R^7$ is independently hydrogen, halo, —CN, —NO$_2$, —C(=O)R', —C(=O)OR', —C(=O)N(R')$_2$, —N(R')$_2$, —OR', —SR', —S(=O)R', —S(=O)$_2$R', optionally substituted alkyl, optionally substituted alkenyl, optionally substituted alkynyl, optionally substituted carbocyclyl, optionally substituted heterocyclyl, optionally substituted aryl, or optionally substituted heteroaryl; and each instance of R' is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R' groups attached to the same nitrogen are joined to form an optionally substituted heterocyclyl ring or optionally substituted heteroaryl ring.

* * * * *

UNITED STATES PATENT AND TRADEMARK OFFICE
CERTIFICATE OF CORRECTION

PATENT NO. : 9,718,816 B2
APPLICATION NO. : 14/775197
DATED : August 1, 2017
INVENTOR(S) : Richard Chesworth et al.

Page 1 of 3

It is certified that error appears in the above-identified patent and that said Letters Patent is hereby corrected as shown below:

In the Claims

Claim 5, Column 239, Line 15, please replace the current compound formula (i-c) with the below formula:

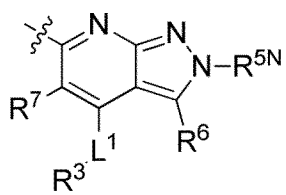

pyrazolopyridinyl

Claim 5, Column 240, Line 5, please replace the current compound formula (i-h) with the below formula:

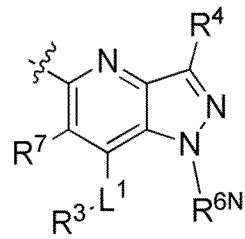

pyrazolopyridinyl

Signed and Sealed this
Twenty-eighth Day of August, 2018

Andrei Iancu
*Director of the United States Patent and Trademark Office*

CERTIFICATE OF CORRECTION (continued)

Claim 5, Column 240, Line 60, please replace the current compound formula (i-m) with the below formula:

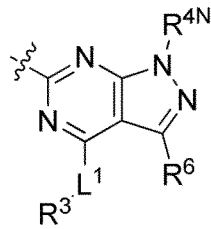

pyrazolopyrimidinyl

Claim 5, Column 243, Line 50, please replace the current compound formula (ii-h) with the below formula:

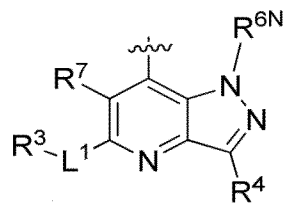

pyrazolopyridinyl

Claim 16, Column 273, Line 5, please replace the current compound formula with the below formula:

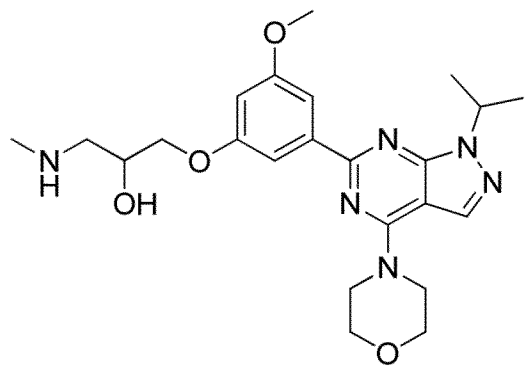

Claim 16, Column 274, Line 15, please replace the current compound formula with the below formula:

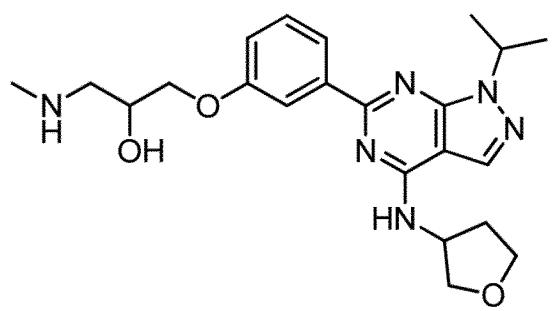

Claim 16, Column 284, Line 55, please replace the current compound formula with the below formula:

CERTIFICATE OF CORRECTION (continued)
U.S. Pat. No. 9,718,816 B2

Page 3 of 3

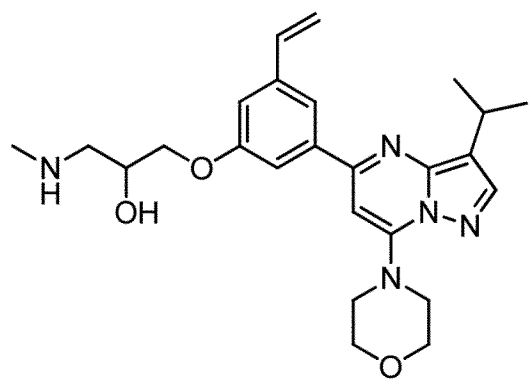

Claim 28, Column 301, Line 60, please replace the current compound formula (ii-o) with the below formula:

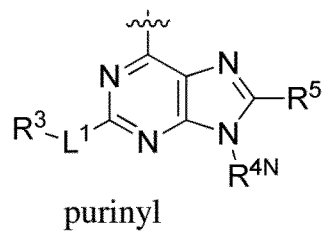

purinyl

SEQUENCE LISTING

<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 1

Xaa Pro Arg Lys Gln Leu Ala Thr Lys Ala Ala Arg Lys Ser Ala Pro
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 2

```
Met Asp Tyr Lys Asp Asp Asp Lys
1               5
```

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

```
Glu Gly His His His His His His
1               5
```

<210> SEQ ID NO 4
<211> LENGTH: 601
<212> TYPE: PRT
<213> ORGANISM: Artificial Sequence
<220> FEATURE:
<223> OTHER INFORMATION: Synthetic Polypeptide

<400> SEQUENCE: 4

```
Met Asp Tyr Lys Asp Asp Asp Lys Ala Ala Ala Ala Ala Val
1               5                   10                  15

Gly Pro Gly Ala Gly Gly Ala Gly Ser Ala Val Pro Gly Gly Ala Gly
                20                  25                  30

Pro Cys Ala Thr Val Ser Val Phe Pro Gly Ala Arg Leu Leu Thr Ile
            35                  40                  45

Gly Asp Ala Asn Gly Glu Ile Gln Arg His Ala Glu Gln Gln Ala Leu
    50                  55                  60

Arg Leu Glu Val Arg Ala Gly Pro Asp Ser Ala Gly Ile Ala Leu Tyr
65                  70                  75                  80

Ser His Glu Asp Val Cys Val Phe Lys Cys Ser Val Ser Arg Glu Thr
                85                  90                  95

Glu Cys Ser Arg Val Gly Lys Gln Ser Phe Ile Ile Thr Leu Gly Cys
            100                 105                 110

Asn Ser Val Leu Ile Gln Phe Ala Thr Pro Asn Asp Phe Cys Ser Phe
        115                 120                 125

Tyr Asn Ile Leu Lys Thr Cys Arg Gly His Thr Leu Glu Arg Ser Val
    130                 135                 140

Phe Ser Glu Arg Thr Glu Glu Ser Ser Ala Val Gln Tyr Phe Gln Phe
145                 150                 155                 160

Tyr Gly Tyr Leu Ser Gln Gln Gln Asn Met Met Gln Asp Tyr Val Arg
                165                 170                 175

Thr Gly Thr Tyr Gln Arg Ala Ile Leu Gln Asn His Thr Asp Phe Lys
            180                 185                 190

Asp Lys Ile Val Leu Asp Val Gly Cys Gly Ser Gly Ile Leu Ser Phe
        195                 200                 205

Phe Ala Ala Gln Ala Gly Ala Arg Lys Ile Tyr Ala Val Glu Ala Ser
    210                 215                 220

Thr Met Ala Gln His Ala Glu Val Leu Val Lys Ser Asn Asn Leu Thr
225                 230                 235                 240

Asp Arg Ile Val Val Ile Pro Gly Lys Val Glu Glu Val Ser Leu Pro
                245                 250                 255

Glu Gln Val Asp Ile Ile Ile Ser Glu Pro Met Gly Tyr Met Leu Phe
            260                 265                 270

Asn Glu Arg Met Leu Glu Ser Tyr Leu His Ala Lys Lys Tyr Leu Lys
```

```
                275                 280                 285
Pro Ser Gly Asn Met Phe Pro Thr Ile Gly Asp Val His Leu Ala Pro
    290                 295                 300
Phe Thr Asp Glu Gln Leu Tyr Met Glu Gln Phe Thr Lys Ala Asn Phe
305                 310                 315                 320
Trp Tyr Gln Pro Ser Phe His Gly Val Asp Leu Ser Ala Leu Arg Gly
                325                 330                 335
Ala Ala Val Asp Glu Tyr Phe Arg Gln Pro Val Val Asp Thr Phe Asp
            340                 345                 350
Ile Arg Ile Leu Met Ala Lys Ser Val Lys Tyr Thr Val Asn Phe Leu
            355                 360                 365
Glu Ala Lys Glu Gly Asp Leu His Arg Ile Glu Ile Pro Phe Lys Phe
    370                 375                 380
His Met Leu His Ser Gly Leu Val His Gly Leu Ala Phe Trp Phe Asp
385                 390                 395                 400
Val Ala Phe Ile Gly Ser Ile Met Thr Val Trp Leu Ser Thr Ala Pro
                405                 410                 415
Thr Glu Pro Leu Thr His Trp Tyr Gln Val Arg Cys Leu Phe Gln Ser
            420                 425                 430
Pro Leu Phe Ala Lys Ala Gly Asp Thr Leu Ser Gly Thr Cys Leu Leu
        435                 440                 445
Ile Ala Asn Lys Arg Gln Ser Tyr Asp Ile Ser Ile Val Ala Gln Val
    450                 455                 460
Asp Gln Thr Gly Ser Lys Ser Ser Asn Leu Leu Asp Leu Lys Asn Pro
465                 470                 475                 480
Phe Phe Arg Tyr Thr Gly Thr Thr Pro Ser Pro Pro Gly Ser His
                485                 490                 495
Tyr Thr Ser Pro Ser Glu Asn Met Trp Asn Thr Gly Ser Thr Tyr Asn
            500                 505                 510
Leu Ser Ser Gly Met Ala Val Ala Gly Met Pro Thr Ala Tyr Asp Leu
            515                 520                 525
Ser Ser Val Ile Ala Ser Gly Ser Ser Val Gly His Asn Asn Leu Ile
    530                 535                 540
Pro Leu Gly Ser Ser Gly Ala Gln Gly Ser Gly Gly Ser Thr Ser
545                 550                 555                 560
Ala His Tyr Ala Val Asn Ser Gln Phe Thr Met Gly Gly Pro Ala Ile
                565                 570                 575
Ser Met Ala Ser Pro Met Ser Ile Pro Thr Asn Thr Met His Tyr Gly
            580                 585                 590
Ser Glu Gly His His His His His His
    595                 600
```